US011116776B2

(12) United States Patent
Williams et al.

(10) Patent No.: US 11,116,776 B2
(45) Date of Patent: *Sep. 14, 2021

(54) INTRAVITREAL DRUG DELIVERY SYSTEMS FOR THE TREATMENT OF OCULAR CONDITIONS

(71) Applicant: Aerie Pharmaceuticals, Inc., Bedminster, NJ (US)

(72) Inventors: Stuart Williams, Morrisville, NC (US); Sanjib Kumar Das, Morrisville, NC (US); Tomas Navratil, Morrisville, NC (US); Melissa Sandahl, Morrisville, NC (US); Janet Tully, Cary, NC (US); Rozemarijn Verhoeven, Siler City, NC (US)

(73) Assignee: Aerie Pharmaceuticals, Inc., Bedminster, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/712,624

(22) Filed: Dec. 12, 2019

(65) Prior Publication Data

US 2020/0230157 A1 Jul. 23, 2020

Related U.S. Application Data

(63) Continuation of application No. 15/746,797, filed as application No. PCT/US2016/043675 on Jul. 22, 2016, now Pat. No. 10,624,904.

(Continued)

(51) Int. Cl.
*A61K 31/58* (2006.01)
*A61K 9/00* (2006.01)
(Continued)

(52) U.S. Cl.
CPC ............ *A61K 31/58* (2013.01); *A61K 9/0048* (2013.01); *A61K 9/0051* (2013.01); *A61K 9/08* (2013.01);
(Continued)

(58) Field of Classification Search
CPC .............................. A61K 31/713; A61K 31/56
See application file for complete search history.

(56) References Cited

U.S. PATENT DOCUMENTS 3,405,713 A 10/1968 Solowey
4,251,310 A 2/1981 Goldhaber
(Continued)

FOREIGN PATENT DOCUMENTS

WO 2015/085251 A1 6/2015
WO 2016/144832 A1 9/2016
(Continued)

OTHER PUBLICATIONS

International Search Report and Written Opinion for International Application No. PCT/US2016/043675 dated Nov. 29, 2016.
(Continued)

*Primary Examiner* — San Ming R Hui
(74) *Attorney, Agent, or Firm* — K&L Gates LLP; Louis C. Cullman; Benjamin D. Heuberger

(57) ABSTRACT

The disclosure teaches precisely engineered biodegradable drug delivery systems and methods of making and utilizing such systems. In aspects, the biodegradable drug delivery systems taught herein comprise intravitreal ocular implants suitable for delivery of corticosteroids to the posterior segment of a human eye. The intravitreal ocular implants described herein have a desired extended drug release profile suitable for treating inflammation of the human eye.

26 Claims, 57 Drawing Sheets

Related U.S. Application Data

(60) Provisional application No. 62/358,372, filed on Jul. 5, 2016, provisional application No. 62/329,763, filed on Apr. 29, 2016, provisional application No. 62/277,281, filed on Jan. 11, 2016, provisional application No. 62/196,269, filed on Jul. 23, 2015.

(51) Int. Cl.
| | | |
|---|---|---|
| *A61K 9/08* | (2006.01) | |
| *A61K 9/10* | (2006.01) | |
| *A61K 9/16* | (2006.01) | |
| *A61K 31/573* | (2006.01) | |
| *A61K 47/26* | (2006.01) | |
| *A61K 47/36* | (2006.01) | |
| *A61F 9/00* | (2006.01) | |
| *A61M 31/00* | (2006.01) | |

(52) U.S. Cl.
CPC ............ *A61K 9/10* (2013.01); *A61K 9/1647* (2013.01); *A61K 31/573* (2013.01); *A61K 47/26* (2013.01); *A61K 47/36* (2013.01); *A61F 9/0017* (2013.01); *A61M 31/002* (2013.01)

(56) References Cited

U.S. PATENT DOCUMENTS

| | | |
|---|---|---|
| 5,869,079 A | 2/1999 | Wong et al. |
| 6,129,710 A | 10/2000 | Padgett et al. |
| 2004/0151754 A1 | 8/2004 | Ashton |
| 2004/0171598 A1 | 9/2004 | Bingaman et al. |
| 2005/0154399 A1 | 7/2005 | Weber |
| 2005/0244467 A1 | 11/2005 | Nivaggioli |
| 2005/0244468 A1 | 11/2005 | Huang |
| 2006/0233860 A1 | 10/2006 | Chang |
| 2008/0033351 A1 | 2/2008 | Trogden et al. |
| 2008/0071246 A1 | 3/2008 | Nazzaro et al. |
| 2010/0124565 A1 | 5/2010 | Spada et al. |
| 2010/0278897 A1 | 11/2010 | Shi et al. |
| 2011/0229551 A1 | 9/2011 | Doshi et al. |
| 2013/0138047 A1 | 5/2013 | Takemoto et al. |
| 2013/0158561 A1 | 6/2013 | Bhagat et al. |
| 2013/0218102 A1 | 8/2013 | Iwase et al. |
| 2013/0253528 A1 | 9/2013 | Haffner et al. |
| 2015/0118279 A1 | 4/2015 | Ghebremeskel et al. |
| 2015/0209180 A1 | 7/2015 | Prausnitz et al. |
| 2016/0067426 A1 | 3/2016 | Ujaoney |
| 2018/0368886 A1 | 12/2018 | Navratil et al. |
| 2019/0083512 A1 | 3/2019 | Williams et al. |
| 2019/0374380 A1 | 12/2019 | Navratil et al. |

FOREIGN PATENT DOCUMENTS

| | | |
|---|---|---|
| WO | 2017/015604 A1 | 1/2017 |
| WO | 2018/045386 A1 | 3/2018 |

OTHER PUBLICATIONS

Singaporean Search Report and Written Opinion for Singaporean Application No. 11201800538R (date of actual completion of search: Nov. 2, 2018).
Supplementary European Search Report for European Patent Application No. 16762267.9 dated Oct. 15, 2018 (8 pages).
International Search Report and Written Opinion for International Application No. PCT/US2016/021081 dated Jul. 18, 2016.
International Search Report and Written Opinion for International Application No. PCT/US2017/050122 dated Nov. 16, 2017.
Singaporean Written Opinion (Second) for Singaporean Application No. 11201800538R (dated Oct. 11, 2019).

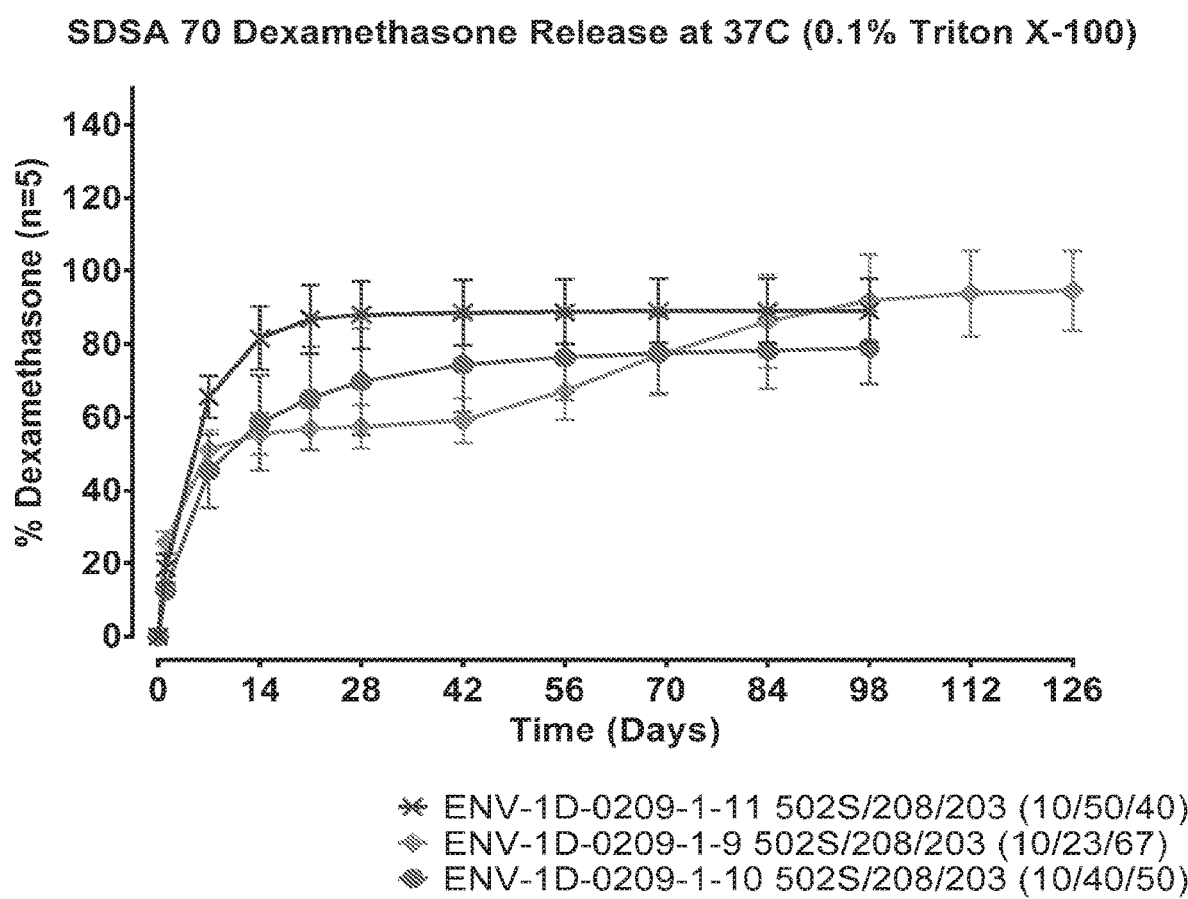

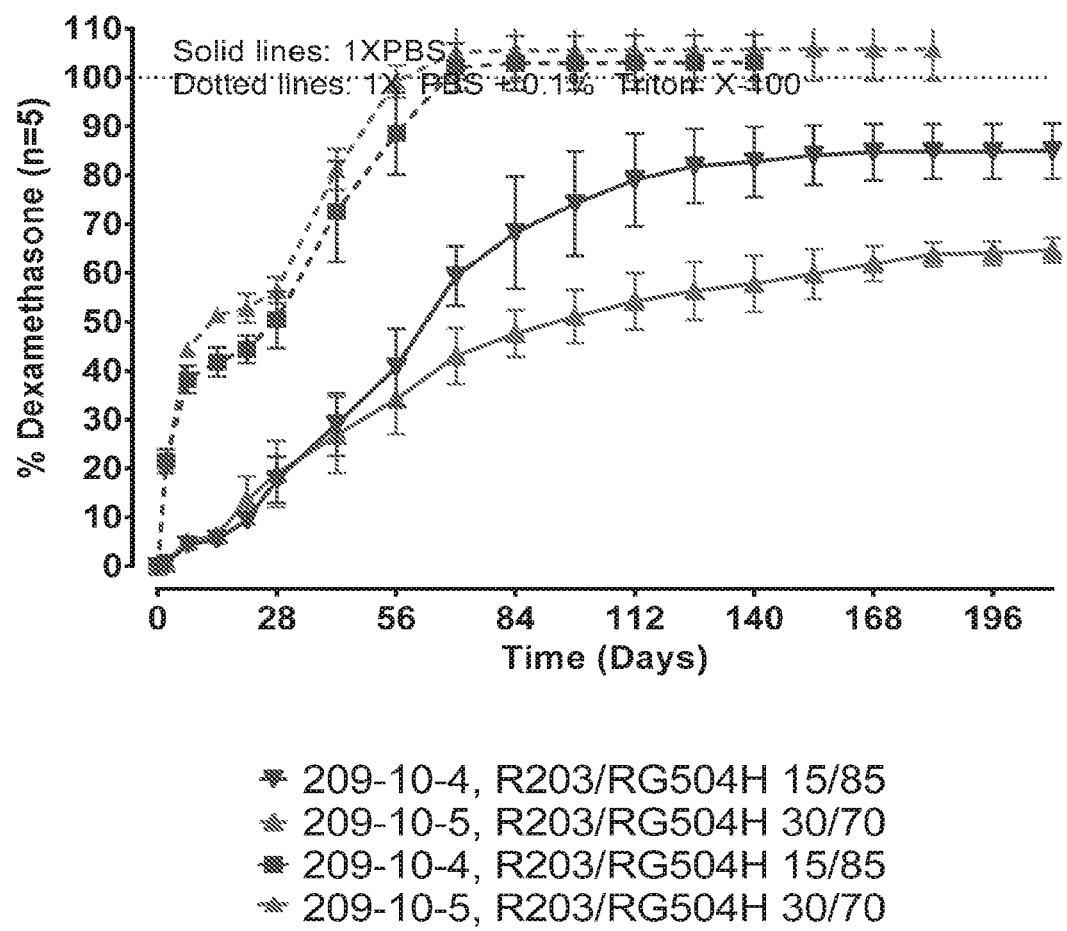

FIG. 32

Dexamethasone Concentration in Albino Rabbit Aqueous Humor
Mean, ±SD (n=4 eyes/group)

- Group 1
- Group 2
- Group 3
- Group 4
- Group 5
- Group 6
- Group 7
- LLOQ/Ki

INTRAVITREAL DRUG DELIVERY SYSTEMS FOR THE TREATMENT OF OCULAR CONDITIONS

CROSS-REFERENCE TO RELATED APPLICATIONS

The present application is a continuation of U.S. patent application Ser. No. 15/746,797, filed Jan. 22, 2018, which is a 35 U.S.C. § 371 national stage entry of International Patent Application No. PCT/US2016/043675, filed Jul. 22, 2016, which claims priority to: U.S. Provisional Application No. 62/196,269, filed on Jul. 23, 2015; U.S. Provisional Application No. 62/277,281, filed on Jan. 11, 2016; U.S. Provisional Application No. 62/329,763, filed on Apr. 29, 2016; and U.S. Provisional Application No. 62/358,372, filed on Jul. 5, 2016, the entire contents of each of which are hereby incorporated by reference in their entirety.

FIELD

The present disclosure relates to the field of pharmaceutical compositions, implants formed from pharmaceutical compositions, methods of forming implants, and methods of treating ocular conditions.

BACKGROUND

Ocular inflammatory diseases, such as macular edema, retinal vein occlusion, and uveitis, can cause blurry vision, double vision, floaters, ocular pain, loss of vision, and may result in blindness.

For treatment, corticosteroids, such as dexamethasone or triamcinolone acetonide (TRIESENCE®), can be injected via intravitreal injection (IVT). Repeated bolus injections of corticosteroids such as TRIESENCE are associated with cataract formation, increased intraocular pressure, vitreous floaters, endophthalmitis, decreased visual acuity, and retinal injury. Patients are administered numerous injections over the course of treatment. This regimen is burdensome for patients and medical care providers.

Intravitreal implants have been developed which deliver a sustained concentration of drug over a period of time. These implants are injected or surgically implanted in the vitreous of the eye for the sustained release of drug to the posterior of the eye. For example, OZURDEX® is an intravitreal implant used for the extended release of dexamethasone to treat various ocular conditions. However, sufficient levels of the drug are released for only approximately 30 to 60 days, and a new implant must be injected into the eye of the patient. Repeated injections may result in pain, headache, conjunctival blood spot, intraocular infection, globe perforation, fibrosis of the extraocular muscles, vitreous detachment, reactions to the delivery vehicle, increased intraocular pressure, and cataract development. Alternatively, an intravitreal implant containing fluocinolone acetonide, ILUVIEN®, has been developed, which releases fluocinolone acetonide over a period of approximately 3 years. This duration of corticosteroid exposure is often too extensive for many patients, and may result in increased risk of corticosteroid-associated adverse effects, including cataract formation and increased intraocular pressure.

Therefore, there is a great need in the medical field for an alternative treatment using a sustained-release delivery system with an improved safety and efficacy profile. An improved sustained release pharmaceutical formulation administered directly to the posterior of an eye would likely improve both compliance and the adverse event profile of current intravitreal implants. Moreover, any extended release implant is highly dependent on the selection of polymers, co-polymers, drug-polymer interaction, load uniformity, porosity, size, surface-area to volume ratio, and the like for providing its drug release and degradation characteristics and the manufacturing techniques used in the prior art implants can induce inherent drawbacks in each of these parameters.

BRIEF SUMMARY

The present disclosure addresses a crucial need in the art, by providing a sustained-release pharmaceutical formulation that may be directly administered to the posterior of an eye and that does not suffer from the drawbacks of the current art.

Moreover, the present disclosure provides implants with highly uniform, tunable and reproducible size, shape, loading, composition, and load distribution, which provide implants having a desired extended drug release profile suitable for treating desired indications. In a particular embodiment, the implant is utilized to treat an ocular indication of inflammation.

In certain embodiments, the disclosure relates to precisely engineered biodegradable drug delivery systems and methods of making and utilizing such systems.

The biodegradable drug delivery systems taught herein are, in some embodiments, engineered using a Particle Replication in Non-wetting Template (PRINT®) technology. The PRINT® Technology utilized in some embodiments allows for uniform size, shape, and dose concentration in the disclosed drug delivery systems.

Further, the disclosure provides methods of utilizing the taught precisely engineered biodegradable drug delivery systems to treat, inter alia, conditions of the eye.

Conditions treatable according to the present disclosure include edema, retinal vein occlusion, and uveitis.

In certain embodiments, the present disclosure relates to pharmaceutical compositions for treating an ocular condition, comprising: a biodegradable polymer matrix and at least one therapeutic agent.

In certain embodiments, the present disclosure provides for pharmaceutical compositions for treating an ocular condition, comprising: an ocular implant or a particle suspension. In aspects, the ocular implant or particle suspension comprises a biodegradable polymer matrix that contains a homogenously dispersed therapeutic agent therein. In some embodiments, the ocular implant is a "non-extruded" ocular implant, such as for example a molded implant. In some embodiments, the ocular implant is an intravitreal implant.

In certain embodiments, the therapeutic agent is a corticosteroid. In embodiment, the corticosteroid is selected from the group consisting of dexamethasone, fluocinolone acetonide, and combinations thereof. In a particular embodiment, the therapeutic agent is dexamethasone.

In embodiments, the biodegradable polymer matrix contains a mixture of polymers selected from the group consisting of: an ester end-capped biodegradable poly(D,L-lactide) homopolymer, an acid end-capped biodegradable poly(D,L-lactide) homopolymer, an ester end-capped biodegradable poly(D,L-lactide-co-glycolide) copolymer, and an acid end-capped biodegradable poly(D,L-lactide-co-glycolide) copolymer.

In embodiments, the biodegradable polymer matrix comprises as weight of the pharmaceutical composition (e.g., intravitreal implant or particle suspension): about 1 µg to about 1,000 µg, about 1 µg to about 500 µg, or about 1 µg to about 400 µg, or about 1 g to about 300 µg, or about 1 µg to about 250 µg, or about 1 µg to about 200 µg, or about 1 µg to about 150 µg, or about 1 µg to about 100 µg, or about 1 µg to about 50 µg, or about 1 µg to about 40 µg, or about 1 µg to about 30 µg, or about 1 µg to about 20 µg, or about 1 µg to about 10 µg, or about 1 to about 5 µg, including all values and subranges in between. In certain embodiments, the biodegradable polymer matrix comprises as weight of the pharmaceutical composition: about 50 µg to about 1,000 µg, about 50 µg to about 500 µg, or about 50 µg to about 400 µg, or about 50 µg to about 300 µg, or about 50 µg to about 250 µg, about 50 µg to about 200 µg, or about 50 µg to about 175 µg, or about 50 µg to about 160 µg to about, or about 60 µg to about 75 µg to about, or about 120 µg to about 160 µg to about, or about 165 µg to about 205 µg to about, or about 180 µg to about 220 µg.

In certain embodiments, the biodegradable polymer matrix comprises as a % w/w of the pharmaceutical composition (e.g., intravitreal implant or particle suspension): about 1% to about 99%, w/w, about 10% to about 90%, or about 10% to about 80%, or about 10% to about 70%, or about 10% to about 65%, or about 10% to about 60%, or about 10% to about 55%, or about 10% to about 50%, or about 20% to about 90%, or about 20% to about 80%, or about 20% to about 70%, or about 20% to about 65%, or about 20% to about 60%, or about 20% to about 55%, or about 20% to about 50%, or about 30% to about 90%, or about 30% to about 80%, or about 30% to about 70%, or about 30% to about 65%, or about 30% to about 60%, or about 30% to about 55%, or about 40% to about 90%, or about 40% to about 80%, or about 40% to about 70%, or about 40% to about 65%, or about 40% to about 60%, or about 40% to about 55%, or about 50% to about 90%, or about 50% to about 80%, or about 50% to about 70%, or about 50% to about 65%, or about 50% to about 60%, or about 60% to about 90%, or about 60% to about 80%, or about 60% to about 75%, or about 60% to about 70%, or about 55% to about 65%, or about 70% to about 90%, or about 75% to about 85%, or about 80% to about 85%, including all values and subranges in between.

In certain embodiments, the biodegradable polymer matrix comprises as a % w/w of the intravitreal implant: about 1% to about 99%, w/w, about 10% to about 90%, or about 10% to about 80%, or about 10% to about 70%, or about 10% to about 65%, or about 10% to about 60%, or about 10% to about 55%, or about 10% to about 50%, or about 20% to about 90%, or about 20% to about 80%, or about 20% to about 70%, or about 20% to about 65%, or about 20% to about 60%, or about 20% to about 55%, or about 20% to about 50%, or about 30% to about 90%, or about 30% to about 80%, or about 30% to about 70%, or about 30% to about 65%, or about 30% to about 60%, or about 30% to about 55%, or about 40% to about 90%, or about 40% to about 80%, or about 40% to about 70%, or about 40% to about 65%, or about 40% to about 60%, or about 40% to about 55%, or about 50% to about 90%, or about 50% to about 80%, or about 50% to about 70%, or about 50% to about 65%, or about 50% to about 60%, or about 60% to about 90%, or about 60% to about 80%, or about 60% to about 75%, or about 60% to about 70%, or about 55% to about 65%, including all values and subranges in between.

In certain embodiments, the biodegradable polymer matrix includes a first polymer. In aspects, the first polymer comprises as a % w/w of the biodegradable polymer matrix: about 1% to about 100%, or about 1% to about 90% w/w, or about 1% to about 80%, or about 1% to about 70%, or about 1% to about 60%, or about 1% to about 50%, or about 1% to about 40%, or about 1% to about 30%, or about 1% to about 20%, or about 1% to about 10%; or 10% to about 100%, or about 10% to about 90% w/w, or about 10% to about 80%, or about 10% to about 70%, or about 10% to about 60%, or about 10% to about 50%, or about 10% to about 40%, or about 10% to about 30%, or about 10% to about 20%; or about 15% to about 100%, or about 15% to about 95%, or about 15% to about 90%, or about 15% to about 85%, or about 15% to about 80%, or about 15% to about 70%, or about 15% to about 60%, or about 15% to about 50%, or about 15% to about 40%, or about 15% to about 30%, or about 15% to about 20%, or 20% to about 100%, or about 20% to about 90% w/w, or about 20% to about 80%, or about 20% to about 70%, or about 20% to about 60%, or about 20% to about 50%, or about 20% to about 40%, or about 20% to about 30%; or 30% to about 100%, or about 30% to about 90% w/w, or about 30% to about 80%, or about 30% to about 70%, or about 30% to about 60%, or about 30% to about 50%, or about 30% to about 40%; or 40% to about 100%, or about 40% to about 90% w/w, or about 40% to about 80%, or about 40% to about 70%, or about 40% to about 60%, or about 40% to about 50%; or 50% to about 100%, or about 50% to about 90% w/w, or about 50% to about 80%, or about 50% to about 70%, or about 50% to about 60%; or 60% to about 100%, or about 60% to about 90% w/w, or about 60% to about 80%, or about 60% to about 70%; or 70% to about 100%, or about 70% to about 90%, or about 70% to about 80%; or 80% to about 100%, or about 80% to about 90%; or 90% to about 100% w/w; or about 15%; or about 30%; or about 50%; or about 60%; or about 70%; or about 85%; or about 95%, including all values and subranges in between. In aspects, the first polymer is a PLA or a PLGA polymer. In aspects, the PLA polymer is R 203 S or R 205 S. In aspects, the PLGA polymer is RG 502 S, RG 503 H, RG 504 H, RG 653 H, RG 752 S, DLG 1A, DLG 2A, DLG 3A, or DLG 4A. In aspects, the PLA polymer or the PLGA polymer can be present as the sole polymer in the biodegradable polymer matrix. In aspects, the PLA polymer or the PLGA polymer can be present as a mixture of polymers in the biodegradable polymer matrix.

In certain embodiments, the biodegradable polymer matrix includes a first polymer. In aspects, the first polymer comprises as a % w/w of the pharmaceutical composition (e.g., intravitreal implant or particle suspension): about 1% to about 99%, or about 1% to about 90% w/w, or about 1% to about 80%, or about 1% to about 70%, or about 1% to about 60%, or about 1% to about 50%, or about 1% to about 40%, or about 1% to about 30%, or about 1% to about 20%, or about 1% to about 10%; or 10% to about 100%, or about 10% to about 90% w/w, or about 10% to about 80%, or about 10% to about 70%, or about 10% to about 60%, or about 10% to about 50%, or about 10% to about 40%, or about 10% to about 30%, or about 10% to about 20%; or 15% to about 100%, or about 15% to about 95%, or about 15% to about 90%, or about 15% to about 85%, or about 15% to about 80%, or about 15% to about 70%, or about 15% to about 60%, or about 15% to about 50%, or about 15% to about 40%, or about 15% to about 30%, or about 15% to about 20%, or 20% to about 100%, or about 20% to about 90% w/w, or about 20% to about 80%, or about 20% to about 70%, or about 20% to about 60%, or about 20% to about 50%, or about 20% to about 40%, or about 20% to about 30%; or 30% to about 100%, or about 30% to about 90% w/w, or about 30% to about 80%, or about 30% to about 70%, or about 30% to about 60%, or about 30% to about 50%, or about 30% to about 40%; or 40% to about 100%, or about 40% to about 90% w/w, or about 40% to about 80%, or about 40% to about 70%, or about 40% to about 60%, or about 40% to about 50%; or 50% to about 100%, or about 50% to about 90% w/w, or about 50% to about 80%, or about 50% to about 70%, or about 50% to about 60%; or 60% to about 100%, or about 60% to about 90% w/w, or about 60% to about 80%, or about 60% to about 70%; or about 7% to about 10%; or about 48% to about 58%, or about 32% to about 39%; or about 30% to about 34%; or about 36% to about 46%; or about 31% to about 36%; or about 53% to about 63%; including all values and subranges in between. In aspects, the first polymer is a PLA or a PLGA polymer. In aspects, the PLA polymer is R 203 S or R 205 S. In aspects, the PLGA polymer is RG 502 S, RG 503 H, RG 504 H, RG 653 H, RG 752 S, DLG 1A, DLG 2A, DLG 3A, or DLG 4A. In aspects, the PLA polymer or the PLGA polymer can be present as the sole polymer in the biodegradable polymer matrix. In aspects, the PLA polymer or the PLGA polymer can be present as a mixture of polymers in the biodegradable polymer matrix.

In certain embodiments, the biodegradable polymer matrix includes a first polymer. In aspects, the first polymer comprises as a weight of the biodegradable polymer matrix: about 1 µg to about 1,000 µg, about 1 µg to about 500 µg, or about 1 µg to about 400 µg, or about 1 µg to about 300 µg, or about 1 µg to about 250 µg, or about 1 g to about 200 µg, or about 1 µg to about 150 µg, or about 1 µg to about 100 µg, or about 1 µg to about 90 µg, or about 1 µg to about 80 µg, or about 1 µg to about 70 µg, or about 1 µg to about 60 µg, or about 1 µg to about 50 µg, or about 1 µg to about 40 µg, or about 1 µg to about 30 µg, or about 1 µg to about 20 µg, or about 1 µg to about 10 µg, including all values and subranges in between. In aspects, the first polymer comprises as weight of the biodegradable polymer matrix: 5 µg to about 1,000 µg, about 5 µg to about 500 µg, or about 5 µg to about 400 µg, or about 5 µg to about 300 µg, or about 5 µg to about 250 µg, or about 5 µg to about 200 µg, about 5 µg to about 150 µg, about 9 µg to about 141 µg, or about 40 µg to about 141 µg, or about 74 µg to about 141 µg, or about 118 µg to about 131 µg, or about 81 µg to about 87 µg, or about 74 µg to about 76 µg, or about 40 µg to about 41 µg, or about 76 µg to about 80 µg, or about 129 µg to about 141 µg, or about 8 to about 12 µg, or about 9 µg to about 11 µg, including all values and subranges in between. In aspects, the first polymer is a PLA polymer. In aspects, the first polymer is a PLA or a PLGA polymer. In aspects, the PLA polymer is R 203 S or R 205 S. In aspects, the PLGA polymer is RG 502 S, RG 503 H, RG 504 H, RG 653 H, RG 752 S, DLG 1A, DLG 2A, DLG 3A, or DLG 4A. In aspects, the PLA polymer or the PLGA polymer can be present as the sole polymer in the biodegradable polymer matrix. In aspects, the PLA polymer or the PLGA polymer can be present as a mixture of polymers in the biodegradable polymer matrix.

In certain embodiments, the biodegradable polymer matrix includes a second polymer. In aspects, the second polymer comprises as a % w/w of the biodegradable polymer matrix: about 1% to about 99%, or about 1% to about 90% w/w, or about 1% to about 80%, or about 1% to about 70%, or about 1% to about 60%, or about 1% to about 50%, or about 1% to about 40%, or about 1% to about 30%, or about 1% to about 20%, or about 1% to about 10%; or 10% to about 100%, or about 10% to about 90% w/w, or about 10% to about 80%, or about 10% to about 70%, or about 10% to about 60%, or about 10% to about 50%, or about 10% to about 40%, or about 10% to about 30%, or about 10% to about 20%; or 20% to about 100%, or about 20% to about 90% w/w, or about 20% to about 80%, or about 20% to about 70%, or about 20% to about 60%, or about 20% to about 50%, or about 20% to about 40%, or about 20% to about 30%; or 30% to about 100%, or about 30% to about 90% w/w, or about 30% to about 80%, or about 30% to about 70%, or about 30% to about 60%, or about 30% to about 50%, or about 30% to about 40%; or 40% to about 100%, or about 40% to about 90% w/w, or about 40% to about 80%, or about 40% to about 70%, or about 40% to about 60%, or about 40% to about 50%; or 50% to about 100%, or about 50% to about 90% w/w, or about 50% to about 80%, or about 50% to about 70%, or about 50% to about 60%; or 60% to about 100%, or about 60% to about 90% w/w, or about 60% to about 80%, or about 60% to about 70%; or 70% to about 100%, or about 70% to about 90% w/w, or about 70% to about 80%; or 80% to about 100%, or about 80% to about 90% w/w; or 90% to about 100%; or about 5%; or about 15%; or about 40%; or about 50%; or about 60%; or about 70%; or about 85%; or about 90%; or about 95%, including all values and subranges in between. In aspects, the second polymer is a PLA or PLDA polymer. In aspects, the PLA polymer is R 203 S or R 205 S. In aspects, the PLGA polymer is RG 502 S, RG 503 H, RG 504 H, RG 653 H, RG 752 S, DLG 1A, DLG 2A, DLG 3A, or DLG 4A. In aspects, the PLA polymer or the PLGA polymer can be present as a mixture of polymers in the biodegradable polymer matrix.

In certain embodiments, the biodegradable polymer matrix includes a second polymer. In aspects, the second polymer comprises as a % w/w of the pharmaceutical composition (e.g., intravitreal implant or particle suspension): about 1% to about 99%, or about 1% to about 90% w/w, or about 1% to about 80%, or about 1% to about 70%, or about 1% to about 60%, or about 1% to about 50%, or about 1% to about 40%, or about 1% to about 30%, or about 1% to about 20%, or about 1% to about 10%; or 10% to about 100%, or about 10% to about 90% w/w, or about 10% to about 80%, or about 10% to about 70%, or about 10% to about 60%, or about 10% to about 50%, or about 10% to about 40%, or about 10% to about 30%, or about 10% to about 20%; or about 15% to about 100%, or about 15% to about 95%, or about 15% to about 90%, or about 15% to about 85%, or about 15% to about 80%, or about 15% to about 70%, or about 15% to about 60%, or about 15% to about 50%, or about 15% to about 40%, or about 15% to about 30%, or about 15% to about 20%; or 20% to about 100%, or about 20% to about 90% w/w, or about 20% to about 80%, or about 20% to about 70%, or about 20% to about 60%, or about 20% to about 50%, or about 20% to about 40%, or about 20% to about 30%; or 30% to about 100%, or about 30% to about 90% w/w, or about 30% to about 80%, or about 30% to about 70%, or about 30% to about 60%, or about 30% to about 50%, or about 30% to about 40%; or 40% to about 100%, or about 40% to about 90% w/w, or about 40% to about 80%, or about 40% to about 70%, or about 40% to about 60%, or about 40% to about 50%; or 50% to about 100%, or about 50% to about 90% w/w, or about 50% to about 80%, or about 50% to about 70%, or about 50% to about 60%; or 60% to about 100%, or about 60% to about 90% w/w, or about 60% to about 80%, or about 60% to about 70%; or about 8% to about 10%; or about 22% to about 26%; or about 30% to about 34%; or about 38% to about 42%; or about 31% to about 36%; or about 27% to about 33%; or about 39% to about 55%; including all values and subranges in between. In aspects, the second polymer is a PLA or a PLGA polymer. In aspects, the PLA polymer is R 203 S or R 205 S. In aspects, the PLGA polymer is RG 502 S, RG 503 H, RG 504 H, RG 653 H, RG 752 S, DLG 1A, or DLG 2A. In aspects, the PLA polymer or the PLGA polymer can be present as a mixture of polymers in the biodegradable polymer matrix.

In certain embodiments, the biodegradable polymer matrix includes a second polymer. In aspects, the second polymer comprises as a weight of the biodegradable polymer matrix: about 1 μg to about 1,000 μg, about 1 μg to about 500 μg, or about 1 μg to about 400 μg, or about 1 μg to about 300 μg, or about 1 μg to about 250 μg, or about 1 g to about 200 μg, or about 1 μg to about 150 μg, or about 1 μg to about 100 μg, or about 1 μg to about 50 μg, or about 1 μg to about 40 μg, or about 1 μg to about 30 μg, or about 1 μg to about 20 μg, or about 1 μg to about 10 μg, or about 1 to about 5 μg, including all values and subranges in between. In aspects, the second polymer comprises as weight of the biodegradable polymer matrix: about 15 μg to about 1,000 μg, about 15 g to about 500 μg, or about 15 μg to about 400 μg, or about 15 μg to about 300 μg, or about 15 μg to about 250 μg, or about 15 μg to about 200 μg, or about 15 μg to about 150 μg, about 15 μg to about 100 μg, or about 20 μg to about 95 μg, or about 20 μg to about 23 μg, or about 54 μg to about 58 μg, or about 74 μg to about 76 μg, or about 93 μg to about 95 μg, or about 76 μg to about 80 μg, or about 68 μg to about 74 μg, or about 51 g to about 61 μg, including all values and subranges in between. In aspects, the second polymer is a PLA or a PLGA polymer. In aspects, the PLA polymer is R 203 S or R 205 S. In aspects, the PLGA polymer is RG 502 S, RG 503 H, RG 504 H, RG 653 H, RG 752 S, DLG 1A, DLG 2A, DLG 3A, or DLG 4A. In aspects, the PLA polymer or the PLGA polymer can be present as a mixture of polymers in the biodegradable polymer matrix.

In certain embodiments, the biodegradable polymer matrix includes a third polymer. In aspects, the third polymer comprises as a % w/w of the biodegradable polymer matrix: about 1% to about 99%, or about 1% to about 90% w/w, or about 1% to about 80%, or about 1% to about 70%, or about 1% to about 60%, or about 1% to about 50%, or about 1% to about 40%, or about 1% to about 30%, or about 1% to about 20%, or about 1% to about 10%; or 10% to about 100%, or about 10% to about 90% w/w, or about 10% to about 80%, or about 10% to about 70%, or about 10% to about 60%, or about 10% to about 50%, or about 10% to about 40%, or about 10% to about 30%, or about 10% to about 20%; or 20% to about 100%, or about 20% to about 90% w/w, or about 20% to about 80%, or about 20% to about 70%, or about 20% to about 60%, or about 20% to about 50%, or about 20% to about 40%, or about 20% to about 30%; or 30% to about 100%, or about 30% to about 90% w/w, or about 30% to about 80%, or about 30% to about 70%, or about 30% to about 60%, or about 30% to about 50%, or about 30% to about 40%; or 40% to about 100%, or about 40% to about 90% w/w, or about 40% to about 80%, or about 40% to about 70%, or about 40% to about 60%, or about 40% to about 50%; or 50% to about 100%, or about 50% to about 90% w/w, or about 50% to about 80%, or about 50% to about 70%, or about 50% to about 60%; or 60% to about 100%, or about 60% to about 90% w/w, or about 60% to about 80%, or about 60% to about 70%; or 70% to about 100%, or about 70% to about 90% w/w, or about 70% to about 80%; or 80% to about 100%, or about 80% to about 90% w/w; or 90% to about 100%; or about 5%; or about 15%; or about 40%; or about 50%; or about 60%; or about 70%; or about 85%; or about 90%; or about 95%, including all values and subranges in between. In aspects, the third polymer is a PLA or PLGA polymer. In aspects, the PLA polymer is R 203 S or R 205 S. In aspects, the PLGA polymer is RG 502 S, RG 503 H, RG 504 H, RG 653 H, RG 752 S, DLG 1A, DLG 2A, DLG 3A, or DLG 4A. In aspects, the PLA polymer or the PLGA polymer can be present as a mixture of polymers in the biodegradable polymer matrix.

In certain embodiments, the biodegradable polymer matrix includes a third polymer. In aspects, the third polymer comprises as a % w/w of the pharmaceutical composition (e.g., intravitreal implant or particle suspension): about 1% to about 99%, or about 1% to about 90% w/w, or about 1% to about 80%, or about 1% to about 70%, or about 1% to about 60%, or about 1% to about 50%, or about 1% to about 40%, or about 1% to about 30%, or about 1% to about 20%, or about 1% to about 10%; or 10% to about 100%, or about 10% to about 90% w/w, or about 10% to about 80%, or about 10% to about 70%, or about 10% to about 60%, or about 10% to about 50%, or about 10% to about 40%, or about 10% to about 30%, or about 10% to about 20%; or about 15% to about 100%, or about 15% to about 95%, or about 15% to about 90%, or about 15% to about 85%, or about 15% to about 80%, or about 15% to about 70%, or about 15% to about 60%, or about 15% to about 50%, or about 15% to about 40%, or about 15% to about 30%, or about 15% to about 20%, or 20% to about 100%, or about 20% to about 90% w/w, or about 20% to about 80%, or about 20% to about 70%, or about 20% to about 60%, or about 20% to about 50%, or about 20% to about 40%, or about 20% to about 30%; or 30% to about 100%, or about 30% to about 90% w/w, or about 30% to about 80%, or about 30% to about 70%, or about 30% to about 60%, or about 30% to about 50%, or about 30% to about 40%; or 40% to about 100%, or about 40% to about 90% w/w, or about 40% to about 80%, or about 40% to about 70%, or about 40% to about 60%, or about 40% to about 50%; or 50% to about 100%, or about 50% to about 90% w/w, or about 50% to about 80%, or about 50% to about 70%, or about 50% to about 60%; or 60% to about 100%, or about 60% to about 90% w/w, or about 60% to about 80%, or about 60% to about 70%; or about 8% to about 10%; or about 22% to about 26%; or about 30% to about 34%; or about 38% to about 42%; or about 31% to about 36%; or about 27% to about 33%; or about 39% to about 55%; including all values and subranges in between. In aspects, the third polymer is a PLA or a PLGA polymer. In aspects, the PLA polymer is R 203 S or R 205 S. In aspects, the PLGA polymer is RG 502 S, RG 503 H, RG 504 H, RG 653 H, RG 752 S, DLG 1A, DLG 2A, DLG 3A, or DLG 4A. In aspects, the PLA polymer or the PLGA polymer can be present as a mixture of polymers in the biodegradable polymer matrix.

In certain embodiments, the biodegradable polymer matrix includes a third polymer. In aspects, the third polymer comprises as a weight of the biodegradable polymer matrix: about 1 μg to about 1,000 μg, about 1 μg to about 500 μg, or about 1 μg to about 400 μg, or about 1 μg to about 300 μg, or about 1 μg to about 250 μg, or about 1 g to about 200 μg, or about 1 μg to about 150 μg, or about 1 μg to about 100 μg, or about 1 μg to about 50 μg, or about 1 μg to about 40 μg, or about 1 μg to about 30 μg, or about 1 μg to about 20 μg, or about 1 μg to about 10 μg, or about 1 to about 5 μg, including all values and subranges in between. In aspects, the second polymer comprises as weight of the biodegradable polymer matrix: about 15 μg to about 1,000 μg, about 15 g to about 500 μg, or about 15 μg to about 400 μg, or about 15 μg to about 300 μg, or about 15 μg to about 250 μg, or about 15 μg to about 200 μg, or about 15 μg to about 150 μg, about 15 μg to about 100 μg, or about 20 μg to about 95 μg, or about 20 μg to about 23 μg, or about 54 μg to about 58 µg, or about 74 µg to about 76 µg, or about 93 µg to about 95 µg, or about 76 µg to about 80 µg, or about 68 µg to about 74 µg, or about 51 g to about 61 Gig, including all values and subranges in between. In aspects, the third is a PLA or a PLGA polymer. In aspects, the PLA polymer is R 203 S or R 205 S. In aspects, the PLGA polymer is RG 502 S, RG 503 H, RG 504 H, RG 653 H, RG 752 S, DLG 1A, DLG 2A, DLG 3A, or DLG 4A. In aspects, the PLA polymer or the PLGA polymer can be present as a mixture of polymers in the biodegradable polymer matrix.

In certain embodiments, the biodegradable polymer matrix includes a first polymer and a second polymer. In aspects, the first polymer and the second polymer comprise as a % w/w ratio of the biodegradable polymer matrix: about 1%/99% to about 99%/1%, or about 5%/95% to about 95%/5%, or about 10%/90% to about 90%/10%, or about 15%/85% to about 85%/15%, or about 20%/80% to about 80%/20%, or about 25%/75% to about 75%/25%, or about 30%/70% to about 70%/30%, or about 35%/65% to about 65%/35%, or about 40%/60% to about 60%/40%, or about 45%/55% to about 55%/45%, or about 50%/50%. In aspects, the first polymer and the second polymer comprises as a % w/w ratio of the biodegradable polymer matrix: about 95%/5%, or about 85%/15%, or about 75%/25%, or about 70%/30%, or about 60%/40%, or about 50%/50%, or about 30%/70%, or about 25%/75%, or about 10%/90%. In aspects, the first polymer and the second polymer is a PLA polymer, a PLGA polymer, or combinations thereof. In aspects, the PLA polymer is R 203 S or R 205 S. In aspects, the PLGA polymer is RG 502 S, RG 503 H, RG 504 S, RG 504 H, RG 653 H, RG 752 S, DLG 1A, or DLG 2A. In aspects, the PLA polymer or the PLGA polymer can be present as the sole polymer in the biodegradable polymer matrix. In aspects, the first polymer and the second polymer can be a mixture of PLA polymers. In aspects, the first polymer and the second polymer can be a mixture of PLGA polymers. In aspects, biodegradable polymer matrix can include a mixture of PLA and PLGA polymers.

In certain embodiments, the biodegradable polymer matrix is comprised of a first polymer and a second polymer. In aspects, the first polymer and the second polymer comprises as a weight of the biodegradable polymer matrix: about 1 µg to about 1000 µg; and about 1 µg to about 500 µg; or about 1 µg to about 400 µg; or about 1 µg to about 300 µg; or about 1 µg to about 300 µg; or about 1 µg to about 200 µg; or about 50 µg to about 400 µg; or about 50 µg to about 300 µg; or about 50 µg to about 200 µg; or about 50 µg to about 190 µg; or about 50 µg to about 180 µg; or about 50 µg to about 170 µg; or about 50 µg to about 160 µg; or about 100 µg to about 200 µg; or about 100 µg to about 190 µg; or about 100 µg to about 180 µg; or about 100 µg to about 170 µg; or about 100 µg to about 180 µg; or about 100 µg to about 160 µg; or about 130 µg to about 160 µg; or about 139 µg to about 153 µg; or about 135 g to about 145 µg; or about 149 µg to about 151 µg; or about 133 µg to about 136 µg; or about 152 µg to about 160 µg; or about 136 µg to about 148 µg; or about 60 µg to about 72 µg. In aspects, the first polymer and the second polymer is a PLA polymer, a PLGA polymer, or combinations thereof. In aspects, the PLA polymer is R 203 S or R 205 S. In aspects, the PLGA polymer is RG 502 S, RG 503 H, RG 504 S, RG 504 H, RG 653 H, RG 752 S, DLG 1A, or DLG 2A. In aspects, the PLA polymer or the PLGA polymer can be present as the sole polymer in the biodegradable polymer matrix. In aspects, the first polymer and the second polymer can be a mixture of PLA polymers. In aspects, the first polymer and the second polymer can be a mixture of PLGA polymers. In aspects, biodegradable polymer matrix can include a mixture of PLA and PLGA polymers.

In certain embodiments, the intravitreal implant comprises as a biodegradable polymer matrix content: about 1 µg to about 1000 µg, or about 1 µg to about 900 µg, or about 1 µg to about 800 µg, or about 1 µg to about 700 µg, or about 1 µg to about 600 µg, or about 1 µg to about 500 µg, or about 1 µg to about 450 µg, or about 1 µg to about 400 µg, or about 1 µg to about 350 µg, or about 1 µg to about 300 µg, or about 1 µg to about 250 µg, or about 1 µg to about 200 µg, or about 1 µg to about 150 µg, or about 1 g to about 100 µg, or about 1 µg to about 90 µg, or about 1 µg to about 80 µg, or about 1 µg to about 70 µg, or about 1 µg to about 60 µg, or about 1 µg to about 50 µg, or about 1 µg to about 40 µg. or about 1 µg to about 30 µg, or about 1 µg to about 20 µg. In certain embodiments, the intravitreal implant comprises as a biodegradable polymer matrix content: or about 50 µg to about 400 µg; or about 50 µg to about 300 µg; or about 50 µg to about 200 µg; or about 50 µg to about 190 µg; or about 50 µg to about 180 µg; or about 50 µg to about 170 µg; or about 50 µg to about 160 µg; or about 100 µg to about 200 µg; or about 100 µg to about 190 µg; or about 100 µg to about 180 µg; or about 100 g to about 170 µg; or about 100 µg to about 180 µg; or about 100 µg to about 170 µg; or about 100 µg to about 160 µg; or about 130 µg to about 160 µg; or about 139 µg to about 153 µg; or about 135 µg to about 145 µg; or about 149 µg to about 151 µg; or about 133 µg to about 136 µg; or about 152 µg to about 160 µg; or about 136 µg to about 148 µg; or about 60 µg to about 72 µg. In aspects, the first polymer and the second polymer is a PLA polymer, a PLGA polymer, or combinations thereof. In aspects, the PLA polymer is R 203 S or R 205 S. In aspects, the PLGA polymer is RG 502 S, RG 503 H, RG 504 S, RG 504 H, RG 653 H, RG 752 S, DLG 1A, or DLG 2A. In aspects, the PLA polymer or the PLGA polymer can be present as the sole polymer in the biodegradable polymer matrix. In aspects, the first polymer and the second polymer can be a mixture of PLA polymers. In aspects, the first polymer and the second polymer can be a mixture of PLGA polymers. In aspects, biodegradable polymer matrix can be a mixture of PLA and PLGA polymers.

In certain embodiments, the biodegradable polymer matrix contains one or more polymers, wherein the one or polymers is a biodegradable a poly(D,L-lactide) homopolymer, a biodegradable poly(D,L-lactide-co-glycolide) copolymer, or combinations thereof, wherein the biodegradable polymer matrix comprises about about 80-90 weight percent of the pharmaceutical composition, and wherein the at least one therapeutic agent comprises about 10-20 weight percent of the pharmaceutical composition. In embodiments, the biodegradable a poly(D,L-lactide) homopolymer is PLA polymer. In embodiments, the PLA polymer is R 203 S or R 207 S. In embodiments, the biodegradable poly(D,L-lactide-co-glycolide) copolymer is a PLGA polymer. In embodiments, the PLGA polymer is RG 503 H, RG 504 H, RG 504 S, or 858 S.

In certain embodiments, the biodegradable polymer matrix includes a mixture of two or more polymers, wherein one of said polymers is a biodegradable a poly(D,L-lactide) homopolymer and one of said polymers is a biodegradable poly(D,L-lactide-co-glycolide) copolymer, wherein the biodegradable polymer matrix comprises about 55-65 weight percent of the pharmaceutical composition, and wherein the at least one therapeutic agent comprises about 35-45 weight percent of the pharmaceutical composition. In embodiments, the biodegradable a poly(D,L-lactide) homopolymer is a PLA polymer. In embodiments, the PLA polymer is R 203

S or R 205 S. In embodiments, the PLA polymer is R 203 S or R 205 S. In embodiments, the biodegradable poly(D,L-lactide-co-glycolide) copolymer is a PLGA polymer. In embodiments, the PLGA polymer is RG 502 S, RG 503 H, RG 504 H, RG 653 H, RG 752 S, DLG 1A, or DLG 2A.

In aspects, the biodegradable polymer matrix contains a mixture of polymers comprising as a wt % of the polymer matrix: i) 85±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 15±5% of a biodegradable poly(D,L-lactide-co-glycolide) copolymer having an inherent viscosity of 0.16 to 0.24 dL/g measured at 0.1% w/v in $CHCl_3$ at 25° C. with a Ubbelhode size 0c glass capillary viscometer. In aspects, polymer i) is a PLA polymer, and polymer ii) is a PLGA polymer. In aspects, polymer ii) is a R 203 S polymer, and polymer ii) is a RG 752 S polymer.

In aspects, the biodegradable polymer matrix contains a mixture of polymers comprising as a wt % of the polymer matrix: i) 60±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 40±5% of a biodegradable poly(D,L-lactide-co-glycolide) copolymer having an inherent viscosity of 0.32 to 0.44 dL/g measured at 0.1% w/v in $CHCl_3$ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 653 H polymer.

In aspects, the biodegradable polymer matrix contains a mixture of polymers comprising as a wt % of the polymer matrix: i) 50±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 50±5% of a biodegradable poly(D,L-lactide-co-glycolide) copolymer having an inherent viscosity of 0.16 to 0.24 dL/g measured at 0.1% w/v in $CHCl_3$ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 502 S polymer.

In aspects, the biodegradable polymer matrix contains a mixture of polymers comprising as a wt % of the polymer matrix: i) 15±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 85±5% of a biodegradable poly(D,L-co-glycolide) copolymer having an inherent viscosity of 0.32 to 0.44 dL/g measured at 0.1% w/v in $CHCl_3$ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 503 H polymer.

In aspects, the biodegradable polymer matrix contains a mixture of polymers comprising as a wt % of the polymer matrix: i) 30±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 70±5% of a biodegradable poly(D,L-lactide-co-glycolide) copolymer having an inherent viscosity of 0.45 to 0.60 dL/g measured at 0.1% w/v in $CHCl_3$ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 504 H polymer.

In aspects, the biodegradable polymer matrix contains a mixture of polymers comprising as a wt % of the polymer matrix: i) 50±5% of a biodegradable poly(D,L-lactide) homopolymer having an inherent viscosity of 0.55 to 0.75 dL/g measured at 0.1% w/v in $CHCl_3$ at 25° C. with a Ubbelhode size 0c glass capillary viscometer; and ii) 50±5% of a biodegradable poly(D,L-lactide-co-glycolide) copolymer having an inherent viscosity of 0.32 to 0.44 dL/g measured at 0.1% w/v in $CHCl_3$ at 25° C. with a Ubbelhode size 0c glass capillary viscometer. In aspects, polymer i) is a PLA polymer, and polymer ii) is a PLGA polymer. In aspects, polymer i) is a R 205 S polymer, and polymer ii) is a RG 653 H polymer.

In aspects, the biodegradable polymer matrix contains a mixture of polymers comprising as a wt % of the polymer matrix: i) 95±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 5±5% of a biodegradable poly(D,L-lactide-co-glycolide) copolymer having an inherent viscosity of 0.05 to 0.15 dL/g measured at 0.1% w/v in $CHCl_3$ at 25° C. with a Ubbelhode size 0c glass capillary viscometer. In aspects, polymer i) a PLA polymer and polymer ii) is a PLGA polymer. In aspects, polymer i) is a R 205 S polymer, and polymer ii) is a DLG 1A polymer.

In aspects, the biodegradable polymer matrix contains a mixture of polymers comprising as a wt % of the polymer matrix: i) 50±5% of a biodegradable poly(D,L-lactide-co-glycolide) copolymer having an inherent viscosity of 0.16 to 0.24 dL/g measured at 0.1% w/v in $CHCl_3$ at 25° C. with a Ubbelhode size 0c glass capillary viscometer; and ii) 50±5% of a biodegradable poly(D,L-lactide-co-glycolide) copolymer having an inherent viscosity of 0.16 to 0.24 dL/g measured at 0.1% w/v in $CHCl_3$ at 25° C. with a Ubbelhode size 0c glass capillary viscometer. In aspects, polymer i) is a PLGA polymer, and polymer ii) is a PLGA polymer. In aspects, polymer i) is a RG 502 S polymer, and polymer ii) is a RG 502 H polymer.

In aspects, the biodegradable polymer matrix contains as a sole polymer comprising as a wt % of the polymer matrix: a biodegradable poly(D,L-lactide-co-glycolide) copolymer having an inherent viscosity of 0.16 to 0.24 dL/g measured at 0.1% w/v in $CHCl_3$ at 25° C. with a Ubbelhode size 0c glass capillary viscometer. In aspects, the sole polymer is a PLGA polymer. In aspects, the sole polymer is a RG 502 S polymer.

In aspects, the biodegradable polymer matrix contains a mixture of polymers comprising as a wt % of the polymer matrix: i) 85±5% of a biodegradable poly(D,L-lactide-co-glycolide) copolymer having an inherent viscosity of 0.16 to 0.24 dL/g measured at 0.1% w/v in $CHCl_3$ at 25° C. with a Ubbelhode size 0c glass capillary viscometer; and ii) 50±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer. In aspects, polymer i) a PLGA polymer, and polymer ii) is a PLA polymer. In aspects, polymer i) is a RG 502 S polymer, and polymer ii) is a R 203 S polymer.

In aspects, the biodegradable polymer matrix contains a mixture of polymers comprising as a wt % of the polymer matrix: i) 85±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 50±5% of a biodegradable poly(D,L-lactide-co-glycolide) copolymer having an inherent viscosity of 0.15 to 0.25 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a DLG 2A polymer.

In aspects, the pharmaceutical composition (e.g., an intravitreal implant) contains a mixture of polymers comprising as a wt % of the pharmaceutical composition: i) 53±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 9±5% of a biodegradable poly(D,L-lactide-co-glycolide) copolymer having an inherent viscosity of 0.16 to 0.24 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 752 S polymer.

In aspects, the pharmaceutical composition (e.g., an intravitreal implant) contains a mixture of polymers comprising as a wt % of the pharmaceutical composition: i) 35±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 24±5% of a biodegradable poly(D,L-lactide-co-glycolide) copolymer having an inherent viscosity of 0.32 to 0.44 dL/g measured at 0.1% w/v in CHCl₃ at 25° C. with a Ubbelhode size 0c glass capillary viscometer. In aspects, polymer i) a PLA polymer, and polymer ii) is a PLGA polymer. In aspects, the polymer i) is a R 203 S polymer, and polymer ii) is a RG 653 H polymer.

In aspects, the pharmaceutical composition (e.g., an intravitreal implant) contains a mixture of polymers comprising as a wt % of the pharmaceutical composition: i) 32±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 32±5% of a biodegradable poly(D,L-lactide-co-glycolide) copolymer having an inherent viscosity of 0.16 to 0.24 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 502 S polymer.

In aspects, the pharmaceutical composition (e.g., an intravitreal implant) contains a mixture of polymers comprising as a wt % of the pharmaceutical composition: i) 41±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 40±5% of a biodegradable poly(D,L-lactide-co-glycolide) copolymer having an inherent viscosity of 0.45 to 0.60 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 504 H polymer.

In aspects, the pharmaceutical composition (e.g., an intravitreal implant) contains a mixture of polymers comprising as a wt % of the pharmaceutical composition: i) 33±5% of a biodegradable poly(D,L-lactide) homopolymer having an inherent viscosity of 0.55 to 0.75 dL/g measured at 0.1% w/v in CHCl₃ at 25° C. with a Ubbelhode size 0c glass capillary viscometer; and ii) 33±5% of a biodegradable poly(D,L-lactide-co-glycolide) copolymer having an inherent viscosity of 0.32 to 0.44 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 205 S polymer, and polymer ii) is a RG 653 H polymer.

In aspects, the pharmaceutical composition (e.g., an intravitreal implant) contains a mixture of polymers comprising as a wt % of the pharmaceutical composition: i) 58±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 30±5% of a biodegradable poly(D,L-lactide-co-glycolide) copolymer having an inherent viscosity of 0.05 to 0.15 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 205 S polymer, and polymer ii) is a DLG 1A polymer.

In aspects, the pharmaceutical composition (e.g., an intravitreal implant) contains a mixture of polymers comprising as a wt % of the pharmaceutical composition: i) 8±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 48±10% of a biodegradable poly(D,L-co-glycolide) copolymer having an inherent viscosity of 0.32 to 0.44 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 503 H polymer.

In aspects, the pharmaceutical composition (e.g., a particle suspension) contains a mixture of polymers comprising as a wt % of the biodegradable polymer matrix: i) 25-75±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 25-75±5% of a biodegradable poly(D,L-co-glycolide) copolymer having an inherent viscosity of 0.45 to 0.60 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 504 S polymer.

In aspects, the pharmaceutical composition (e.g., particle suspension) contains a mixture of polymers comprising as a wt % of the biodegradable polymer matrix: i) 25-75±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 25-75±5% of a biodegradable poly(D,L-co-glycolide) copolymer having an inherent viscosity of 0.32 to 0.44 dL/g measured at 0.1% w/v in CHCl₃ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 503 H polymer.

In aspects, the pharmaceutical composition (e.g., a particle suspension) comprises as a wt % of the pharmaceutical composition about 85±5% of a biodegradable poly(D,L-co-glycolide) copolymer having an inherent viscosity of 0.45 to 0.60 dL/g measured at 0.1% w/v in CHCl₃ at 25° C. with a Ubbelhode size 0c glass capillary viscometer. In aspects, the biodegradable polymer is a RG 504 H polymer or an RG 504 S polymer.

In aspects, the pharmaceutical composition (e.g., a particle suspension) comprises as a wt % of the pharmaceutical composition about 85±5% of a biodegradable poly(D,L-co-glycolide) copolymer having an inherent viscosity of 1.3 to 1.7 dL/g measured at 0.1% w/v in $CHCl_3$ at 25° C. with a Ubbelhode size 0c glass capillary viscometer. In aspects, the biodegradable polymer is a RG 858 S polymer.

In aspects, the pharmaceutical composition (e.g., a particle suspension) comprises as a wt % of the pharmaceutical composition about 85±5% of a biodegradable biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer. In aspects, the biodegradable polymer is a R 203 S.

In aspects, the pharmaceutical composition (e.g., a particle suspension) comprises as a wt % of the pharmaceutical composition about 85±5% of a biodegradable biodegradable poly(D,L-lactide) homopolymer having an inherent viscosity of 1.3 to 1.7 dL/g measured at 0.1% w/v in $CHCl_3$ at 25° C. with a Ubbelhode size 0c glass capillary viscometer. In aspects, the biodegradable polymer is a R 207 S.

In aspects, the pharmaceutical composition (e.g., a particle suspension) contains a mixture of polymers comprising as a wt % of the pharmaceutical composition: i) 50±5 wt % of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 50±5 wt % of a biodegradable poly(D,L-lactide-co-glycolide) copolymer having an inherent viscosity of 0.45 to 0.60 dL/g measured at 0.1% w/v in $CHCl_3$ at 25° C. with a Ubbelhode size 0c glass capillary viscometer. In embodiments, polymer i) is R 203 S. In embodiments, polymer ii) is R 504 S.

In certain aspects, the pharmaceutical composition comprises as a therapeutic agent content: about 1% to about 99%, or about 1% to about 90% w/w, or about 1% to about 80%, or about 1% to about 70%, or about 1% to about 60%, or about 1% to about 50%, or about 1% to about 40%, or about 1% to about 30%, or about 1% to about 20%, or about 1% to about 10%; or 10% to about 100%, or about 10% to about 90% w/w, or about 10% to about 80%, or about 10% to about 70%, or about 10% to about 60%, or about 10% to about 50%, or about 10% to about 40%, or about 10% to about 30%, or about 10% to about 20%; or 20% to about 100%, or about 20% to about 90% w/w, or about 20% to about 80%, or about 20% to about 70%, or about 20% to about 60%, or about 20% to about 50%, or about 20% to about 40%, or about 20% to about 30%; or 30% to about 100%, or about 30% to about 90% w/w, or about 30% to about 80%, or about 30% to about 70%, or about 30% to about 60%, or about 30% to about 50%, or about 30% to about 40%; or 40% to about 100%, or about 40% to about 90% w/w, or about 40% to about 80%, or about 40% to about 70%, or about 40% to about 60%, or about 40% to about 50%, or about 20% to about 35% w/w, or about 25% to about 35% w/w, or about 25%, or about 26%, or about 27%, or about 28%, or about 29%, or about 30%, or about 31%, or about 32%, or about 33%, or about 34%, or about 35%, or about or about 36%, or about 37%, or about 38%, or about 39%, or about 40%, of the pharmaceutical composition.

In certain aspects, the intravitreal implant comprises as a therapeutic agent content: about 1% to about 100%, or about 1% to about 90% w/w, or about 1% to about 80%, or about 1% to about 70%, or about 1% to about 60%, or about 1% to about 50%, or about 1% to about 40%, or about 1% to about 30%, or about 1% to about 20%, or about 1% to about 10%; or 10% to about 100%, or about 10% to about 90% w/w, or about 10% to about 80%, or about 10% to about 70%, or about 10% to about 60%, or about 10% to about 50%, or about 10% to about 40%, or about 10% to about 30%, or about 10% to about 20%; or 20% to about 100%, or about 20% to about 90% w/w, or about 20% to about 80%, or about 20% to about 70%, or about 20% to about 60%, or about 20% to about 50%, or about 20% to about 40%, or about 20% to about 30%; or 30% to about 100%, or about 30% to about 90% w/w, or about 30% to about 80%, or about 30% to about 70%, or about 30% to about 60%, or about 30% to about 50%, or about 30% to about 40%; or 40% to about 100%, or about 40% to about 90% w/w, or about 40% to about 80%, or about 40% to about 70%, or about 40% to about 60%, or about 40% to about 50%, or about 20% to about 35% w/w, or about 25% to about 35% w/w, or about 25%, or about 26%, or about 27%, or about 28%, or about 29%, or about 30%, or about 31%, or about 32%, or about 33%, or about 34%, or about 35%, or about or about 36%, or about 37%, or about 38%, or about 39%, or about 40%, of the pharmaceutical composition.

In certain embodiments, the therapeutic agent comprises as a % w/w of the composition: about 1% to about 90%, or about 1% to about 80%, or about 1% to about 70%, or about 1% to about 60%, or about 1% to about 55%, or about 1% to about 50%, or about 1% to about 45%, or about 1% to about 40%, or about 1% to about 35%, or about 1% to about 30%, or about 1% to about 25%, or about 1% to about 20%, or about 1% to about 15%, or about 1% to about 10%, or about 1% to about 5%, or about 5% to about 90%, or about 5% to about 80%, or about 5% to about 70%, or about 5% to about 60%, or about 5% to about 55%, or about 5% to about 50%, or about 5% to about 45%, or about 5% to about 40%, or about 5% to about 35%, or about 5% to about 30%, or about 5% to about 25%, or about 5% to about 20%, or about 5% to about 15%, or about 5% to about 10%, or about 10% to about 90%, or about 10% to about 80%, or about 10% to about 70%, or about 10% to about 60%, or about 10% to about 55%, or about 10% to about 50%, or about 10% to about 45%, or about 10% to about 40%, or about 10% to about 35%, or about 10% to about 30%, or about 10% to about 25%, or about 10% to about 20%, or about 10% to about 15%, or about 15% to about 90%, or about 15% to about 80%, or about 15% to about 70%, or about 15% to about 60%, or about 15% to about 55%, or about 15% to about 50%, or about 15% to about 45%, or about 15% to about 40%, or about 15% to about 35%, or about 15% to about 30%, or about 15% to about 25%, or about 15% to about 20%, or about 20% to about 90%, or about 20% to about 80%, or about 20% to about 70%, or about 20% to about 60%, or about 20% to about 55%, or about 20% to about 50%, or about 20% to about 45%, or about 20% to about 40%, or about 20% to about 35%, or about 20% to about 30%, or about 20% to about 25%, or about 30% to about 90%, or about 30% to about 80%, or about 30% to about 70%, or about 30% to about 60%, or about 30% to about 55%, or about 30% to about 50%, or about 30% to about 45%, or about 30% to about 40%, or about 30% to about 35%, or about 40% to about 90%, or about 40% to about 80%, or about 40% to about 70%, or about 40% to about 60%, or about 40% to about 55%, or about 40% to about 50%, or about 40% to about 45%, or about 45% to about 90%, or about 45% to about 80%, or about 45% to about 75%, or about 45% to about 70%, or about 45% to about 65%, or about 45% to about 60%, or about 45% to about 55%, or about 45% to about 50%, or about 50% to about 90%, or about 50% to about 80%, or about 50% to about 70%, or about 50% to about 60%, or about 50% to about 55%, or about 25% to about 40%, or about 28% to about 35%, or about 30%, to about 33%.

In certain embodiments, the pharmaceutical composition comprises as a therapeutic agent content: of from about 1 μg to about 1000 μg; or about 1 μg to about 700 μg; or about 1 μg to about 500 μg; or about 1 μg to about 400 μg; or about 1 μg to about 300 μg; or about 1 μg to about 200 μg; or about 1 μg to about 100 μg; or about 1 g to about 90 μg; or about 1 μg to about 80 μg; or about 1 μg to about 70 μg; or about 1 g to about 60 μg; or about 1 μg to about 50 μg; or about 1 μg to about 40 μg; or about 1 g to about 30 μg; or about 1 μg to about 20 μg; or about 1 μg to about 10 μg; or about g to about 100 μg; or about 10 μg to about 50 μg; or about 10 μg to about 90 μg; or about 10 μg to about 80 μg; or about 10 μg to about 70 μg; or about 10 μg to about 60 μg; or about 10 μg to about 50 μg; or about 10 μg to about 40 μg; or about 10 μg to about 30 μg; or about 10 μg to about 20 μg; or about 100 μg to about 700 μg; or about 100 μg to about 600 μg; or about 100 μg to about 500 μg; or about 100 μg to about 400 μg; or about 200 μg to about 400 μg; or about 250 μg to about 350 μg.

In certain embodiments, the intravitreal implant comprises as a therapeutic agent content: of from about 1 μg to about 1000 μg; or about 1 μg to about 900 μg; or about 1 g to about 800 μg; or about 1 μg to about 700 μg; or about 1 μg to about 600 μg; or about 1 μg to about 500 μg; or about 1 μg to about 400 μg; or about 1 μg to about 300 μg; or about 1 μg to about 200 μg; or about 1 μg to about 100 μg; or about 1 μg to about 90 μg; or about 1 μg to about 80 μg; or about 1 μg to about 70 μg; or about 1 μg to about 60 μg; or about 1 μg to about 50 μg; or about 1 μg to about 40 μg; or about 1 μg to about 30 μg; or about 1 μg to about 20 μg; or about 1 μg to about 10 μg; or about 10 μg to about 100 μg; or about 10 μg to about 90 μg; or about 10 μg to about 80 μg; or about 10 g to about 70 μg; or about 10 μg to about 60 μg; or about 10 μg to about 50 μg; or about g to about 40 μg; or about 10 μg to about 30 μg; or about 10 μg to about 20 μg; or about 100 μg to about 600 μg; or about 100 μg to about 500 μg; or about 100 μg to about 400 μg; or about 200 μg to about 400 μg; or about 250 μg to about 350 μg.

In certain embodiments, the particle suspension comprises as a therapeutic agent content: of from about 1 μg to about 1000 μg; or about 1 μg to about 900 μg; or about 1 g to about 800 μg; or about 1 μg to about 700 μg; or about 1 μg to about 600 μg; or about 1 μg to about 500 μg; or about 1 μg to about 400 μg; or about 1 μg to about 300 μg; or about 1 μg to about 200 μg; or about 1 μg to about 100 μg; or about 1 μg to about 90 μg; or about 1 μg to about 80 μg; or about 1 μg to about 70 μg; or about 1 μg to about 60 μg; or about 1 μg to about 50 μg; or about 1 μg to about 40 μg; or about 1 μg to about 30 μg; or about 1 μg to about 20 μg; or about 1 μg to about 10 μg; or about 10 μg to about 1000 μg; or about 10 μg to about 900 μg; or about 10 μg to about 800 μg; or about g to about 700 μg; or about 10 μg to about 600 μg; or about 10 μg to about 500 μg; or about 10 μg to about 400 μg; or about 10 μg to about 300 μg; or about 10 μg to about 200 μg; or about 100 μg to about 1000 μg; or about 100 μg to about 900 μg; or about 100 g to about 800 μg; or about 100 μg to about 700 μg; or about 100 μg to about 600 μg; or about 100 μg to about 500 μg; or about 100 μg to about 400 μg; or about 200 μg to about 800 μg; or about 300 μg to about 800 μg; or about 400 μg to about 800 μg; or about 500 g to about 800 μg; or about 600 μg to about 800 μg.

In certain embodiments, the pharmaceutical composition administers via intravitreal injection a total therapeutic agent content per eye: of from about 1 μg to about 1000 μg; or about 1 μg to about 900 μg; or about 1 μg to about 800 μg; or about 1 μg to about 700 μg; or about 1 μg to about 600 μg; or about 1 μg to about 500 μg; or about 1 g to about 400 μg; or about 1 μg to about 300 μg; or about 1 μg to about 200 μg; or about 1 μg to about 100 μg; or about 1 μg to about 90 μg; or about 1 μg to about 80 μg; or about 1 μg to about 70 μg; or about 1 μg to about 60 μg; or about 1 μg to about 50 μg; or about 1 μg to about 40 μg; or about 1 μg to about 30 μg; or about 1 μg to about 20 μg; or about 1 μg to about 10 μg; or about 10 μg to about 1000 μg; or about 10 μg to about 900 μg; or about 10 μg to about 800 μg; or about 10 μg to about 700 μg; or about 10 μg to about 600 μg; or about 10 μg to about 500 μg; or about 10 μg to about 400 μg; or about 10 μg to about 300 μg; or about 10 μg to about 200 μg; or about 100 μg to about 1000 μg; or about 100 μg to about 900 μg; or about 100 μg to about 800 μg; or about 100 g to about 700 μg; or about 100 μg to about 600 μg; or about 100 μg to about 500 μg; or about 100 μg to about 400 μg; or about 200 μg to about 400 μg; or about 250 μg to about 350 μg, or about 200 μg to about 800 μg; or about 300 μg to about 800 μg; or about 400 g to about 800 μg; or about 500 μg to about 800 μg; or about 600 μg to about 800 μg; or about 250 μg to about 750 μg; or about 270 μg to about 700 μg.

In certain embodiments, the pharmaceutical composition for treating an ocular condition is fabricated as an ocular implant. In other embodiments, the pharmaceutical composition for treating an ocular condition is fabricated as a rod-shaped ocular implant. In particular embodiments, the ocular implant is a rod-shaped ocular implant having dimensions of about 150 μm×150 μm×3150 μm, a rod-shaped implant having dimensions of about 225 μm×225 μm×2925 μm or a rod-shaped implant having dimensions of about 300 μm×300 μm×6,000 μm. In other embodiments, the ocular implant is a rod-shaped ocular implant having dimensions of about 225 μm×225 μm×4000 μm, a rod-shaped implant having dimensions of 200 μm×200 μm×4,500 μm a rod-shaped implant having dimensions of about 225 μm×225 μm×6000 μm, a rod-shaped implant having dimensions of about 320 μm×320 μm×6,000 μm, a rod-shaped implant having dimensions of about 300 μm×300 μm×4,500 μm, or a rod-shaped implant having dimensions of about 311 μm×395 μm×6045 μm. In other embodiments, the ocular implant is a the rod-shaped ocular implant has dimensions of about 265 μm×265 μm×4,500 μm, dimensions of about 255 μm×255 μm×4,500 μm, or dimensions of about 238 μm×238 μm×4,500 μm.

In certain embodiments, the pharmaceutical composition for treating an ocular condition is fabricated as a rod-shaped ocular implant and wherein the implant degrades in not less than 4 months after administration to the posterior of a human eye and releases the therapeutic agent at least about 4 months. In embodiments, the implant degrades in about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 2 years, about 3 years, about 4 years, or about 5 years. In embodiments, the therapeutic agent is released for about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 2 years, about 3 years, about 4 years, or about 5 years.

In certain embodiments, the present disclosure provides for an ocular implant for treating an ocular condition. In aspects, the ocular implant comprises a biodegradable polymer matrix that contains a homogenously dispersed therapeutic agent therein. In some embodiments, the ocular implant is a "non-extruded" ocular implant, such as for example a molded implant.

In certain embodiments, the therapeutic agent is a corticosteroid. In another embodiment, the corticosteroid is selected from the group consisting of dexamethasone, fluocinolone acetonide, and combinations thereof. In a particular embodiment, the therapeutic agent is dexamethasone.

Thus, in one embodiment, the disclosure provides for a method of treating an ocular condition in a subject in need thereof comprising: a) administering a pharmaceutical composition to the posterior of said subject's eye, wherein said pharmaceutical composition comprises a biodegradable polymer matrix and at least one corticosteroid homogeneously dispersed therein, wherein the pharmaceutical composition releases the corticosteroid for at least about 4 months (e.g., about 4 months, about 5 months, about 6 months, about 7 months, about 8 months, etc.), and whereby the ocular condition is treated. In embodiments, the ocular condition is characterized by inflammation. In embodiments, the ocular condition is macular edema, retinal vein occlusion, or uveitis. In embodiments, the corticosteroid is dexamethasone or fluocinolone acetonide, or combinations thereof.

In another embodiment, the disclosure provides for a method of treating an ocular condition in a subject in need thereof comprising: a) administering at least one intravitreal implant to the posterior of said subject's eye, wherein said intravitreal implant comprises a biodegradable polymer matrix and at least one corticosteroid homogeneously dispersed therein, wherein the intravitreal implant releases the corticosteroid for at least about 4 months (e.g., about 4 months, about 5 months, about 6 months, about 7 months, about 8 months, etc.), and whereby the ocular condition is treated. In embodiments, the ocular condition is characterized by inflammation. In embodiments, the ocular condition is macular edema, retinal vein occlusion, or uveitis. In embodiments, the corticosteroid is dexamethasone or fluocinolone acetonide, or combinations thereof.

In another embodiment, the disclosure provides for a method of treating ocular inflammation in a subject in need thereof comprising: a) administering at least one intravitreal implant to the posterior of said subject's eye, wherein said intravitreal implant comprises a biodegradable polymer matrix and at least one corticosteroid homogeneously dispersed therein, wherein the corticosteroid is released from pharmaceutical composition for at least about 4 months (e.g., about 4 months, about 5 months, about 6 months, about 7 months, about 8 months etc.), and whereby the ocular condition is treated. In embodiments, the corticosteroid is dexamethasone or fluocinolone acetonide, or combinations thereof. In embodiments, the ocular conditions is macular edema, retinal vein occlusion, or uveitis.

In some aspects, the disclosure provides a method of treating ocular inflammation in a subject by administering, via intravitreal injection, a pharmaceutical composition (e.g., biodegradable, rod-shaped intravitreal implant or particle suspension) to the subject. In aspects, the pharmaceutical composition is delivered directly into the vitreous of the subject's eye. In a particular aspect, the pharmaceutical compositions of the disclosure do not migrate substantially from their initial position. In other aspects, the pharmaceutical compositions may move substantially from their initial position. In embodiments of the disclosed methods, ocular inflammation is controlled for at least about 4 months following implantation, via intravitreal injection, of pharmaceutical compositions having an initial therapeutic agent content ranging from about: 1 to 1000 µg, 1 to 900 µg, 1 to 800 µg, 1 to 700 µg, 1 to 600 µg, 1 to 500 µg per eye, 1 to 400 µg per eye, 1 to 300 µg per eye, 1 to 200 µg per eye, 1 to 150 µg per eye, 1 to 140 µg per eye, 1 to 130 µg per eye, 1 to 120 µg per eye, 1 to 110 µg per eye, 1 to 100 µg per eye, 1 to 90 µg per eye, 1 to 80 µg per eye, 1 to 70 µg per eye, 1 to 60 µg per eye, 1 to 50 µg per eye, 1 to 40 µg per eye, 1 to 30 µg per eye, 1 to 20 µg per eye, or 1 to 10 µg per eye. In some embodiments, the drug is a corticosteroid (e.g., dexamethasone or fluocinolone acetonide), and the corticosteroid is released from the pharmaceutical composition over time treating ocular inflammation.

In certain embodiments, the ocular implant is fabricated as a rod-shaped ocular implant. In particular embodiments, the rod-shaped ocular implant has dimensions of about 150 µm×150 µm×1500 µm, dimensions of about 225 µm×225 µm×2925 µm, or dimensions of about 300 µm×300 µm×6,000 µm. In other embodiments, the rod-shaped ocular implant has dimensions of about 225 µm×225 µm×4000 µm, or dimensions of about 200 µm×200 µm×4,500 µm, or dimensions of about 225 µm×225 µm×6000 µm, dimensions of about 320 µm×320 µm×6,000 µm, of about 300 µm×300 µm×4,500 µm, or dimensions of about 311 µm×395 µm×6045 µm. In other embodiments, the rod-shaped ocular implant has dimensions of about 265 µm×265 µm×4,500 µm, dimensions of about 255 µm×255 µm×4,500 µm, or dimensions of about 238 µm×238 µm×4,500 µm.

In certain embodiments, the rod-shaped ocular implant degrades in not less than 4 months (e.g., about 4 months, about 5 months, about 6 months, about 7 months, about 8 months etc.) in the posterior of a human eye and releases the therapeutic agent for more than 4 months (e.g., about 4 months, about 5 months, about 6 months, about 7 months, about 8 months etc.).

In certain embodiments, the pharmaceutical composition is fabricated as a particle suspension. In particular embodiments, the particles have dimensions of about 12.5 µm×12.5 µm×25 µm, dimensions of about 25 µm×25 µm×25 µm, dimensions of about 25 m×25 µm×50 µm, dimensions of about 50 µm×50 µm×30 µm, or dimensions of about 50 µm×50 µm×50 µm.

In certain embodiments, the particle suspension degrades in not less than 4 months (e.g., about 4 months, about 5 months, about 6 months, about 7 months, about 8 months etc.) in the posterior of a human eye and releases the therapeutic agent for more than 4 months (e.g., about 4 months, about 5 months, about 6 months, about 7 months, about 8 months etc.).

In certain embodiments, a kit for delivery of a biodegradable implant is disclosed. The kit includes a needle for inserting a treatment to a patient and a biodegradable implant for treating the patient, wherein the biodegradable implant is configured with a maximum linear cross-section dimension smaller than an inner diameter of the needle.

In some embodiments, the ocular implant is a rod-shaped implant comprising a shortest dimension of between about 100 µm to about 500 µm and a longest dimension of about 1,500 µm to about 8,000 µm. In embodiments, the rod-shaped ocular implant has dimensions of about 175-275 µm×175-275 µm×3,500-5,000 µm.

In some aspects, the disclosure provides a pharmaceutical composition for treating an ocular condition, wherein the composition is fabricated as a rod-shaped ocular implant having dimensions of about 150 μm×150 μm×1500 μm (W×H×L)+50 μm of each dimension, a rod-shaped ocular implant having dimensions of about 225 μm×225 μm×2,925 μm (W×H×L)+50 μm of each dimension, or a rod-shaped ocular implant having dimensions of 300 μm×300 μm×6,000 μm (W×H×L)+50 μm of each dimension. In some aspects, the disclosure provides a pharmaceutical composition for treating an ocular condition, wherein the composition is fabricated as a rod-shaped ocular implant having dimensions of about 200 μm×200 μm×4500 μm (W×H×L)+50 μm of each dimension, a rod-shaped ocular implant having dimensions of about 225 m×225 μm×4000 μm (W×H×L)+50 μm of each dimension, a rod-shaped ocular implant having dimensions of about 225 μm×225 μm×6000 μm (W×H×L)+50 μm of each dimension, a rod-shaped ocular implant having dimensions of 320 μm×320 μm×6,000 μm (W×H×L)+50 μm of each dimension, a rod-shaped ocular implant having dimensions of 300 μm×300 μm×4500 μm (W×H×L)+50 μm of each dimension, or a rod-shaped implant having dimensions of about 311 μm×395 μm×6045 μm (W×H×L)+50 μm of each dimension. In some aspects, the disclosure provides a pharmaceutical composition for treating an ocular condition, wherein the composition is fabricated as a rod-shaped ocular implant having dimensions of about 175 μm×215 μm×2925 μm (W×H×L)+50 μm of each dimension, a rod-shaped ocular implant having dimensions of about 225 μm×240 μm×2925 μm (W×H×L)+50 μm of each dimension, a rod-shaped ocular implant having dimensions of 395 μm×311 μm×6,045 m (W×H×L)+50 μm of each dimension, a rod-shaped ocular implant having dimensions of 205 μm×305 μm×3500 μm (W×H×L)+50 μm of each dimension, a rod-shaped implant having dimensions of about 250 μm×250 μm×4000 μm (W×H×L)+50 μm of each dimension, or a rod-shaped implant having dimensions of about 300 m×300 μm×6000 μm (W×H×L)+50 μm of each dimension. In aspects, the disclosure provides a pharmaceutical composition for treating an ocular condition, wherein the composition is fabricated as a rod-shaped implant has dimensions of about 265 μm×265 μm×4,500 μm (W×H×L)+50 μm of each dimension, a rod-shaped ocular implant having dimensions of about 255 μm×255 μm×4,500 μm (W×H×L)+50 μm of each dimension, or a rod-shaped ocular implant having dimensions of about 238 μm×238 μm×4,500 μm (W×H×L)+50 μm of each dimension.

In some aspects, the disclosure provides a pharmaceutical composition for treating an ocular condition, wherein the composition is fabricated as a rod-shaped ocular implant having dimensions of about 150 μm×150 μm×1500 μm (W×H×L)+40 μm of each dimension, a rod-shaped ocular implant having dimensions of about 225 μm×225 μm×2,925 μm (W×H×L)+40 μm of each dimension, or a rod-shaped ocular implant having dimensions of 300 μm×300 μm×6,000 μm (W×H×L)+40 μm of each dimension. In some aspects, the disclosure provides a pharmaceutical composition for treating an ocular condition, wherein the composition is fabricated as a rod-shaped ocular implant having dimensions of about 200 μm×200 μm×4500 μm (W×H×L)+40 μm of each dimension, a rod-shaped ocular implant having dimensions of about 225 μm×225 μm×4000 μm (W×H×L)+40 μm of each dimension, a rod-shaped ocular implant having dimensions of about 225 μm×225 μm×6000 μm (W×H×L)+40 μm of each dimension, a rod-shaped ocular implant having dimensions of 320 μm×320 μm×6,000 μm (W×H×L)+40 μm of each dimension, a rod-shaped ocular implant having dimensions of 300 μm×300 μm×4500 μm (W×H×L)+40 μm of each dimension, a rod-shaped implant having dimensions of about 311 μm×395 μm×6045 m (W×H×L)+0 μm of each dimension. In some aspects, the disclosure provides a pharmaceutical composition for treating an ocular condition, wherein the composition is fabricated as a rod-shaped ocular implant having dimensions of about 175 μm×215 μm×2925 μm (W×H×L)+40 μm of each dimension, a rod-shaped ocular implant having dimensions of about 225 μm×240 μm×2925 μm (W×H×L)+40 μm of each dimension, a rod-shaped ocular implant having dimensions of 395 μm×311 μm×6,045 m (W×H×L)+40 μm of each dimension, a rod-shaped ocular implant having dimensions of 205 μm×305 μm×3500 μm (W×H×L)+40 μm of each dimension, a rod-shaped implant having dimensions of about 250 μm×250 μm×4000 μm (W×H×L)+40 μm of each dimension, or a rod-shaped implant having dimensions of about 300 m×300 μm×6000 μm (W×H×L)+40 μm of each dimension. In aspects, the disclosure provides a pharmaceutical composition for treating an ocular condition, wherein the composition is fabricated as a rod-shaped implant has dimensions of about 265 μm×265 μm×4,500 μm (W×H×L)+40 μm of each dimension, a rod-shaped ocular implant having dimensions of about 255 μm×255 μm×4,500 μm (W×H×L)+m of each dimension, or a rod-shaped ocular implant having dimensions of about 238 μm×238 μm×4,500 μm (W×H×L)+40 μm of each dimension.

In some aspects, the disclosure provides a pharmaceutical composition for treating an ocular condition, wherein the composition is fabricated as a rod-shaped ocular implant having dimensions of about 150 μm×150 μm×1500 μm (W×H×L)+30 μm of each dimension, a rod-shaped ocular implant having dimensions of 225 μm×225 μm×2,925 μm (W×H×L)+30 μm of each dimension, or a rod-shaped ocular implant having dimensions of 300 μm×300 μm×6,000 μm (W×H×L)+30 μm of each dimension. In some aspects, the disclosure provides a pharmaceutical composition for treating an ocular condition, wherein the composition is fabricated as a rod-shaped ocular implant having dimensions of about 200 μm×200 μm×4500 μm (W×H×L)+30 μm of each dimension, a rod-shaped ocular implant having dimensions of about 225 μm×225 μm×4000 μm (W×H×L)+30 μm of each dimension, a rod-shaped ocular implant having dimensions of about 225 μm×225 μm×6000 μm (W×H×L)+30 μm of each dimension, a rod-shaped ocular implant having dimensions of 320 μm×320 μm×6,000 μm (W×H×L)+30 μm of each dimension, a rod-shaped ocular implant having dimensions of 300 μm×300 μm×4500 μm (W×H×L)+30 μm of each dimension, or a rod-shaped implant having dimensions of about 311 μm×395 μm×6045 μm (W×H×L)+30 μm of each dimension. In some aspects, the disclosure provides a pharmaceutical composition for treating an ocular condition, wherein the composition is fabricated as a rod-shaped ocular implant having dimensions of about 175 μm×215 μm×2925 μm (W×H×L)+30 μm of each dimension, a rod-shaped ocular implant having dimensions of about 225 μm×240 μm×2925 μm (W×H×L)+30 μm of each dimension, a rod-shaped ocular implant having dimensions of 395 μm×311 μm×6,045 m (W×H×L)+30 μm of each dimension, a rod-shaped ocular implant having dimensions of 205 μm×305 μm×3500 μm (W×H×L)+30 μm of each dimension, a rod-shaped implant having dimensions of about 250 μm×250 μm×4000 μm (W×H×L)+30 μm of each dimension, or a rod-shaped implant having dimensions of about 300 m×300 μm×6000 μm (W×H×L)+30 μm of each dimension. In aspects, the disclosure provides a pharmaceutical composition for treating an ocular condition, wherein the composition is fabricated as a rod-shaped implant has dimensions of about 265 μm×265 μm×4,500 μm (W×H×L)+30 μm of each dimension, a rod-shaped ocular implant having dimensions of about 255 μm×255 μm×4,500 μm (W×H×L)+m of each dimension, or a rod-shaped ocular implant having dimensions of about 238 μm×238 μm×4,500 μm (W×H×L)+30 μm of each dimension.

In some aspects, the disclosure provides a pharmaceutical composition for treating an ocular condition, wherein the composition is fabricated as a rod-shaped ocular implant having dimensions of about 150 μm×150 μm×1500 μm (W×H×L)+20 μm of each dimension, a rod-shaped ocular implant having dimensions of 225 μm×225 μm×2,925 μm (W×H×L)+20 μm of each dimension, or a rod-shaped ocular implant having dimensions of 300 μm×300 μm×6,000 μm (W×H×L)+20 μm of each dimension. In some aspects, the disclosure provides a pharmaceutical composition for treating an ocular condition, wherein the composition is fabricated as a rod-shaped ocular implant having dimensions of about 200 μm×200 μm×4500 μm (W×H×L)+20 μm of each dimension, a rod-shaped ocular implant having dimensions of about 225 μm×225 μm×4000 μm (W×H×L)+20 μm of each dimension, a rod-shaped ocular implant having dimensions of about 225 μm×225 μm×6000 μm (W×H×L)+20 μm of each dimension, a rod-shaped ocular implant having dimensions of 320 μm×320 μm×6,000 μm (W×H×L)+20 μm of each dimension, or a rod-shaped ocular implant having dimensions of 300 μm×300 μm×4500 μm (W×H×L)+20 μm of each dimension, or a rod-shaped implant having dimensions of about 311 μm×395 μm×6045 μm (W×H×L)+20 μm of each dimension. In some aspects, the disclosure provides a pharmaceutical composition for treating an ocular condition, wherein the composition is fabricated as a rod-shaped ocular implant having dimensions of about 175 m×215 μm×2925 μm (W×H×L)+20 μm of each dimension, a rod-shaped ocular implant having dimensions of about 225 μm×240 μm×2925 μm (W×H×L)+20 μm of each dimension, a rod-shaped ocular implant having dimensions of 395 μm×311 μm×6,045 μm (W×H×L)+20 μm of each dimension, a rod-shaped ocular implant having dimensions of 205 μm×305 μm×3500 μm (W×H×L)+20 μm of each dimension, a rod-shaped implant having dimensions of about 250 μm×250 μm×4000 μm (W×H×L)+20 μm of each dimension, or a rod-shaped implant having dimensions of about 300 m×300 μm×6000 μm (W×H×L)+20 μm of each dimension. In aspects, the disclosure provides a pharmaceutical composition for treating an ocular condition, wherein the composition is fabricated as a rod-shaped implant has dimensions of about 265 μm×265 μm×4,500 μm (W×H×L)+20 μm of each dimension, a rod-shaped ocular implant having dimensions of about 255 μm×255 μm×4,500 μm (W×H×L)+m of each dimension, or a rod-shaped ocular implant having dimensions of about 238 μm×238 μm×4,500 μm (W×H×L)+20 μm of each dimension.

In some aspects, the disclosure provides a pharmaceutical composition for treating an ocular condition, wherein the composition is fabricated as a rod-shaped ocular implant having dimensions of about 150 μm×150 μm×1500 μm (W×H×L)+10 μm of each dimension, a rod-shaped ocular implant having dimensions of 225 μm×225 μm×2,925 μm (W×H×L)+10 μm of each dimension, or a rod-shaped ocular implant having dimensions of 300 μm×300 μm×6,000 μm (W×H×L)+10 μm of each dimension. In some aspects, the disclosure provides a pharmaceutical composition for treating an ocular condition, wherein the composition is fabricated as a rod-shaped ocular implant having dimensions of about 200 μm×200 μm×4500 μm (W×H×L)+10 μm of each dimension, a rod-shaped ocular implant having dimensions of about 225 μm×225 μm×4000 μm (W×H×L)+10 μm of each dimension, a rod-shaped ocular implant having dimensions of about 225 μm×225 μm×6000 μm (W×H×L)+10 μm of each dimension, a rod-shaped ocular implant having dimensions of 320 μm×320 μm×6,000 μm (W×H×L)+10 μm of each dimension, or a rod-shaped ocular implant having dimensions of 300 μm×300 μm×4500 μm (W×H×L)+10 μm of each dimension, or a rod-shaped implant having dimensions of about 311 μm×395 μm×6045 μm (W×H×L)+10 μm of each dimension. In some aspects, the disclosure provides a pharmaceutical composition for treating an ocular condition, wherein the composition is fabricated as a rod-shaped ocular implant having dimensions of about 175 m×215 μm×2925 μm (W×H×L)+10 μm of each dimension, a rod-shaped ocular implant having dimensions of about 225 μm×240 μm×2925 μm (W×H×L)+10 μm of each dimension, a rod-shaped ocular implant having dimensions of 395 μm×311 μm×6,045 μm (W×H×L)+10 μm of each dimension, a rod-shaped ocular implant having dimensions of 205 μm×305 μm×3500 μm (W×H×L)+10 μm of each dimension, a rod-shaped implant having dimensions of about 250 μm×250 μm×4000 μm (W×H×L)+10 μm of each dimension, or a rod-shaped implant having dimensions of about 300 m×300 μm×6000 μm (W×H×L)+10 μm of each dimension. In aspects, the disclosure provides a pharmaceutical composition for treating an ocular condition, wherein the composition is fabricated as a rod-shaped implant has dimensions of about 265 μm×265 μm×4,500 μm (W×H×L)+10 μm of each dimension, a rod-shaped ocular implant having dimensions of about 255 μm×255 μm×4,500 μm (W×H×L)+m of each dimension, or a rod-shaped ocular implant having dimensions of about 238 μm×238 μm×4,500 μm (W×H×L)+10 μm of each dimension.

In some aspects, the disclosure provides a pharmaceutical composition for treating an ocular condition, wherein the composition is fabricated as a rod-shaped ocular implant having dimensions of about 150 μm×150 μm×1500 μm (W×H×L)+5 μm of each dimension, a rod-shaped ocular implant having dimensions of 225 μm×225 μm×2,925 μm (W×H×L)+5 μm of each dimension, or a rod-shaped ocular implant having dimensions of 300 μm×300 μm×6,000 μm (W×H×L)+5 μm of each dimension. In some aspects, the disclosure provides a pharmaceutical composition for treating an ocular condition, wherein the composition is fabricated as a rod-shaped ocular implant having dimensions of about 200 μm×200 μm×4500 μm (W×H×L)+5 μm of each dimension, a rod-shaped ocular implant having dimensions of about 225 μm×225 μm×4000 μm (W×H×L)+5 μm of each dimension, a rod-shaped ocular implant having dimensions of about 225 μm×225 μm×6000 μm (W×H×L)+5 μm of each dimension, a rod-shaped ocular implant having dimensions of 320 μm×320 μm×6,000 m (W×H×L)+5 μm of each dimension, a rod-shaped ocular implant having dimensions of 300 μm×300 μm×4500 μm (W×H×L)+5 μm of each dimension, or a rod-shaped implant having dimensions of about 311 μm×395 μm×6045 μm (W×H×L)+5 μm of each dimension. In some aspects, the disclosure provides a pharmaceutical composition for treating an ocular condition, wherein the composition is fabricated as a rod-shaped ocular implant having dimensions of about 175 μm×215 μm×2925 μm (W×H×L)+5 μm of each dimension, a rod-shaped ocular implant having dimensions of about 225 μm×240 μm×2925 μm (W×H×L)+5 μm of each dimension, a rod-shaped ocular implant having dimensions of 395 μm×311 μm×6,045 μm (W×H×L)±5 μm of each dimension, a rod-shaped ocular implant having dimensions of 205 μm×305 μm×3500 μm (W×H×L)+50 μm of each dimension, a rod-shaped implant having dimensions of about 250 μm×250 μm×4000 μm (W×H×L)+5 μm of each dimension, or a rod-shaped implant having dimensions of about 300 µm×300 µm×6000 µm (W×H×L)+5 µm of each dimension. In aspects, the disclosure provides a pharmaceutical composition for treating an ocular condition, wherein the composition is fabricated as a rod-shaped implant has dimensions of about 265 µm×265 µm×4,500 m (W×H×L)+5 µm of each dimension, a rod-shaped ocular implant having dimensions of about 255 µm×255 µm×4,500 µm (W×H×L)+5 µm of each dimension, or a rod-shaped ocular implant having dimensions of about 238 µm×238 µm×4,500 µm (W×H×L)+5 µm of each dimension.

In some aspects, the disclosure provides a pharmaceutical composition for treating an ocular condition, wherein the composition is fabricated a particle suspension having dimensions of about 12.5 µm×12.5 µm×25 µm (W×H×L)+10 µm, a particle suspension having dimensions of about 25 µm×25 µm×25 µm (W×H×L)+10 µm, dimensions of about 25 µm×25 µm×50 µm (W×H×L)+10 µm, a particle suspension having dimensions of about 50 µm×50 µm×30 µm (W×H×L)+10 µm, or a particle suspension having dimensions of about 50 µm×50 µm×50 µm (W×H×L)+10 µm.

In some aspects, the disclosure provides a pharmaceutical composition for treating an ocular condition, wherein the composition is fabricated a particle suspension having dimensions of about 12.5 µm×12.5 µm×25 µm (W×H×L)+5 µm, a particle suspension having dimensions of about 25 µm×25 µm×25 µm (W×H×L)+5 µm, dimensions of about 25 µm×25 µm×50 µm (W×H×L)+5 µm, a particle suspension having dimensions of about 50 µm×50 µm×30 µm (W×H×L)+5 µm, or a particle suspension having dimensions of about 50 µm×50 µm×50 µm (W×H×L)+5 µm.

In some aspects, the disclosure provides a pharmaceutical composition for treating an ocular condition, wherein the composition is fabricated a particle suspension having dimensions of about 12.5 µm×12.5 µm×25 µm (W×H×L)+2 µm, a particle suspension having dimensions of about 25 µm×25 µm×25 µm (W×H×L)+2 µm, dimensions of about 25 µm×25 µm×50 µm (W×H×L)+2 µm, a particle suspension having dimensions of about 50 µm×50 µm×30 µm (W×H×L)+2 µm, or a particle suspension having dimensions of about 50 µm×50 µm×50 µm (W×H×L)+2 µm.

In embodiments, the implants may have a volume of 180,000,000 cubic microns, or 202,500,000 cubic microns, or 316,012,500 cubic microns, or 292,612,500 cubic microns, or 254,898,000 cubic microns, or 33,750,000 cubic microns, or 148,078,125 cubic microns, or 742,598,025 cubic microns. In some embodiments, the volume from implant to implant may vary by about 0.1% to about 10%. The disclosure provides for compositions comprising the implants, kits comprising the implants, methods of utilizing the aforementioned implants, and systems comprising the implants with the stated cubic micron volumes.

In certain embodiments, the pharmaceutical formulations exclude implants that are not of the following volumes: 180,000,000 cubic microns±10%, or 202,500,000 cubic microns±10%, or 316,012,500 cubic microns±10% or 292,612,500 cubic microns±10%, or 254,898,000 cubic microns±10%, or 33,750,000 cubic microns±10%, or 148,078,125 cubic microns±10%, or 742,598,025 cubic microns±10%. Some embodiments exclude implants that are not of the following dimensions: about 150 µm×about 150 µm×about 1,500 µm, or about 200 µm×about 200 µm×about 4,500 µm, or about 238 µm×about 238 µm×about 4,500 µm, or about 225 µm×about 225 µm×about 4,000 µm, or about 255 µm×about 255 µm×about 4,500 µm, or about 265 µm×about 265 µm×about 4,500 µm, or about 225 µm×about 225 µm×about 2,925 µm, or about 311 µm×about 395 µm×about 6,045 µm. Some embodiments taught herein exclude implants that are not fabricated in a mold based method, such as for example by PRINT® technology fabrication.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the biocompatible polymer matrix comprises PLA and PLGA. In some embodiments, the biodegradable polymer matrix contains a mixture of polymers comprising as a wt % of the polymer matrix: i) 85±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 15±5% of a biodegradable poly(D,L-lactide-co-glycolide) copolymer having an inherent viscosity of 0.16 to 0.24 dL/g measured at 0.1% w/v in $CHCl_3$ at 25° C. with a Ubbelhode size 0c glass capillary viscometer. In embodiments, polymer i) is R 203 S, and polymer ii) is RG 752 S polymer. In some embodiments, the therapeutic agent is dexamethasone. In some embodiments, the implant is a rod-shaped implant having dimensions of about 200 µm×about 200 µm×about 4,500. In embodiments, the implant comprises dexamethasone in an amount of about 86 to about 92 µg per implant. In embodiments, the implant has a volume of 180,000,000 cubic microns±10%. In aspects, the implant is designed and structured to allow for administration in a 27 gauge needle.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the biocompatible polymer matrix comprises PLA and PLGA. In embodiments, the biodegradable polymer matrix contains a mixture of polymers comprising as a wt % of the polymer matrix: i) 60±5% of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and ii) 40±5% of a biodegradable poly(D,L-lactide-co-glycolide) copolymer having an inherent viscosity of 0.32 to 0.44 dL/g measured at 0.1% w/v in $CHCl_3$ at 25° C. with a Ubbelhode size 0c glass capillary viscometer. In embodiments, polymer i) is R 203 S, and polymer ii) is RG 653 H polymer. In some embodiments, the therapeutic agent is dexamethasone. In some embodiments, the implant is a rod-shaped implant having dimensions of about 200 µm×about 200 µm×about 4,500. In embodiments, the implant comprises dexamethasone in an amount of about 90 to about 100 µg per implant and the biodegradable polymer matrix in an amount of about 225 µg to about 245 µg. In embodiments, the implant has a volume of 180,000,000 cubic microns±10%. In aspects, the implant is designed and structured to allow for administration in a 27 gauge needle.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the biodegradable polymer matrix contains a mixture of polymers comprising as a wt % of the polymer matrix: i) 50±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 50±5% of a biodegradable poly(D,L-lactide-co-glycolide) copolymer having an inherent viscosity of 0.16 to 0.24 dL/g measured at 0.1% w/v in CHCl₃ at 25° C. with a Ubbelhode size 0c glass capillary viscometer. In embodiments, polymer i) is R 203 S, and polymer ii) is RG 502 S polymer. In some embodiments, the therapeutic agent is dexamethasone. In some embodiments, the implant is a rod-shaped implant having dimensions of about 200 µm×about 200 µm×about 4,500. In embodiments, the implant comprises dexamethasone in an amount of about 76 to about 94 µg per implant and the biodegradable polymer matrix in an amount of about 225 µg to about 245 µg. In embodiments, the implant has a volume of 180,000,000 cubic microns±10%. In aspects, the implant is designed and structured to allow for administration in a 27 gauge needle.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the biodegradable polymer matrix contains a mixture of polymers comprising as a wt % of the polymer matrix: i) 30±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 70±5% of a biodegradable poly(D,L-lactide-co-glycolide) copolymer having an inherent viscosity of 0.45 to 0.60 dL/g measured at 0.1% w/v in CHCl₃ at 25° C. with a Ubbelhode size 0c glass capillary viscometer. In embodiments, polymer i) is R 203 S, and polymer ii) is RG 504 H polymer. In some embodiments, the therapeutic agent is dexamethasone. In some embodiments, the implant is a rod-shaped implant having dimensions of about 200 µm×about 200 µm×about 4,500. In embodiments, the implant comprises dexamethasone in an amount of about 89 to about 112 µg per implant and the biodegradable polymer matrix in an amount of about 225 µg to about 245 µg. In embodiments, the implant has a volume of 180,000,000 cubic microns±10%. In aspects, the implant is designed and structured to allow for administration in a 27 gauge needle.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the biodegradable polymer matrix contains a mixture of polymers comprising as a wt % of the polymer matrix: i) 50±5% of a biodegradable poly(D,L-lactide) homopolymer having an inherent viscosity of 0.55 to 0.75 dL/g measured at 0.1% w/v in CHCl₃ at 25° C. with a Ubbelhode size 0c glass capillary viscometer; and ii) 50±5% of a biodegradable poly(D,L-lactide-co-glycolide) copolymer having an inherent viscosity of 0.32 to 0.44 dL/g measured at 0.1% w/v in CHCl₃ at 25° C. with a Ubbelhode size 0c glass capillary viscometer. In embodiments, polymer i) is R 205 S, and polymer ii) is RG 653 H polymer. In some embodiments, the therapeutic agent is dexamethasone. In some embodiments, the implant is a rod-shaped implant having dimensions of about 200 µm×about 200 µm×about 4,500. In embodiments, the implant comprises dexamethasone in an amount of about 73 to about 85 µg per implant and the biodegradable polymer matrix in an amount of about 225 µg to about 245 µg. In embodiments, the implant has a volume of 180,000,000 cubic microns±10%. In aspects, the implant is designed and structured to allow for administration in a 27 gauge needle.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the biodegradable polymer matrix contains a mixture of polymers comprising as a wt % of the polymer matrix: i) 95±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 5±5% of a biodegradable poly(D,L-lactide-co-glycolide) copolymer having an inherent viscosity of 0.05 to 0.15 dL/g measured at 0.1% w/v in CHCl₃ at 25° C. with a Ubbelhode size 0c glass capillary viscometer. In embodiments, polymer i) is R 205 S, and polymer ii) is DLG1A polymer. In some embodiments, the therapeutic agent is dexamethasone. In some embodiments, the implant is a rod-shaped implant having dimensions of about 200 µm×about 200 µm×about 4,500. In embodiments, the implant comprises dexamethasone in an amount of about 89 to about 97 µg per implant and the biodegradable polymer matrix in an amount of about 225 µg to about 245 µg. In embodiments, the implant has a volume of 180,000,000 cubic microns±10%. In aspects, the implant is designed and structured to allow for administration in a 27 gauge needle.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the biodegradable polymer matrix contains a mixture of polymers comprising as a wt % of the polymer matrix: i) 15±5% of a biodegradable poly(D,L-lactide) homopolymer having an inherent viscosity of 0.25 to 0.35 dL/g measured at 0.1% w/v in CHCl₃ at 25° C. with a Ubbelhode size 0c glass capillary viscometer; and ii) 85±5% of a biodegradable poly(D,L-co-glycolide) copolymer having an inherent viscosity of 0.32 to 0.44 dL/g measured at 0.1% w/v in CHCl₃ at 25° C. with a Ubbelhode size 0c glass capillary viscometer. In embodiments, polymer i) is R 203 S, and polymer ii) is RG 502 S polymer. In some embodiments, the therapeutic agent is dexamethasone. In some embodiments, the implant is a rod-shaped implant having dimensions of about 225 µm×about 225 µm×about 4,000. In embodiments, the implant comprises dexamethasone in an amount of about 50 to about 58 µg per implant and the biodegradable polymer matrix in an amount of about 110 µg to about 130 µg. In embodiments, the implant has a volume of 202,500,000 cubic microns±10%. In aspects, the implant is designed and structured to allow for administration in a 25 gauge needle.

In certain embodiments, the disclosure provides for particle suspension comprising: A) a biodegradable polymer matrix; and B) at least one therapeutic agent homogenously dispersed therein, wherein the biocompatible polymer matrix comprises about 80% w/w to about 90% w/w of the particle and the therapeutic agent comprises about 10% w/w to about 20% w/w. In embodiments, the biodegradable polymer matrix comprises about 85±5% of a biodegradable poly(D,L-co-glycolide) copolymer having an inherent viscosity of 0.45 to 0.60 dL/g measured at 0.1% w/v in CHCl$_3$ at 25° C. with a Ubbelhode size 0c glass capillary viscometer. In embodiments, the biodegradable polymer is a RG 504 H polymer or an RG 504 S polymer. In some embodiments, the therapeutic agent is dexamethasone. In some embodiments, the particles have dimensions of about 25 μm×about 25 μm×about 25 or of about 25 μm×about 25 μm×about 50. In embodiments, the particle has a volume of 15,625-31,250 cubic microns±10%. In aspects, the particle is designed and structured to allow for administration in a 27 gauge needle or smaller.

In certain embodiments, the disclosure provides for particle suspension comprising: A) a biodegradable polymer matrix; and B) at least one therapeutic agent homogenously dispersed therein, wherein the biocompatible polymer matrix comprises about 80% w/w to about 90% w/w of the particle and the therapeutic agent comprises about 10% w/w to about 20% w/w. In embodiments, the biodegradable polymer matrix comprises about 85±5% of a biodegradable poly(D,L-co-glycolide) copolymer having an inherent viscosity of 1.3 to 1.7 dL/g measured at 0.1% w/v in CHCl$_3$ at 25° C. with a Ubbelhode size 0c glass capillary viscometer. In aspects, the biodegradable polymer is a RG 858 S polymer. n some embodiments, the therapeutic agent is dexamethasone. In some embodiments, the particles have dimensions of about 50 μm×about 50 μm×about 50. In embodiments, the particle has a volume of cubic microns 125,000±10%. In aspects, the particle is designed and structured to allow for administration in a 27 gauge needle or smaller.

In certain embodiments, the disclosure provides for particle suspension comprising: A) a biodegradable polymer matrix; and B) at least one therapeutic agent homogenously dispersed therein, wherein the biocompatible polymer matrix comprises about 80% w/w to about 90% w/w of the particle and the therapeutic agent comprises about 10% w/w to about 20% w/w. In embodiments, the biodegradable polymer matrix comprises about 85±5% of a biodegradable biodegradable poly(D,L-lactide) homopolymer having an inherent viscosity of 0.25 to 0.35 dL/g measured at 0.1% w/v in CHCl$_3$ at 25° C. with a Ubbelhode size 0c glass capillary viscometer. In aspects, the biodegradable polymer is a R 203 S. In some embodiments, the therapeutic agent is dexamethasone. In some embodiments, the particles have dimensions of about 25 μm×about 25 μm×about 50. In embodiments, the particle has a volume of 31,250 cubic microns±10%. In aspects, the particle is designed and structured to allow for administration in a 27 gauge needle or smaller.

In certain embodiments, the disclosure provides for particle suspension comprising: A) a biodegradable polymer matrix; and B) at least one therapeutic agent homogenously dispersed therein, wherein the biocompatible polymer matrix comprises about 80% w/w to about 90% w/w of the particle and the therapeutic agent comprises about 10% w/w to about 20% w/w. In embodiments, the biodegradable polymer matrix comprises about 85±5% of a biodegradable biodegradable poly(D,L-lactide) homopolymer having an inherent viscosity of 1.3 to 1.7 dL/g measured at 0.1% w/v in CHCl$_3$ at 25° C. with a Ubbelhode size 0c glass capillary viscometer. In aspects, the biodegradable polymer is a R 207 S. In some embodiments, the therapeutic agent is dexamethasone. In some embodiments, the particles have dimensions of about 25 μm×about 25 μm×about 50. In embodiments, the particle has a volume of 31,250 cubic microns±10%. In aspects, the particle is designed and structured to allow for administration in a 27 gauge needle or smaller.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the pharmaceutical composition contains a mixture of polymers comprising as a wt % of the biodegradable polymer matrix: i) 25-75±5% of a biodegradable poly(D,L-lactide) homopolymer having an inherent viscosity of 0.25 to 0.35 dL/g measured at 0.1% w/v in CHCl$_3$ at 25° C. with a Ubbelhode size 0c glass capillary viscometer; and ii) 25-75±5% of a biodegradable poly(D,L-co-glycolide) copolymer having an inherent viscosity of 0.45 to 0.60 dL/g measured at 0.1% w/v in CHCl$_3$ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 504 S polymer. In some embodiments, the therapeutic agent is dexamethasone. In some embodiments, the particles have dimensions of about 25 μm×about 25 μm×about 50. In embodiments, the particle has a volume of 31,250 cubic microns±10%. In aspects, the particle is designed and structured to allow for administration in a 27 gauge needle or smaller.

In certain embodiments, the disclosure provides for an ocular implant comprising: A) a biodegradable polymer matrix; and B) at least one therapeutic agent homogenously dispersed therein, wherein the biocompatible polymer matrix comprises about 55% w/w to about 65% w/w of the overall implant and the therapeutic agent comprises about 35% w/w to about 55% w/w. In embodiments, the pharmaceutical composition contains a mixture of polymers comprising as a wt % of the biodegradable polymer matrix: i) 25-75±5% of a biodegradable poly(D,L-lactide) homopolymer having an inherent viscosity of 0.25 to 0.35 dL/g measured at 0.1% w/v in CHCl$_3$ at 25° C. with a Ubbelhode size 0c glass capillary viscometer; and ii) 25-75±5% of a biodegradable poly(D,L-co-glycolide) copolymer having an inherent viscosity of 0.32 to 0.44 dL/g measured at 0.1% w/v in CHCl$_3$ at 25° C. with a Ubbelhode size 0c glass capillary viscometer. In aspects, polymer i) is a PLA polymer, and polymer ii) is a PLGA polymer. In aspects, polymer i) is a R 203 S polymer, and polymer ii) is a RG 503 H polymer. In some embodiments, the therapeutic agent is dexamethasone. In some embodiments, the particles have dimensions of about 25 μm×about 25 μm×about 50. In embodiments, the particle has a volume of 31,250 cubic microns±10%. In aspects, the particle is designed and structured to allow for administration in a 27 gauge needle or smaller.

In certain embodiments, the disclosure provides for an ocular implant comprising: A) a biodegradable polymer matrix; and B) at least one therapeutic agent homogenously dispersed therein, wherein the biocompatible polymer matrix comprises 85% w/w to about 92% w/w of the overall implant and the therapeutic agent comprises about 8% w/w to about 15% w/w. In embodiments, the pharmaceutical composition contains a mixture of polymer comprising as a wt % of the biodegradable polymer matrix: i) 50±5 wt % of a biodegradable poly(D,L-lactide) homopolymer having an inherent viscosity of 0.25 to 0.35 dL/g measured at 0.1% w/v in CHCl$_3$ at 25° C. with a Ubbelhode size 0c glass capillary viscometer; and ii) 50±5 wt % of a biodegradable poly(D, L-lactide-co-glycolide) copolymer having an inherent viscosity of 0.45 to 0.60 dL/g measured at 0.1% w/v in $CHCl_3$ at 25° C. with a Ubbelhode size 0c glass capillary viscometer. In embodiments, polymer i) is R 203 S. In embodiments, polymer ii) is R 504 S. In some embodiments, the therapeutic agent is dexamethasone. In some embodiments, the particles have dimensions of about 25 μm×about 25 μm×about 50. In embodiments, the particle has a volume of 31,250 cubic microns±10%. In aspects, the particle is designed and structured to allow for administration in a 27 gauge needle or smaller.

In embodiments, the PRINT® particle technology can be utilized in the present disclosure to fabricate implants in the size range of 10 micrometers in a broadest dimension or larger, depending on the size designed into the mold cavities (as further described herein and in the art incorporated herein by reference).

Importantly, for intraorbital ophthalmic applications, the density of the implant is fabricated to be greater than the density of the fluid environment in which the implant will be placed, such as for example the aqueous humor or the like, such that the implant settles and remains outside the field of view of the patient and the implant also remains in the eye.

Furthermore, the larger surface area to volume ratio of the particles having smaller overall dimensions, for example, a 10 micron cube compared to a 100 micron cube, will degrade more rapidly. Likewise, a collection of, for example, 10 micron cube particles having total overall volume equal to a 100×100×2000 micron implant will conform to the shape of the space to which they are implanted much more closely than the 100×100×2000 micron implant.

In some embodiments, the implants have a largest cross-sectional dimension of 10 micrometers and a density greater than that of the aqueous humor, vitreous humor, or the like such that the implant settles due to gravitational forces. In some embodiments, the implants have a largest cross-sectional dimension of 20 micrometers and a density greater than that of the aqueous humor, vitreous humor, or the like such that the implant settles due to gravitational forces. In some embodiments, the implants have a largest cross-sectional dimension of 50 micrometers and a density greater than that of the aqueous humor, vitreous humor, or the like such that the implant settles due to gravitational forces. In some embodiments, the implants have a largest cross-sectional dimension of 100 micrometers and a density greater than that of the aqueous humor, vitreous humor, or the like such that the implant settles due to gravitational forces. In some embodiments, the implants have a largest cross-sectional dimension of 200 micrometers and a density greater than that of the aqueous humor, vitreous humor, or the like such that the implant settles due to gravitational forces. In some embodiments, the implants have a largest cross-sectional dimension of 500 micrometers and a density greater than that of the aqueous humor, vitreous humor, or the like such that the implant settles due to gravitational forces.

In embodiments, the present disclosure provides methods of treating an ocular condition in a human in need thereof comprising: administering at least one intravitreal implant to the vitreous humor. In certain embodiments, the intravitreal implant is formulated to achieve a concentration of dexamethasone in the vitreous humor of at least about 150 ng/g at day 28. In embodiments, the concentration of dexamethasone at day 28 is from about 150 ng/g to about 5000 ng/g. In certain embodiments, the intravitreal implant is formulated to maintain a concentration of dexamethasone in the vitreous humor of at least about 100 ng/g for at least about 45 days. In embodiments, the concentration of dexamethasone in the vitreous is maintained for at least about 56 days. In embodiments, the concentration of dexamethasone in the vitreous is maintained for at least about 90 days. In embodiments, the ocular condition is macular edema, retinal vein occlusion, or uveitis.

In embodiments, the methods entail administering at least one intravitreal implant comprising: i) a biodegradable polymer matrix comprising: a) 50±5 wt % of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and b) 50±5 wt % of a biodegradable poly(D,L-lactide-co-glycolide) copolymer having an inherent viscosity of 0.16 to 0.24 dL/g measured at 0.1% w/v in $CHCl_3$ at 25° C. with a Ubbelhode size 0c glass capillary viscometer; and ii) dexamethasone homogenously dispersed within the polymer matrix in an amount of about 35-45 wt % of the intravitreal implant. In embodiments, the intravitreal implant comprises about 42 μg of dexamethasone. In embodiments, the methods entail administering 6 intravitreal implants are administered to the vitreous humor. In embodiments, the dexamethasone is administered to the vitreous in an amount of about 300 g.

In embodiments, the methods entail administering at least one intravitreal implant comprising: i) a biodegradable polymer matrix comprising: a) 50±5 wt % of a biodegradable poly(D,L-lactide) homopolymer having an inherent viscosity of 0.25 to 0.35 dL/g measured at 0.1% w/v in $CHCl_3$ at 25° C. with a Ubbelhode size 0c glass capillary viscometer; and b) 50±5 wt % of a biodegradable poly(D,L-lactide-co-glycolide) copolymer having an inherent viscosity of 0.45 to 0.60 dL/g measured at 0.1% w/v in $CHCl_3$ at 25° C. with a Ubbelhode size 0c glass capillary viscometer; and ii) dexamethasone homogenously dispersed within the polymer matrix in an amount of about 12±5 wt % percent of the intravitreal implant. In embodiments, the dexamethasone is administered to the vitreous in an amount of about 700 μg.

Methods of the present disclosure for treating or preventing an ophthalmic condition include inserting more than 5 sustained release drug loaded biodegradable polymer based implants intraorbitally to treat or prevent the ophthalmic condition for more than 2 weeks. Methods of the present disclosure for treating or preventing an ophthalmic condition include inserting more than 10 sustained release drug loaded biodegradable polymer based implants intraorbitally to treat or prevent the ophthalmic condition for more than 2 weeks. Methods of the present disclosure for treating or preventing an ophthalmic condition include inserting more than 25 sustained release drug loaded biodegradable polymer based implants intraorbitally to treat or prevent the ophthalmic condition for more than 2 weeks. Methods of the present disclosure for treating or preventing an ophthalmic condition include inserting more than 50 sustained release drug loaded biodegradable polymer based implants intraorbitally to treat or prevent the ophthalmic condition for more than 2 weeks. Methods of the present disclosure for treating or preventing an ophthalmic condition include inserting more than 100 sustained release drug loaded biodegradable polymer based implants intraorbitally to treat or prevent the ophthalmic condition for more than 2 weeks. Methods of the present disclosure for treating or preventing an ophthalmic condition include inserting more than 500 sustained release drug loaded biodegradable polymer based implants intraorbitally to treat or prevent the ophthalmic condition for more than 2 weeks. Methods of the present disclosure for treating or preventing an ophthalmic condition include inserting more than 1,000 sustained release drug loaded biodegradable polymer based implants intraorbitally to treat or prevent the ophthalmic condition for more than 2 weeks. Methods of the present disclosure for treating or preventing an ophthalmic condition include inserting more than 10,000 sustained release drug loaded biodegradable polymer based implants intraorbitally to treat or prevent the ophthalmic condition for more than 2 weeks. Methods of the present disclosure for treating or preventing an ophthalmic condition include inserting more than 100,000 sustained release drug loaded biodegradable polymer based implants intraorbitally to treat or prevent the ophthalmic condition for more than 2 weeks. Methods of the present disclosure for treating or preventing an ophthalmic condition include inserting more than 1,000,000 sustained release drug loaded biodegradable polymer based implants intraorbitally to treat or prevent the ophthalmic condition for more than 2 weeks.

The polymer composition and ratios of each implant in these collections of small implants can be varied between implants within a single dose such that an aggregate degradation profile of the collection of implants is achieved for delivery of the active agent for greater than 2 weeks, greater than 1 month, greater than 3 months, greater than 4 months, greater than 6 months, greater than 9 months and greater than 12 months.

Delivery of such implants disclosed herein include delivery through a 21 gauge needle or smaller. In some embodiments, the needle is 22 gauge, 23 gauge, 24 gauge, 25 gauge, 26 gauge, or 27 gauge, or smaller.

In one embodied delivery method the needle is a 28 gauge, 29 gauge, 30 gauge, 31 gauge, 32 gauge, 33 gauge, or 34 gauge needle.

In some aspects, the ocular implant is formulated for treating an ocular condition characterized by inflammation.

In some aspects, the ocular implant is sized and structured to allow for administration with a needle for delivery. In some embodiments, the needle is 27 gauge. In some embodiments, the needle is 25 gauge.

An important aspect of some embodiments of the present disclosure is the uniformity and control of overall size to the tolerances discussed herein to provide for use of the smallest needle gauge as possible. An implant will have between 10-50 micron clearance between overall maximum implant cross-sectional width and inside needle diameter. In other embodiments, an implant-needle clearance shall be between 20-40 micron between overall maximum implant cross-sectional width and inside needle diameter. In other embodiments, an implant-needle clearance shall be not less than 40 micron between overall maximum implant cross-sectional width and inside needle diameter. In other embodiments, an implant-needle clearance shall be not less than 30 micron between overall maximum implant cross-sectional width and inside needle diameter. In other embodiments, an implant-needle clearance shall be not less than 20 micron between overall maximum implant cross-sectional width and inside needle diameter. In other embodiments, an implant-needle clearance shall be not less than 10 micron between overall maximum implant cross-sectional width and inside needle diameter. It will be appreciated by one of ordinary skill in the art that the three-dimensional shape of the implant can be designed to maximize the volume of the inner opening of the needle or to facilitate the desired loading, insertion, tissue deposition or other parameter of the implant or treatment. In some embodiments, the molds and implants of the present disclosure are designed as cylindrical implants. In some embodiments the cylindrical implants are fabricated with a cross-sectional diameter that is not less than 30 micrometers smaller than the inner diameter of the needle. In some embodiments the implant, mold, or master from which the mold is made is fabricated utilizing additive manufacturing techniques.

In a particular embodiment, the ocular implant is manufactured by a process comprising: 1) providing a mold, wherein the mold comprises a plurality of recessed areas formed therein; 2) disposing a volume of liquid material in the plurality of recessed areas; 3) forming a plurality of substantially uniform implants; and 4) harvesting the implants from the patterned template, wherein each of said implants substantially mimics the recessed areas.

Some embodiments comprise a kit for administering a biodegradable sustained release ocular implant, comprising: (a) at least one biodegradable sustained release ocular implant; wherein said at least one biodegradable sustained release ocular implant comprises at least one therapeutic agent that is homogeneously dispersed within a biodegradable polymer matrix; and (b) a single use ocular implant applicator that comprises a needle or needlelike device.

In some aspects, the implants produced according to the present disclosure exhibit a therapeutic agent release profile that has very low inter-implant variability. The therapeutic agent release profiles exhibited by some implants of the present disclosure are consistent across implants and demonstrate variation that is not statistically significant. Consequently, the drug release profiles demonstrated by embodiments of the implants exhibit coefficients of variation that are within a confidence interval and not biologically relevant.

In some aspects, the therapeutic agent content amongst implants of a given configuration is highly consistent. In particular embodiments, the implants of the present disclosure possess a therapeutic agent content that does not vary significantly amongst implants of a given configuration. In an embodiment, the therapeutic agent content of implants having a given configuration does not vary in a statistically significant manner from one another.

In an aspect, the pharmaceutical composition for treating an ocular condition taught herein is fabricated as an ocular implant.

In an aspect, the pharmaceutical composition for treating an ocular condition taught herein is fabricated as an ocular implant and said fabrication does not comprise hot-melt extrusion.

BRIEF DESCRIPTION OF THE DRAWINGS

FIG. 6F shows in-vitro release of dexamethasone measured for implant formulations ENV-1D-0209-1-9 through ENV-1D-0209-1-11 in Table 1F; dexamethasone release was measured at 37° C. in 1×PBS with 0.1% Triton X-100.

FIG. 7B shows in-vitro release of dexamethasone measured for implant formulations ENV-1D-0209-10-4 and ENV-1D-0209-10-5 in Table 1G; dexamethasone release was measured at 37° C. in 1×PBS (solid lines) or 1×PBS with 0.1% Triton X-100 (dotted lines).

FIG. 32 illustrates ocular pharmacokinetics from nonclinical study ENV1105-PRE-003: aqueous humor concentration of dexamethasone following a single bilateral administration of various formulations of ENV1105 intravitreal implant.

DETAILED DESCRIPTION

Figure 1A:
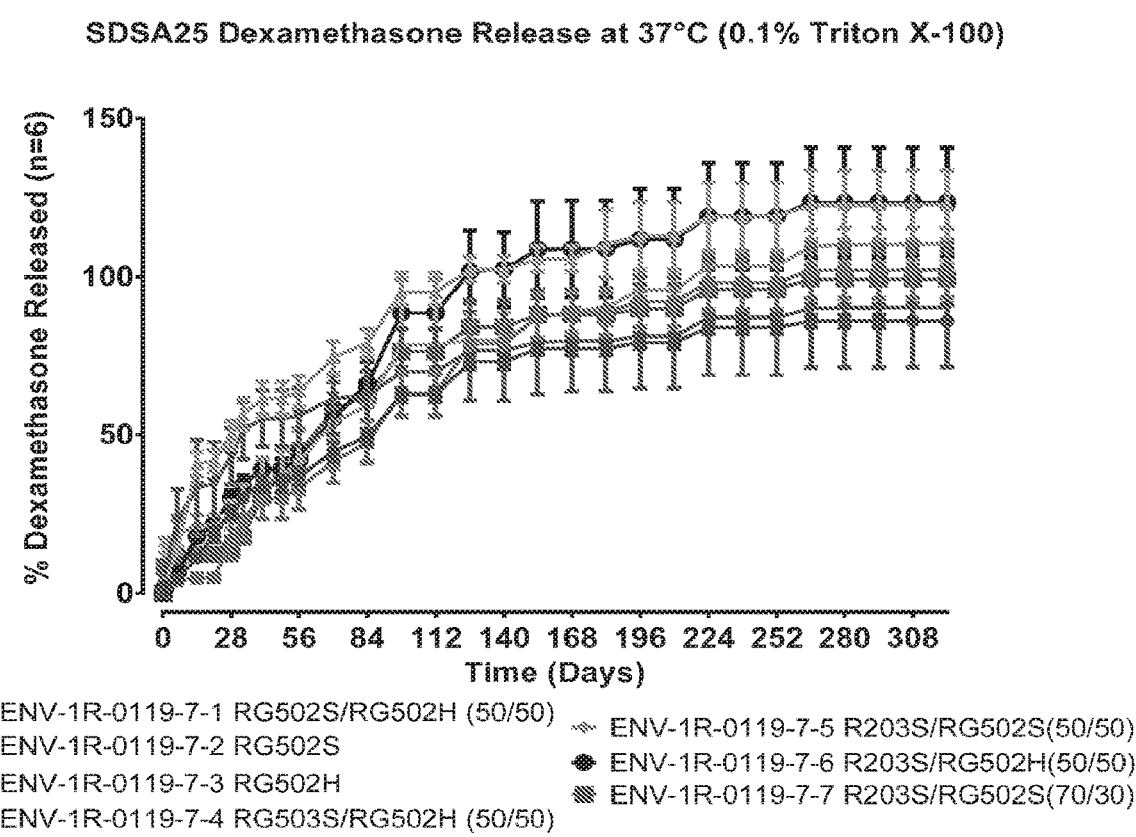
FIG. 1A shows in-vitro release of dexamethasone measured for the implant formulations ENV-1R-0119-7-1 through ENV-1R-0119-7-7 in Table 1A; dexamethasone release was measured at 37° C. in 1×PBS with 0.1% Triton X-100.
Figure 1B:
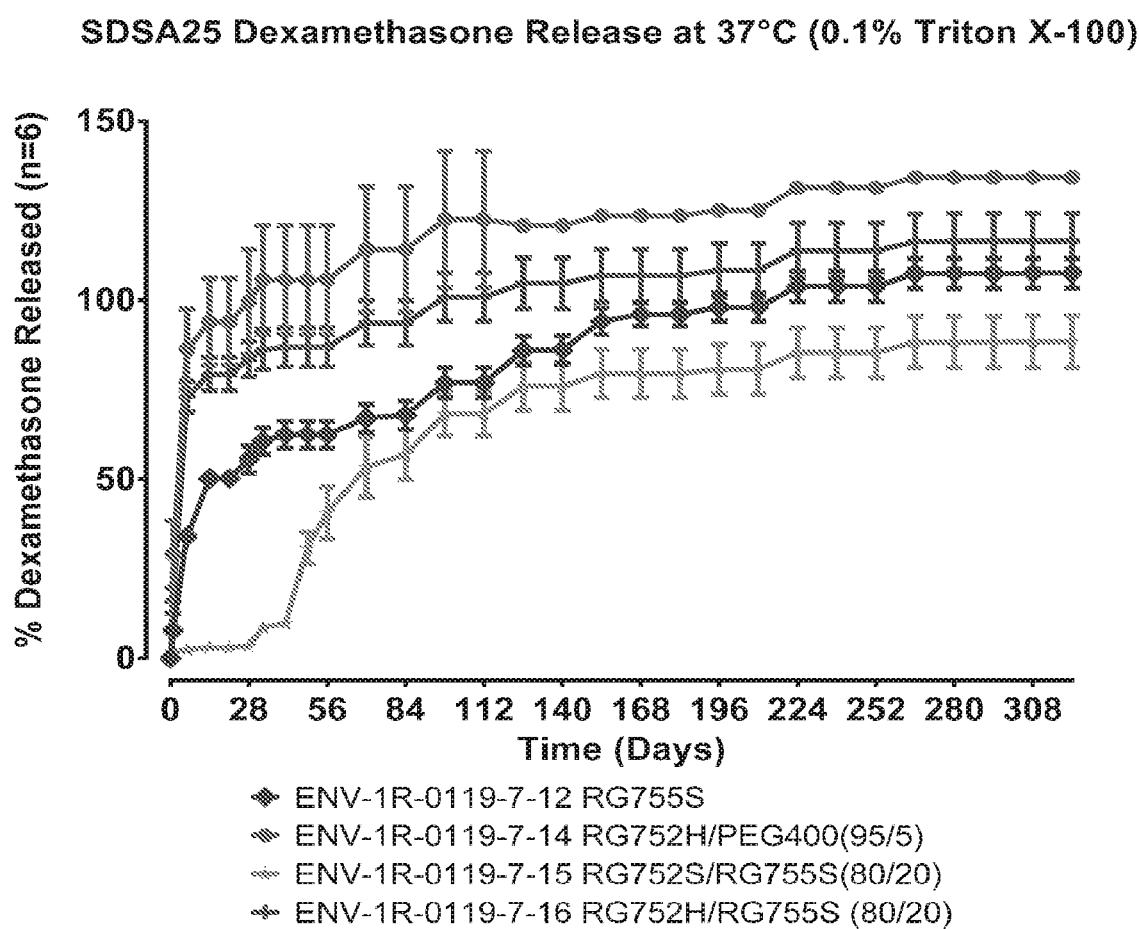
FIG. 1B shows in-vitro release of dexamethasone measured for the implant formulations ENV-1R-0119-7-12 through ENV-1R-0119-7-16 in Table 1A; dexamethasone release was measured at 37° C. in 1×PBS with 0.1% Triton X-100.
Figure 1C:
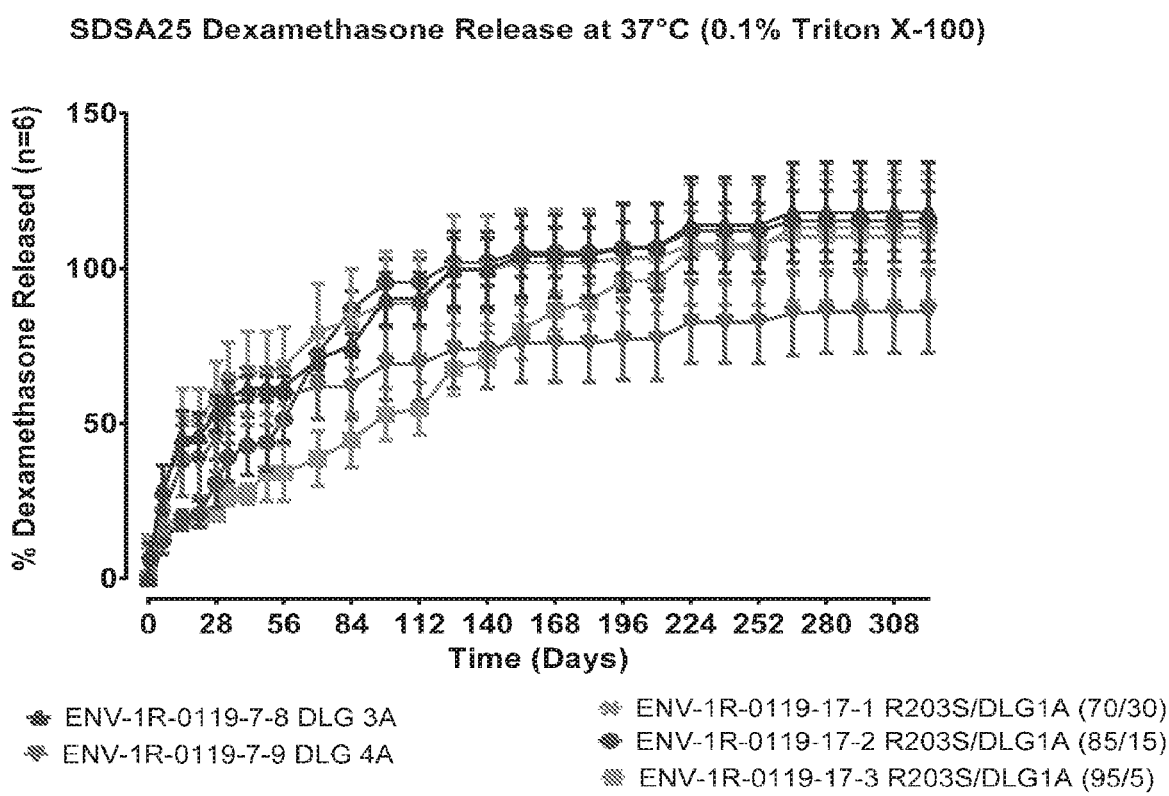
FIG. 1C shows in-vitro release of dexamethasone measured for the implant formulations ENV-1R-0119-7-8, ENV-1R-0119-7-9 and ENV-1R-0119-17-1 through ENV-1R-0119-17-1 in Table 1A; dexamethasone release was measured at 37° C. in 1×PBS with 0.1% Triton X-100.
Figure 2:
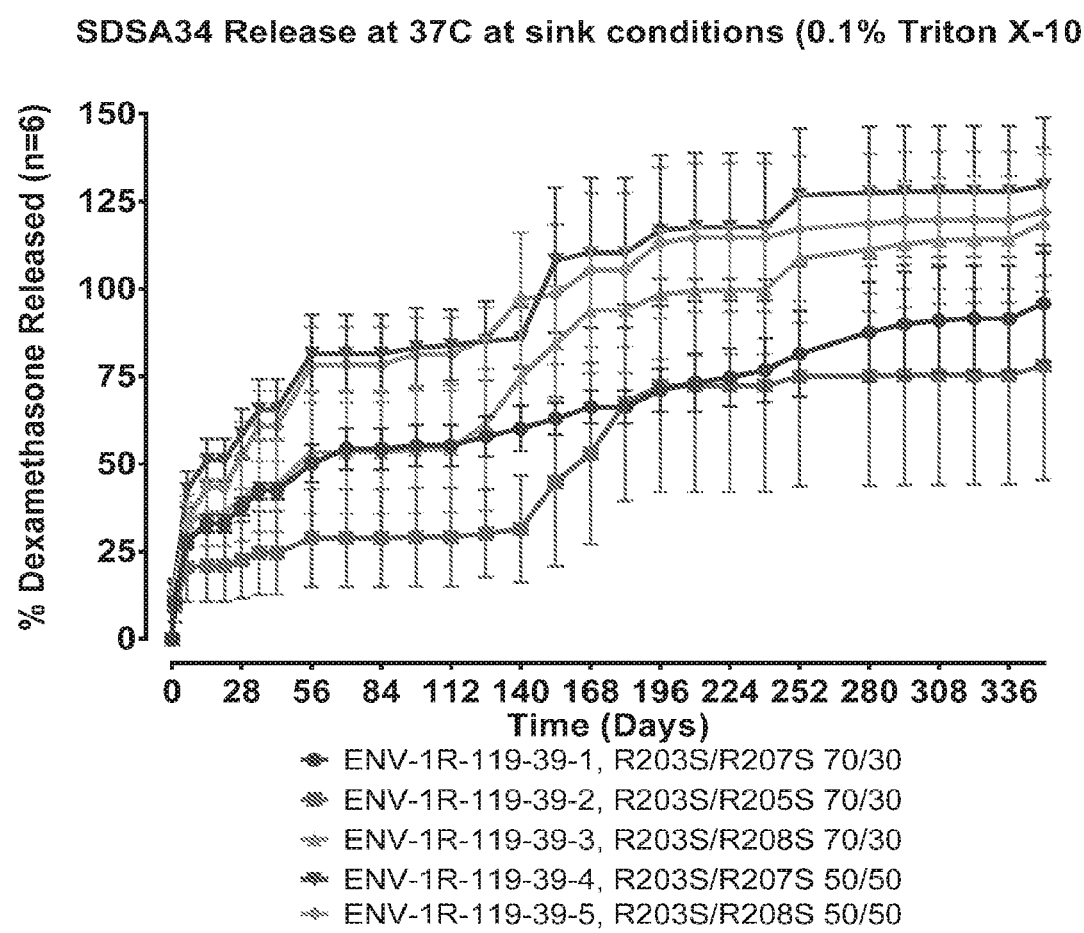
FIG. 2 illustrates the in-vitro release studies for dexamethasone implant formulations in Table 1B. Dexamethasone release was measured at 37° C. in 1×PBS with 0.1% Triton X-100.
Figure 3:
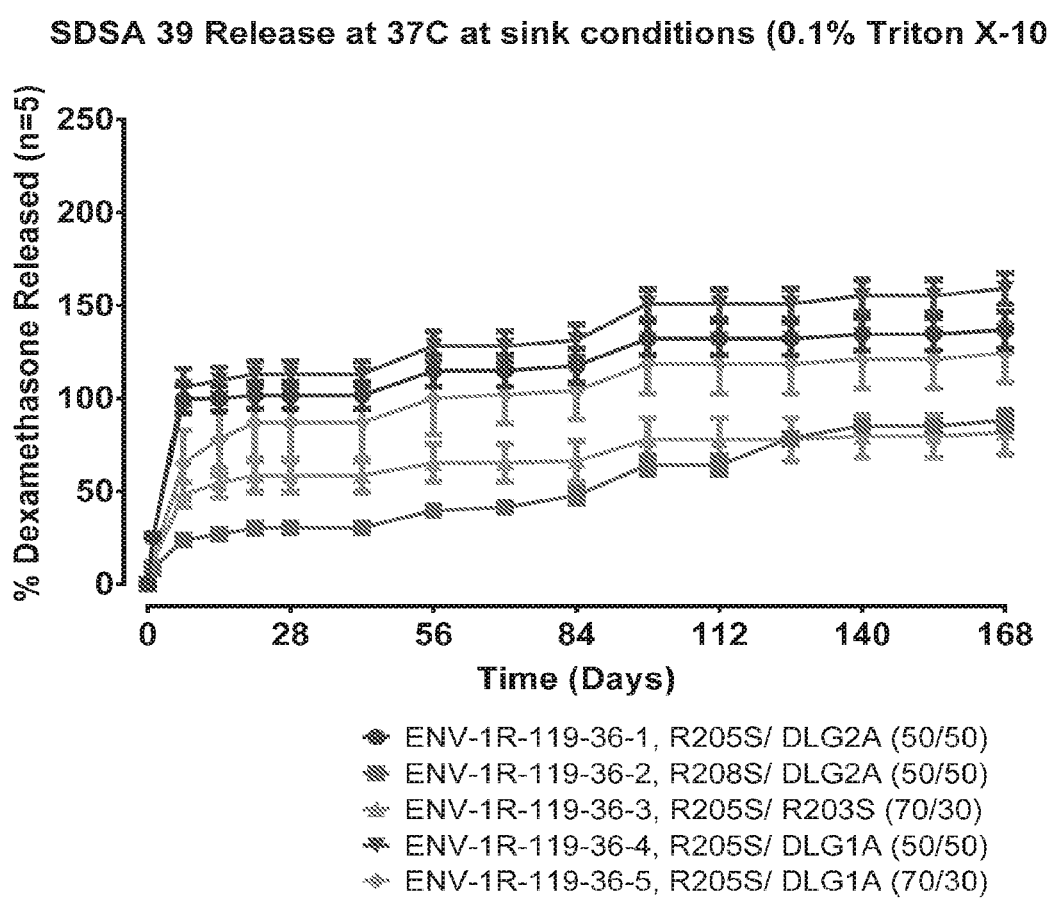
FIG. 3 illustrates in-vitro release studies for dexamethasone implant formulations in Table 1C. Dexamethasone release was measured at 37° C. in 1×PBS with 0.1% Triton X-100.
Figure 4A:
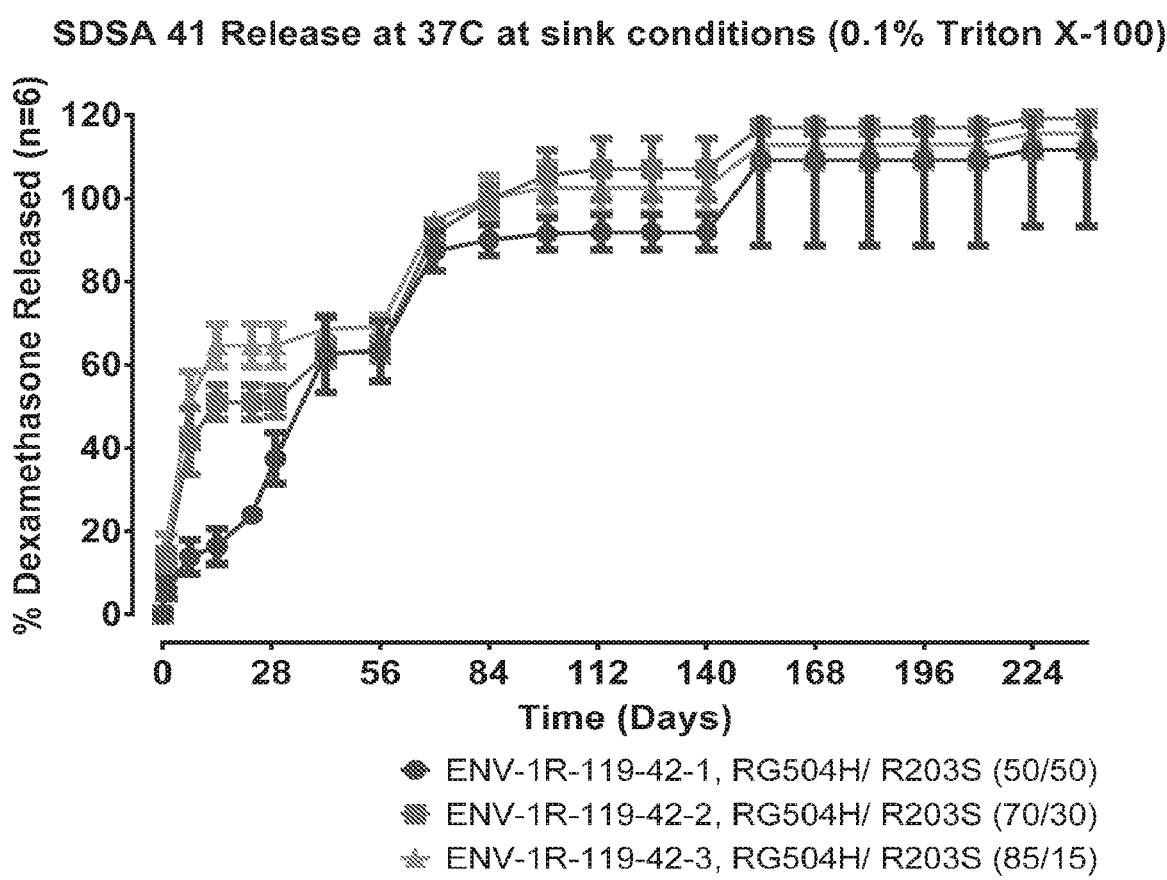
FIG. 4A shows in-vitro release of dexamethasone measured for implant formulations ENV-1R-119-42-1 through ENV-1R-119-42-3 in Table 1D; dexamethasone release was measured at 37° C. in 1×PBS with 0.1% Triton X-100.
Figure 4B:
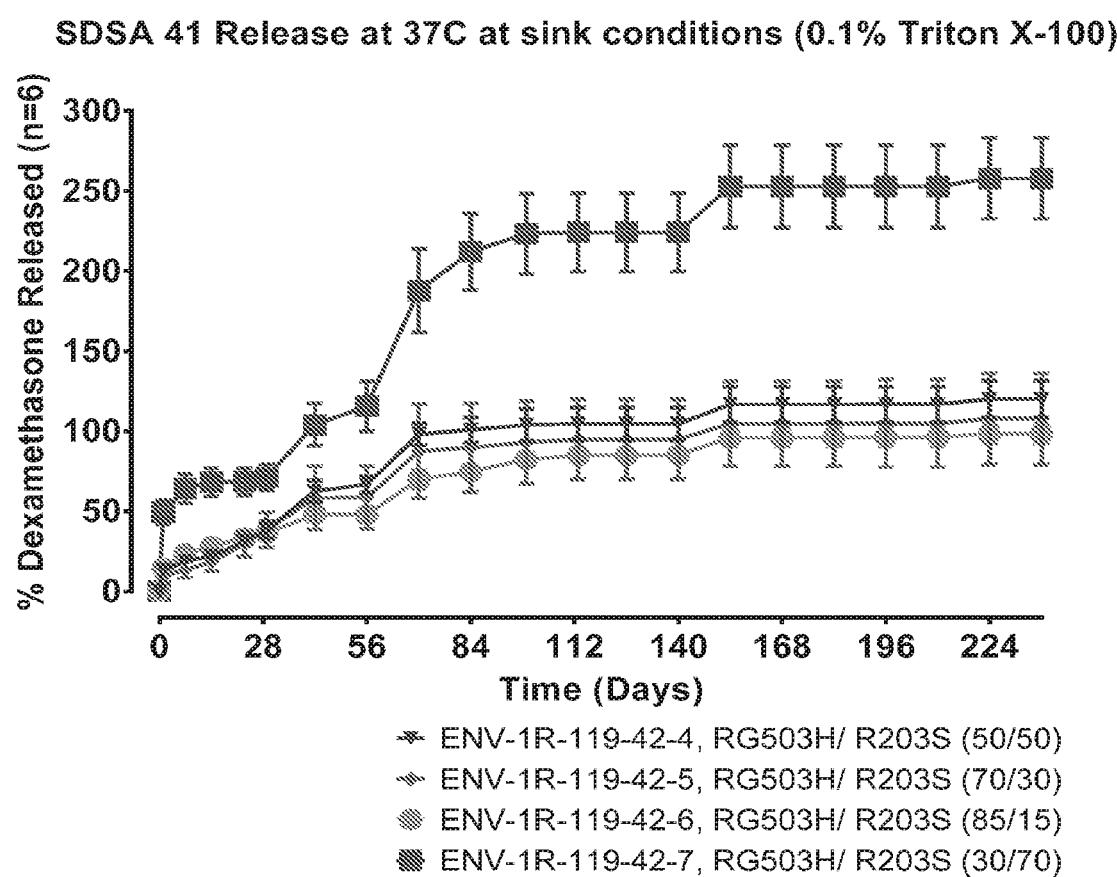
FIG. 4B shows in-vitro release of dexamethasone measured for implant formulations ENV-1R-119-42-4 through ENV-1R-119-42-7 in Table 1D; dexamethasone release was measured at 37° C. in 1×PBS with 0.1% Triton X-100.
Figure 4C:
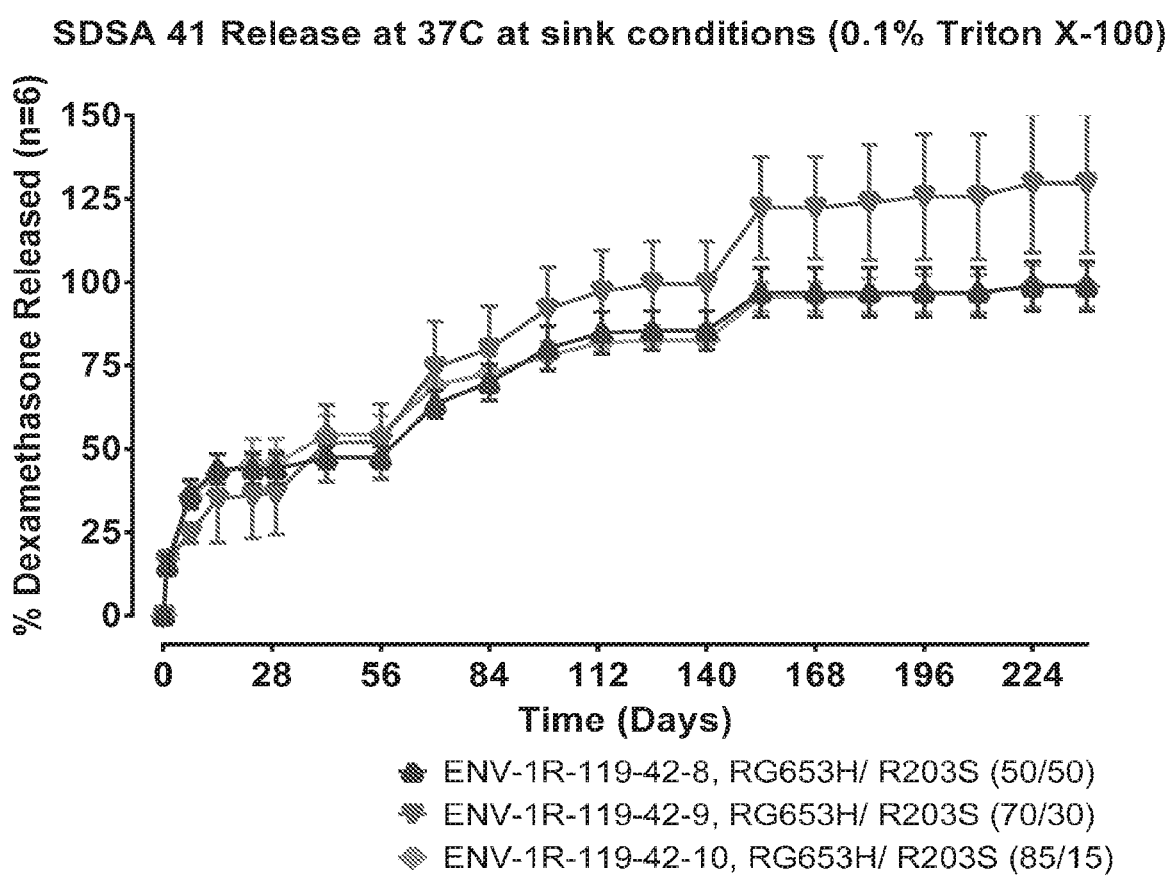
FIG. 4C shows in-vitro release of dexamethasone measured for implant formulations ENV-1R-119-42-8 through ENV-1R-119-42-10 in Table 1D; dexamethasone release was measured at 37° C. in 1×PBS with 0.1% Triton X-100.
Figure 4D:
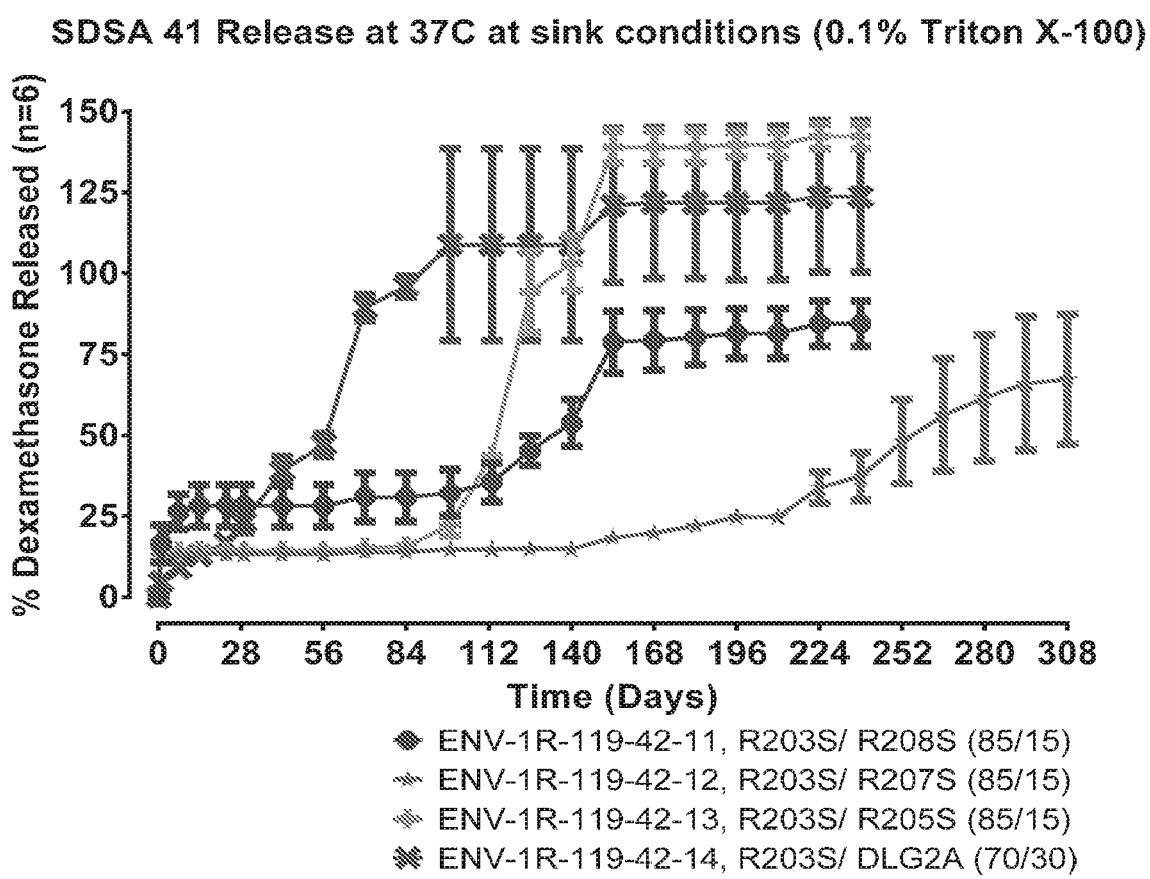
FIG. 4D shows in-vitro release of dexamethasone measured for implant formulations ENV-1R-119-42-11 through ENV-1R-119-42-14 in Table 1D; dexamethasone release was measured at 37° C. in 1×PBS with 0.1% Triton X-100.
Figure 5:
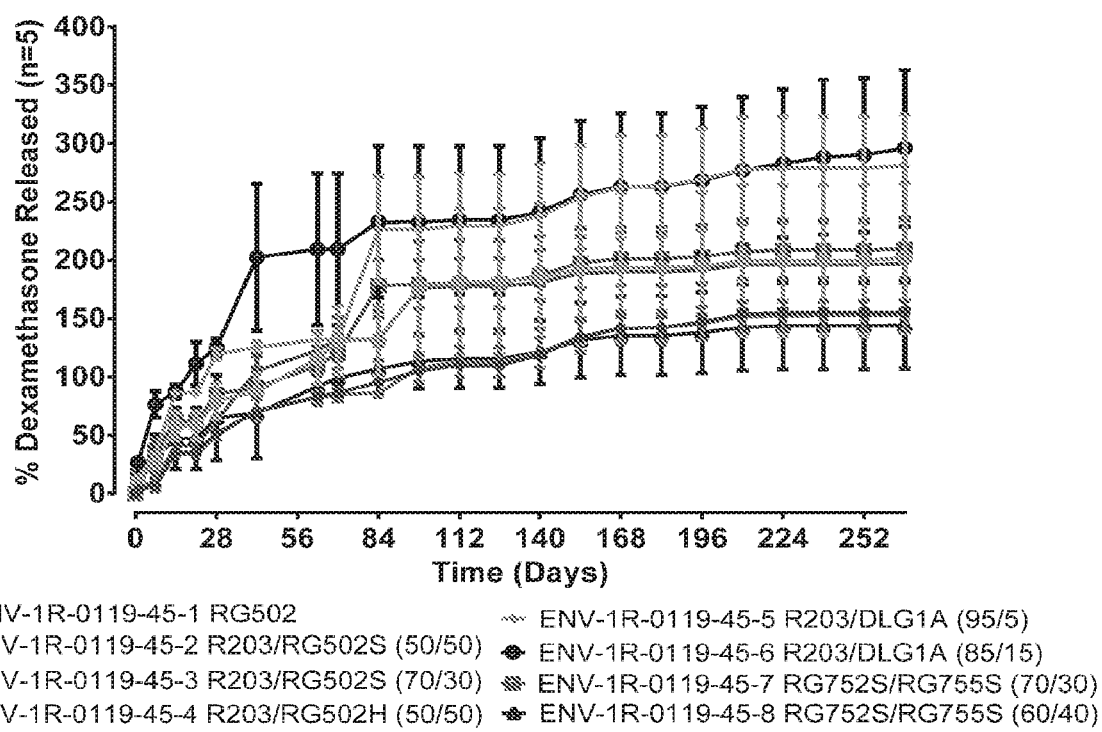
FIG. 5 illustrates In-vitro release studies for dexamethasone implant formulations in Table 1E. Dexamethasone release was measured at 37° C. in 1×PBS with 0.1% Triton X-100.
Figure 6A:
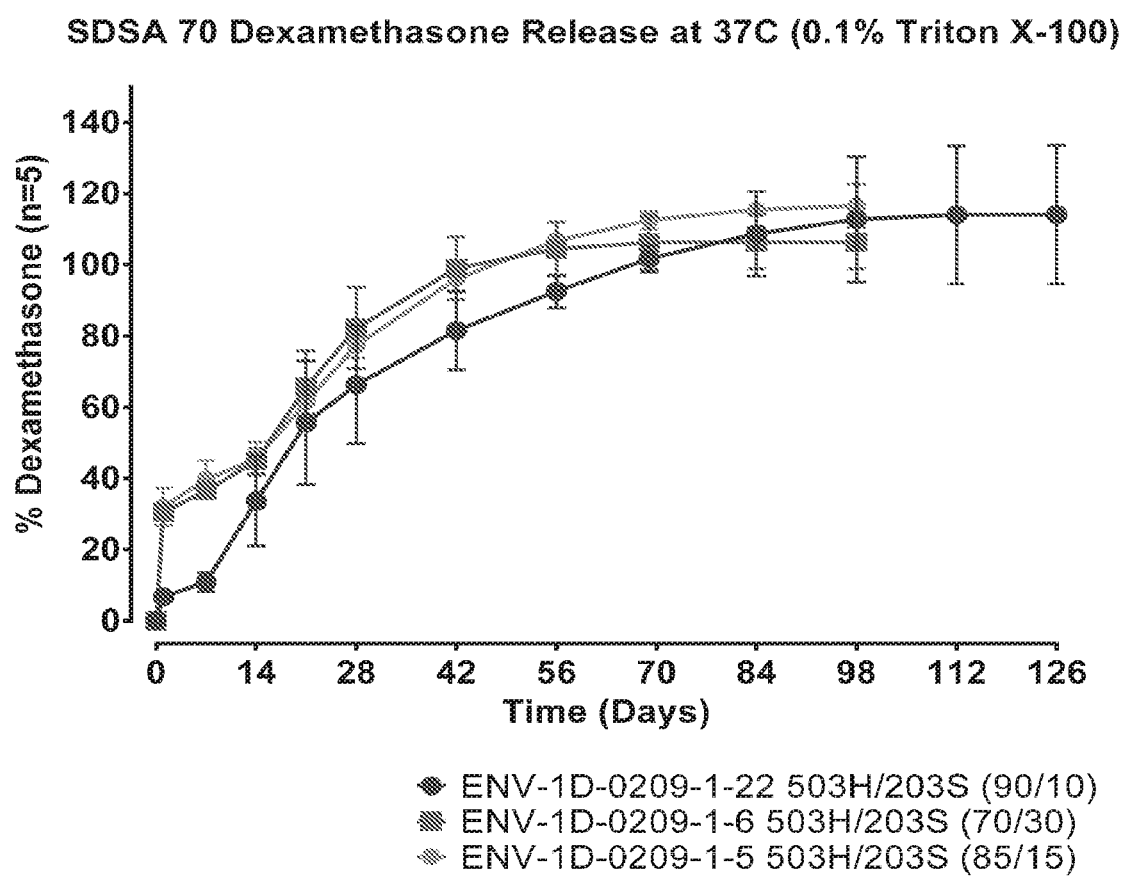
FIG. 6A shows in-vitro release of dexamethasone measured for implant formulations ENV-1D-0209-1-22, ENV-1D-0209-1-5, and ENV-1D-0209-1-6 in Table 1F; dexamethasone release was measured at 37° C. in 1×PBS with 0.1% Triton X-100.
Figure 6B:
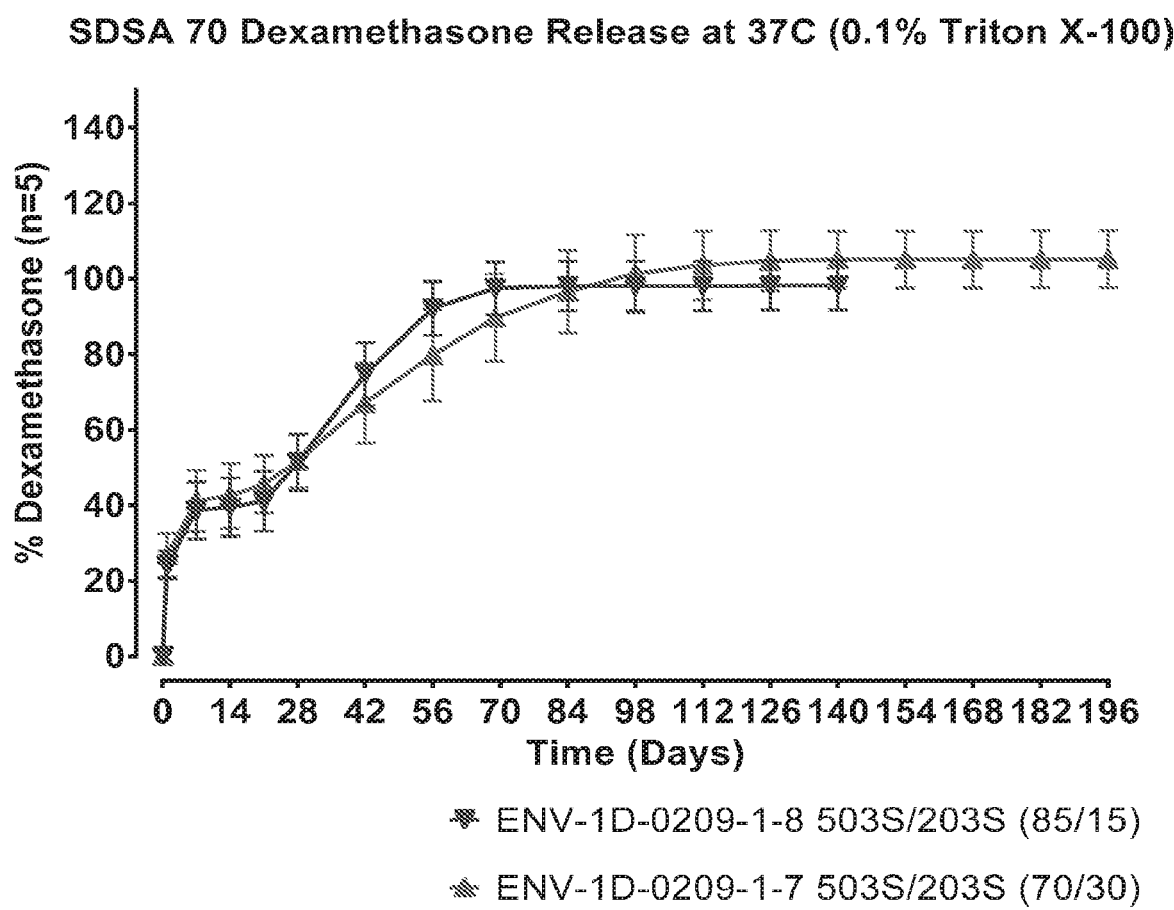
FIG. 6B shows in-vitro release of dexamethasone measured for implant formulations ENV-1D-0209-1-7 and ENV-1D-0209-1-8 in Table 1F; dexamethasone release was measured at 37° C. in 1×PBS with 0.1% Triton X-100.
Figure 6C:
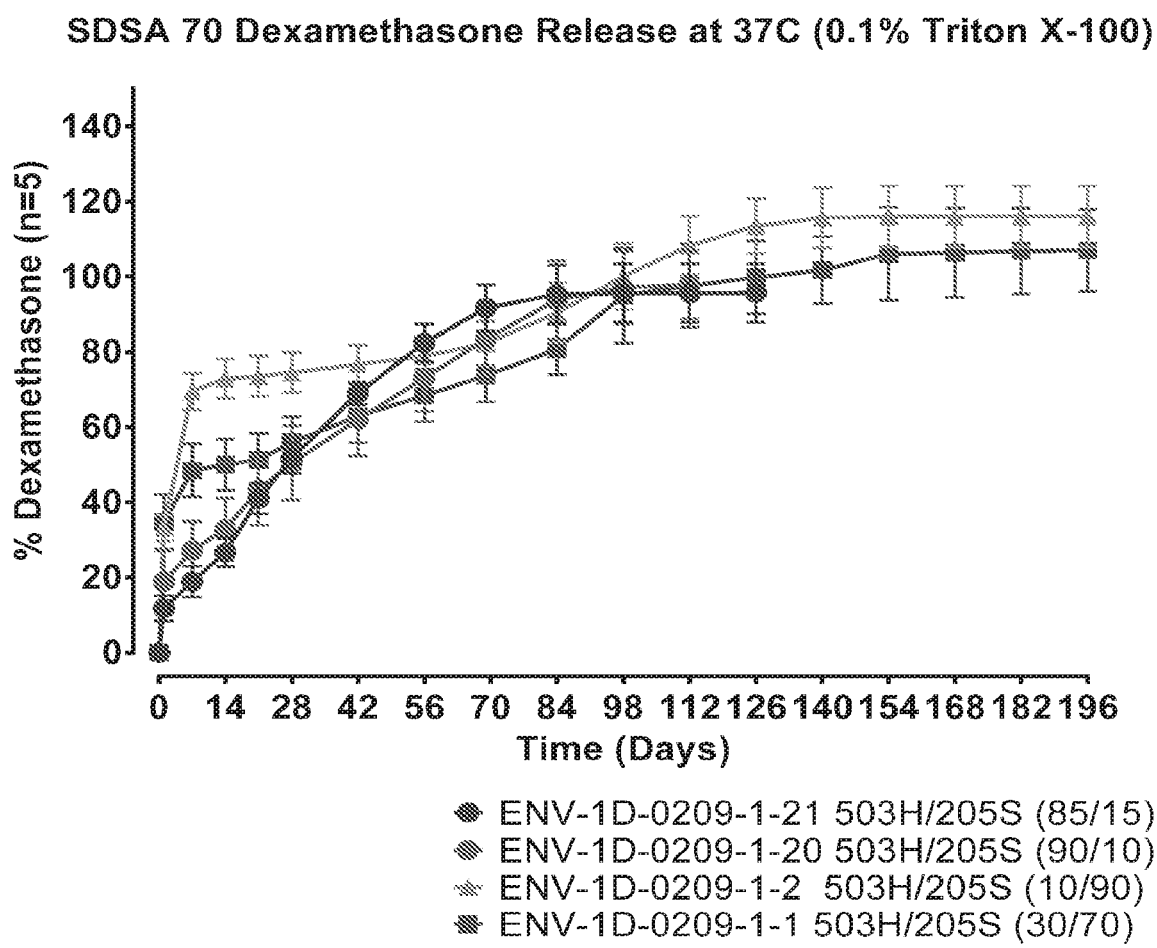
FIG. 6C shows in-vitro release of dexamethasone measured for implant formulations ENV-1D-0209-1-1, ENV-1D-0209-1-2, ENV-1D-0209-1-20, and ENV-1D-0209-1-21 in Table 1F; dexamethasone release was measured at 37° C. in 1×PBS with 0.1% Triton X-100.
Figure 6D:
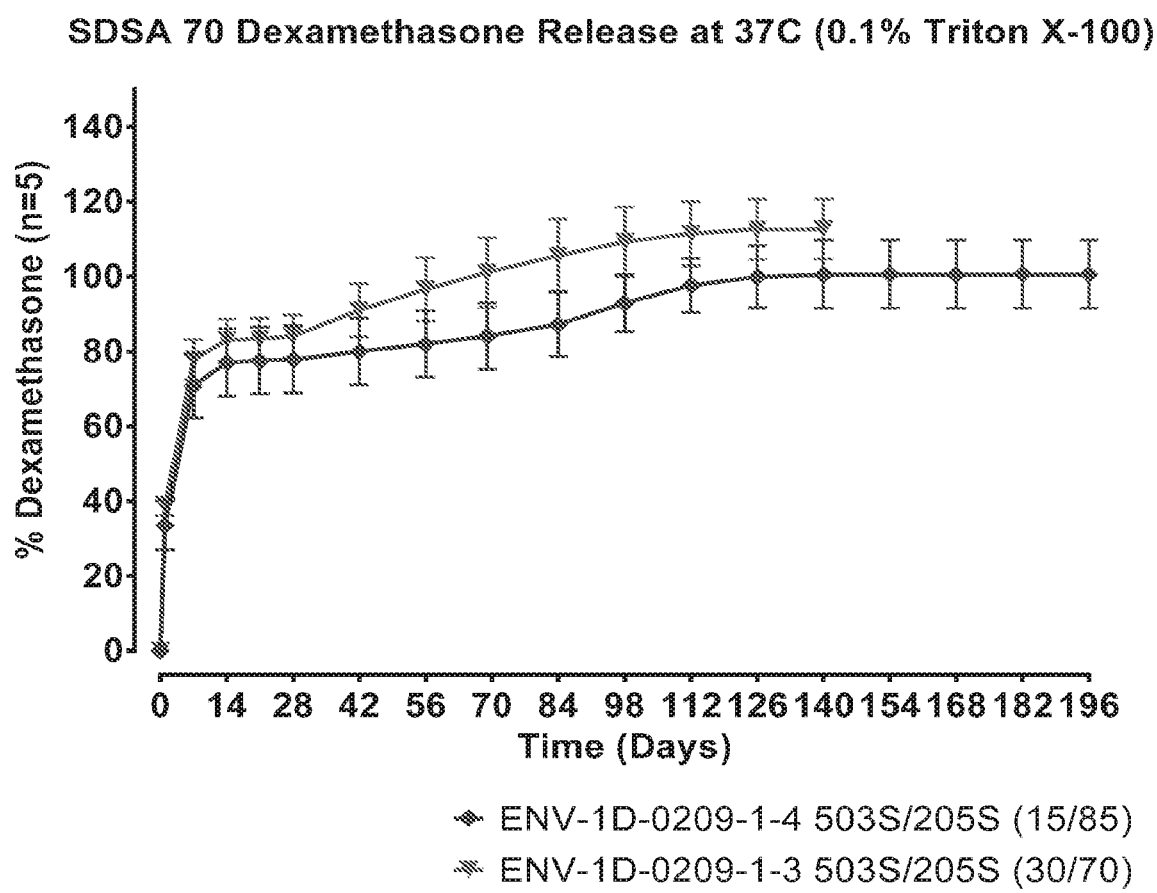
FIG. 6D shows in-vitro release of dexamethasone measured for implant formulations ENV-1D-0209-1-3 and ENV-1D-0209-1-4 in Table 1F; dexamethasone release was measured at 37° C. in 1×PBS with 0.1% Triton X-100.
Figure 6E:
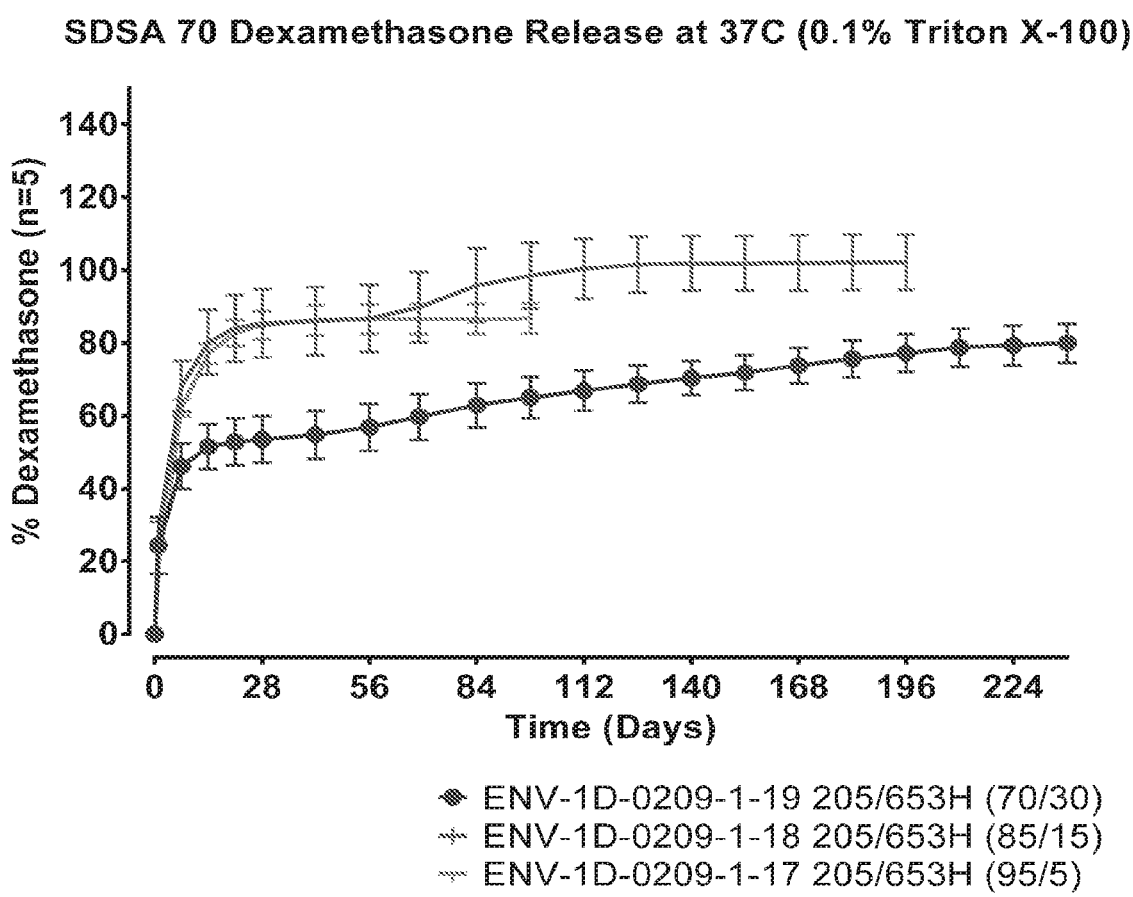
FIG. 6E shows in-vitro release of dexamethasone measured for implant formulations ENV-1D-0209-1-17 through ENV-1D-0209-1-19 in Table 1F; dexamethasone release was measured at 37° C. in 1×PBS with 0.1% Triton X-100.
Figure 6G:
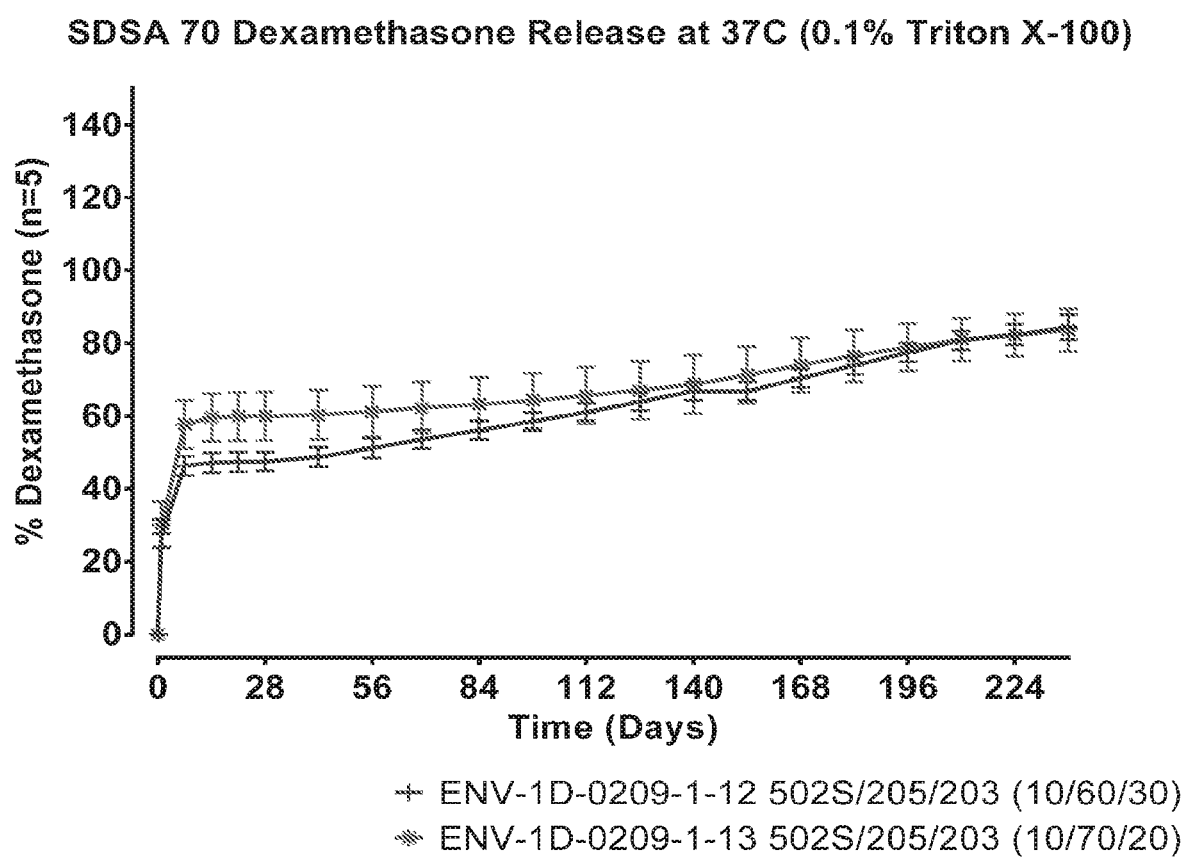
FIG. 6G shows in-vitro release of dexamethasone measured for implant formulations ENV-1D-0209-1-12 and ENV-1D-0209-1-13 in Table 1F; dexamethasone release was measured at 37° C. in 1×PBS with 0.1% Triton X-100.
Figure 6H:
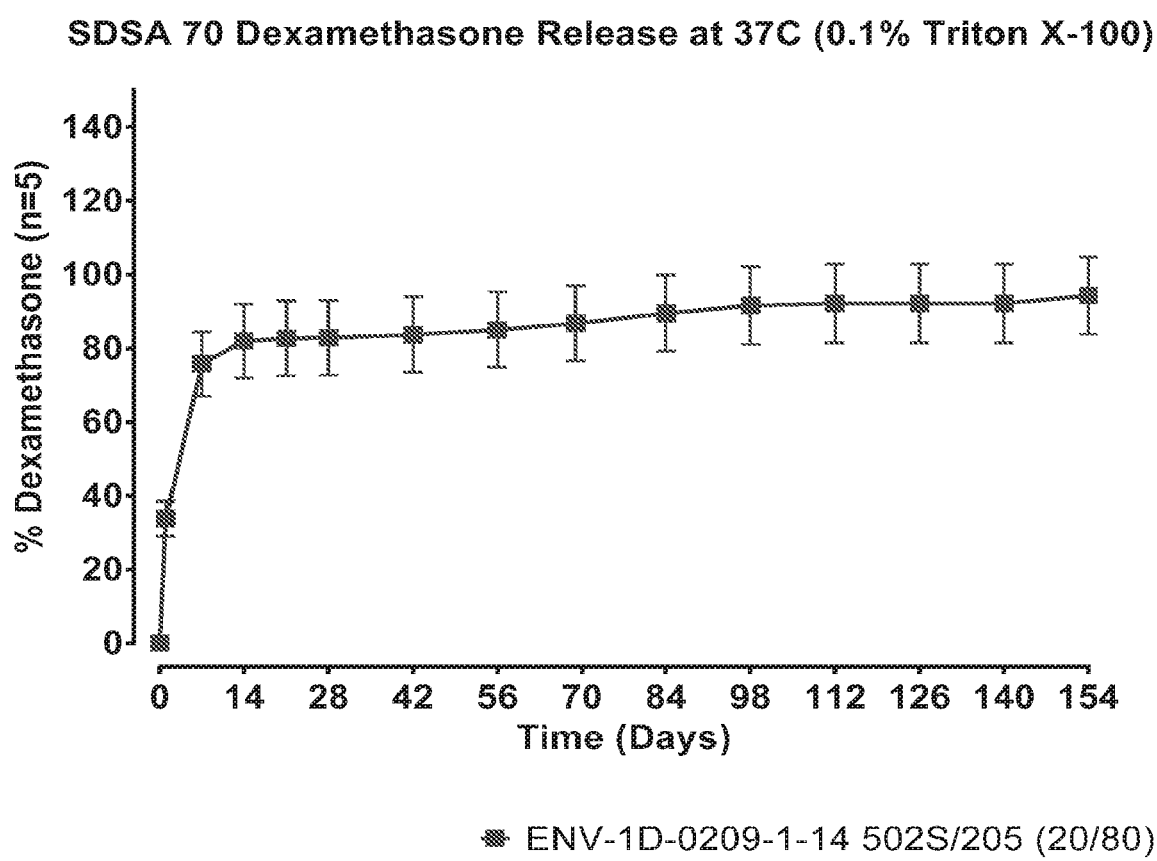
FIG. 6H shows in-vitro release of dexamethasone measured for implant formulations ENV-1D-0209-1-14 in Table 1F; dexamethasone release was measured at 37° C. in 1×PBS with 0.1% Triton X-100.
Figure 6I:
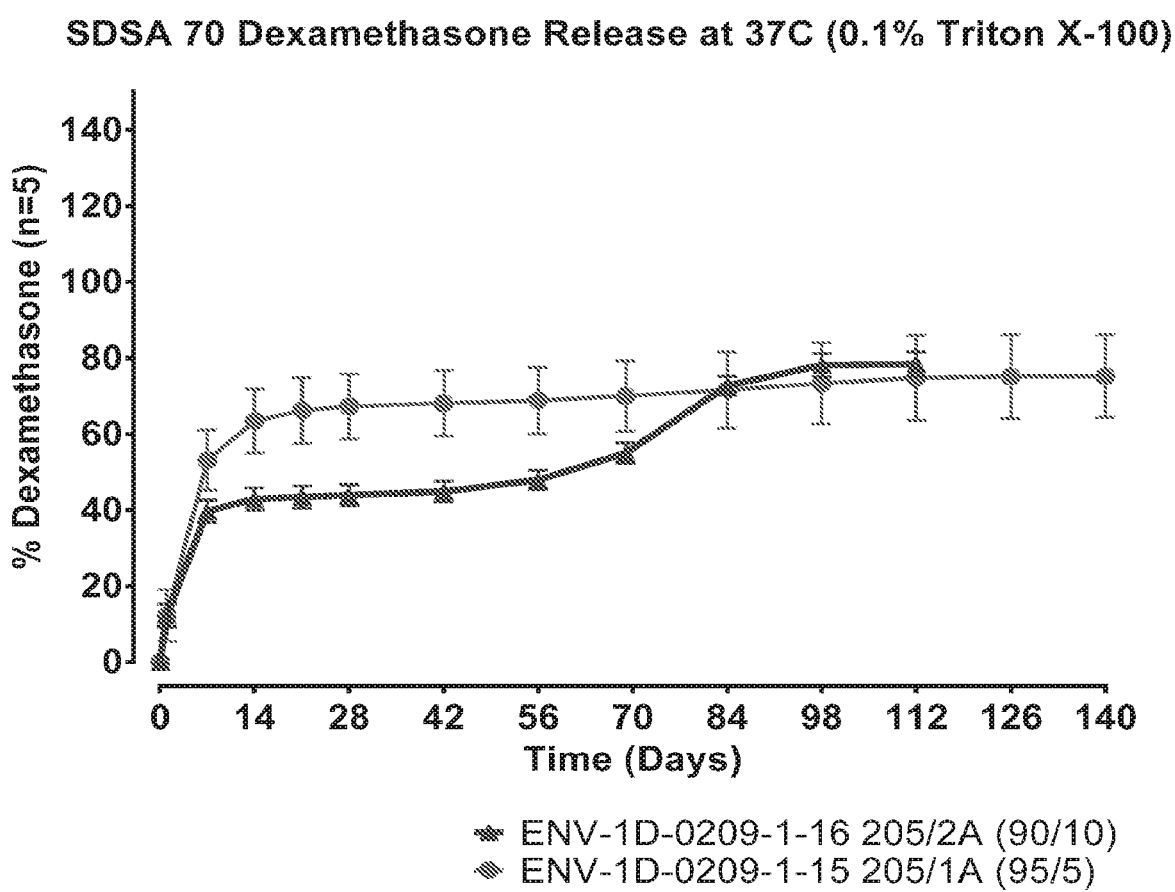
FIG. 6I shows in-vitro release of dexamethasone measured for implant formulations ENV-1D-0209-1-15 and ENV-1D-0209-1-16 in Table 1F; dexamethasone release was measured at 37° C. in 1×PBS with 0.1% Triton X-100.
Figure 7A:
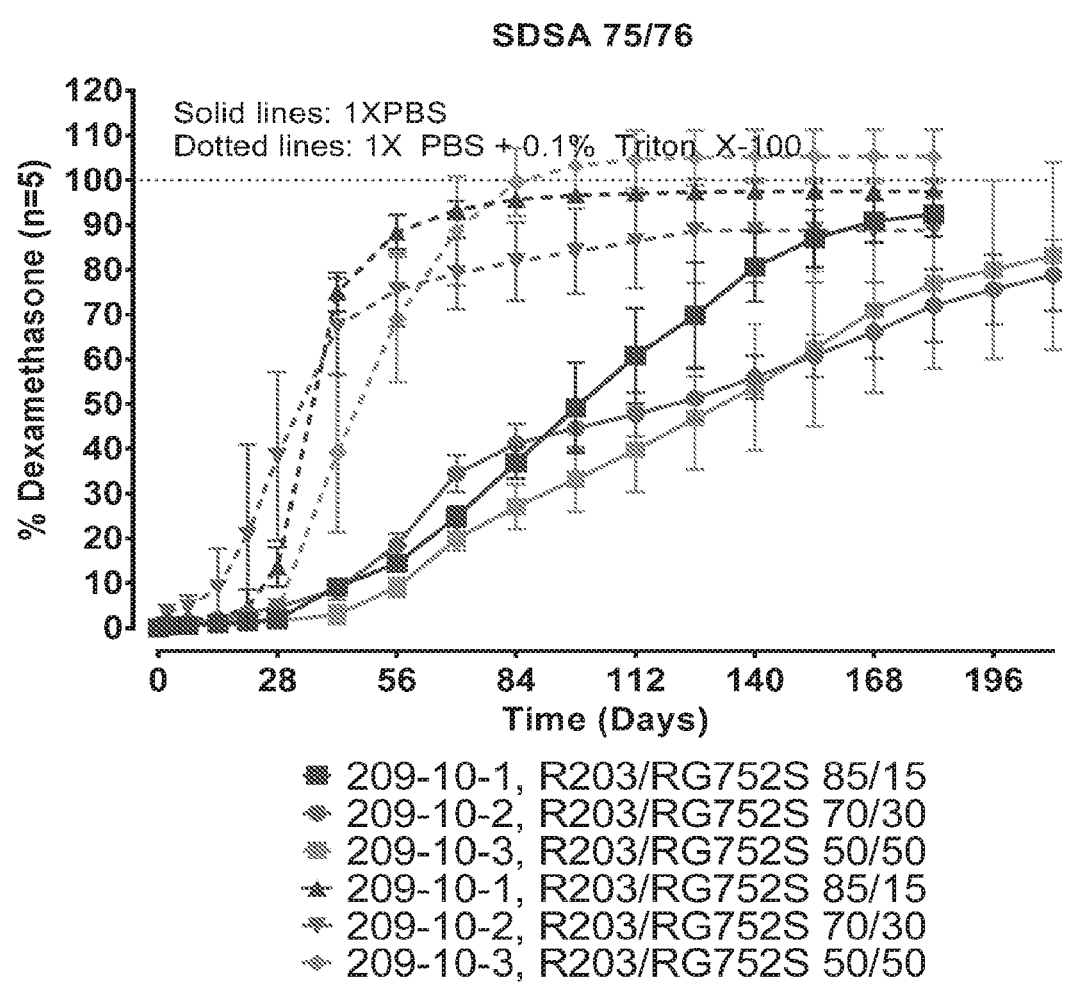
FIG. 7A shows in-vitro release of dexamethasone measured for implant formulations ENV-1D-0209-10-1 through ENV-1D-0209-10-3 in Table 1G; dexamethasone release was measured at 37° C. in 1×PBS (solid lines) or 1×PBS with 0.1% Triton X-100 (dotted lines).
Figure 7C:
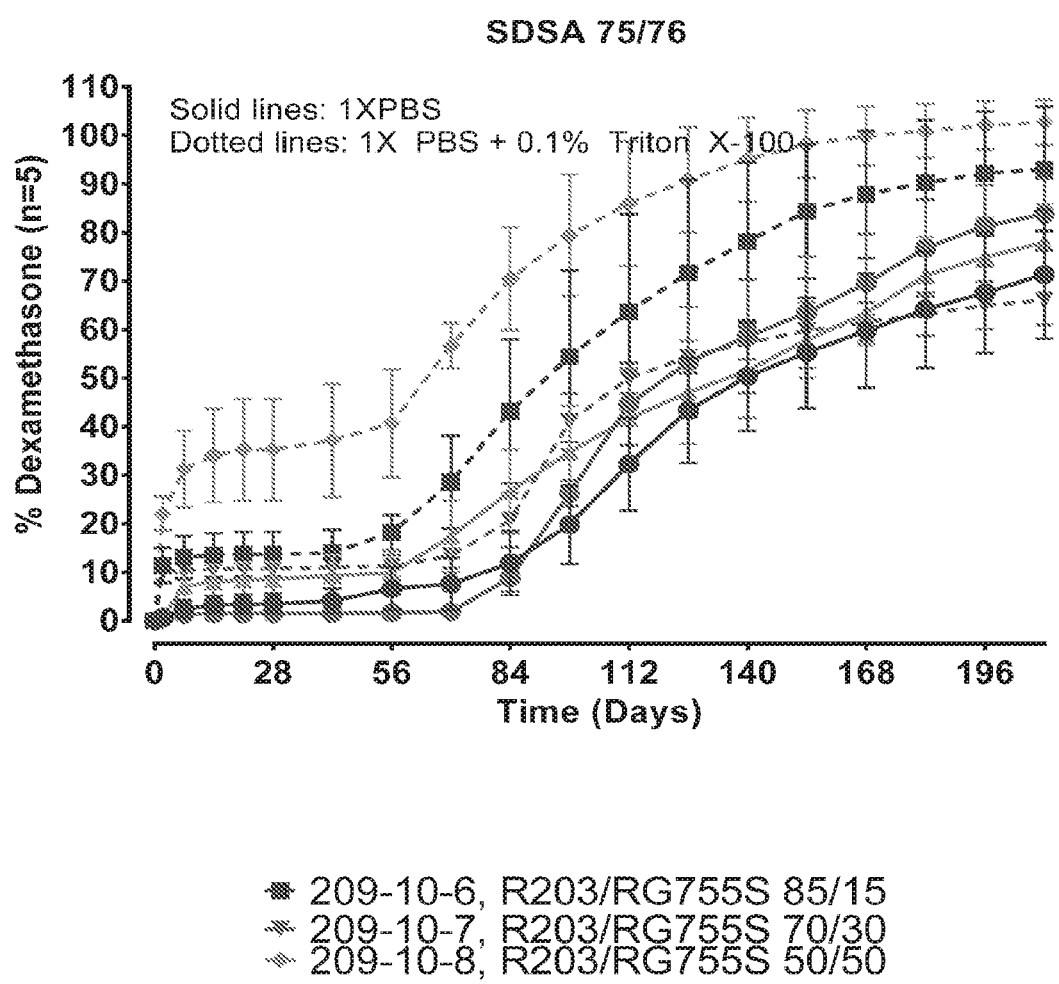
FIG. 7C shows in-vitro release of dexamethasone measured for implant formulations ENV-1D-0209-10-6 through ENV-1D-0209-10-8 in Table 1G; dexamethasone release was measured at 37° C. in 1×PBS (solid lines) or 1×PBS with 0.1% Triton X-100 (dotted lines).
Figure 7D:
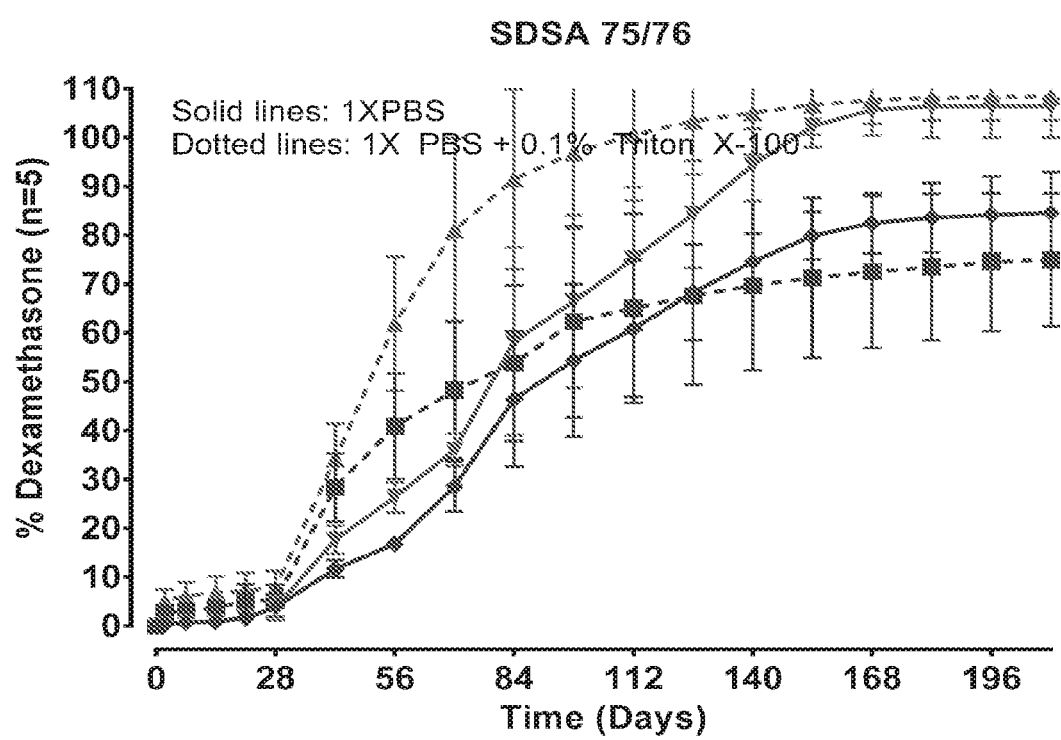
FIG. 7D shows in-vitro release of dexamethasone measured for implant formulations ENV-1D-0209-10-9 and ENV-1D-0209-10-10 in Table 1G; dexamethasone release was measured at 37° C. in 1×PBS (solid lines) or 1×PBS with 0.1% Triton X-100 (dotted lines).
Figure 7E:
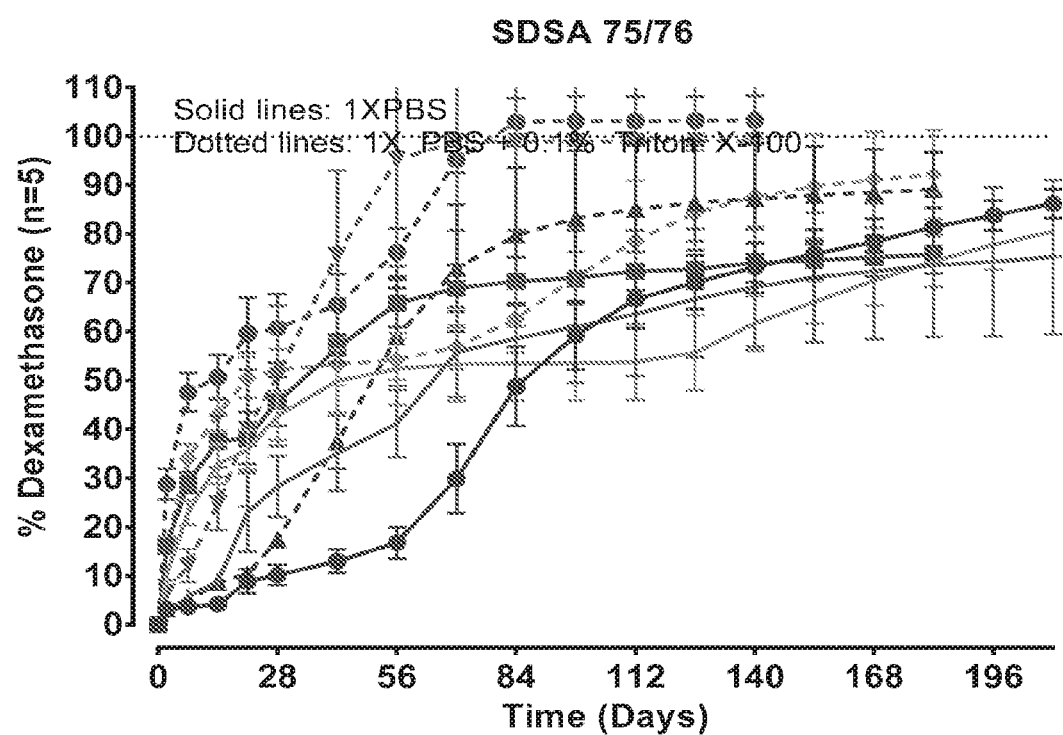
FIG. 7E shows in-vitro release of dexamethasone measured for implant formulations ENV-1D-0209-10-11 through ENV-1D-0209-10-14 in Table 1G; dexamethasone release was measured at 37° C. in 1×PBS (solid lines) or 1×PBS with 0.1% Triton X-100 (dotted lines).
Figure 7F:
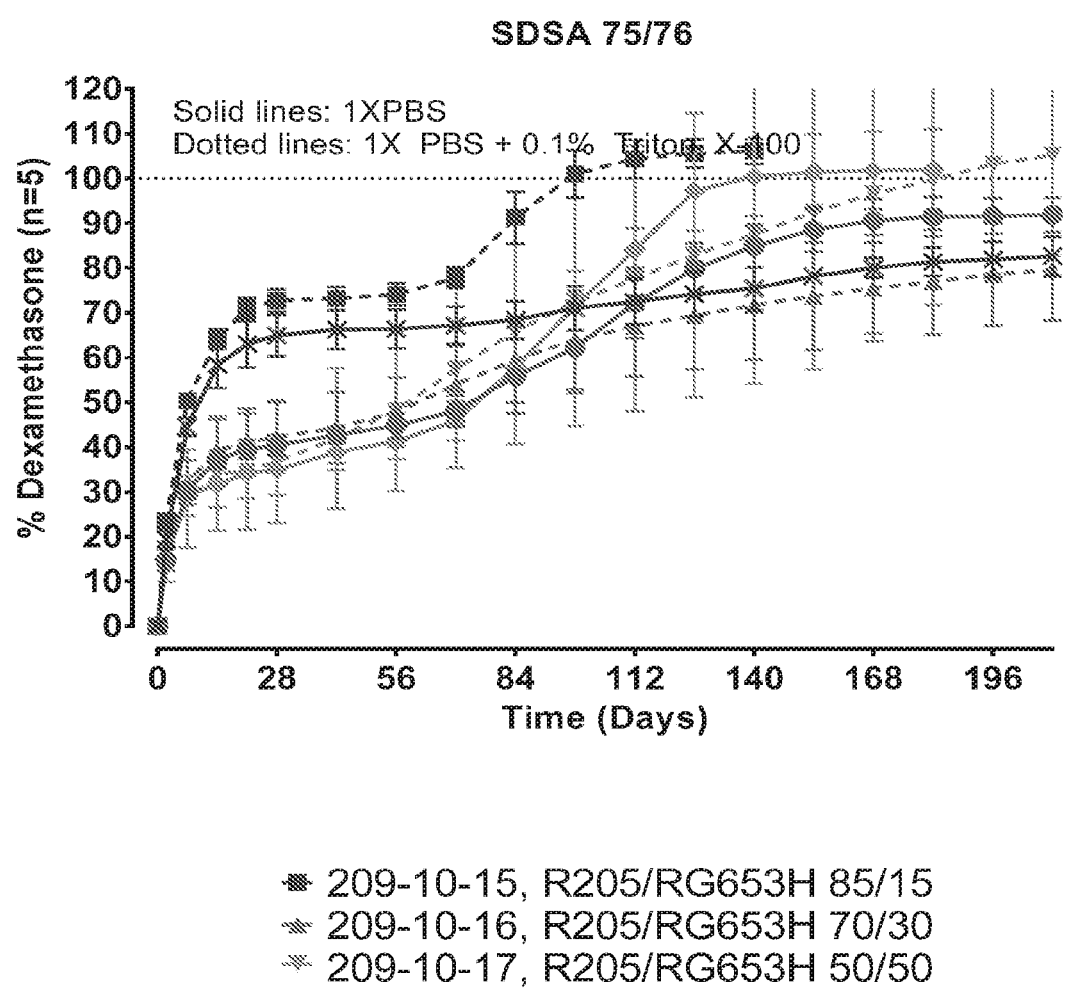
FIG. 7F shows in-vitro release of dexamethasone measured for implant formulations ENV-1D-0209-10-15 through ENV-1D-0209-10-17 in Table 1G; dexamethasone release was measured at 37° C. in 1×PBS (solid lines) or 1×PBS with 0.1% Triton X-100 (dotted lines).
Figure 7G:
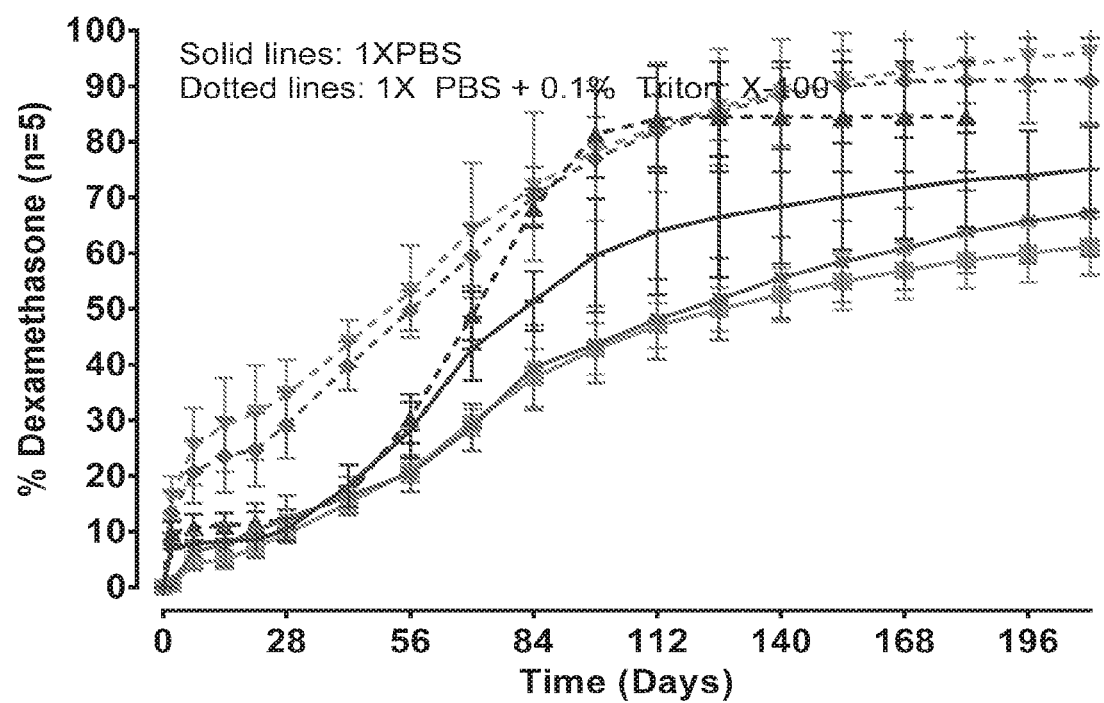
FIG. 7G shows in-vitro release of dexamethasone measured for implant formulations ENV-1D-0209-10-18 through ENV-1D-0209-10-20 in Table 1G; dexamethasone release was measured at 37° C. in 1×PBS (solid lines) or 1×PBS with 0.1% Triton X-100 (dotted lines).
Figure 7H:
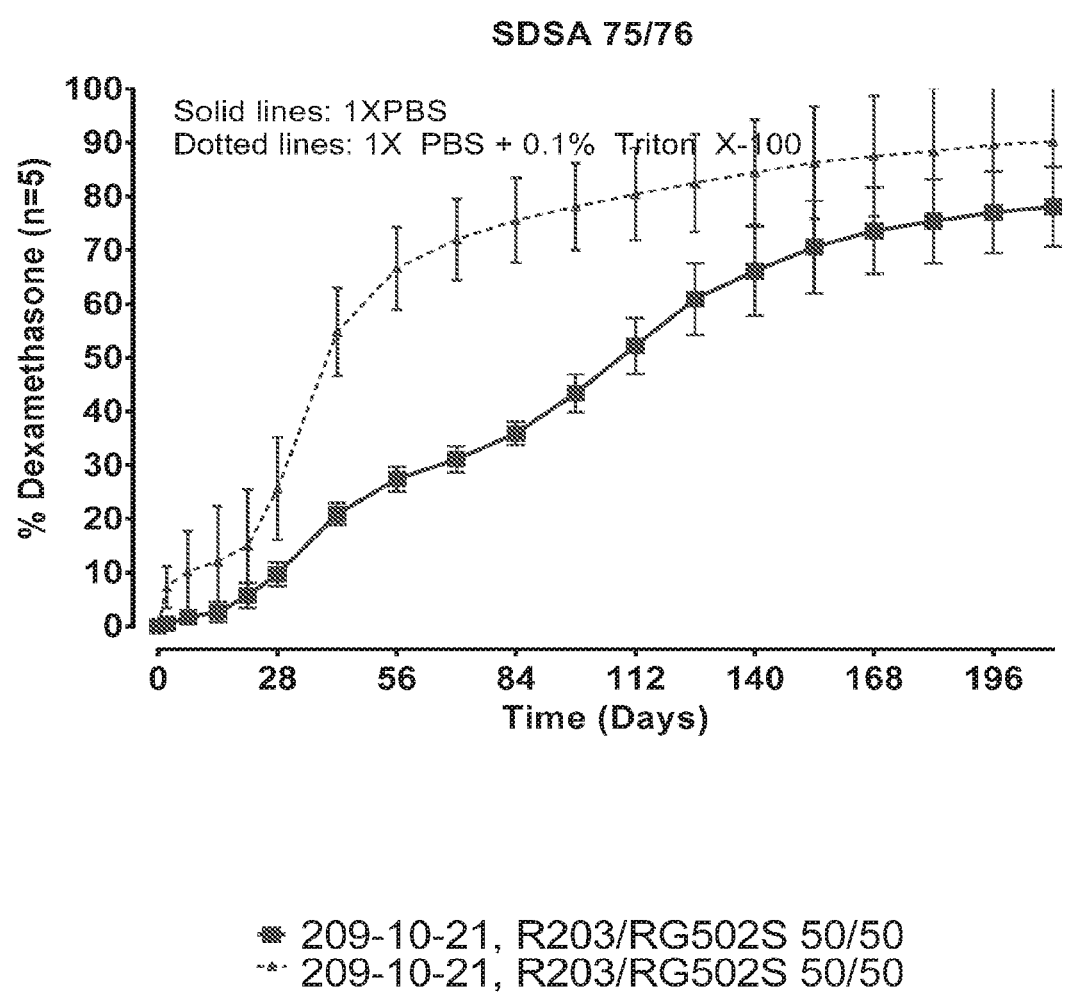
FIG. 7H shows in-vitro release of dexamethasone measured for implant formulations ENV-1D-0209-10-21 in Table 1G; dexamethasone release was measured at 37° C. in 1×PBS (solid lines) or 1×PBS with 0.1% Triton X-100 (dotted lines).
Figure 8:
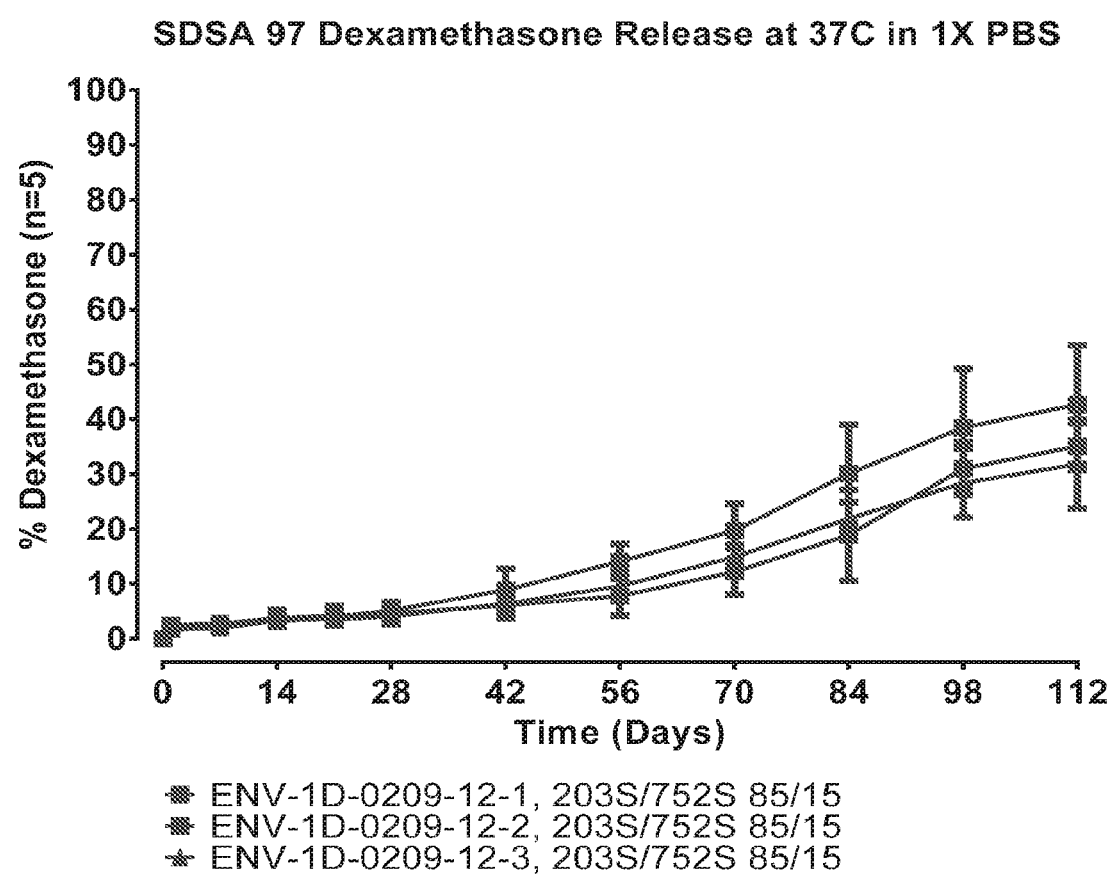
FIG. 8 illustrates in-vitro release studies for dexamethasone implant formulations in Table 1H. Dexamethasone release was measured at 37° C. in 1×PBS with 0.1% Triton X-100.
Figure 9:
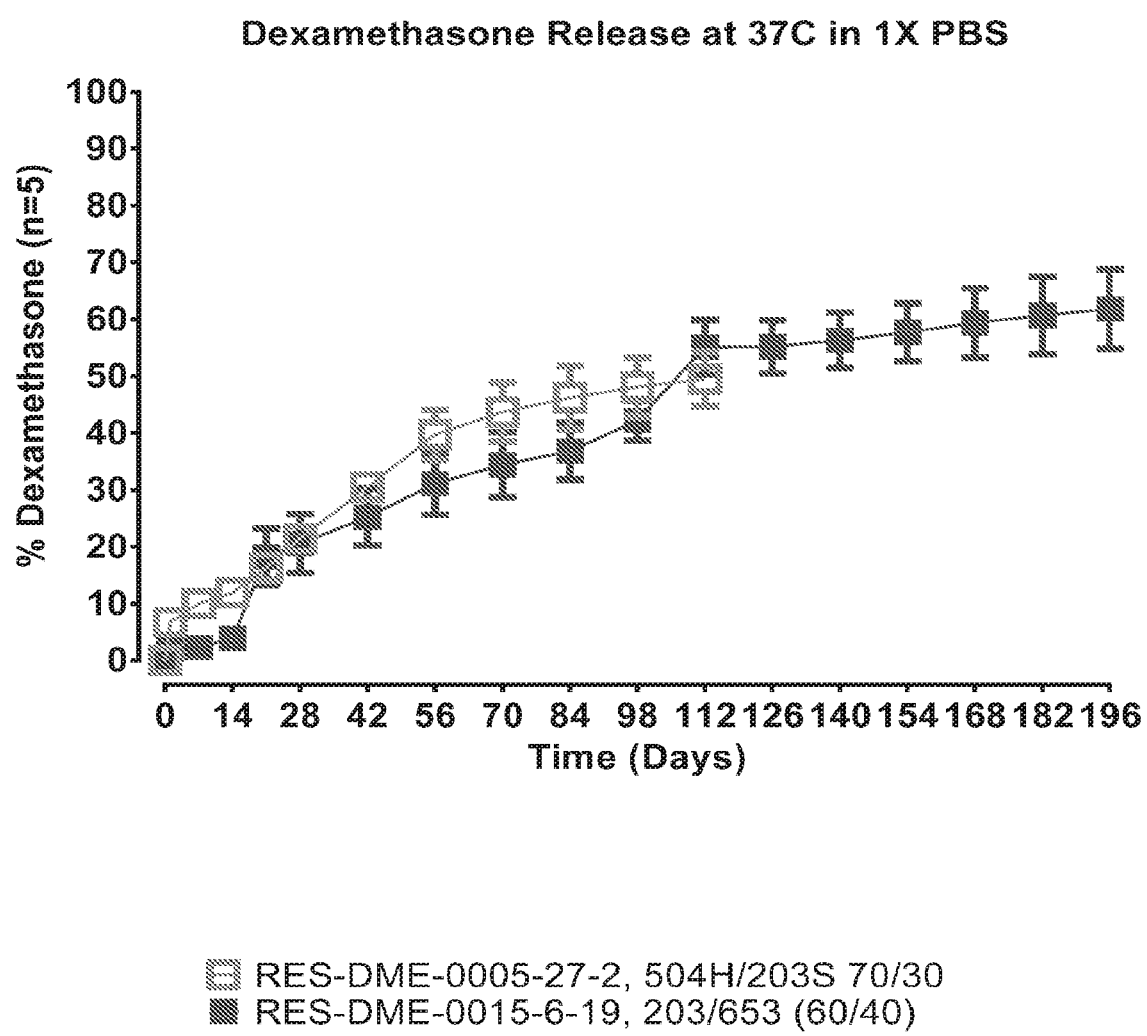
FIG. 9 illustrates in-vitro release studies for dexamethasone implant formulations in Table 11I. Dexamethasone was measured at 37° C. in 1×PBS with 0.1% Triton X-100.
Figure 10:
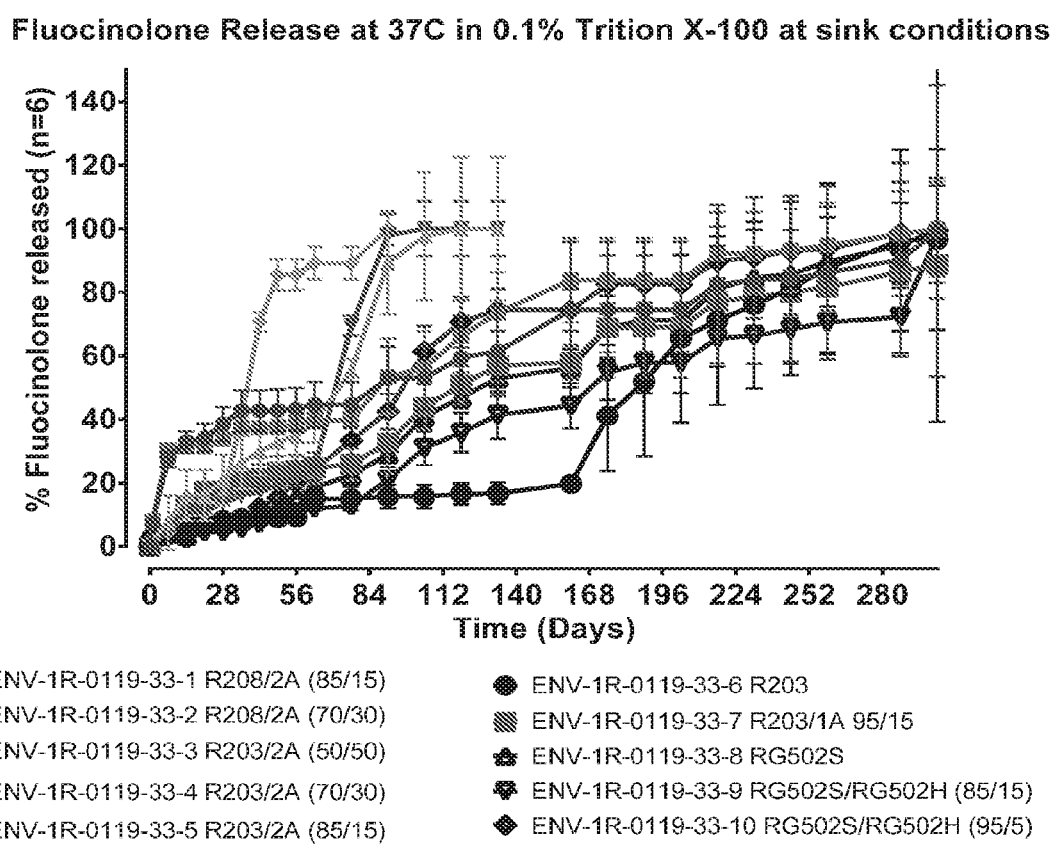
FIG. 10 illustrates in-vitro release studies for fluocinolone acetonide implant formulations in Table 3A. Fluocinolone acetonide release was measured at 37° C. in 1×PBS with 0.1% Triton X-100.
Figure 11:
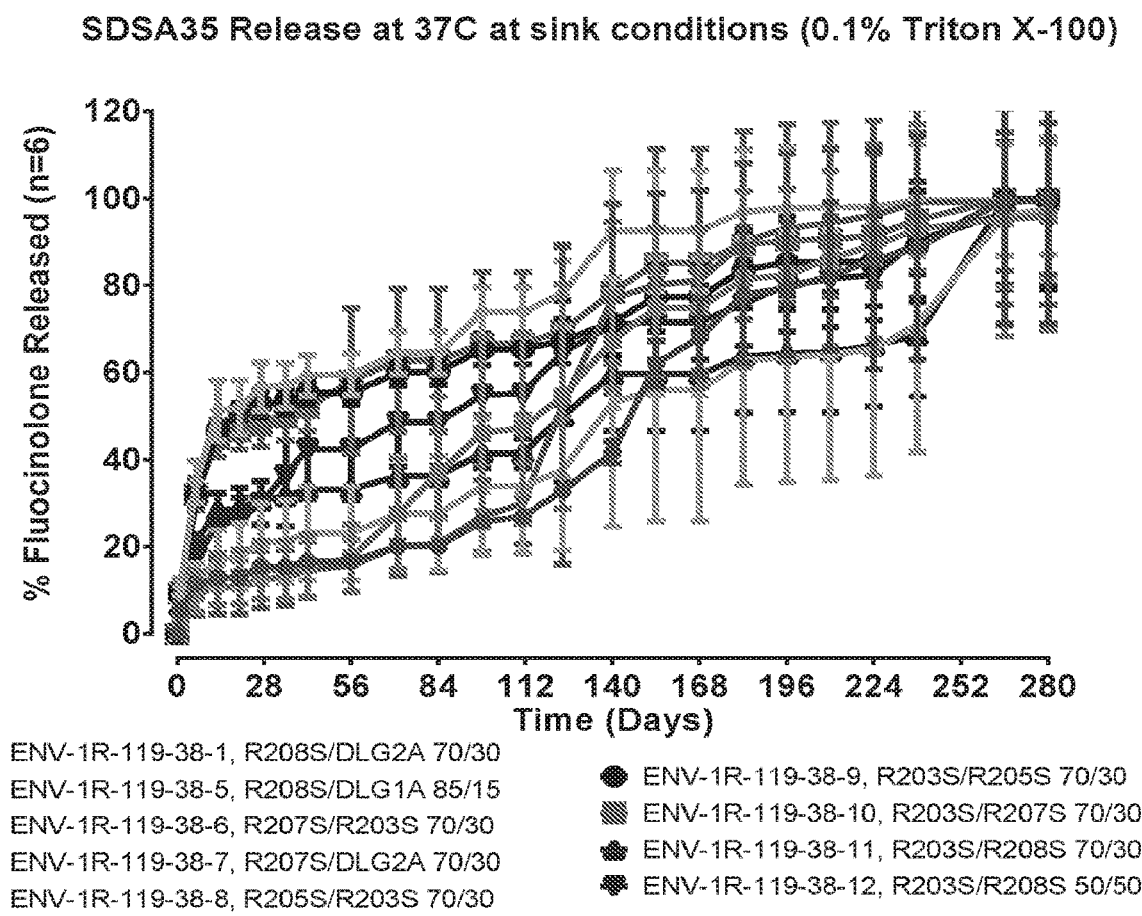
FIG. 11 illustrates in-vitro release studies for fluocinolone acetonide implant formulations in Table 3B. Fluocinolone acetonide release was measured at 37° C. in 1×PBS with 0.1% Triton X-100.
Figure 12:
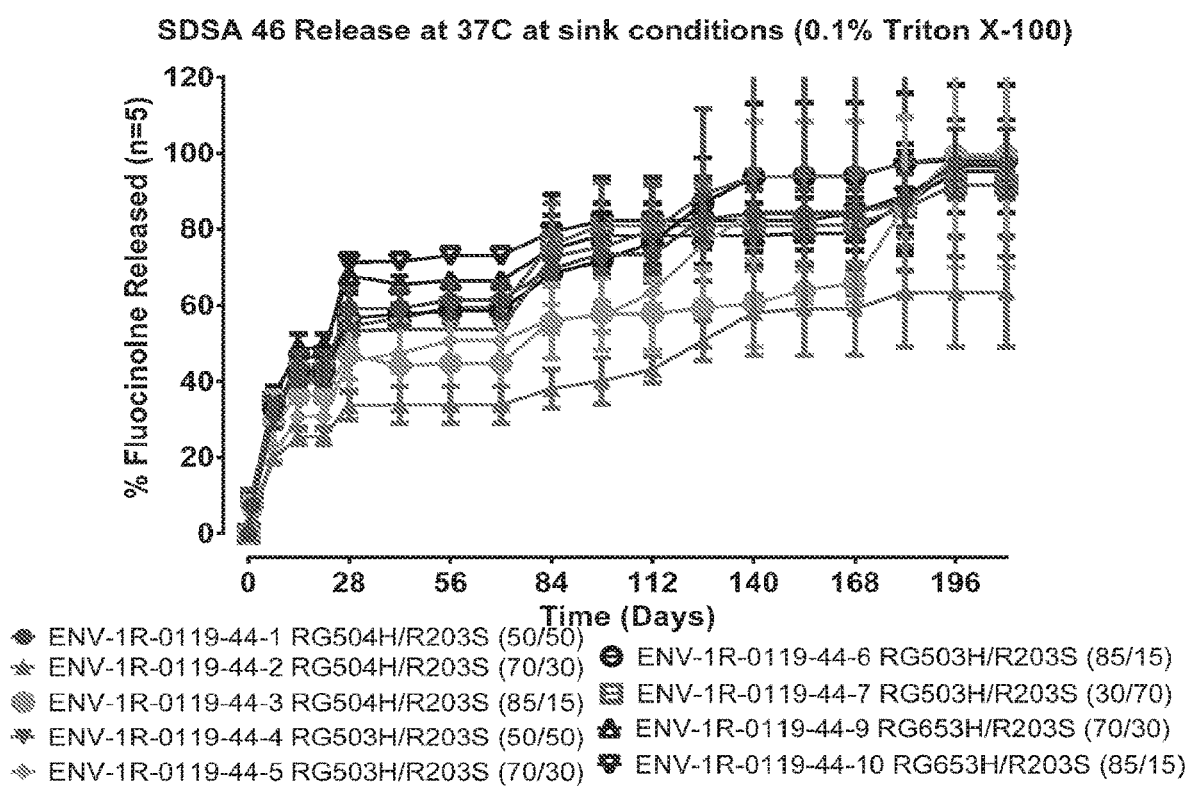
FIG. 12 illustrates in-vitro release studies for fluocinolone acetonide implant formulations in Table 3C. Fluocinolone acetonide release was measured at 37° C. in 1×PBS with 0.1% Triton X-100.
Figure 13A:
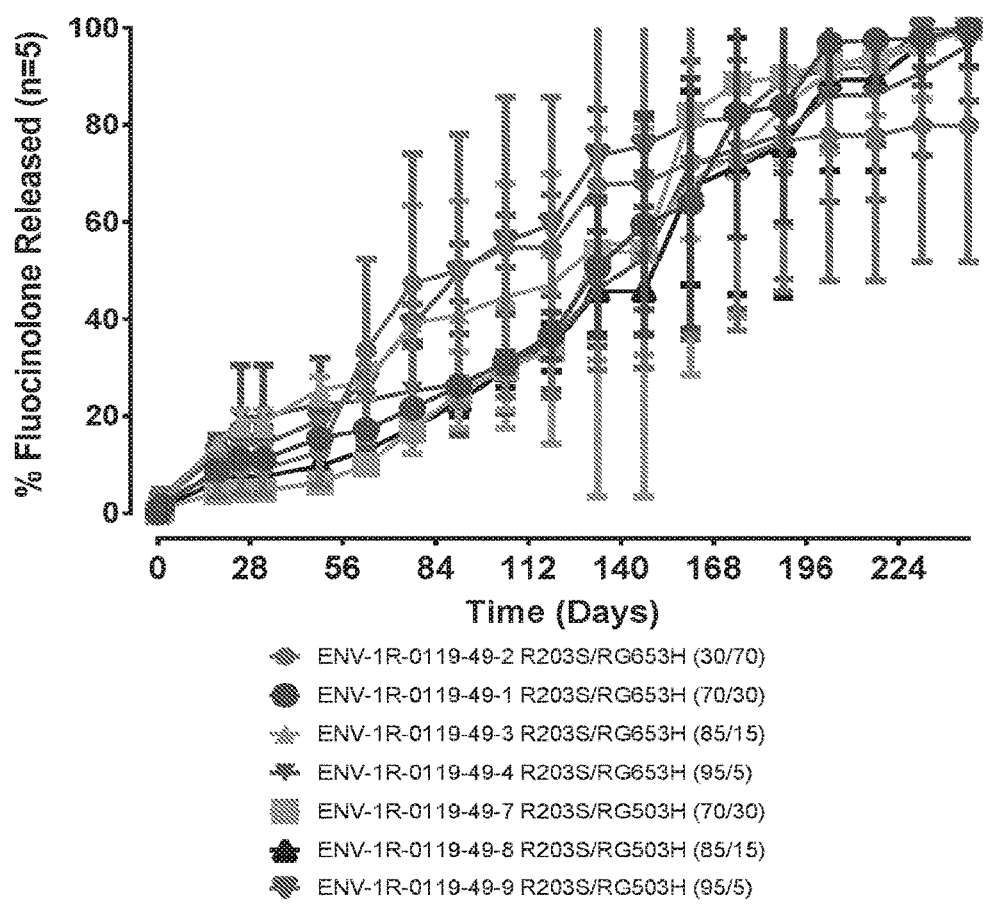
FIG. 13A shows in-vitro release of fluocinolone acetonide measured for implant formulations ENV-1R-0119-49-1 through ENV-1R-0119-49-4 and ENV-1R-0119-49-7 through ENV-1R-0119-49-9 in Table 3D; fluocinolone acetonide release was measured at 37° C. in 1×PBS with 0.1% Triton X-100.
Figure 13B:
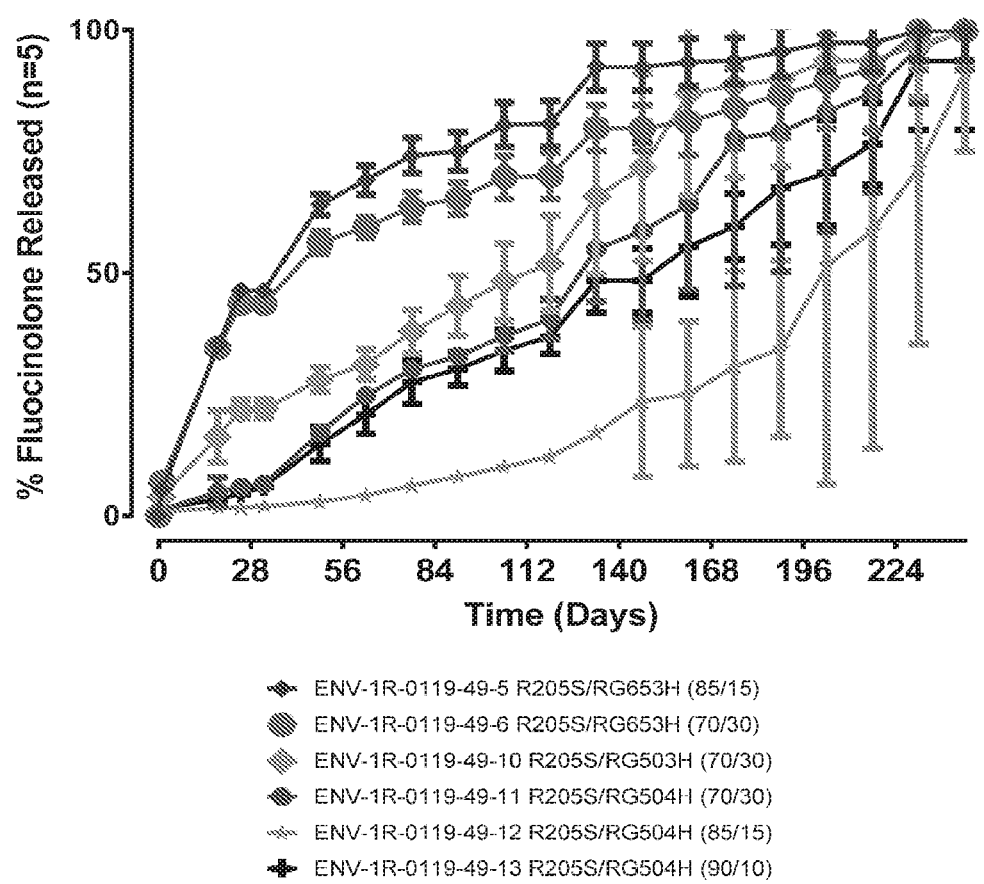
FIG. 13B shows in-vitro release of fluocinolone acetonide measured for implant formulations ENV-1R-0119-49-5, ENV-1R-0119-49-6, and ENV-1R-0119-49-10 through ENV-1R-0119-49-13 in Table 3D; fluocinolone acetonide release was measured at 37° C. in 1×PBS with 0.1% Triton X-100.
Figure 14A:
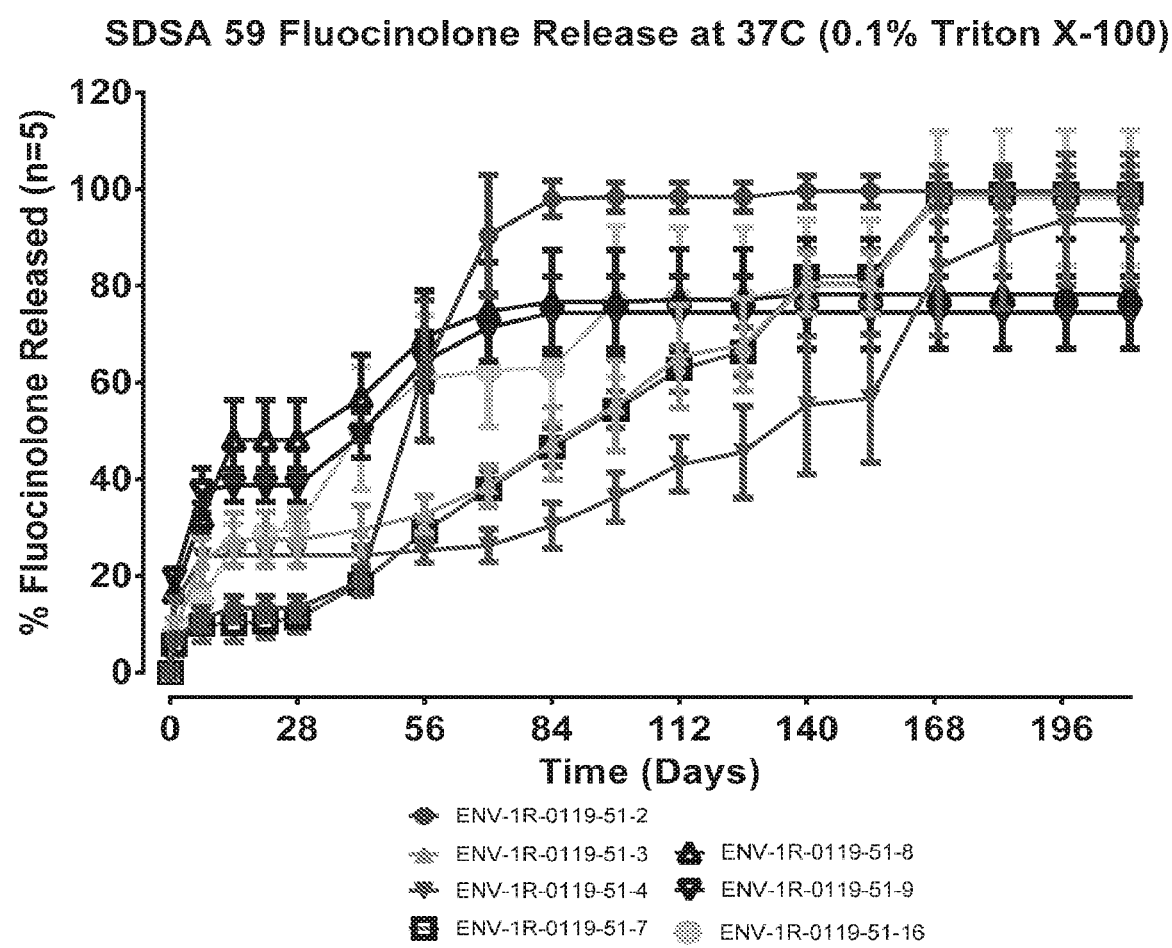
FIG. 14A shows in-vitro release of fluocinolone acetonide measured for implant formulations ENV-1R-0119-51-2 through ENV-1R-0119-51-4, ENV-1R-0119-51-7 through and ENV-1R-0119-51-9, and ENV-1R-0119-51-16 in Table 3E; fluocinolone acetonide release was measured at 37° C. in 1×PBS with 0.1% Triton X-100.
Figure 14B:
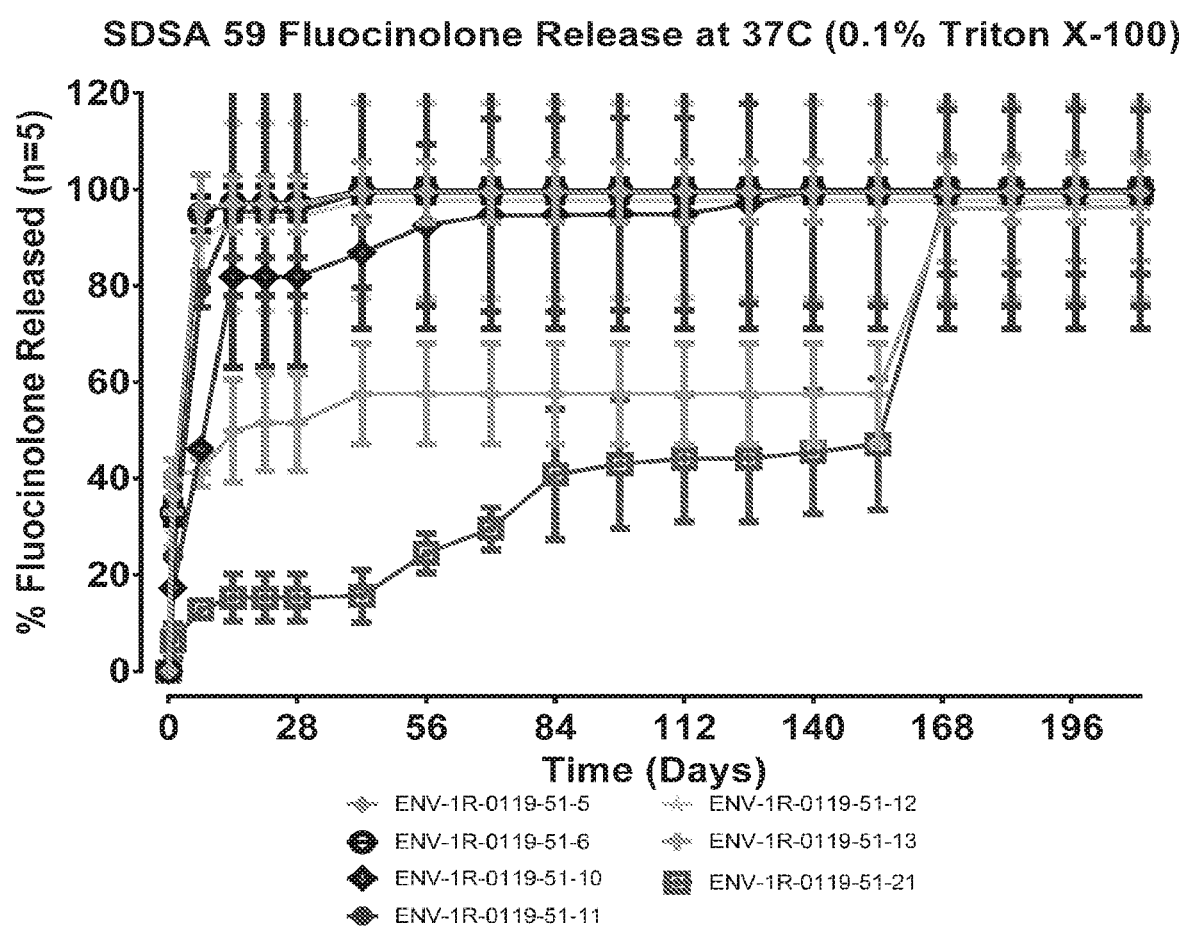
FIG. 14B shows in-vitro release of fluocinolone acetonide measured for implant formulations ENV-1R-0119-51-5, ENV-1R-0119-51-6, ENV-1R-0119-51-10 through ENV-1R-0119-51-13, and ENV-1R-0119-51-21 in Table 3E; fluocinolone acetonide release was measured at 37° C. in 1×PBS with 0.1% Triton X-100.
Figure 14C:
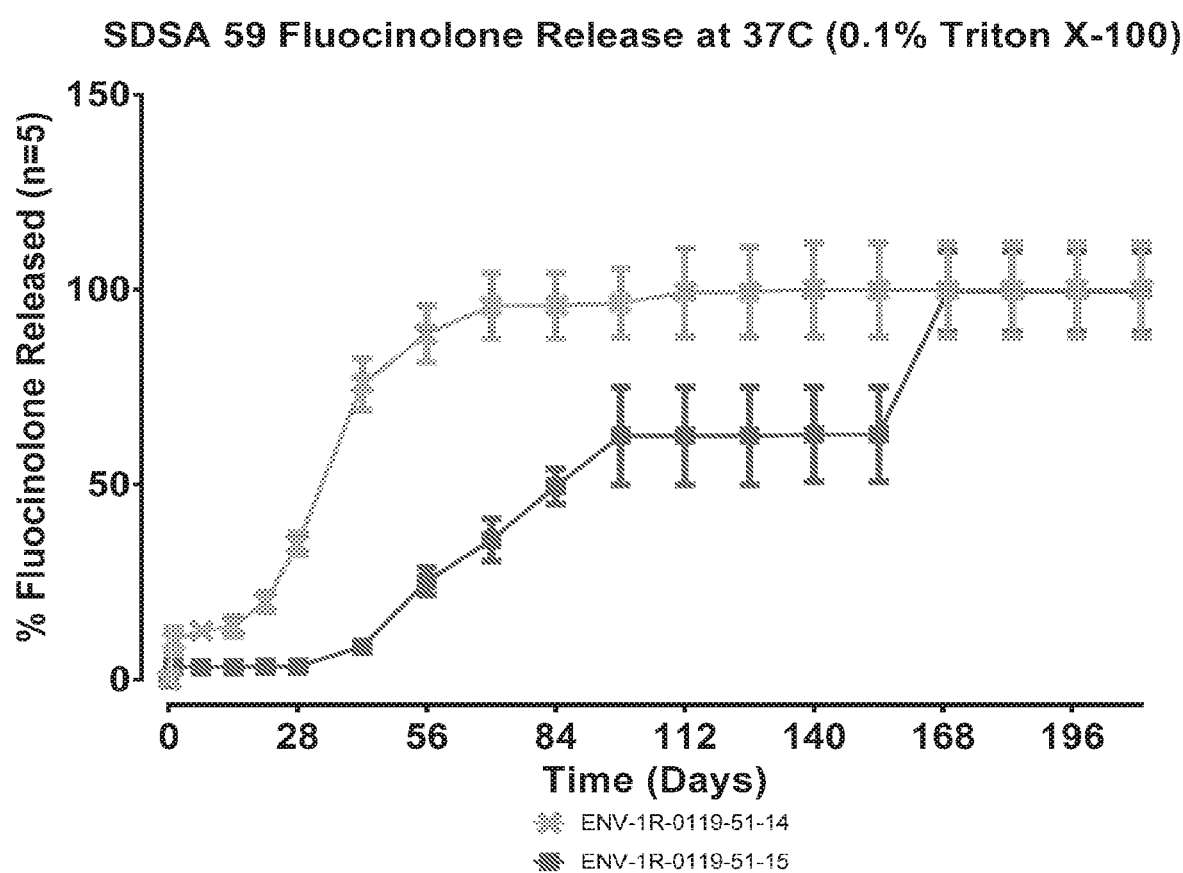
FIG. 14C shows in-vitro release of fluocinolone acetonide measured for implant formulations ENV-1R-0119-51-14 and ENV-1R-0119-51-15 in Table 3E; fluocinolone acetonide release was measured at 37° C. in 1×PBS with 0.1% Triton X-100.
Figure 15:
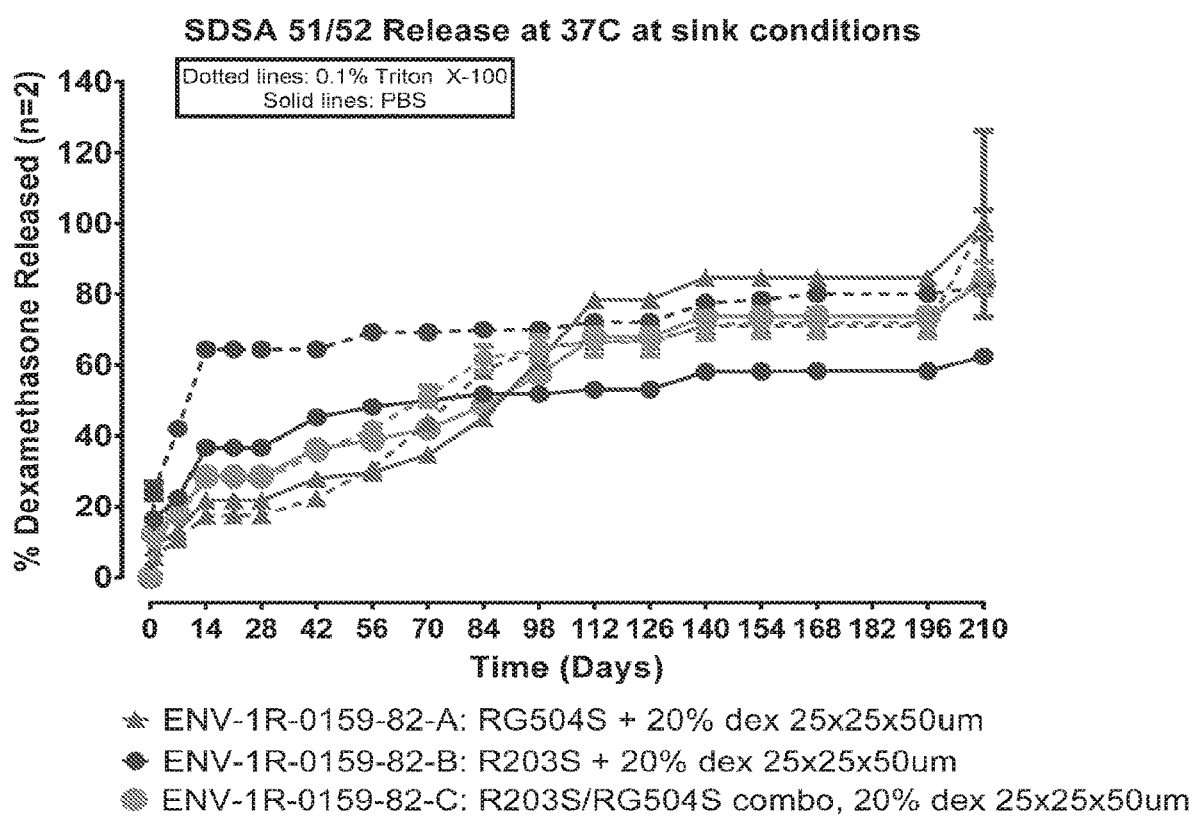
FIG. 15 illustrates in-vitro release studies for dexamethasone particle suspension formulations in Table 5A. Dexamethasone release was measured at 37° C. in 1×PBS (solid lines) and 1×PBS with 0.1% Triton X-100 (dotted lines).
Figure 16:
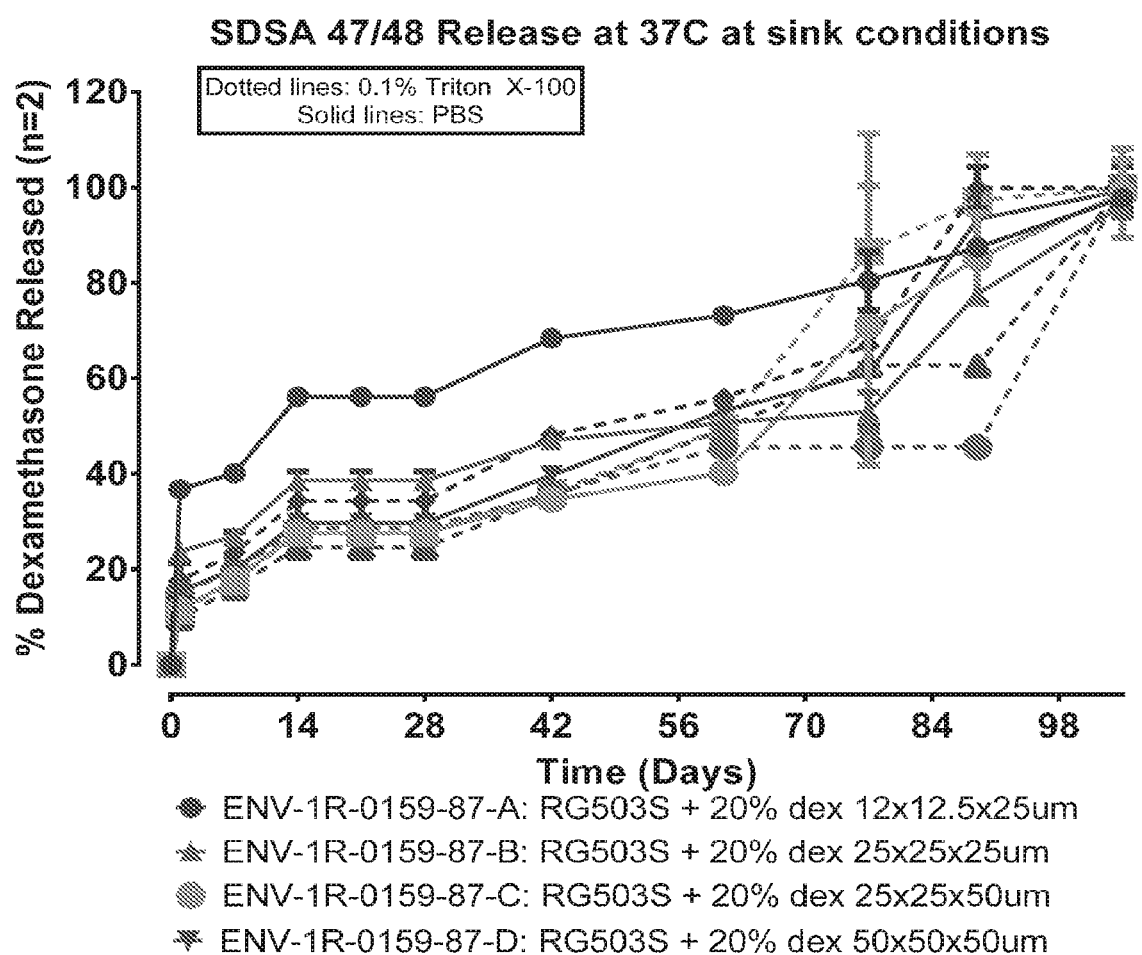
FIG. 16 illustrates in-vitro release studies for dexamethasone particle suspension formulations in Table 5B. Dexamethasone release was measured at 37° C. in 1×PBS (solid lines) and 1×PBS with 0.1% Triton X-100 (dotted lines).
Figure 17:
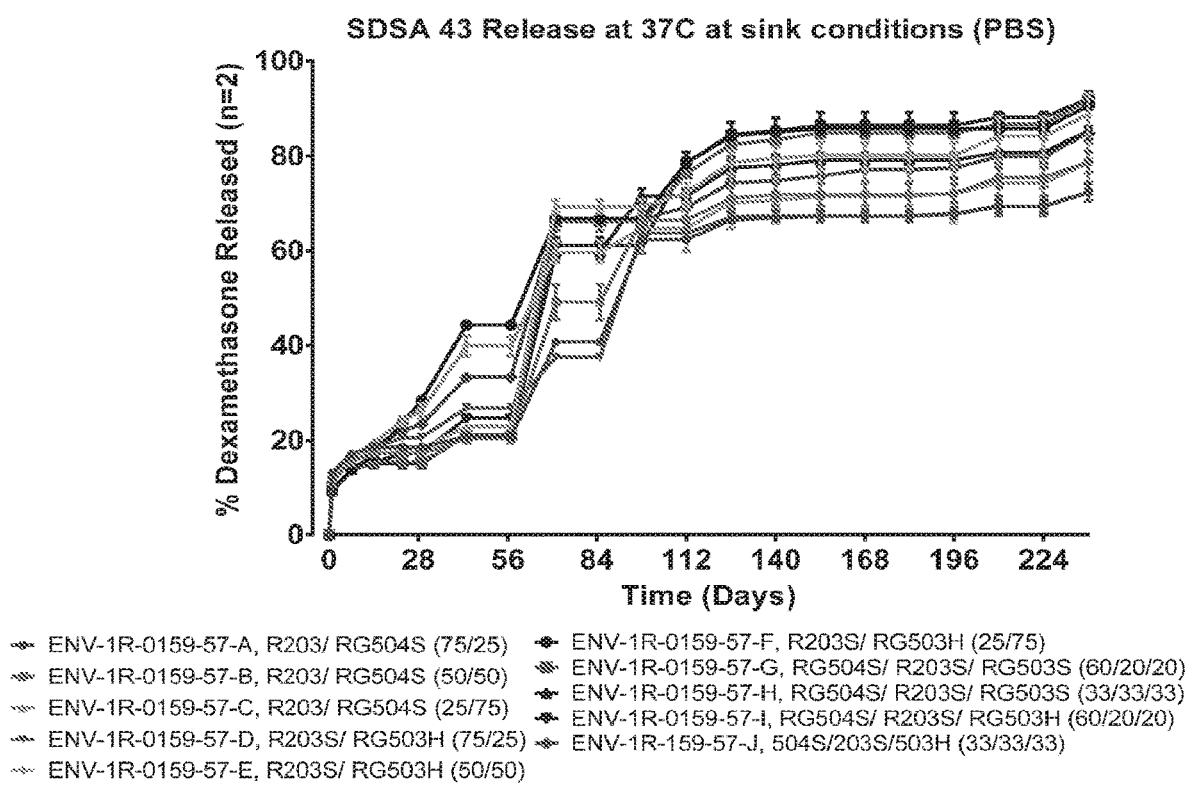
FIG. 17 illustrates in-vitro release studies for dexamethasone particle suspension formulations in Table 5C. Dexamethasone release was measured at 37° C. in 1×PBS.
Figure 18:
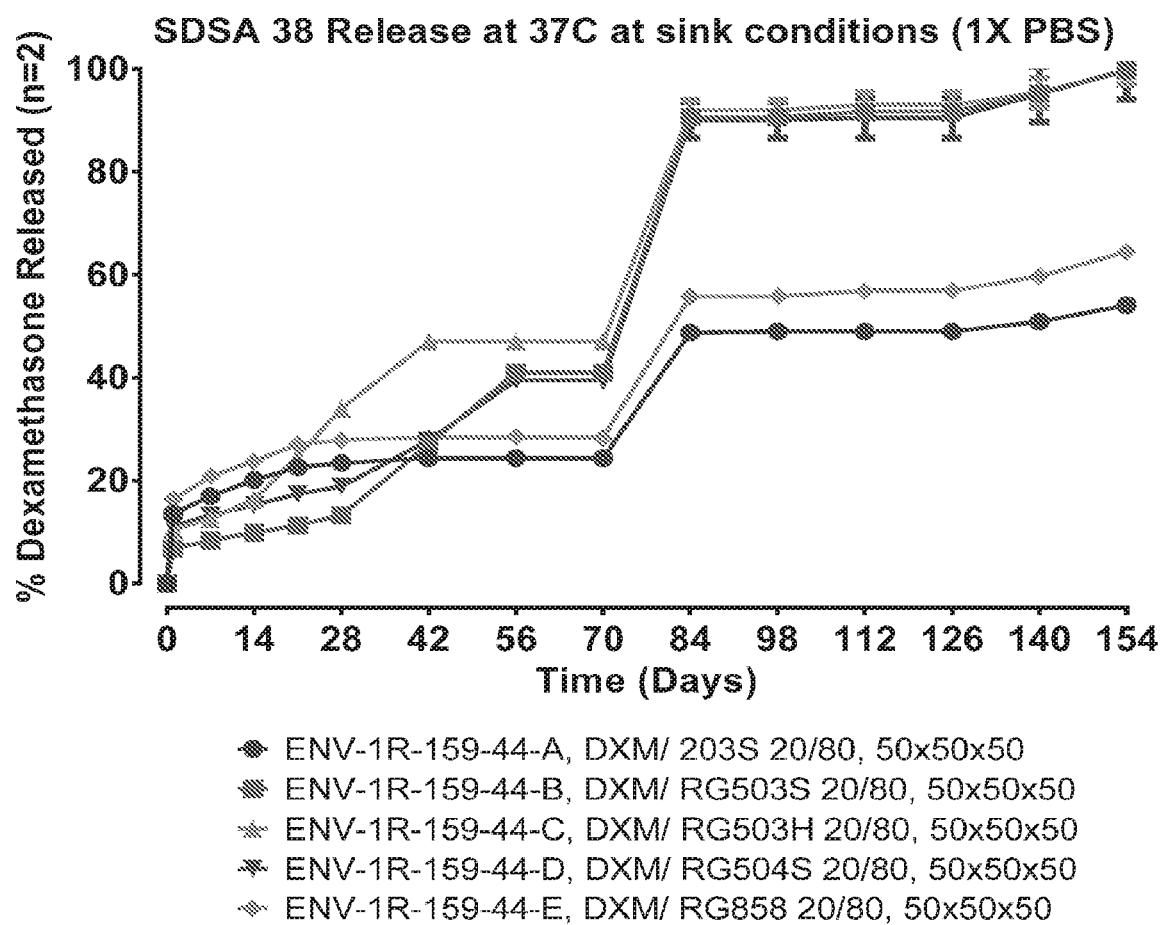
FIG. 18 illustrates in-vitro release studies for dexamethasone particle suspension formulations in Table 5D. Dexamethasone release was measured at 37° C. in 1×PBS.
Figure 19:
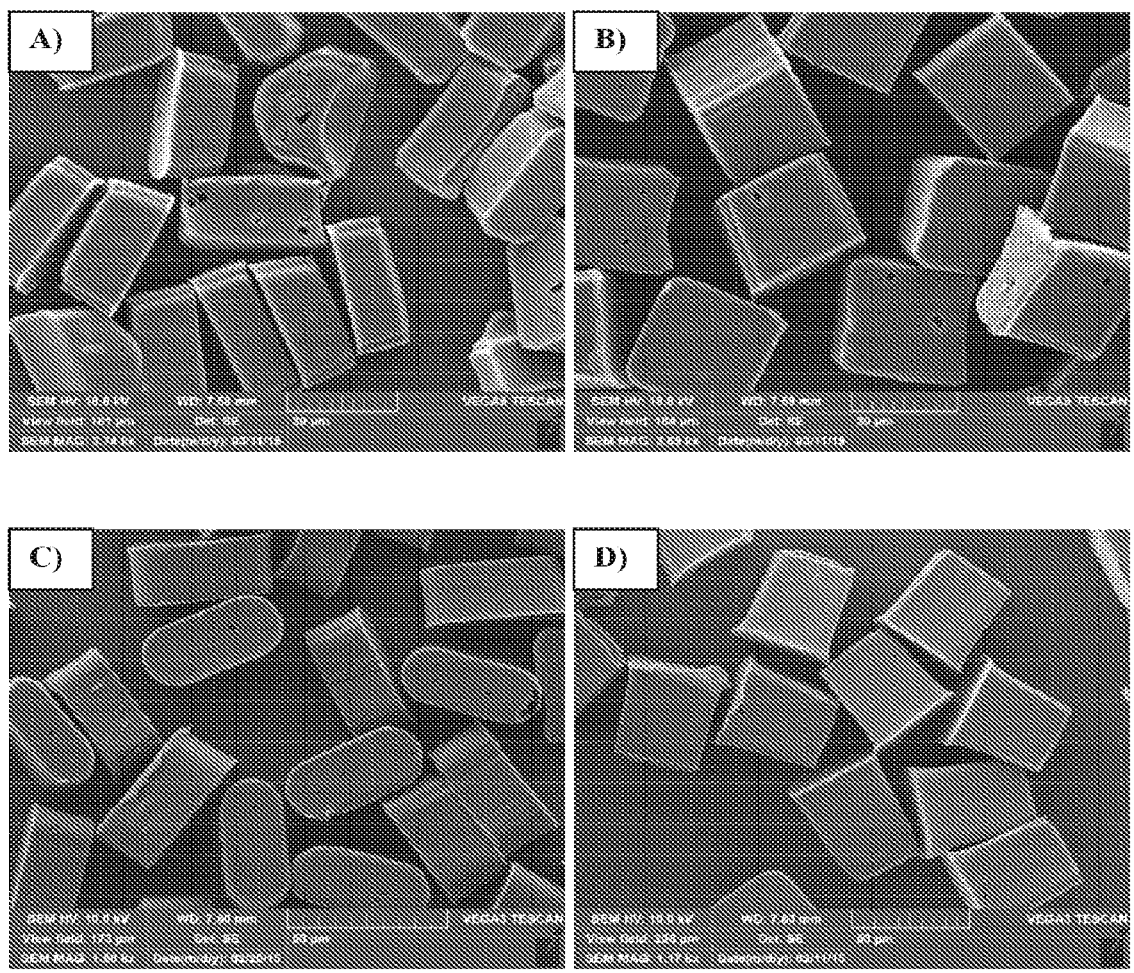
FIG. 19 shows illustrative scanning electron micrographs of dexamethasone particle suspensions having dimensions of: A) 12.5×12.5×25 μm; B) 25×25×25 μm; C) 25×25×50 μm; and D) 50×50×50 μm.
Figure 20:
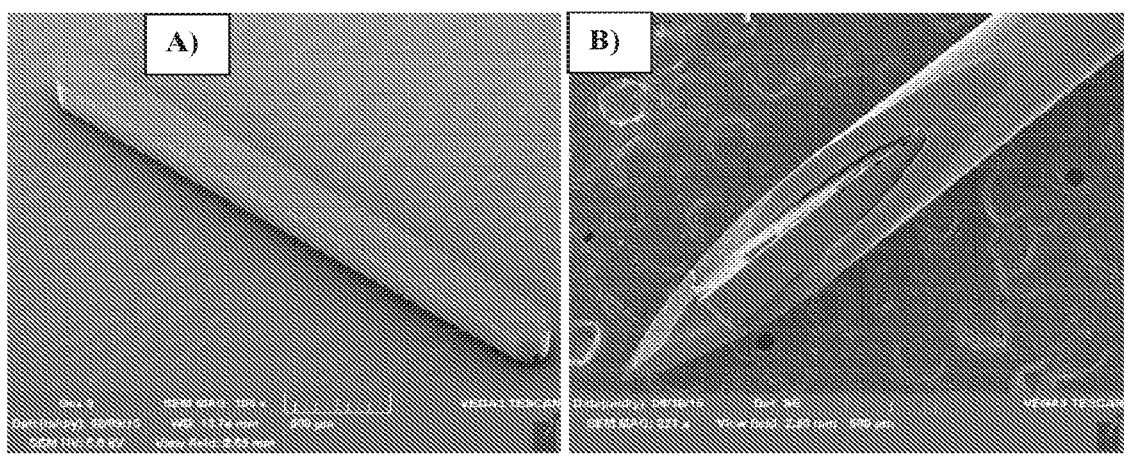
FIG. 20 shows illustrative scanning electron micrographs of dexamethasone implant: A) having dimensions of 225 μm×225 μm×4000 μm; and B) loaded in a 25G needle.
Figure 21:
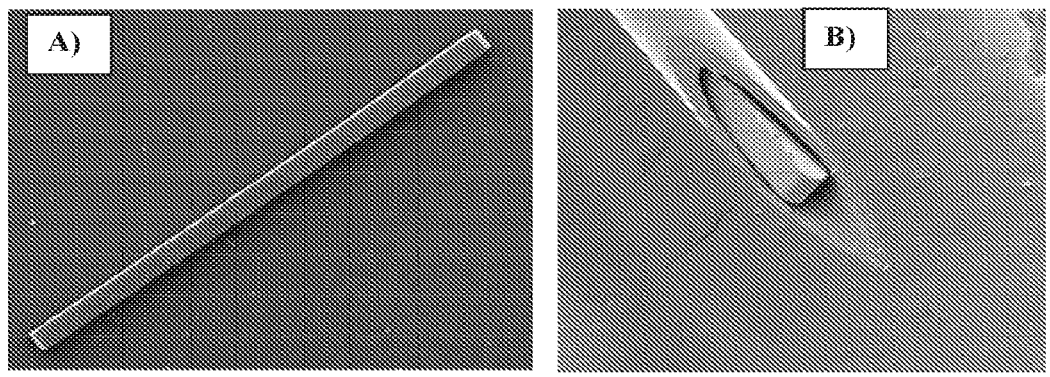
FIG. 21 shows illustrative scanning electron micrographs of dexamethasone implant: A) having dimensions of 200 μm×200 μm×4500 μm; and B) loaded in a 27G ultra-thin-walled (UTW) needle.
Figure 22:
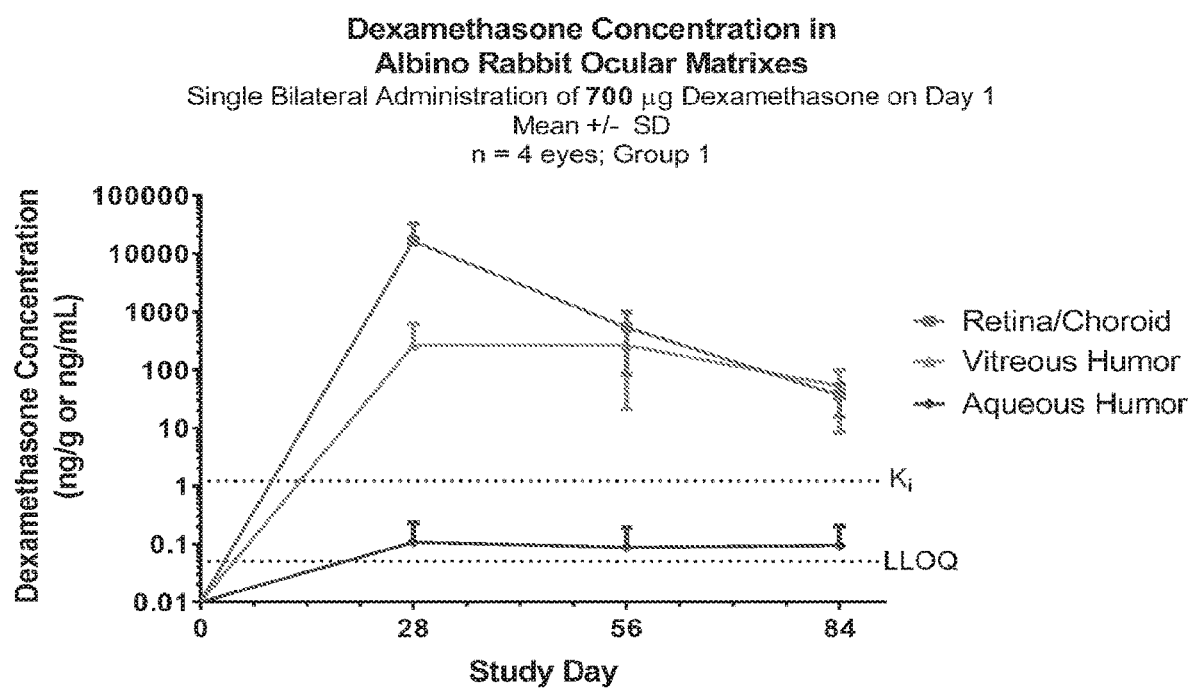
FIG. 22 illustrates ocular pharmacokinetics from nonclinical study ENVRES-PRE-002: Group 1, single bilateral administration of 700 μg dexamethasone in an intravitreal particle suspension.
Figure 23:
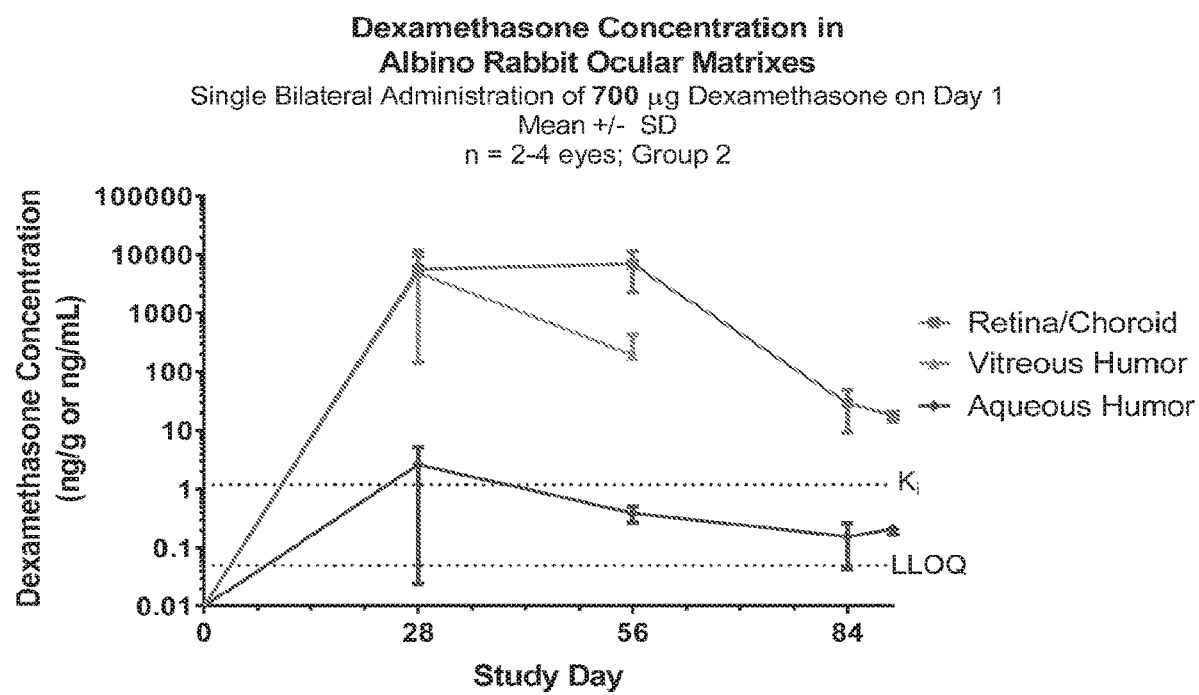
FIG. 23 illustrates ocular pharmacokinetics from nonclinical study ENVRES-PRE-002: Group 2, single bilateral administration of 700 ug dexamethasone in an intravitreal particle suspension
Figure 24:
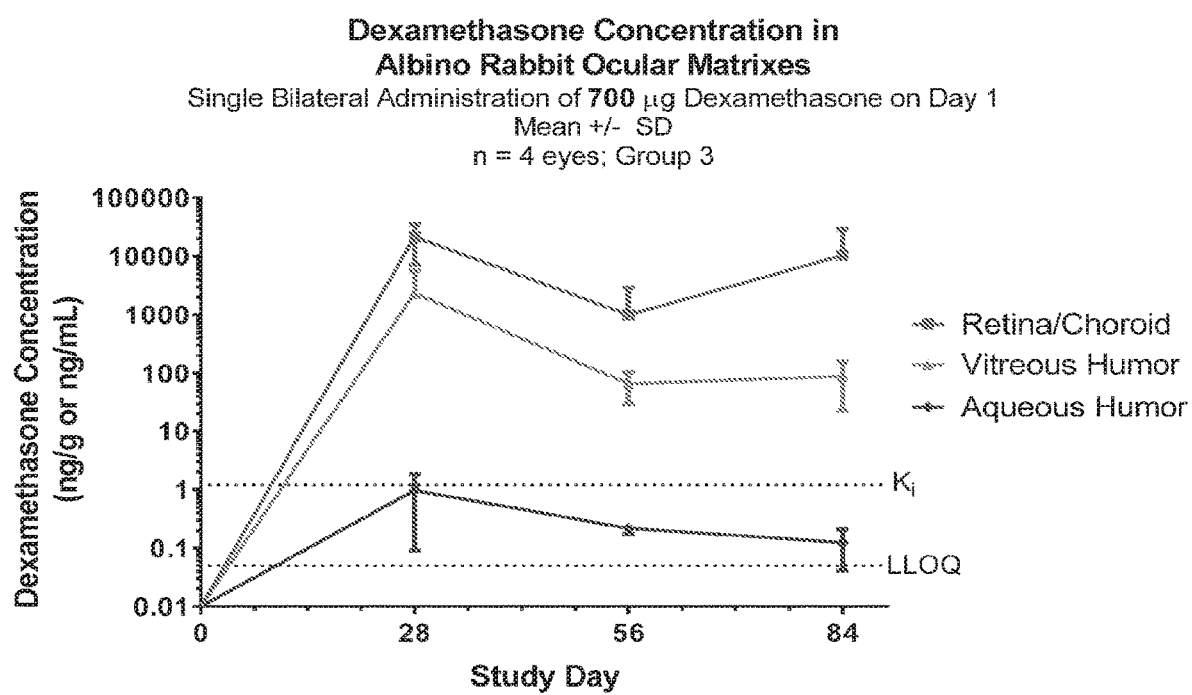
FIG. 24 illustrates ocular pharmacokinetics from nonclinical study ENVRES-PRE-002: Group 3, single bilateral administration of 700 ug dexamethasone in an intravitreal particle suspension
Figure 25:
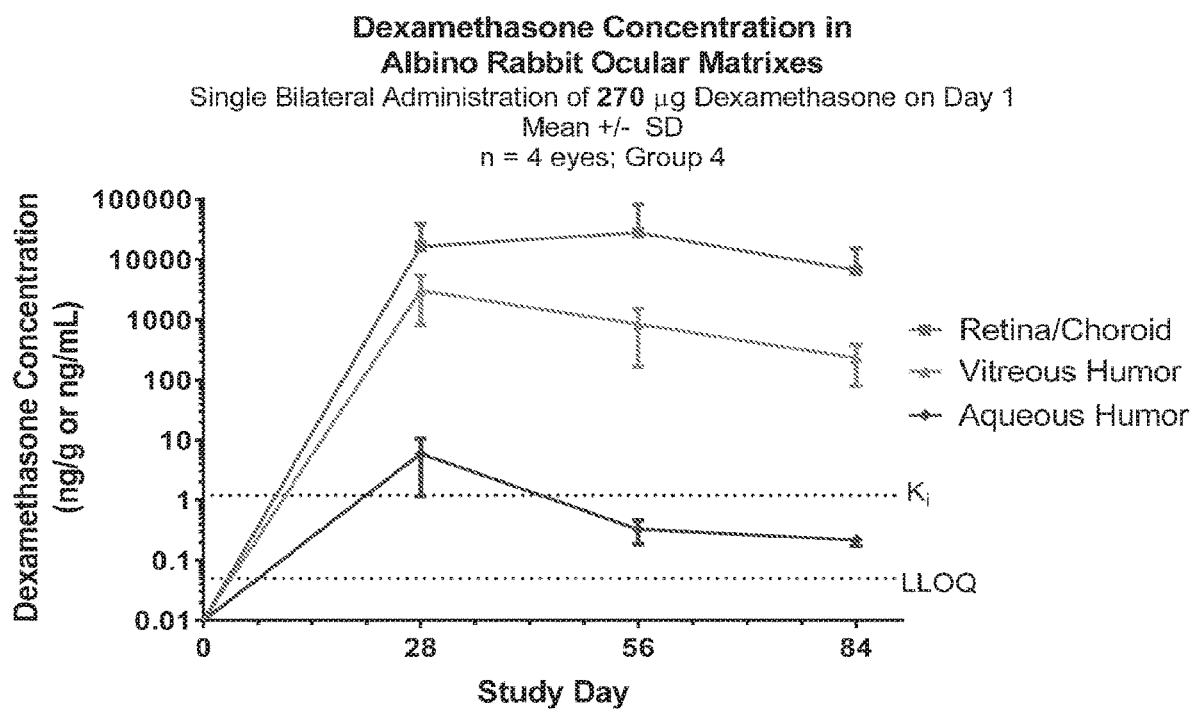
FIG. 25 illustrates ocular pharmacokinetics from nonclinical study ENVRES-PRE-002: Group 4, single bilateral administration of 270 ug dexamethasone in an intravitreal implant formulation.
Figure 26:
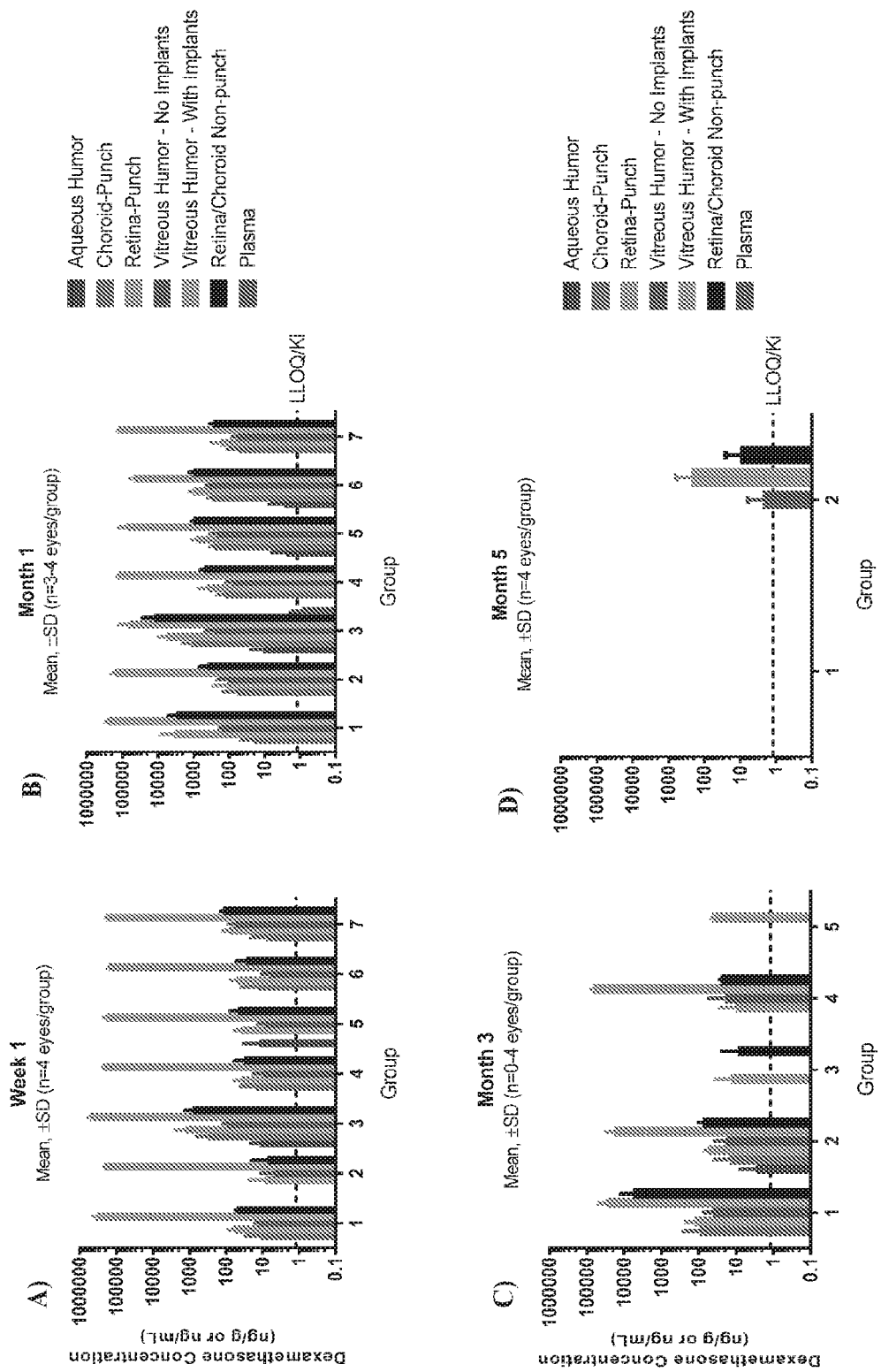
FIG. 26 illustrates ocular and systemic pharmacokinetics from nonclinical study ENV1105-PRE-003: all groups and all matrices following a single bilateral administration of various formulations of ENV1105 intravitreal implants. Data was measured: A) one week after administration; B) one month after administration; C) three months after administration; and D) five months after administration.
Figure 27:
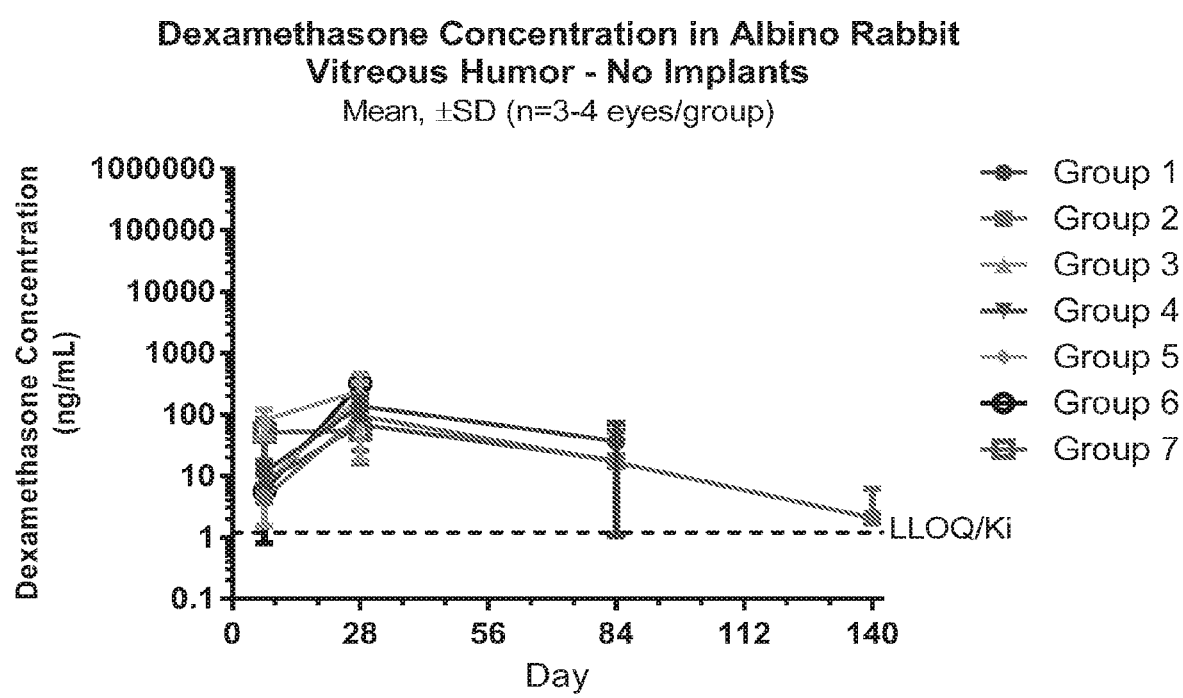
FIG. 27 illustrates ocular pharmacokinetics from nonclinical study ENV1105-PRE-003: vitreous humor concentration of dexamethasone following a single bilateral administration of various formulations of ENV1105 intravitreal implant.
Figure 28:
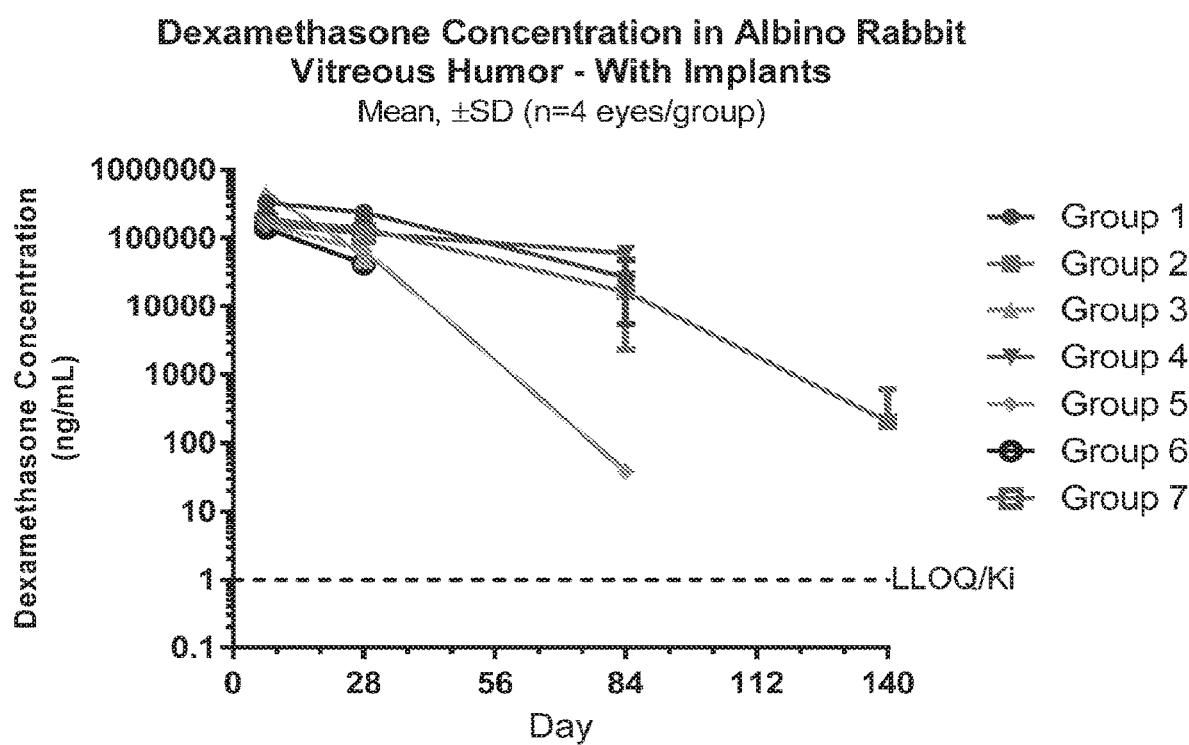
FIG. 28 illustrates ocular pharmacokinetics from nonclinical study ENV1105-PRE-003: vitreous humor with implants concentration of dexamethasone following a single bilateral administration of various formulations of ENV1105 intravitreal implant.
Figure 29:
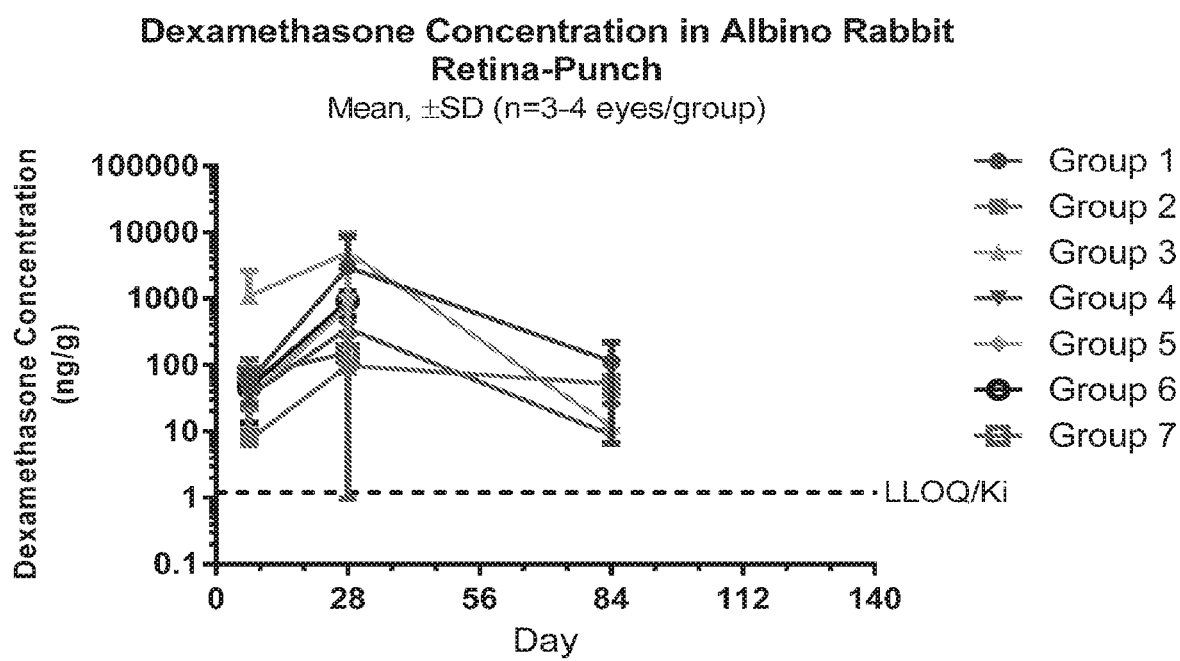
FIG. 29 illustrates ocular pharmacokinetics from nonclinical study ENV1105-PRE-003: retina ("macula" punch) concentration of dexamethasone following a single bilateral administration of various formulations of ENV1105 intravitreal implant.
Figure 30:
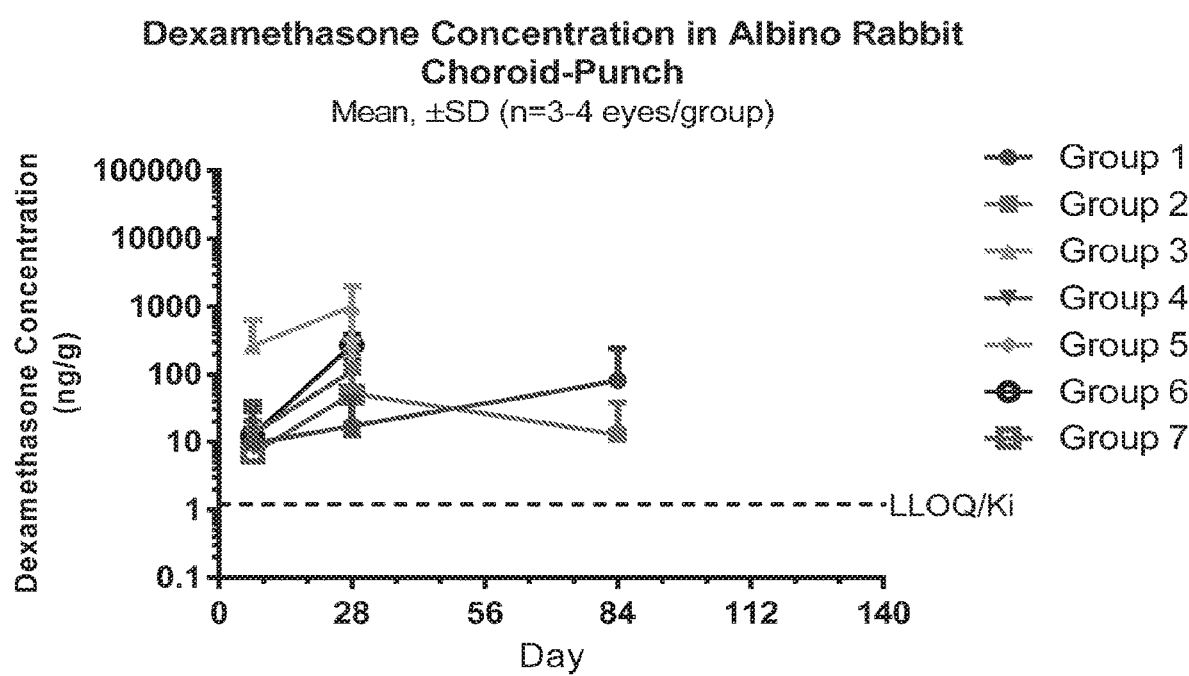
FIG. 30 illustrates ocular pharmacokinetics from nonclinical study ENV1105-PRE-003: choroid ("macula" punch) concentration of dexamethasone following a single bilateral administration of various formulations of ENV1105 intravitreal implant.
Figure 31:
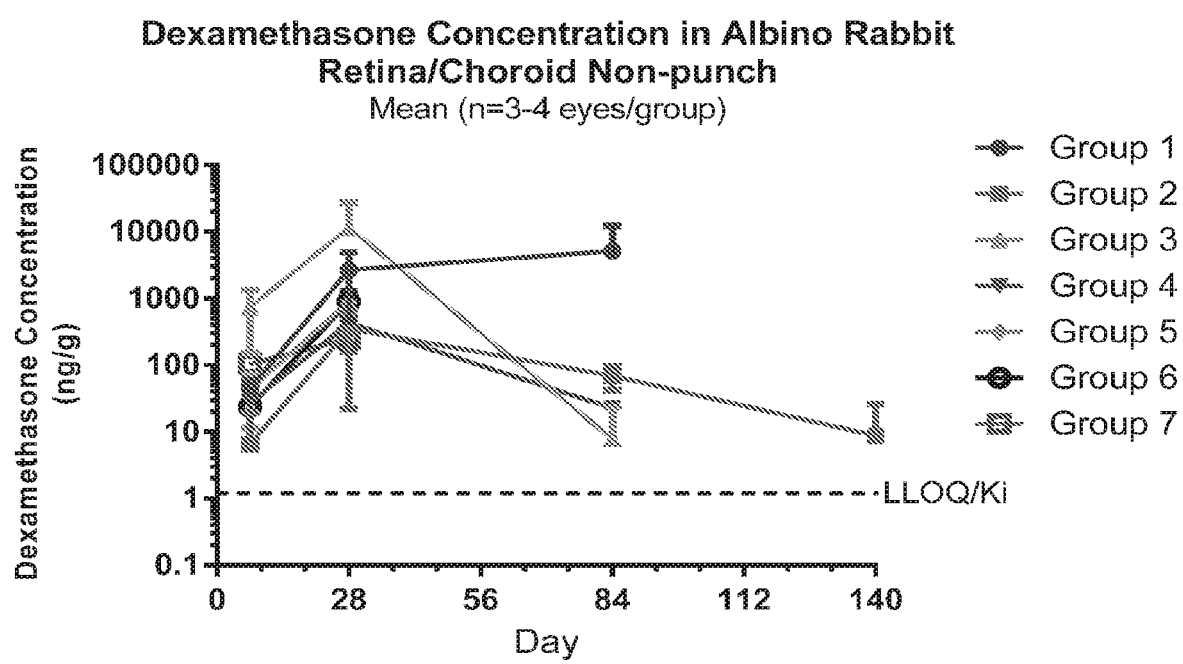
FIG. 31 illustrates ocular pharmacokinetics from nonclinical study ENV1105-PRE-003: retina/choroid (remaining) concentration of dexamethasone following a single bilateral administration of various formulations of ENV1105 intravitreal implant.
Figure 33:
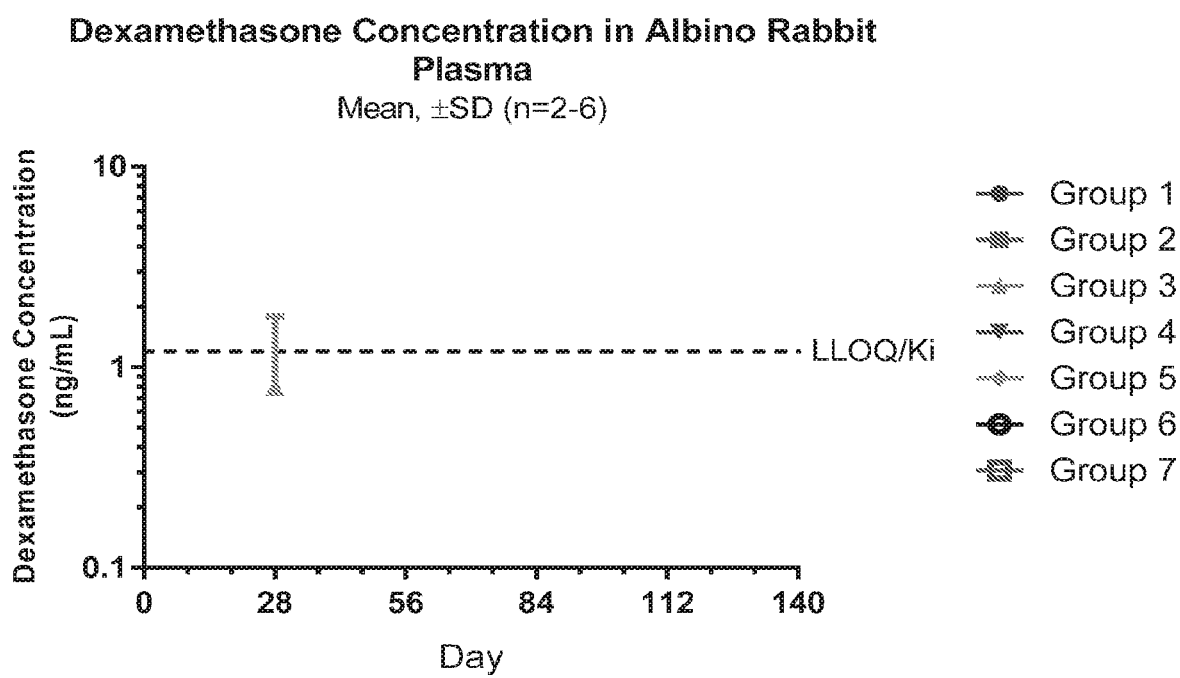
FIG. 33 illustrates ocular pharmacokinetics from nonclinical study ENV1105-PRE-003: plasma concentration of dexamethasone following a single bilateral administration of various formulations of ENV1105 intravitreal implant.

Provided herein are pharmaceutical compositions for treating an ocular condition. In embodiments, the pharmaceutical composition comprises: a biodegradable polymer matrix and a therapeutic agent, which is included in the polymer matrix. In embodiments, the therapeutic agent is dispersed homogeneously throughout the polymer matrix.

As described herein, multiple pharmaceutical compositions have been fabricated and/or contemplated in the form of an implant, resulting in highly effective pharmaceutically active products including ocular therapeutic treatments including sustained release ocular implants.

In various embodiments, these pharmaceutical compositions include a therapeutic agent dispersed throughout a polymer matrix formed into an ocular implant.

In a particular embodiment, the pharmaceutical composition of the present disclosure comprises: i) a biodegradable polymer or blend of biodegradable polymers, and ii) a therapeutic agent such as, for example, a drug effective for use in the treatment of an ocular condition.

Definitions

"About" means plus or minus a percent (e.g., +5%) of the number, parameter, or characteristic so qualified, which would be understood as appropriate by a skilled artisan to the scientific context in which the term is utilized. Furthermore, since all numbers, values, and expressions referring to quantities used herein, are subject to the various uncertainties of measurement encountered in the art, and then unless otherwise indicated, all presented values may be understood as modified by the term "about."

As used herein, the articles "a," "an," and "the" may include plural referents unless otherwise expressly limited to one-referent, or if it would be obvious to a skilled artisan from the context of the sentence that the article referred to a singular referent.

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include any and all subranges between the minimum value of 1 and the maximum value of 10.

As used herein, the term "polymer" is meant to encompass both homopolymers (polymers having only one type of repeating unit) and copolymers (a polymer having more than one type of repeating unit).

"Biodegradable polymer" means a polymer or polymers, which degrade in vivo, under physiological conditions. The release of the therapeutic agent occurs concurrent with, or subsequent to, the degradation of a biodegradable polymer over time.

The terms "biodegradable" and "bioerodible" are used interchangeably herein. A biodegradable polymer may be a homopolymer, a copolymer, or a polymer comprising more than two different polymeric units.

As used herein, the term "polymer matrix" refers to a homogeneous mixture of polymers. In other words, the matrix does not include a mixture wherein one portion thereof is different from the other portion by ingredient, density, and etc. For example, the matrix does not include a composition containing a core and one or more outer layers, nor a composition containing a drug reservoir and one or more portions surrounding the drug reservoir. The mixture of polymers may be of the same type, e.g. two different PLA polymers, or of different types, e.g. PLA polymers combined with PLGA polymers.

"Ocular condition" means a disease, ailment, or condition, which affects or involves the ocular region.

The term "hot-melt extrusion" or "hot-melt extruded" is used herein to describe a process, whereby a blended composition is heated and/or compressed to a molten (or softened) state and subsequently forced through an orifice, where the extruded product (extrudate) is formed into its final shape, in which it solidifies upon cooling.

The term "non-extruded implant" or "non-hot melt extruded implant" refers to an implant that was not manufactured in a process that utilizes an extrusion step, for example, through molding in a mold cavity.

"Sustained release" or "controlled release" refers to the release of at least one therapeutic agent, or drug, from an implant at a sustained rate. Sustained release implies that the therapeutic agent is not released from the implant sporadically, in an unpredictable fashion. The term "sustained release" may include a partial "burst phenomenon" associated with deployment. In some example embodiments, an initial burst of at least one therapeutic agent may be desirable, followed by a more gradual release thereafter. The release rate may be steady state (commonly referred to as "timed release" or zero order kinetics), that is the at least one therapeutic agent is released in even amounts over a predetermined time (with or without an initial burst phase), or may be a gradient release. For example, sustained release can have substantially constant release over a given time period or as compared to topical administration.

"Therapeutically effective amount" means a level or amount of a therapeutic agent needed to treat an ocular condition; the level or amount of a therapeutic agent that produces a therapeutic response or desired effect in the subject to which the therapeutic agent was administered. Thus, a therapeutically effective amount of a therapeutic agent, such as a travoprost, is an amount that is effective in reducing at least one symptom of an ocular condition.

Ocular Anatomy

In particular embodiments, the implants described herein are intravitreal implants manufactured for placement at or into the posterior of the human eye. In one embodiment, the implants described herein are intravitreal implants.

In these embodiments, the sustained release of therapeutic agent from the implant achieves a concentration of drug in the vitreous of the patient's eye that significantly lowers inflammation over the period of sustained release. Furthermore, in embodiments, the intravitreal implant placed at or into the vitreous of a patient's eye achieves a drug concentration in the posterior of the eye that does not fluctuate below a therapeutic level for any consecutive period of 48 hours or more over the sustained release period of the implant and thus overcomes an inherent problem associated with a topical administration paradigm and prior art implants.

Biodegradable Polymers

In certain embodiments, the implants described herein are engineered in size, shape, composition, and combinations thereof, to provide maximal approximation of the implant to the iridocorneal angle of a human eye. In certain embodiments, the implants are made of polymeric materials.

In embodiments, the polymer materials used to form the implants described herein are biodegradable. In embodiments, the polymer materials may be any combination of polylactic acid, glycolic acid, and co-polymers thereof that provides sustained-release of the therapeutic agent into the eye over time.

Suitable polymeric materials or compositions for use in the implants include those materials which are compatible, that is biocompatible, with the eye so as to cause no substantial interference with the functioning or physiology of the eye. Such polymeric materials may be biodegradable, bioerodible or both biodegradable and bioerodible.

In particular embodiments, examples of useful polymeric materials include, without limitation, such materials derived from and/or including organic esters and organic ethers, which when degraded result in physiologically acceptable degradation products. Also, polymeric materials derived from and/or including, anhydrides, amides, orthoesters and the like, by themselves or in combination with other monomers, may also find use in the present disclosure. The polymeric materials may be addition or condensation polymers. The polymeric materials may be cross-linked or non-cross-linked. For some embodiments, besides carbon and hydrogen, the polymers may include at least one of oxygen and nitrogen. The oxygen may be present as oxy, e.g. hydroxy or ether, carbonyl, e.g. non-oxo-carbonyl, such as carboxylic acid ester, and the like. The nitrogen may be present as amide, cyano and amino.

In one embodiment, polymers of hydroxyaliphatic carboxylic acids, either homopolymers or copolymers, and polysaccharides are useful in the implants. Polyesters can include polymers of D-lactic acid, L-lactic acid, racemic lactic acid, glycolic acid, polycaprolactone, co-polymers thereof, and combinations thereof.

Some characteristics of the polymers or polymeric materials for use in embodiments of the present disclosure may include biocompatibility, compatibility with the selected therapeutic agent, ease of use of the polymer in making the therapeutic agent delivery systems described herein, a desired half-life in the physiological environment, and hydrophilicity.

In one embodiment, the biodegradable polymer matrix used to manufacture the implant is a synthetic aliphatic polyester, for example, a polymer of lactic acid and/or glycolic acid, and includes poly-(D,L-lactide) (PLA), poly-(D-lactide), poly-(L-lactide), polyglycolic acid (PGA), and/or the copolymer poly-(D, L-lactide-co-glycolide) (PLGA).

PLGA and PLA polymers are known to degrade via backbone hydrolysis (bulk erosion) and the final degradation products are lactic and glycolic acids, which are non-toxic and considered natural metabolic compounds. Lactic and glycolic acids are eliminated safely via the Krebs cycle by conversion to carbon dioxide and water.

PLGA is synthesized through random ring-opening co-polymerization of the cyclic dimers of glycolic acid and lactic acid. Successive monomeric units of glycolic or lactic acid are linked together by ester linkages. The ratio of lactide to glycolide can be varied, altering the biodegradation characteristics of the product. By altering the ratio it is possible to tailor the polymer degradation time. Importantly, drug release characteristics are affected by the rate of biodegradation, molecular weight, and degree of crystallinity in drug delivery systems. By altering and customizing the biodegradable polymer matrix, the drug delivery profile can be changed.

PLA, PGA, and PLGA are cleaved predominantly by non-enzymatic hydrolysis of its ester linkages throughout the polymer matrix, in the presence of water in the surrounding tissues. PLA, PGA, and PLGA polymers are biocompatible, because they undergo hydrolysis in the body to produce the original monomers, lactic acid and/or glycolic acid. Lactic and glycolic acids are nontoxic and eliminated safely via the Krebs cycle by conversion to carbon dioxide and water. The biocompatibility of PLA, PGA and PLGA polymers has been further examined in both non-ocular and ocular tissues of animals and humans. The findings indicate that the polymers are well tolerated.

PLA, PGA, and PLGA can include terminal esters or acids.

Examples of PLA polymers, which may be utilized in an embodiment of the disclosure, include the RESOMER® Product line available from Evonik Industries identified as, but are not limited to, R 207 S, R 202 S, R 202 H, R 203 S, R 203 H, R 205 S, R 208, R 206, and R 104. Examples of suitable PLA polymers include both acid and ester terminated polymers with inherent viscosities ranging from approximately 0.15 to approximately 2.2 dL/g when measured at 0.1% w/v in $CHCl_3$ at 25° C. with an Ubbelhode size 0c glass capillary viscometer.

The synthesis of various molecular weights and of various inherent viscosities of PLA is possible. For example, and not by limitation, in one embodiment, PLA, such as RESOMER® R208S, with an inherent viscosity of approximately 1.8 to approximately 2.2 dl/g, can be used. In another embodiment, PLA, such as RESOMER® R203 S, with an inherent viscosity of approximately 0.25 to approximately 0.35 dl/g can be used. In yet another embodiment, PLA, such as RESOMER® R205S, with an inherent viscosity of approximately 0.55 to approximately 0.75 dl/g can be used.

Resomers identified by an "R" in the product name, such as R 203S and R208S, are poly(D,L-lactide) or PLA having the general structure (1):

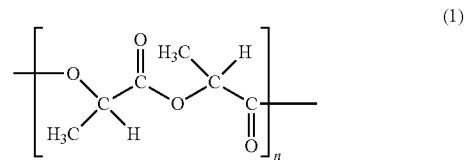

(1)

These polymer can be ester-terminated polymers, as identified by a terminal "S" in the product name, or acid-terminated polymers, as identified by a terminal "H".

Examples of PLGA polymers, which may be utilized in an embodiment of the disclosure, include the RESOMER® Product line from Evonik Industries identified as, but are not limited to, RG 502, RG 502 S, RG 502 H, RG 503, RG 503 H, RG 504, RG 504 H, RG 505, RG 506, RG 653 H, RG 752 H, RG 752 S, RG 753 H, RG 753 S, RG 755, RG 755 S, RG 756, RG 756 S, RG 757 S, RG 750 S, RG 858, and RG 858 S. Such PLGA polymers include both acid and ester terminated polymers with inherent viscosities ranging from approximately 0.14 to approximately 1.7 dl/g when measured at 0.1% w/v in $CHCl_3$ at 25° C. with an Ubbelhode size 0c glass capillary viscometer. Example polymers used in various embodiments of the disclosure may include variation in the mole ratio of D,L-lactide to glycolide from approximately 50:50 to approximately 85:15, including, but not limited to, 50:50, 65:35, 75:25, and 85:15.

The synthesis of various molecular weights of PLGA with various D,L-lactide-glycolide ratios is possible. In one embodiment, PLGA, such as RESOMER® RG752S, with an inherent viscosity of approximately 0.16 to approximately 0.24 dl/g can be used. In another embodiment, PLGA, such as RESOMER® RG653H, with an inherent viscosity of approximately 0.32 to approximately 0.44 dl/g can be used. In yet another embodiment, PLGA, such as RESOMER® RG653H, with an inherent viscosity of approximately 0.32 to approximately 0.44 dl/g can be used. In still another embodiment, PLGA, such as RESOMER® RG502S, with an inherent viscosity of approximately 0.16 to approximately 0.24 dl/g can be used. In still yet another embodiment, PLGA, such as RESOMER® RG503H, with an inherent viscosity of approximately 0.32 to approximately 0.44 dl/g can be used. In still yet another embodiment, PLGA, such as RESOMER® RG504H, with an inherent viscosity of approximately 0.45 to approximately 0.60 dl/g can be used.

Other examples of PLGA polymers which may be utilized in an embodiment of the disclosure include those produced by Lakeshore Biomaterials identified as, but are not limited to, DLG 1A, DLG 3A, or DLG 4A. Such DLG polymers include both acid (A) and ester (E) terminated polymers with inherent viscosities ranging from approximately 0.0.5 to approximately 1.0 dl/g when measured at 0.1% w/v in CHC13 at 25° C. with an Ubbelhode size 0c glass capillary viscometer. Example polymers used in various embodiments of the disclosure may include variation in the mole ratio of D,L-lactide to glycolide from approximately 1:99 to approximately 99:1, including, but not limited to, 50:50, 65:35, 75:25, and 85:15.

The synthesis of various molecular weights of DLG with various D,L-lactide-glycolide ratios is possible. In one embodiment, DLG, such as 1A, with an inherent viscosity of approximately 0.05 to approximately 0.15 dl/g can be used. In another embodiment, DLG, such as 2A, with an inherent viscosity of approximately 0.15 to approximately 0.25 dl/g can be used.

Resomers identified by an "RG" or "DLG" in the product name, such as RG752S, is a poly(D,L-lactide-co-glycolide) or PLGA having the general structure (2):

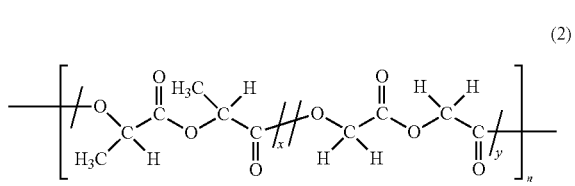

(2)

Poly(D,L-lactide-co-glycolide) or PLGA copolymers can be synthesized at different ratios of lactide to glycolide, such as a lactide:glycolide ratio of 75:25. These copolymers can be an ester-terminated PLGA copolymer, as identified by the terminal "S" in the product name, or an acid-terminated PLGA copolymer, as identified by the terminal "H" in the product name.

In another embodiment, the biodegradable polymer matrix used to manufacture the implant is polyethylene glycol (PEG). PEG can be synthesis at various molecular weights and of various inherent viscosities. The polymer matric can be composed of PEG or the PEG can exist in combination with other polymers disclosed herein.

In another embodiment, polymer blends described herein can be used with particle suspensions. In one embodiments, the polymer suspension is delivered by sorbitol-modified hyaluronic acid (HS/sorbitol) vehicle.

The polymers used to form the implants of the disclosure have independent properties associated with them that when combined provide the properties needed to provide sustained release of a therapeutically effective amount of a therapeutic agent.

A few of the primary polymer characteristics that control therapeutic agent release rates are the molecular weight distribution, polymer endgroup (i.e., acid or ester), and the ratio of polymers and/or copolymers in the polymer matrix. The present disclosure provides examples of polymer matrices that possess desirable therapeutic agent release characteristics by manipulating one or more of the aforementioned properties to develop a suitable ocular implant.

The biodegradable polymeric materials which are included to form the implant's polymeric matrix are often subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implants. Different molecular weights of the same or different polymeric compositions may be included to modulate the release profile of the at least one therapeutic agent.

In an embodiment of the present disclosure, the polymers of the present implants are selected from biodegradable polymers, disclosed herein, that do not substantially swell when in the presence of the aqueous humor. By way of example but not limitation, PLGA polymers swell when used as the matrix material of drug delivery implants whereas PLA based polymer blends do not appreciably swell in the presence of the aqueous humor. Therefore, PLA polymer matrix materials are polymer matrix materials in embodiments of the present disclosure.

Particle Suspension

In aspects, the present compositions include liquid formulations and delivery systems. Thus, the present compositions may be understood to include solutions, suspensions, emulsions, and the like, such as other liquid-containing compositions used in ophthalmic therapies.

In particular embodiments, the liquid formulations are particle suspensions. Particle suspensions, as used herein, are micronized pharmaceutical compositions formulated as a suspension in an aqueous phase containing necessary excipient, such as a delivery vehicle. Particles are generally smaller than the implants disclosed herein and may vary in shape. For example, certain embodiments of the present disclosure use substantially cylindrical particles. The drug delivery system may comprise a population of such particles with a predetermined size distribution. In embodiments, suspension may comprise a population of particles having a desired diameter measurement.

As discussed above, polymer blends described herein can be used with particle suspensions. Thus, in embodiments, the above disclosed PLA, PGA, and PLGA polymers and a therapeutic agent can be formulated as a particle suspension for ocular administration. Additional agents including, but not limited to, tocopherol (e.g., α-tocopherol, β-tocopherol, γ-tocopherol, and δ-tocopherol) can be used in the particle suspensions described herein. The particle suspension can include one polymer or a blend of polymers.

In embodiments, the particles have a size less than 100 μm in any dimension. In embodiments, the largest dimensions may be from 10 μm to about 100 μm, or about 12.5 μm to about 50 μm, or about 25 μm to about 50 μm. In other embodiments, the smallest dimension may be from 10 μm to about 100 μm, or about 12.5 μm to about 25 μm.

In embodiments, the particles comprises as a therapeutic agent content of from about 1% to about 90%, or about 1% to about 80%, or about 1% to about 70%, or about 1% to about 60%, or about 1% to about 50%, or about 1% to about 40%, or about 1% to about 30%, or about 1% to about 20%, or about 1% to about 10%, or about 10% to about 50%, or about 10% to about 40%, or about 10% to about 30%, or about 10% to about 25%, or about 10% to about 23%, or about 10% to about 20%, or about 15% to about 35%, or about 15% to about 30%, or about 15% to about 25%.

Delivery vehicles can be used in the administration, via intravitreal injection, of the particle suspensions described herein. For example, a hyaluronic acid (HA) delivery vehicle can be used to formulate an injectable vehicle for administering a particle suspension, such as the one described in U.S. Pat. Nos. 7,582,311 and 7,651,703, which is incorporated herein by reference in its entirety. Hyaluronic acid (HA) is a polyanionic, polysaccharide that consists of N-acetyl-D-glucosamine and beta-glucoronic acid. The unique viscoelastic nature of HA along with its biocompatibility and non-immunogenicity has led to its use in a number of clinical applications, which include: the supplementation of joint fluid in arthritis; as a surgical aid in eye surgery; and to facilitate the healing and regeneration of surgical wounds. More recently, HA has been investigated as a drug delivery agent for various routes of administration, including ophthalmic, nasal, pulmonary, parenteral and topical.

In embodiments, the particle suspension is delivered by an aqueous solution. In one embodiment, the particle suspension is delivered by an aqueous solution containing sorbitol and hyaluronic acid (HA/sorbitol) vehicle. In embodiments, the aqueous solution comprises from about 0.1-99% HA and about 1-99% sorbitol, or about 0.1-50% HA, and about 20-90% sorbitol, or about 0.1-10% HA and about 40-60% sorbitol. In certain embodiments, the aqueous solution comprises about 1% HA and about 50% sorbitol.

Drug Release Profile Manipulation

The rate of drug release from biodegradable implants and particle suspensions depends on several factors. For example, the surface area of the implant, therapeutic agent content, and water solubility of the therapeutic agent, and speed of polymer degradation. For a homopolymer such as PLA, the drug release is also determined by (a) the lactide stereoisomeric composition (i.e. the amound of L- vs. D,L-lactide) and (b) molecular weight. Three additional factors that determine the degradation rate of PLGA copolymers are: (a) the lactide:glycolide ratio, (b) the lactide stereoisomeric composition (i.e., the amount of L- vs. DL-lactide), and (c) molecular weight.

The lactide:glycolide ratio and stereoisomeric composition are generally considered most important for PLGA degradation, as they determine polymer hydrophilicity and crystallinity. For instance, PLGA with a 1:1 ratio of lactic acid to glycolic acid degrades faster than PLA or PGA, and the degradation rate can be decreased by increasing the content of either lactide or glycolide. Polymers with degradation times ranging from weeks to years can be manufactured simply by customizing the lactide:glycolide ratio and lactide stereoisomeric composition.

The versatility of PGA, PLA, and PLGA allows for construction of delivery systems to tailor the drug release for treating a variety of ocular diseases.

When the versatility of PGA, PLA, and PLGA polymers are combined with the manufacturing techniques of the present disclosure, i.e. PRINT® technology (Envisia Therapeutics Inc.) particle fabrication, then a host of custom tailored and highly consistent and predictable drug release profiles can be created, which were not possible based upon the technology of the prior art, such as for example extrusion.

That is, with the present mold based particle fabrication technology, implants can be manufactured that exhibit a drug release profile that has highly reproducible characteristics from implant to implant. The drug release profiles exhibited by various implants of the present disclosure are consistent implant to implant and demonstrate variation that is not statistically significant. Consequently, the drug release profiles demonstrated by embodiments of the implants exhibit coefficients of variation that are within a confidence interval and does not impact the therapeutic delivery. The ability to produce implants that demonstrate such a high degree of consistent drug loading or release is an advancement over the state of the art.

Drug Release Kinetics

Drug release from PLA- and PLGA-based polymer matrix drug delivery systems generally follows pseudo first-order or square root kinetics.

Drug release is influenced by many factors including: polymer composition, therapeutic agent content, implant morphology, porosity, tortuosity, surface area, method of manufacture, and deviation from sink conditions, just to name a few. The present mold based manufacturing techniques-utilized in embodiments of the disclosure—are able to manipulate implant morphology, porosity, tortuosity, and surface area in ways that the prior art methods were incapable of doing. For instance, the highly consistent drug release profiles, highly consistent implant morphologies, and highly consistent homogeneous drug dispersions achievable by the present methods, were not available to prior art practitioners relegated to utilizing an extrusion based method of manufacture.

In general, therapeutic agent release occurs in 3 phases: (a) an initial burst release of therapeutic agent from the surface, (b) followed by a period of diffusional release, which is governed by the inherent dissolution of therapeutic agent (diffusion through internal pores into the surrounding media) and lastly, (c) therapeutic agent release associated with biodegradation of the polymer matrix. The rapid achievement of high therapeutic agent concentrations, followed by a longer period of continuous lower-dose release, makes such delivery systems ideally suited for acute-onset diseases that require a loading dose of therapeutic agent followed by tapering doses over a 1-day to 3-month period.

More recent advancements in PLGA-based drug delivery systems have allowed for biphasic release characteristics with an initial high (burst) rate of therapeutic agent release followed by substantially sustained zero-order (linear) kinetic release (i.e., therapeutic agent release rate from the polymer matrix is steady and independent of the therapeutic agent concentration in the surrounding milieu) over longer periods. In addition, when desired for treating chronic diseases such as elevated IOP, these therapeutic agent delivery systems can be designed to have substantially steady state release following zero order kinetics from the onset.

Therapeutic Agents

Suitable therapeutic agents for use in various embodiments of the disclosure may be found in the Orange Book published by the Food and Drug Administration, which lists therapeutic agents approved for treating ocular diseases including macular edema, retinal vein occlusion, and uveitis.

In some embodiments, the therapeutic agents that can be used according to the disclosure include: corticosteroids, corticosteroids prodrugs, corticosteroids analogues, pharmaceutically acceptable salts, solvates, esters, and polymorphs thereof, and combinations thereof.

Examples include dexamethasone and fluocinolone acetonide.

The chemical structure (3) of dexamethasone is illustrated below:

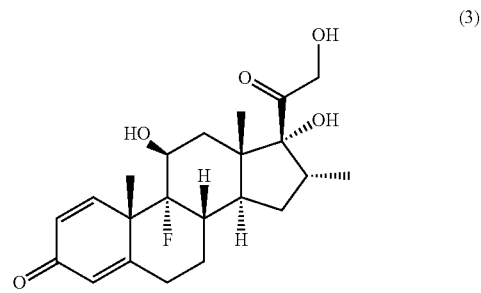

IUPAC Name: (8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one The chemical structure (4) of fluocinolone acetonide is illustrated below:

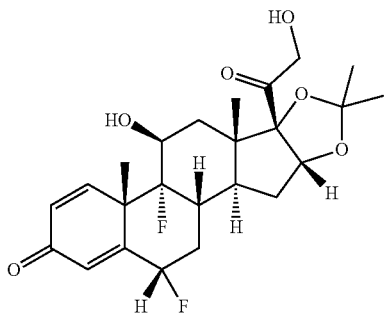

IUPAC Name: (1S,2S,4R,8S,9S,11S,12R,13S,19S)-12,19-difluoro-11-hydroxy-8-(2-hydroxyacetyl)-6,6,9,13-tetramethyl-5,7-dioxapentacyclo[10.8.0.0$^{2,9}$.0$^{4,8}$.0$^{13,18}$]icosa-14,17-dien-16-one Pharmaceutical Compositions In embodiments, the pharmaceutical composition is comprised of the biodegradable polymer matrix and at least one therapeutic agent.

The biodegradable polymer matrix is comprised of polymers meeting the desired characteristics. For example, desired characteristics may include a specific therapeutic agent release rate or a specific duration of action. The biodegradable polymer matrix may be comprised of one polymer, two polymers, or many polymers, such as three, four, five polymers, or more polymers.

In some embodiments, the compositions may comprise polymers utilizing the same monomer, such as compositions comprising various poly(D,L-lactide) homopolymers, or compositions comprising various poly(D,L-lactide-co-glycolide) copolymers. However, even if the polymers of the composition utilize the same monomer, the polymers may differ in other characteristics, such as, for example, inherent viscosity or mole ratio of D,L-lactide to glycolide.

In other embodiments, the compositions may comprise polymers utilizing different monomers, such as compositions comprising a poly(D, L-lactide-co-glycolide) copolymer and a poly(D,L-lactide) homopolymer. However, even if the polymers of the compositions utilize different monomers, the polymers may be similar in other characteristics, such as for example, inherent viscosity.

In one embodiment, the pharmaceutical composition comprises a biodegradable polymer matrix and at least one therapeutic agent homogeneously dispersed throughout the polymer matrix.

In one embodiment, the therapeutic agent is dexamethasone, and the pharmaceutical composition is an implant.

In one embodiment, the therapeutic agent is fluocinolone acetonide, and the pharmaceutical composition is an implant.

In one embodiment, the therapeutic agent is dexamethasone, and the pharmaceutical composition is a particle suspension.

The aforementioned mold cavities used to fabricate the ocular implants may vary from the recited dimensions by +50 μm, or +40 μm, or +30 μm, or +20 μm, or +10 μm, or ±5 μm, in various aspects.

In embodiments, the therapeutic agent is blended with the biodegradable polymer matrix to form the pharmaceutical composition. The amount of therapeutic agent used in the pharmaceutical composition depends on several factors such as: biodegradable polymer matrix selection, therapeutic agent selection, rate of release, duration of release desired, configuration of pharmaceutical composition, and ocular PK, to name a few.

For example, the therapeutic agent content of the overall implant may comprise approximately 0.1 to approximately 60.0 weight percent of the total implants pharmaceutical composition. In some embodiments, the therapeutic agent comprises approximately 10.0 to approximately 50.0 weight percent of the pharmaceutical composition. In other embodiments, the therapeutic agent comprises approximately 20.0 to approximately 40.0 weight percent of the pharmaceutical composition. In other embodiments, the therapeutic agent comprises approximately 30.0 to approximately 40.0 weight percent of the pharmaceutical composition. In yet other embodiments, the therapeutic agent comprises approximately 30.0 to approximately 35.0 weight percent of the pharmaceutical composition. In yet still other embodiments, the therapeutic agent comprises approximately 30.0 weight percent of the pharmaceutical composition. Or in other embodiments the therapeutic agent comprises approximately 33.0 weight percent of the pharmaceutical composition. In still other embodiments, the therapeutic agent comprises approximately 15.0 to approximately 20.0 weight percent of the pharmaceutical composition. Or in other embodiments the therapeutic agent comprises approximately 33.0 weight percent of the pharmaceutical composition. In a particular embodiment, dexamethasone comprises approximately 20.0 weight percent of the pharmaceutical composition.

In embodiments, the pharmaceutical composition is prepared by dissolving the polymer or polymers and the therapeutic agent in a suitable solvent to create a homogeneous solution. For example, acetone, alcohol, acetonitrile, tetrahydrofuran, chloroform, and ethyl acetate may be used as solvents. Other solvents known in the art are also contemplated. The solvent is then allowed to evaporate, leaving behind a homogeneous film. The solution can be aseptically filtered prior to evaporation of the solvent.

Fabrication of an Ocular Implant

Various methods may be used to produce the implants or particle suspensions. Methods include, but are not limited to, solvent casting, phase separation, interfacial methods, molding, compression molding, injection molding, extrusion, co-extrusion, heat extrusion, die cutting, heat compression, and combinations thereof. In certain embodiments, the implants are molded, preferably in polymeric molds.

In particular embodiments, the implants of the present disclosure are fabricated through the PRINT® Technology (Liquidia Technologies, Inc.) particle fabrication. In particular, the implants are made by molding the materials intended to make up the implants in mold cavities.

The molds can be polymer-based molds and the mold cavities can be formed into any desired shape and dimension. Uniquely, as the implants and particles are formed in the cavities of the mold, the implants are highly uniform with respect to shape, size, and composition. Due to the consistency among the physical and compositional makeup of each implant of the present pharmaceutical compositions, the pharmaceutical compositions of the present disclosure provide highly uniform release rates and dosing ranges. The methods and materials for fabricating the implants of the present disclosure are further described and disclosed in the Applicant's issued patents and co-pending patent applications, each of which are incorporated herein by reference in their entirety: U.S. Pat. Nos. 8,518,316; 8,444,907; 8,420,124; 8,268,446; 8,263,129; 8,158,728; 8,128,393; 7,976,759; U.S. Pat. Application Publications Nos. 2013-0249138, 2013-0241107, 2013-0228950, 2013-0202729, 2013-0011618, 2013-0256354, 2012-0189728, 2010-0003291, 2009-0165320, 2008-0131692; and pending U.S. application Ser. No. 13/852,683 filed Mar. 28, 2013 and Ser. No. 13/950,447 filed Jul. 25, 2013.

The mold cavities can be formed into various shapes and sizes. For example, the cavities may be shaped as a prism, rectangular prism, triangular prism, pyramid, square pyramid, triangular pyramid, cone, cylinder, torus, or rod. The cavities within a mold may have the same shape or may have different shapes. In certain aspects of the disclosure, the shapes of the implants are a cylinder, rectangular prism, or a rod. In a particular embodiment, the implant is a rod.

The mold cavities can be dimensioned from nanometer to micrometer to millimeter dimensions and larger. For certain embodiments of the disclosure, mold cavities are dimensioned in the micrometer and millimeter range. For example, cavities may have a smallest dimension of between approximately 50 nanometers and approximately 750 µm. In some aspects, the smallest mold cavity dimension may be between approximately 100 µm and approximately 300 µm. In other aspects, the smallest mold cavity dimension may be between approximately 125 µm and approximately 250 µm. In still other aspects, the smallest mold cavity dimension may be between approximately 10 µm and approximately 100 µm. In some aspects, the smallest mold cavity dimension may be between approximately 12.5 µm and approximately 50 µm, e.g., 25 µm and 30 µm. The mold cavities may also have a largest dimension of between approximately 750 µm and approximately 10,000 µm. In other aspects, the largest mold cavity dimension may be between approximately 1,000 µm and approximately 5000 µm. In other aspects, the largest mold cavity dimension may be between approximately 1,000 m and approximately 3,500 µm. In still other aspects, the largest mold cavity dimension may be between approximately 25 µm and approximately 100 µm. In some aspects, the smallest mold cavity dimension may be between approximately 25 µm and approximately 50 µm, e.g., 25 µm and 30 µm.

In one embodiment, a mold cavity with dimensions of 12.5 µm×12.5 µm×25 µm (W×H×L) is utilized to fabricate the particles of the present disclosure.

In one embodiment, a mold cavity with dimensions of 25 µm×25 µm×25 µm (W×H×L) is utilized to fabricate the particles of the present disclosure.

In one embodiment, a mold cavity with dimensions of 25 µm×25 µm×50 µm (W×H×L) is utilized to fabricate the particles of the present disclosure.

In one embodiment, a mold cavity with dimensions of 50 µm×50 µm×30 µm (W×H×L) is utilized to fabricate the particles of the present disclosure.

In one embodiment, a mold cavity with dimensions of 50 µm×50 µm×50 µm (W×H×L) is utilized to fabricate the particles of the present disclosure.

In one embodiment, a mold cavity having generally a rod shape with dimensions of 140 µm×140 µm×1325 µm (W×H×L) is utilized to fabricate the implants of the present disclosure.

In a further embodiment, a mold cavity having a rod shape with dimensions of 225 µm×225 µm×2965 µm (W×H×L) is used to fabricate the implants of the present disclosure.

In another embodiment, a mold cavity having generally a rod shape with dimensions of 395 µm×311 µm×6045 µm (W×H×L) is used to fabricate the implants of the present disclosure.

In one embodiment, a mold cavity having generally a rod shape with dimensions of 100 µm×100 µm×1500 µm (W×H×L) is utilized to fabricate the implants of the present disclosure.

In a further embodiment, a mold cavity having a rod shape with dimensions of 150 µm×150 µm×3150 µm (W×H×L) is used to fabricate the implants of the present disclosure.

In another embodiment, a mold cavity having generally a rod shape with dimensions of 180 µm×180 µm×3000 µm (W×H×L) is used to fabricate the implants of the present disclosure.

In one embodiment, a mold cavity having generally a rod shape with dimensions of 200 µm×200 µm×2000 µm (W×H×L) is utilized to fabricate the implants of the present disclosure.

In a further embodiment, a mold cavity having a rod shape with dimensions of 200 µm×200 µm×1000 µm (W×H×L) is used to fabricate the implants of the present disclosure.

In another embodiment, a mold cavity having generally a rod shape with dimensions of 225 µm×225 µm×2700 µm (W×H×L) is used to fabricate the implants of the present disclosure.

In another embodiment, a mold cavity having generally a rod shape with dimensions of 250 µm×250 µm×1500 µm (W×H×L) is used to fabricate the implants of the present disclosure.

In another embodiment, a mold cavity having generally a rod shape with dimensions of 200 µm×200 µm×4500 µm (W×H×L) is used to fabricate the implants of the present disclosure.

In another embodiment, a mold cavity having generally a rod shape with dimensions of 265 µm×265 µm×4500 µm (W×H×L) is used to fabricate the implants of the present disclosure.

In another embodiment, a mold cavity having generally a rod shape with dimensions of 255 µm×255 µm×4500 µm (W×H×L) is used to fabricate the implants of the present disclosure.

Once fabricated, the implants and particles may remain on an array for storage, or may be harvested immediately for storage and/or utilization. Implants and particles described herein may be fabricated using sterile processes, or may be sterilized after fabrication. Thus, the present disclosure contemplates kits that include a storage array that has fabricated implants and particles attached thereon. These storage array/implant kits provide a convenient method for mass shipping and distribution of the manufactured implants.

In other embodiments, the implants and particles can be fabricated through the application of additive manufacturing techniques. Additive manufacturing, such as disclosed in US published application US 2013/0295212 and the like can be utilized to either make the master template used in the PRINT process, utilized to make the mold used into the PRINT process otherwise disclosed herein or utilized to fabricate the implants directly.

In a particular embodiment, the implants and particles are fabricated through the process of i) dissolving the polymer and active agent in a solvent, for example acetone; ii) casting the solution into a thin film; iii) drying the film; iv) folding the thin film onto itself; v) heating the folded thin film on a substrate to form a substrate; vi) positioning the thin film on the substrate onto a mold having mold cavities; vii) applying pressure, and in some embodiments heat, to the mold-thin film-substrate combination such that the thin film enters the mold cavities; ix) cooling; x) removing the substrate from the mold to provide implants that substantially mimic the size and shape of the mold cavities.

Delivery Devices

In embodiments, a delivery device may be used to insert the implant or particles into the eye or eyes for treatment of ocular diseases.

Suitable devices can include a needle or needle-like applicator. In some embodiments, the smallest dimension of an implant may range from approximately 50 m to approximately 750 µm, and therefore a needle or needle-like applicator with a gauge ranging from approximately 15 to approximately 30 may be utilized. In certain embodiments, the need gauge is 15, 16, 17, 18, 19, 20, 21, 22, 23, 24, 25, 26, 27, 28, 29, or 30. In one embodiment, the device uses a 25 gauge needle for an implant with a smallest dimension of 265 µm. In another embodiment, the device uses a 21 or 22 gauge needle for an implant with a smallest dimension of 395 µm. In yet another embodiment, the device uses a 27 gauge needle for a particle suspension or for an implant with the smallest dimension of 200 µm. The delivery implant may be a syringe with an appropriately sized needle or may be a syringe-like implant with a needle-like applicator. In an embodiment, the device uses a 27 gauge ultra thin wall needle having an inner diameter of 300+/−10 micrometers.

Delivery routes include punctual, intravitreal, subconjunctival, lens, intrascleral, fornix, anterior sub-Tenon's, suprachoroidal, posterior sub-Tenon's, subretinal, anterior chamber, and posterior chamber, to name a few.

In embodiments, an implant or implants are delivered to the anterior chamber of a patient's eye to treat glaucoma and/or elevated intraocular pressure.

Kits

In embodiments, the implant and delivery device may be combined and presented as a kit for use.

The implant may be packaged separately from the delivery device and loaded into the delivery device just prior to use.

Alternatively, the implant may be loaded into the delivery implant prior to packaging. In this case, once the kit is opened, the delivery implant is ready for use.

Components may be sterilized individually and combined into a kit, or may be sterilized after being combined into a kit.

Further, as aforementioned, a kit may include an array with implants bound thereon.

Use of Ocular Implant for Treatment

In one aspect of the disclosure, there is presented a method of treating inflammation of the eye. The method comprises placing a biodegradable implant in an eye, degrading the implant, releasing a therapeutic agent which is effective to reduce ocular inflammation, and thereby treating edema, retinal vein occlusion, uveitis, to name a few.

In aspects of the disclosure, the eye is that of an animal. For example, a dog, cat, horse, cow (or any agricultural livestock), or human.

Course of Treatment

Over the course of treatment, the biodegradable polymer matrix degrades releasing the therapeutic agent. Once the therapeutic agent has been completely released, the polymer matrix is expected to be gone. Complete polymer matrix degradation may take longer than the complete release of the therapeutic agent. Polymer matrix degradation may occur at the same rate as the release of the therapeutic agent.

Current treatments for inflammation require the patient to place drops in their eyes each day or to receive multiple steroidal injections into the eye. The pharmaceutical composition of the disclosure is designed for sustained release of an effective amount of therapeutic agent, thus eliminating the need for daily drops and multiple steroidal injections.

For example, the pharmaceutical composition may be designed to release an effective amount of therapeutic agent for approximately one month, two months, three months, four months, five months, six months, seven months, eight months, nine months, ten months, eleven months, twelve months, or longer. In aspects, the pharmaceutical composition is designed to release an effective amount of therapeutic agent for one month, two months, three months, four months, five months, six months, or more. In other aspects, the pharmaceutical composition is designed to release an effective amount of therapeutic agent for three months, four months, five months, six months, or more.

In an embodiment, the pharmaceutical composition is dosed in a repetitive manner. The dosing regimen provides a second dose of the pharmaceutical composition implants is dosed following the first dose releases its drug cargo. The dosing regimen also provides that a fourth dose of the pharmaceutical composition implants is not dosed until the polymer matrix of the implants of the first dosing are sufficiently degraded. In an embodiment the implant of the first dose fully degrade before the third dosing is administered.

The following non-limiting examples illustrate certain aspects of the present disclosure.

EXAMPLES

The following examples are provided to illustrate embodiments of the disclosure.

Examples

Example 1. Implant Fabrication

A series of polymer matrix/therapeutic agent blends were prepared prior to fabrication of implants. Two separate methods were used to produce polymer matrix/therapeutic agent blends in which the therapeutic agent is homogenously dispersed therapeutic agent throughout the polymer matrix: (1) Hot melt extrusion; and (2) Solvent mixing.

1.1 Hot Melt Mixing—

Polymer powder was added to a vessel containing micronized dexamethasone. The vessel was allowed to heat to above the Tg of the polymers, at which point a metal spatula was used to mix the materials into a thick, viscous, uniform paste.

1.2 Solvent Mixing—

Acetone was added directly to polymer powder and the polymer was allowed to dissolve. The polymer solution was then aseptically filtered and added directly to micronized dexamethasone. The acetone was evaporated leaving a thin film of homogenous material.

Example 2. Fabrication of Molds

A series of templated molds of various dimensions were fabricated by Envisia Therapeutics utilizing Particle Replication in Non-wetting Template (PRINT®) technology.

Molds utilized included: a) a rod shape with dimensions of 225×225×2925 μm; b) a rod shape with dimensions of 200×200×4500 μm; and c) a rod shape with dimensions of 225×225×4000 μm; d) a rod shape with dimensions of 311×395×6045 m; e) a rod shape with dimensions of 25×25×50 μm; f) a cube shape with dimensions of 12.5× 12.5×25 μm; g) a cube shape with dimensions of 25×25×25 μm; and h) a cube shape with dimensions of 50×50×50 μm.

Example 3. Dexamethasone Implant Fabrication

A series of implants were fabricated utilizing the polymer matrix/therapeutic agent blends obtained using the method described in Example 1.1 and the molds described in Example 2. The therapeutic agent was dexamethasone. A portion of polymer matrix/therapeutic agent blend was spread over a PET sheet and was heated. Once heated, the blend was covered with the mold of Example 2 which had the desired dimensions. Light pressure was applied using a roller to spread the blend over the mold area. The mold/blend laminate was then passed through a commercially available thermal laminator using the parameters in the tables below. The blend flowed into the mold cavities and assumed the shape of the mold cavities. The blend was allowed to cool to room temperature and created individual implants in the mold cavities. The mold was then removed leaving a two-dimensional array of implants resting on the film. Individual implants were removed from the PET film utilizing forceps. The blend compositions and mold designs produced by the above method are located below in Tables 1A-1H.

TABLE 1A

Blend compositions and mold designs for SDSA 25

| Sample ID | Resomer polymer name | Mold Design |
| --- | --- | --- |
| ENV-1R-0119-7-1 | 502S/502H (50/50) | 225 × 225 × 2925 μm |
| ENV-1R-0119-7-2 | RG 502 | 225 × 225 × 2925 μm |
| ENV-1R-0119-7-3 | RG 502H | 225 × 225 × 2925 μm |
| ENV-1R-0119-7-4 | RG 503/RG 502H 50/50 | 225 × 225 × 2925 μm |
| ENV-1R-0119-7-5 | RG 203/RG502S 50/50 | 225 × 225 × 2925 μm |
| ENV-1R-0119-7-6 | RG 203/RG502H 50/50 | 225 × 225 × 2925 μm |
| ENV-1R-0119-7-7 | RG 203/RG502S 70/30 | 225 × 225 × 2925 μm |
| ENV-1R-0119-7-8 | DLG 3A | 225 × 225 × 2925 μm |
| ENV-1R-0119-7-9 | DLG 4A | 225 × 225 × 2925 μm |
| ENV-1R-0119-7-10 | RG752S | 225 × 225 × 2925 μm |
| ENV-1R-0119-7-11 | RG752H | 225 × 225 × 2925 μm |
| ENV-1R-0119-7-12 | 755S | 225 × 225 × 2925 μm |
| ENV-1R-0119-7-13 | RG 752/PEG 400 95/5 | 225 × 225 × 2925 μm |
| ENV-1R-0119-7-14 | RG 752H/PEG 400 95/5 | 225 × 225 × 2925 μm |
| ENV-1R-0119-7-15 | 752S/755S 80/20 | 225 × 225 × 2925 μm |
| ENV-1R-0119-7-16 | 752H/755S 80/20 | 225 × 225 × 2925 μm |

TABLE 1B

Blend compositions and mold designs for SDSA 34

| Sample ID | Resomer polymer name | Mold Design |
| --- | --- | --- |
| ENV-1R-0119-39-1A | 203/207 (70/30) | 225 × 225 × 2925 μm |
| ENV-1R-0119-39-2A | 203/205 (70/30) | 225 × 225 × 2925 μm |
| ENV-1R-0119-39-3A | 203/208 (70/30) | 225 × 225 × 2925 μm |
| ENV-1R-0119-39-4A | 203/207 (50/50) | 225 × 225 × 2925 μm |
| ENV-1R-0119-39-5A | 203/208 (50/50) | 225 × 225 × 2925 μm |

TABLE 1C

Blend compositions and mold designs for SDSA 39

| Sample ID | Resomer polymer name | Mold Design |
| --- | --- | --- |
| ENV-1R-0119-36-1 | 205/2A (50/50) | 225 × 225 × 2925 μm |
| ENV-1R-0119-36-2 | 208/2A (50/50) | 225 × 225 × 2925 μm |
| ENV-1R-0119-36-3 | 205/203 (70/30) | 225 × 225 × 2925 μm |
| ENV-1R-0119-36-4 | 205/1A (50/50) | 225 × 225 × 2925 μm |
| ENV-1R-0119-36-5 | 205/1A (70/30) | 225 × 225 × 2925 μm |

TABLE 1D

Blend compositions and mold designs for SDSA 41

| Sample ID | Resomer polymer name | Mold Design |
| --- | --- | --- |
| ENV-1R-0119-42-1 | 504H/203S (50/50) | 225 × 225 × 2925 μm |
| ENV-1R-0119-42-2 | 504H/203S (70/30) | 225 × 225 × 2925 μm |
| ENV-1R-0119-42-3 | 504H/203S (85/15) | 225 × 225 × 2925 μm |
| ENV-1R-0119-42-4 | 503H/203S (50/50) | 225 × 225 × 2925 μm |
| ENV-1R-0119-42-5 | 503H/203S (70/30) | 225 × 225 × 2925 μm |
| ENV-1R-0119-42-6 | 503H/203S (85/15) | 225 × 225 × 2925 μm |
| ENV-1R-0119-42-7 | 503H/203S (30/70) | 225 × 225 × 2925 μm |
| ENV-1R-0119-42-8 | 653H/203S (50/50) | 225 × 225 × 2925 μm |
| ENV-1R-0119-42-9 | 653H/203S (70/30) | 225 × 225 × 2925 μm |
| ENV-1R-0119-42-10 | 653H/203S (85/15) | 225 × 225 × 2925 μm |
| ENV-1R-0119-42-11 | 203/208(85/15) | 225 × 225 × 2925 μm |
| ENV-1R-0119-42-12 | 203/207(85/15) | 225 × 225 × 2925 μm |
| ENV-1R-0119-42-13 | 203/205(85/15) | 225 × 225 × 2925 μm |
| ENV-1R-0119-42-14 | 203/2A(70/30) | 225 × 225 × 2925 μm |

TABLE 1E

Blend compositions and mold designs for SDSA 53

| Sample ID | Resomer polymer name | Mold Design |
| --- | --- | --- |
| ENV-1R-0119-45-1 | RG502 | 311 × 395 × 6045 μm |
| ENV-1R-0119-45-2 | R203/RG502S (50/50) | 311 × 395 × 6045 μm |
| ENV-1R-0119-45-3 | R203/RG502H (70/30) | 311 × 395 × 6045 μm |
| ENV-1R-0119-45-4 | R203/RG502H (50/50) | 311 × 395 × 6045 μm |
| ENV-1R-0119-45-5 | R203/DLG1A (95/5) | 311 × 395 × 6045 μm |
| ENV-1R-0119-45-6 | R203/DLG1A (85/15) | 311 × 395 × 6045 μm |
| ENV-1R-0119-45-7 | RG752S/RG755S (70/30) | 311 × 395 × 6045 μm |
| ENV-1R-0119-45-8 | RG752S/RG755S (60/40) | 311 × 395 × 6045 μm |

TABLE 1F

Blend compositions and mold designs for SDSA 70

| Sample ID | Resomer polymer name | Mold Design (um) |
| --- | --- | --- |
| ENV-1D-0209-1-1 | 503H/205S (30/70) | 225 × 225 × 4000 |
| ENV-1D-0209-1-2 | 503H/205S (10/90) | 225 × 225 × 4000 |
| ENV-1D-0209-1-3 | 503S/205S (30/70) | 225 × 225 × 4000 |
| ENV-1D-0209-1-4 | 503S/205S (15/85) | 225 × 225 × 4000 |
| ENV-1D-0209-1-5 | 503H/203S (85/15) | 225 × 225 × 4000 |
| ENV-1D-0209-1-6 | 503H/203S (70/30) | 225 × 225 × 4000 |
| ENV-1D-0209-1-7 | 503S/203S (70/30) | 225 × 225 × 4000 |
| ENV-1D-0209-1-8 | 503S/203S (85/15) | 225 × 225 × 4000 |
| ENV-1D-0209-1-9 | 502S/208/203 (10/23/67) | 225 × 225 × 4000 |
| ENV-1D-0209-1-10 | 502S/208/203 (10/40/50) | 225 × 225 × 4000 |
| ENV-1D-0209-1-11 | 502S/208/203 (10/50/40) | 225 × 225 × 4000 |
| ENV-1D-0209-1-12 | 502S/205/203 (10/60/30) | 225 × 225 × 4000 |
| ENV-1D-0209-1-13 | 502S/205/203 (10/70/20) | 225 × 225 × 4000 |
| ENV-1D-0209-1-14 | 502S/205 (20/80) | 225 × 225 × 4000 |
| ENV-1D-0209-1-15 | 205/1A (95/5) | 225 × 225 × 4000 |
| ENV-1D-0209-1-16 | 205/2A (90/10) | 225 × 225 × 4000 |
| ENV-1D-0209-1-17 | 205/653H (95/5) | 225 × 225 × 4000 |
| ENV-1D-0209-1-18 | 205/653H (85/15) | 225 × 225 × 4000 |
| ENV-1D-0209-1-19 | 205/653H (70/30) | 225 × 225 × 4000 |

TABLE 1F-continued

Blend compositions and mold designs for SDSA 70

| Sample ID | Resomer polymer name | Mold Design (um) |
|---|---|---|
| ENV-1D-0209-1-20 | 503H/205S (90/10) | 225 × 225 × 4000 |
| ENV-1D-0209-1-21 | 503H/205S (85/15) | 225 × 225 × 4000 |
| ENV-1D-0209-1-22 | 503H/203S (90/10) | 225 × 225 × 4000 |

TABLE 1G

Blend compositions and mold designs for SDSA 75&76

| Sample ID | Resomer polymer name | Mold Design |
|---|---|---|
| ENV-1D-0209-10-1 | 203/752S (85/15) | 200 × 200 × 4500 μm |
| ENV-1D-0209-10-2 | 203/752S (70/30) | 200 × 200 × 4500 μm |
| ENV-1D-0209-10-3 | 203/752S (50/50) | 200 × 200 × 4500 μm |
| ENV-1D-0209-10-4 | 504H/203S (85/15) | 200 × 200 × 4500 μm |
| ENV-1D-0209-10-5 | 504H/203S (70/30) | 200 × 200 × 4500 μm |
| ENV-1D-0209-10-6 | 203/755S (85/15) | 200 × 200 × 4500 μm |
| ENV-1D-0209-10-7 | 203/755S (70/30) | 200 × 200 × 4500 μm |
| ENV-1D-0209-10-8 | 203/755S (50/50) | 200 × 200 × 4500 μm |
| ENV-1D-0209-10-9 | 752S/755S (80/20) | 200 × 200 × 4500 μm |
| ENV-1D-0209-10-10 | 752S/755S (65/35) | 200 × 200 × 4500 μm |
| ENV-1D-0209-10-11 | 203/1A (95/5) | 200 × 200 × 4500 μm |
| ENV-1D-0209-10-12 | 203/1A (80/20) | 200 × 200 × 4500 μm |
| ENV-1D-0209-10-13 | 205/1A (95/5) | 200 × 200 × 4500 μm |
| ENV-1D-0209-10-14 | 205/2A (90/10) | 200 × 200 × 4500 μm |
| ENV-1D-0209-10-15 | 205/653H (85/15) | 200 × 200 × 4500 μm |
| ENV-1D-0209-10-16 | 205/653H (70/30) | 200 × 200 × 4500 μm |
| ENV-1D-0209-10-17 | 205/653H (50/50) | 200 × 200 × 4500 μm |
| ENV-1D-0209-10-18 | 203/653H (85/15) | 200 × 200 × 4500 μm |
| ENV-1D-0209-10-19 | 203/653H (60/40) | 200 × 200 × 4500 μm |
| ENV-1D-0209-10-20 | 203/653H (50/50) | 200 × 200 × 4500 μm |
| ENV-1D-0209-10-21 | 203/502S (50/50) | 200 × 200 × 4500 μm |

TABLE 1H

Blend compositions and mold designs for SDSA 97

| Sample ID | Resomer polymer name | Mold Design |
|---|---|---|
| ENV-1D-0209-12-1 | 203/752S (85/15) | 200 × 200 × 4500 μm |
| ENV-1D-0209-12-2 | 203/752S (85/15) | 200 × 200 × 4500 μm |
| ENV-1D-0209-12-3 | 203/752S (85/15) | 200 × 200 × 4500 μm |

TABLE 1I

Blend compositions and mold designs for Select Formulations

| Sample ID | Resomer polymer name | Mold Design |
|---|---|---|
| RES-DME-0015-6-19 | 203/653H (60/40) | 200 × 200 × 4500 μm |
| RES-DME-0005-27-2 | 203/504H (30/70) | 200 × 200 × 4500 μm |

Example 4. Analysis of Dexamethasone Content

Dexamethasone content was measured by RP-HPLC using a Phenomenex Luna Phenyl-Hexyl, 3 μm particle size, 4.6×100 mm analytical column. The mobile phase consisted of a gradient of 0.1% TFA in purified water and 0.1% TFA in acetonitrile over 5 minutes at 1.0 mL/min. UV absorbance of the steroid was measured at 245 nm. The dexamethasone content for the formulations described in Example 3 (Tables 1A-1I) are provided below in Tables 2A-2I.

TABLE 2A

Dexamethasone Content for SDSA 25

| Sample ID | Total Mass Dexamethasone (ug) |
|---|---|
| ENV-1R-0119-7-1 | 74 |
| ENV-1R-0119-7-2 | 68.1 |
| ENV-1R-0119-7-3 | 55.5 |
| ENV-1R-0119-7-4 | 40 |
| ENV-1R-0119-7-5 | 45.0 |
| ENV-1R-0119-7-6 | 56.3 |
| ENV-1R-0119-7-7 | 71.1 |
| ENV-1R-0119-7-8 | 41.9 |
| ENV-1R-0119-7-9 | 33.2 |
| ENV-1R-0119-7-10 | NA |
| ENV-1R-0119-7-11 | 43.5 |
| ENV-1R-0119-7-12 | 64.1 |
| ENV-1R-0119-7-13 | NA |
| ENV-1R-0119-7-14 | 62 |
| ENV-1R-0119-7-15 | 80 |
| ENV-1R-0119-7-16 | 70 |

TABLE 2B

Dexamethasone Content for SDSA 39

| Sample ID | Total Mass Dexamethasone (ug) |
|---|---|
| ENV-1R-0119-36-1 | 47.3 |
| ENV-1R-0119-36-2 | 48.4 |
| ENV-1R-0119-36-3 | 60.4 |
| ENV-1R-0119-36-4 | 34.5 |
| ENV-1R-0119-36-5 | 48.5 |

TABLE 2C

Dexamethasone Content for SDSA 34

| Sample ID | Total Mass Dexamethasone (ug) |
|---|---|
| ENV-1R-0119-39-1A | NA |
| ENV-1R-0119-39-2A | NA |
| ENV-1R-0119-39-3A | NA |
| ENV-1R-0119-39-4A | NA |
| ENV-1R-0119-39-5A | NA |

TABLE 2D

Dexamethasone Content for SDSA 41

| Sample ID | Total Mass Dexamethasone (ug) |
|---|---|
| ENV-1R-0119-42-1 | 58.7 |
| ENV-1R-0119-42-2 | 52.2 |
| ENV-1R-0119-42-3 | 52.2 |
| ENV-1R-0119-42-4 | 41.5 |
| ENV-1R-0119-42-5 | 58 |
| ENV-1R-0119-42-6 | 46 |
| ENV-1R-0119-42-7 | 16.9 |
| ENV-1R-0119-42-8 | 47.5 |
| ENV-1R-0119-42-9 | 45.2 |
| ENV-1R-0119-42-10 | 47.7 |
| ENV-1R-0119-42-11 | 43.8 |
| ENV-1R-0119-42-12 | 44.6 |

TABLE 2D-continued

Dexamethasone Content for SDSA 41

| Sample ID | Total Mass Dexamethasone (ug) |
|---|---|
| ENV-1R-0119-42-13 | 65.2 |
| ENV-1R-0119-42-14 | 59.1 |

TABLE 2E

Dexamethasone Content for SDSA 53

| Sample ID | Total Mass Dexamethasone (ug) |
|---|---|
| ENV-1R-0119-45-1 | 306.5 |
| ENV-1R-0119-45-2 | 318.8 |
| ENV-1R-0119-45-3 | 318.3 |
| ENV-1R-0119-45-4 | 314.8 |
| ENV-1R-0119-45-5 | 198.4 |
| ENV-1R-0119-45-6 | 195 |
| ENV-1R-0119-45-7 | 242.2 |
| ENV-1R-0119-45-8 | 294.7 |

TABLE 2F

Dexamethasone Content for SDSA 75&76

| Sample ID | Total Mass Dexamethasone (ug) |
|---|---|
| ENV-1D-0209-10-1 | 88.9 ± 2.9 |
| ENV-1D-0209-10-2 | 112.4 ± 4.5 |
| ENV-1D-0209-10-3 | 80.6 ± 5.5 |
| ENV-1D-0209-10-4 | 74.8 ± 5.3 |
| ENV-1D-0209-10-5 | 81.7 ± 3.6 |
| ENV-1D-0209-10-6 | 78.5 ± 4.5 |
| ENV-1D-0209-10-7 | 80.1 ± 6.8 |
| ENV-1D-0209-10-8 | 76.6 ± 3.1 |
| ENV-1D-0209-10-9 | 94.9 ± 7.7 |
| ENV-1D-0209-10-10 | 82.0 ± 6.0 |
| ENV-1D-0209-10-11 | 93.3 ± 4.3 |
| ENV-1D-0209-10-12 | 89.7 ± 11.8 |
| ENV-1D-0209-10-13 | 73.9 ± 10.4 |
| ENV-1D-0209-10-14 | 53.7 ± 2.7 |
| ENV-1D-0209-10-15 | 79.8 ± 1.1 |
| ENV-1D-0209-10-16 | 91.9 ± 2.8 |
| ENV-1D-0209-10-17 | 79.4 ± 6.0 |
| ENV-1D-0209-10-18 | 90.1 ± 3.3 |
| ENV-1D-0209-10-19 | 83.6 ± 6.3 |
| ENV-1D-0209-10-20 | 84.9 ± 7.1 |
| ENV-1D-0209-10-21 | 85.0 ± 9.1 |

TABLE 2G

Dexamethasone Content for SDSA 70

| Sample ID | Total Mass Dexamethasone (ug) |
|---|---|
| ENV-1D-0209-1-1 | 59.3 ± 2.7 |
| ENV-1D-0209-1-2 | 51.7 ± 1.4 |
| ENV-1D-0209-1-3 | 51.7 ± 5.2 |
| ENV-1D-0209-1-4 | 52.3 ± 1.2 |
| ENV-1D-0209-1-5 | 54.2 ± 4.3 |
| ENV-1D-0209-1-6 | 56.5 ± 4.0 |
| ENV-1D-0209-1-7 | 55.2 ± 1.1 |
| ENV-1D-0209-1-8 | 58.9 ± 3.1 |
| ENV-1D-0209-1-9 | 51.3 ± 0.9 |

TABLE 2G-continued

Dexamethasone Content for SDSA 70

| Sample ID | Total Mass Dexamethasone (ug) |
|---|---|
| ENV-1D-0209-1-10 | 47.3 ± 7.8 |
| ENV-1D-0209-1-11 | 70.6 ± 2.2 |
| ENV-1D-0209-1-12 | 49.8 ± 1.5 |
| ENV-1D-0209-1-13 | 57.0 ± 0.7 |
| ENV-1D-0209-1-14 | 52.8 ± 2.0 |
| ENV-1D-0209-1-15 | 51.0 ± 2.4 |
| ENV-1D-0209-1-16 | 51.2 ± 1.2 |
| ENV-1D-0209-1-17 | 58.7 ± 10.3 |
| ENV-1D-0209-1-18 | 51.7 ± 5.7 |
| ENV-1D-0209-1-19 | 68.3 ± 23.7 |
| ENV-1D-0209-1-20 | 62.5 ± 3.4 |
| ENV-1D-0209-1-21 | 45.9 ± 3.7 |
| ENV-1D-0209-1-22 | 47.4 ± 7.9 |

TABLE 2H

Dexamethasone Content for Select Formulations

| Sample ID | Total Mass Dexamethasone (ug) |
|---|---|
| RES-DME-0015-6-19 | 96.5 ± 5.6 |
| RES-DME-0005-27-2 | 100.8 ± 11.0 |

Example 6. In-Vitro Release Analysis of Select Implant Formulations

In vitro release of dexamethasone was determined for the implants of Example 3. Single implants were placed into a 2 mL HPLC vial and were incubated at 37 C in 1 mL of 1×PBS containing 0.1% TRITON-X surfactant. At each time point of interest, the media was removed for analysis. The media was then replaced with 1 mL of fresh media. The media that was removed was analyzed for dexamethasone released via the HPLC method of Example 4. See FIGS. 1-9 for in-vitro release curves for dexamethasone implant formulations in Tables 1A-1I.

The above data indicates that the implant can be formulated to release dexamethasone for 4-6 months.

Example 7. Fluocinolone Acetonide Implant Fabrication

A series of implants were fabricated utilizing the polymer matrix/therapeutic agent blends obtained from the method described in Example 1.1 and the molds described in Example 2. The therapeutic agent was fluocinolone acetonide. The implants were fabricated as described in Example 3. The fluocinolone acetonide implants are provided below in Tables 3A-3E.

TABLE 3A

Blend compositions and mold designs for SDSA 27

| Sample ID | Resomer polymer name | Mold Design |
|---|---|---|
| ENV-1R-0119-33-1 | 208/2A 85/15 | 225 × 225 × 2925 μm |
| ENV-1R-0119-33-2 | 208/2A 70/30 | 225 × 225 × 2925 μm |
| ENV-1R-0119-33-3 | 203/2A 50/50 | 225 × 225 × 2925 μm |
| ENV-1R-0119-33-4 | 203/2A 70/30 | 225 × 225 × 2925 μm |

TABLE 3A-continued

Blend compositions and mold designs for SDSA 27

| Sample ID | Resomer polymer name | Mold Design |
|---|---|---|
| ENV-1R-0119-33-5 | 203/2A 85/15 | 225 × 225 × 2925 μm |
| ENV-1R-0119-33-6 | 203 | 225 × 225 × 2925 μm |
| ENV-1R-0119-33-7 | 203/1A 95/5 | 225 × 225 × 2925 μm |
| ENV-1R-0119-33-8 | 502S | 225 × 225 × 2925 μm |
| ENV-1R-0119-33-9 | 502S/502H 85/15 | 225 × 225 × 2925 μm |
| ENV-1R-0119-33-10 | 502S/502H 95/5 | 225 × 225 × 2925 μm |

TABLE 3B

Blend compositions and mold designs for SDSA 35

| Sample ID | Resomer polymer name | Mold Design |
|---|---|---|
| ENV-1R-0119-38-1 | 208/2A (70/30) | 225 × 225 × 2925 μm |
| ENV-1R-0119-38-2 | 208/203 (70/30) | 225 × 225 × 2925 μm |
| ENV-1R-0119-38-3 | 208/203 (70/30) | 225 × 225 × 2925 μm |
| ENV-1R-0119-38-4 | 208/1A (70/30) | 225 × 225 × 2925 μm |
| ENV-1R-0119-38-5 | 208/1A (85/15) | 225 × 225 × 2925 μm |
| ENV-1R-0119-38-6 | 207/203 (70/30) | 225 × 225 × 2925 μm |
| ENV-1R-0119-38-7 | 207/2A (70/30) | 225 × 225 × 2925 μm |
| ENV-1R-0119-38-8 | 205/203 (70/30) | 225 × 225 × 2925 μm |
| ENV-1R-0119-38-9 | 203/205 (70/30) | 225 × 225 × 2925 μm |
| ENV-1R-0119-38-10 | 203/207 (70/30) | 225 × 225 × 2925 μm |
| ENV-1R-0119-38-11 | 203/208 (70/30) | 225 × 225 × 2925 μm |
| ENV-1R-0119-38-12 | 203/208 (50/50) | 225 × 225 × 2925 μm |

TABLE 3C

Blend compositions and mold designs for SDSA 46

| Sample ID | Resomer polymer name | Mold Design |
|---|---|---|
| ENV-1R-0119-44-1 | 504H/203S (50/50) | 225 × 225 × 2925 μm |
| ENV-1R-0119-44-2 | 504H/203S (70/30) | 225 × 225 × 2925 μm |
| ENV-1R-0119-44-3 | 504H/203S (85/15) | 225 × 225 × 2925 μm |
| ENV-1R-0119-44-4 | 503H/203S (50/50) | 225 × 225 × 2925 μm |
| ENV-1R-0119-44-5 | 503H/203S (70/30) | 225 × 225 × 2925 μm |
| ENV-1R-0119-44-6 | 503H/203S (85/15) | 225 × 225 × 2925 μm |
| ENV-1R-0119-44-7 | 503H/203S (30/70) | 225 × 225 × 2925 μm |
| ENV-1R-0119-44-8 | 653H/203S (50/50) | 225 × 225 × 2925 μm |
| ENV-1R-0119-44-9 | 653H/203S (70/30 | 225 × 225 × 2925 μm |
| ENV-1R-0119-44-10 | 653H/203S (85/15) | 225 × 225 × 2925 μm |

TABLE 3D

Blend compositions and mold designs for SDSA 56

| Sample ID | Resomer polymer name | Mold Design |
|---|---|---|
| ENV-1R-0119-49-1 | 203S/653H (70/30) | 225 × 225 × 2925 μm |
| ENV-1R-0119-49-2 | 203S/653H (30/70) | 225 × 225 × 2925 μm |
| ENV-1R-0119-49-3 | 203S/653H (85/15) | 225 × 225 × 2925 μm |
| ENV-1R-0119-49-4 | 203S/653H (95/5) | 225 × 225 × 2925 μm |
| ENV-1R-0119-49-5 | 205S/653H (85/15) | 225 × 225 × 2925 μm |
| ENV-1R-0119-49-6 | 205S/653H (70/30) | 225 × 225 × 2925 μm |
| ENV-1R-0119-49-7 | 203S/503H (70/30) | 225 × 225 × 2925 μm |
| ENV-1R-0119-49-8 | 203S/503H (85/15) | 225 × 225 × 2925 μm |
| ENV-1R-0119-49-9 | 203S/503H (95/5) | 225 × 225 × 2925 μm |
| ENV-1R-0119-49-10 | 205S/503H (70/30) | 225 × 225 × 2925 μm |
| ENV-1R-0119-49-11 | 205S/504H (70/30) | 225 × 225 × 2925 μm |
| ENV-1R-0119-49-12 | 205S/504H (85/15) | 225 × 225 × 2925 μm |
| ENV-1R-0119-49-13 | 205S/504H (90/10) | 225 × 225 × 2925 μm |

TABLE 3E

Blend compositions and mold designs for SDSA 59

| Sample ID | Resomer polymer name | Mold Design |
|---|---|---|
| ENV-1R-0119-51-1 | 203/1A(9515) | 100 × 100 × 1500 μm |
| ENV-1R-0119-51-2 | 203/2A(70/30) | 100 × 100 × 1500 μm |
| ENV-1R-0119-51-3 | 203/2A(50/50) | 100 × 100 × 1500 μm |
| ENV-1R-0119-51-4 | 208/1A(70/30) | 100 × 100 × 1500 μm |
| ENV-1R-0119-51-5 | 208/1A(80/20) | 100 × 100 × 1500 μm |
| ENV-1R-0119-51-6 | 203/205 (50/50) | 100 × 100 × 1500 μm |
| ENV-1R-0119-51-7 | R203/R207 (50/50) | 100 × 100 × 1500 μm |
| ENV-1R-0119-51-8 | R203/R208 (50/50) | 100 × 100 × 1500 μm |
| ENV-1R-0119-51-9 | RG502S/RG 502H (70/30) | 100 × 100 × 1500 μm |
| ENV-1R-0119-51-10 | RG502S/RG 502H (85/15) | 100 × 100 × 1500 μm |
| ENV-1R-0119-51-11 | 203S/653H (70/30) | 100 × 100 × 1500 μm |
| ENV-1R-0119-51-12 | 203S/653H (30/70) | 100 × 100 × 1500 μm |
| ENV-1R-0119-51-13 | 203S/653H (85/15) | 100 × 100 × 1500 μm |
| ENV-1R-0119-51-14 | 203S/653H (95/5) | 100 × 100 × 1500 μm |
| ENV-1R-0119-51-15 | 205S/653H (85/15) | 100 × 100 × 1500 μm |
| ENV-1R-0119-51-16 | 205S/653H (70/30) | 100 × 100 × 1500 μm |
| ENV-1R-0119-51-17 | 203S/503H (70/30) | 100 × 100 × 1500 μm |
| ENV-1R-0119-51-18 | 203S/503H (80/20) | 100 × 100 × 1500 μm |
| ENV-1R-0119-51-19 | 203S/503H (60/40) | 100 × 100 × 1500 μm |
| ENV-1R-0119-51-20 | 205S/503H (70/30) | 100 × 100 × 1500 μm |
| ENV-1R-0119-51-21 | 205S/504H (70/30) | 100 × 100 × 1500 μm |
| ENV-1R-0119-51-22 | 205S/504H (85/15) | 100 × 100 × 1500 μm |
| ENV-1R-0119-51-23 | 205S/504H (90/10) | 100 × 100 × 1500 μm |
| ENV-1R-0119-51-24 | RG 502S | 100 × 100 × 1500 μm |

Example 8. Analysis of Fluocinolone Acetonide Content

Fluocinolone acetonide content was measured by RP-HPLC using a Phenomenex Luna Phenyl-Hexyl, 3 μm particle size, 4.6×100 mm analytical column. The mobile phase consisted of a gradient of 0.1% TFA in purified water and 0.1% TFA in acetonitrile over 5 minutes at 1.0 mL/min. UV absorbance of the steroid was measured at 244 nm. The fluocinolone acetonide content for the formulations described in Example 7 (Tables 3A-3E) are provided below in Table 4.

TABLE 4

Fluocinolone Acetonide Content

| Sample ID | SDSA | Implant Size (μm) | Polymer | μg/implant |
|---|---|---|---|---|
| ENV-1R-0119-33-1 | 27 | 225 × 225 × 2925 | 208/2A 85/15 | 40.7 |
| ENV-1R-0119-33-2 | 27 | 225 × 225 × 2925 | 208/2A 70/30 | 40 |
| ENV-1R-0119-33-3 | 27 | 225 × 225 × 2925 | 203/2A 50/50 | 49.8 |
| ENV-1R-0119-33-4 | 27 | 225 × 225 × 2925 | 203/2A 70/30 | 47 |
| ENV-1R-0119-33-5 | 27 | 225 × 225 × 2925 | 203/2A 85/15 | 52.6 |
| ENV-1R-0119-33-6 | 27 | 225 × 225 × 2925 | 203 | 45.3 |
| ENV-1R-0119-33-7 | 27 | 225 × 225 × 2925 | 203/1A 95/5 | 40.7 |
| ENV-1R-0119-33-8 | 27 | 225 × 225 × 2925 | 502S | 44.8 |
| ENV-1R-0119-33-9 | 27 | 225 × 225 × 2925 | 502S/502H 85/15 | 57.9 |
| ENV-1R-0119-33-10 | 27 | 225 × 225 × 2925 | 502S/502H 95/5 | 45.1 |
| ENV-1R-0119-38-1 | 35 | 225 × 225 × 2925 | 208/2A (70/30) | NA |

TABLE 4-continued

Fluocinolone Acetonide Content

| Sample ID | SDSA | Implant Size (μm) | Polymer | μg/implant |
|---|---|---|---|---|
| ENV-1R-0119-38-2 | 35 | 225 × 225 × 2925 | 208/203 (70/30) | NA |
| ENV-1R-0119-38-3 | 35 | 225 × 225 × 2925 | 208/203 (70/30) | NA |
| ENV-1R-0119-38-4 | 35 | 225 × 225 × 2925 | 208/1A (70/30) | NA |
| ENV-1R-0119-38-5 | 35 | 225 × 225 × 2925 | 208/1A (85/15) | NA |
| ENV-1R-0119-38-6 | 35 | 225 × 225 × 2925 | 207/203 (70/30) | NA |
| ENV-1R-0119-38-7 | 35 | 225 × 225 × 2925 | 207/2A (70/30) | NA |
| ENV-1R-0119-38-8 | 35 | 225 × 225 × 2925 | 205/203 (70/30) | NA |
| ENV-1R-0119-38-9 | 35 | 225 × 225 × 2925 | 203/205 (70/30) | NA |
| ENV-1R-0119-38-10 | 35 | 225 × 225 × 2925 | 203/207 (70/30) | NA |
| ENV-1R-0119-38-11 | 35 | 225 × 225 × 2925 | 203/208 (70/30) | NA |
| ENV-1R-0119-38-12 | 35 | 225 × 225 × 2925 | 203/208 (50/50) | NA |
| ENV-1R-0119-44-1 | 44 | 225 × 225 × 2925 | 504H/203S (50/50) | 34.9 |
| ENV-1R-0119-44-1 | 44 | 225 × 225 × 2925 | 504H/203S (50/50) | 34.9 |
| ENV-1R-0119-44-2 | 44 | 225 × 225 × 2925 | 504H/203S (70/30) | 41.8 |
| ENV-1R-0119-44-3 | 44 | 225 × 225 × 2925 | 504H/203S (85/15) | 45 |
| ENV-1R-0119-44-4 | 44 | 225 × 225 × 2925 | 503H/203S (50/50) | 32.5 |
| ENV-1R-0119-44-5 | 44 | 225 × 225 × 2925 | 503H/203S (70/30) | 46.5 |
| ENV-1R-0119-44-6 | 44 | 225 × 225 × 2925 | 503H/203S (85/15) | 41.6 |
| ENV-1R-0119-44-7 | 44 | 225 × 225 × 2925 | 503H/203S (30/70) | 35.1 |
| ENV-1R-0119-44-8 | 44 | 225 × 225 × 2925 | 653H/203S (50/50) | NA |
| ENV-1R-0119-44-9 | 44 | 225 × 225 × 2925 | 653H/203S (70/30) | 44.3 |
| ENV-1R-0119-44-10 | 44 | 225 × 225 × 2925 | 653H/203S (85/15) | 44 |
| ENV-1R-0119-49-1 | 56 | 225 × 225 × 2925 | 203S/653H (70/30) | NA |
| ENV-1R-0119-49-2 | 56 | 225 × 225 × 2925 | 203S/653H (30/70) | NA |
| ENV-1R-0119-49-3 | 56 | 225 × 225 × 2925 | 203S/653H (85/15) | NA |
| ENV-1R-0119-49-4 | 56 | 225 × 225 × 2925 | 203S/653H (95/5) | NA |
| ENV-1R-0119-49-5 | 56 | 225 × 225 × 2925 | 205S/653H (85/15) | NA |
| ENV-1R-0119-49-6 | 56 | 225 × 225 × 2925 | 205S/653H (70/30) | NA |
| ENV-1R-0119-49-7 | 56 | 225 × 225 × 2925 | 203S/503H (70/30) | NA |
| ENV-1R-0119-49-8 | 56 | 225 × 225 × 2925 | 203S/503H (85/15) | NA |
| ENV-1R-0119-49-9 | 56 | 225 × 225 × 2925 | 203S/503H (95/5) | NA |
| ENV-1R-0119-49-10 | 56 | 225 × 225 × 2925 | 205S/503H (70/30) | NA |
| ENV-1R-0119-49-11 | 56 | 225 × 225 × 2925 | 205S/504H (70/30) | NA |
| ENV-1R-0119-49-12 | 56 | 225 × 225 × 2925 | 205S/504H (85/15) | NA |
| ENV-1R-0119-49-13 | 56 | 225 × 225 × 2925 | 205S/504H (90/10) | NA |
| ENV-1R-0119-51-1 | 57 | 150 × 150 × 1500 | 203S/653H (70/30) | NA |
| ENV-1R-0119-51-2 | 57 | 150 × 150 × 1500 | 203S/653H (30/70) | 13.5 |
| ENV-1R-0119-51-3 | 57 | 150 × 150 × 1500 | 203S/653H (85/15) | 13.2 |
| ENV-1R-0119-51-4 | 57 | 150 × 150 × 1500 | 203S/653H (95/5) | 12.6 |
| ENV-1R-0119-51-5 | 57 | 150 × 150 × 1500 | 205S/653H (85/15) | 11.5 |
| ENV-1R-0119-51-6 | 57 | 150 × 150 × 1500 | 205S/653H (70/30) | 14.8 |
| ENV-1R-0119-51-7 | 57 | 150 × 150 × 1500 | 203S/503H (70/30) | 13.7 |
| ENV-1R-0119-51-8 | 57 | 150 × 150 × 1500 | 203S/503H (85/15) | 13.4 |
| ENV-1R-0119-51-9 | 57 | 150 × 150 × 1500 | 203S/503H (95/5) | 9.4 |
| ENV-1R-0119-51-10 | 57 | 150 × 150 × 1500 | 205S/503H (70/30) | 12.4 |
| ENV-1R-0119-51-11 | 57 | 150 × 150 × 1500 | 205S/504H (70/30) | 13.7 |
| ENV-1R-0119-51-12 | 57 | 150 × 150 × 1500 | 205S/504H (85/15) | 11.6 |
| ENV-1R-0119-51-13 | 57 | 150 × 150 × 1500 | 205S/504H (90/10) | 11.3 |
| ENV-1R-0119-51-14 | 57 | 150 × 150 × 1500 | RG 502S | 14.2 |
| ENV-1R-0119-51-15 | 57 | 150 × 150 × 1500 | 502S/502H (50/50) | 9.6 |
| ENV-1R-0119-51-16 | 57 | 150 × 150 × 1500 | R203/DLG 1A (95/5) | 13.1 |
| ENV-1R-0119-51-17 | 57 | 150 × 150 × 1500 | R208/DLG 2A (70/30) | NA |
| ENV-1R-0119-51-18 | 57 | 150 × 150 × 1500 | R207/R203S (70/30) | NA |
| ENV-1R-0119-51-19 | 57 | 150 × 150 × 1500 | R207/R203S (60/40) | NA |
| ENV-1R-0119-51-20 | 57 | 150 × 150 × 1500 | R207/DLG 2A (70/30) | NA |
| ENV-1R-0119-51-21 | 57 | 150 × 150 × 1500 | R205/DLG 2A (70/30) | 10.5 |
| ENV-1R-0119-51-22 | 57 | 150 × 150 × 1500 | R207/DLG 2A (85/15) | NA |
| ENV-1R-0119-51-23 | 57 | 150 × 150 × 1500 | 203/1A (95/5) | NA |
| ENV-1R-0119-51-24 | 57 | 150 × 150 × 1500 | 502S/502H (85/15) | NA |
| ENV-1R-0119-51-24 | 57 | 150 × 150 × 1500 | 502S/502H (85/15) | NA |
| ENV-1R-0119-51-7 | 57 | 150 × 150 × 1500 | 203S/503H (70/30) | 13.7 |
| ENV-1R-0119-51-8 | 57 | 150 × 150 × 1500 | 203S/503H (85/15) | 13.4 |
| ENV-1R-0119-51-9 | 57 | 150 × 150 × 1500 | 203S/503H (95/5) | 9.4 |
| ENV-1R-0119-51-10 | 57 | 150 × 150 × 1500 | 205S/503H (70/30) | 12.4 |
| ENV-1R-0119-51-11 | 57 | 150 × 150 × 1500 | 205S/504H (70/30) | 13.7 |
| ENV-1R-0119-51-12 | 57 | 150 × 150 × 1500 | 205S/504H (85/15) | 11.6 |
| ENV-1R-0119-51-13 | 57 | 150 × 150 × 1500 | 205S/504H (90/10) | 11.3 |
| ENV-1R-0119-51-14 | 57 | 150 × 150 × 1500 | RG 502S | 14.2 |
| ENV-1R-0119-51-15 | 57 | 150 × 150 × 1500 | 502S/502H (50/50) | 9.6 |
| ENV-1R-0119-51-16 | 57 | 150 × 150 × 1500 | R203/DLG 1A (95/5) | 13.1 |
| ENV-1R-0119-51-17 | 57 | 150 × 150 × 1500 | R208/DLG 2A (70/30) | NA |
| ENV-1R-0119-51-18 | 57 | 150 × 150 × 1500 | R207/R203S (70/30) | NA |
| ENV-1R-0119-51-19 | 57 | 150 × 150 × 1500 | R207/R203S (60/40) | NA |
| ENV-1R-0119-51-20 | 57 | 150 × 150 × 1500 | R207/DLG 2A (70/30) | NA |

TABLE 4-continued

Fluocinolone Acetonide Content

| Sample ID | SDSA | Implant Size (μm) | Polymer | μg/implant |
|---|---|---|---|---|
| ENV-1R-0119-51-21 | 57 | 150 × 150 × 1500 | R205/DLG 2A (70/30) | 10.5 |
| ENV-1R-0119-51-22 | 57 | 150 × 150 × 1500 | R207/DLG 2A (85/15) | NA |
| ENV-1R-0119-51-23 | 57 | 150 × 150 × 1500 | 203/1A (95/5) | NA |
| ENV-1R-0119-51-24 | 57 | 150 × 150 × 1500 | 502S/502H (85/15) | NA |

Example 9. In-Vitro Release Analysis of Select Implant Formulations Containing Fluocinolone Acetonide In vitro release of fluocinolone acetonide was determined for the implants of Example 3. Single implants were placed into a 2 mL HPLC vial and were incubated at 37C in 1 mL of 1×PBS containing 0.1% TRITON-X surfactant. At each time point of interest, the media was removed for analysis. The media was then replaced with 1 mL of fresh media. The media that was removed was analyzed for fluocinolone acetonide via Reverse Phase HPLC. See FIGS. 10-14 for in-vitro of fluocinolone acetonide implant formulations in Tables 3A-3E.

The above data indicates that the implant can be formulated to controllably release fluocinolone acetonide for 4-6 months.

Example 10. Dexamethasone Particle Fabrication

A series of particles were fabricated utilizing the solvent mixing polymer matrix/therapeutic agent blends of Example 1 and the molds of Example 2. The polymer matrix/therapeutic agent were formed into a dry film on a plastic sheet. The blend was then covered with the mold of Example 2 which had the desired dimensions. Particles were then formed using the PRINT process. The dexamethasone particles are provided below in Tables 5A-5D

TABLE 5A

Blend compositions and mold designs for SDSA 51/52

| Sample ID | Resomer polymer name | Mold Design |
|---|---|---|
| ENV-1R-0159-82-A | 203 | 25 × 25 × 50 μm |
| ENV-1R-0159-82-B | 504S | 25 × 25 × 50 μm |
| ENV-1R-0159-82-C | 203/504S (50/50) | 25 × 25 × 50 μm |

TABLE 5B

Blend compositions and mold designs for SDSA 47/48

| Sample ID | Resomer polymer name | Mold Design |
|---|---|---|
| ENV-1R-0159-87-A | 503S | 12.5 × 12.5 × 25 μm |
| ENV-1R-0159-87-B | 503S | 25 × 25 × 25 μm |
| ENV-1R-0159-87-C | 503S | 25 × 25 × 50 μm |
| ENV-1R-0159-87-D | 503S | 50 × 50 × 50 μm |

TABLE 5C

Blend compositions and mold designs for SDSA 43

| Sample ID | Resomer polymer name | Mold Design |
|---|---|---|
| ENV-1R-0159-57-A | 203/504S (75/25) | 25 × 25 × 50 μm |
| ENV-1R-0159-57-B | 203/504S (50/50) | 25 × 25 × 50 μm |
| ENV-1R-0159-57-C | 203/504S (25/75) | 25 × 25 × 50 μm |
| ENV-1R-0159-57-D | 203/503H (75/25) | 25 × 25 × 50 μm |
| ENV-1R-0159-57-E | 203/503H (50/50) | 25 × 25 × 50 μm |
| ENV-1R-0159-57-F | 203/503H (25/75) | 25 × 25 × 50 μm |
| ENV-1R-0159-57-G | 504S/203/503S (60/20/20) | 25 × 25 × 50 μm |
| ENV-1R-0159-57-H | 504S/203/503S (33.3/33.3/33.3) | 25 × 25 × 50 μm |
| ENV-1R-0159-57-I | 504S/203/503H (60/20/20) | 25 × 25 × 50 μm |
| ENV-1R-0159-57-J | 504S/203/503H (33.3/33.3/33.3) | 25 × 25 × 50 μm |

TABLE 5D

Blend compositions and mold designs for SDSA 38

| Sample ID | Resomer polymer name | Mold Design |
|---|---|---|
| ENV-1R-0159-44-A | 203 | 50 × 50 × 50 μm |
| ENV-1R-0159-44-B | 503S | 50 × 50 × 50 μm |
| ENV-1R-0159-44-C | 503H | 50 × 50 × 50 μm |
| ENV-1R-0159-44-D | 504S | 50 × 50 × 50 μm |
| ENV-1R-0159-44-E | 858S | 50 × 50 × 50 μm |

Example 11. Analysis of Dexamethasone Content

Dexamethasone content was measured by RP-HPLC using a Phenomenex Luna Phenyl-Hexyl, 3 μm particle size, 4.6×100 mm analytical column. The mobile phase consisted of a gradient of 0.1% TFA in purified water and 0.1% TFA in acetonitrile over 5 minutes at 1.0 mL/min. UV absorbance of the steroid was measured at 244 nm. The dexamethasone content for the formulations described in Example 10 (Tables 5A-5E) are provided below in Table 6. Additional formulations are also provided in Table 6.

TABLE 6

Dexamethasone Content

| Sample ID | SDSA ID | Particle Size (μm) | Polymer | % DXM (measured) |
|---|---|---|---|---|
| ENV-1R-0143-9A | 19 | 25 × 25 × 50 | 203S | 10 |
| ENV-1R-0143-9B | 19 | 25 × 25 × 50 | 503S | 23 |
| ENV-1R-0143-9C | 19 | 25 × 25 × 50 | 504H | 13 |
| ENV-1R-0143-9D | 19 | 25 × 25 × 50 | 504S | 16 |
| ENV-1R-0143-9E | 19 | 25 × 25 × 50 | 504S | 23 |
| ENV-1R-0143-9F | 19 | 25 × 25 × 50 | 504S | 17 |
| ENV-1R-0143-33A | 22 | 12.5 × 12.5 × 25 | 203S | 18 |
| ENV-1R-0143-33B | 22 | 25 × 25 × 25 | 203S | 18 |
| ENV-1R-0143-33C | 22 | 25 × 25 × 50 | 203S | 17 |
| ENV-1R-0143-33D | 22 | 12.5 × 12.5 × 25 | 504S | 18 |
| ENV-1R-0143-33E | 22 | 25 × 25 × 25 | 504S | 16 |
| ENV-1R-0143-33F | 22 | 25 × 25 × 50 | 504S | 15 |
| ENV-1R-0143-46A | 24 | 25 × 25 × 50 | 203S | 14 |
| ENV-1R-0143-46K | 24 | 25 × 25 × 50 | 504S | 13 |
| ENV-1R-0159-9A | 36 | 50 × 50 × 30 | 203S | 20* |
| ENV-1R-0159-9B | 36 | 50 × 50 × 30 | 503S | 20* |
| ENV-1R-0159-9C | 36 | 50 × 50 × 30 | 503H | 20* |
| ENV-1R-0159-9D | 36 | 50 × 50 × 30 | 504S | 20* |
| ENV-1R-0159-9E | 36 | 50 × 50 × 30 | 858S | 20* |
| ENV-1R-0159-18A | 37 | 25 × 25 × 50 | 207S/Tocopherol | 15* |
| ENV-1R-0159-18B | 37 | 25 × 25 × 50 | 208S/Tocopherol | 20* |
| ENV-1R-0159-18C | 37 | 25 × 25 × 50 | 858S/Tocopherol | 15* |
| ENV-1R-0159-44A | 38 | 50 × 50 × 50 | 203S | 20* |
| ENV-1R-0159-44B | 38 | 50 × 50 × 50 | 503S | 20* |

TABLE 6-continued

Dexamethasone Content

| Sample ID | SDSA ID | Particle Size (μm) | Polymer | % DXM (measured) |
|---|---|---|---|---|
| ENV-1R-0159-44C | 38 | 50 × 50 × 50 | 503H | 20* |
| ENV-1R-0159-44D | 38 | 50 × 50 × 50 | 504S | 20* |
| ENV-1R-0159-44E | 38 | 50 × 50 × 50 | 858S | 20* |
| ENV-1R-0159-57A-C | 43 | 25 × 25 × 50 | 203S/504S blends (75/25, 50/50, 25/75) | 20* |
| ENV-1R-0159-57D-F | 43 | 25 × 25 × 50 | 203S/503H blends (75/25, 50/50, 25/75) | 20* |
| ENV-1R-0159-57G-H | 43 | 25 × 25 × 50 | 203S/504S/503S blends (20/60/20, 33/33/33) | 20* |
| ENV-1R-0159-57i-J | 43 | 25 × 25 × 50 | 203S/504S/503H blends (20/60/20, 33/33/33) | 20* |
| ENV-1R-0159-58A | 44 | 12.5 × 12.5 × 25 | 504S | 20* |
| ENV-1R-0159-58B | 44 | 25 × 25 × 50 | 504S | 20* |
| ENV-1R-0159-58C | 44 | 50 × 50 × 50 | 504S | 20* |
| ENV-1R-0159-87A | 47/48 | 12.5 × 12.5 × 25 | 503S | 20* |
| ENV-1R-0159-87B | 47/48 | 25 × 25 × 25 | 503S | 20* |
| ENV-1R-0159-87C | 47/48 | 25 × 25 × 50 | 503S | 20* |
| ENV-1R-0159-87D | 47/48 | 50 × 50 × 50 | 503S | 20* |
| ENV-1R-0159-82A | 51/52 | 25 × 25 × 50 | 504S | 12 |
| ENV-1R-0159-82B | 51/52 | 25 × 25 × 50 | 203S | 13 |
| ENV-1R-0159-82C | 51/52 | 25 × 25 × 50 | 504S/203S | 12 |
| ENV-1R-0155-147 | 58 | 25 × 25 × 50 | 203S | 20* |
| ENV-1R-0159-125A | 60 | 25 × 25 × 50 | 503S | 20* |
| ENV-1R-0159-125B | 60 | 25 × 25 × 50 | 503H | 20* |

*theoretical

Example 12. In-Vitro Release Analysis of Particle Suspension Formulations Containing Dexamethasone In vitro release of dexamethasone was determined for the particles of Example 8. Particles in water were centrifuged briefly to remove supernatant and resuspended in a 1% hyaluronic acid solution. Particle concentration was determined by gravimetric weight and 2.5 to 5 mg of particles were added to 50 mL tubes and were incubated at 37C in 50 mL of 1×PBS or 1×PBS containing 0.1% TRITON-X surfactant. At each time point of interest, 1 mL of media was removed for analysis. The media that was removed was analyzed for dexamethasone released via the HPLC method of Example 4. In-vitro release data for the formulations in Tables 4A-4D are shown in FIGS. 15-18.

The above data indicates that PRINT particle suspensions can be formulated to release dexamethasone for 4-6 months.

Example 13. ENV1105 Dexamethasone Intravitreal Implant Nonclinical Studies

The present example demonstrates an embodiment of the disclosure, termed ENV1105, which is a dexamethasone intravitreal implant for the treatment of diabetic macular edema. Embodiments of the dexamethasone intravitreal implant are provided above in Example 3, Tables 1A-1I.

ENV1105 dexamethasone intravitreal implant is an injectable dexamethasone implant formulation using a biocompatible PLGA and/or PLA-based drug delivery system. The implant is designed for ophthalmic administration via intravitreal injection with a duration of action of 4-6 months. The drug delivery system is comprised of a blend of PLGA and/or PLA that functions as binder and release modifier, and was designed for slow erosion of the implant with concurrent release of dexamethasone.

The bioavailability and sustained therapeutic effect of ENV1105 over 4-6 months is governed by multiple factors, including route of administration, erosion of the implant, and the physicochemical properties of the drug substance dexamethasone.

The present example illustrates the functionality of various formulation of ENV1105 intravitreal implants.

Characterization and Overview of ENV1105

ENV1105 is a biocompatible implant formulation containing the corticosteroid dexamethasone in a PLA and/or PLGA-based drug delivery system. The characteristics of the ENV1105 implants administered in nonclinical studies can be found in examples 3 through 11.

ENV1105 implants can be loaded into the needle of a single-use implant applicator and delivered directly into the vitreous. ENV1105 was designed to deliver therapeutic concentrations of dexamethasone for approximately 4-6 months in certain aspects.

ENV1105 implants, of various configurations, have been well tolerated in efficacy and tolerability studies in albino rabbits following intravitreal administration. This generalization will be supported by the below data.

Following intravitreal insertion, ENV1105 implants are retained in the vitreous, remain largely immobile, cause no apparent discomfort, and disintegrate over time.

Potential Mechanism of Action for ENV1105 Embodiments

Without wishing to be bound to a particular mechanistic theory of action, the following description provides one possible mechanism of action for the ENV1105 ocular implants disclosed herein.

Corticosteroids inhibit the inflammatory response to a variety of inciting agents. They inhibit edema, fibrin deposition, capillary dilation, leukocyte migration, capillary proliferation, fibroblast proliferation, deposition of collagen, and scar formation associated with inflammation.

Corticosteroid activity is mediated by intracellular activation of the glucocorticoid receptor (GR). Binding of the corticosteroid ligand results in translocation of the ligand-bound GR from the cell cytosol into the nucleus, where it functions as a transcription factor and binds to the glucocorticoid response elements in the promoter regions of responsive genes or interacts directly with other transcription factors. The actions result in consequent anti-inflammatory effects due to down-regulation of pro-inflammatory molecule production. In the eye, corticosteroids are thought to act by the induction of phospholipase A2 inhibitory proteins, collectively called lipocortins. It is postulated that these proteins control the biosynthesis of potent mediators of inflammation such as prostaglandins and leukotrienes by inhibiting the release of their common precursor arachidonic acid (Walner 1986). Dexamethasone, a corticosteroid, has been shown to suppress inflammation by inhibiting multiple inflammatory cytokines resulting in decreased edema, fibrin deposition, capillary leakage and migration of inflammatory cells.

The ENV1105 embodiments can decrease ocular inflammation associated with diabetic macular edema for approximately 4-6 months following a single administration via intravitreal injection, by effectively delivering dexamethasone to targeted areas of the eye in a sustained manner.

Nonclinical Pharmacology of Dexamethasone in Ocular Formulations

Dexamethasone was first approved in the United States as an intravitreal implant in 2009 under the trade name OZURDEX for retinal vein occlusion. Since then, OZURDEX has also been approved by the FDA for non-infectious uveitis and most recently diabetic macular edema. OZURDEX is formulated as an intravitreal implant containing dexamethasone 0.7 mg in the NOVADUR solid polymer drug delivery system. The NOVADUR system contains PLGA (poly lactic-co-glycolic acid) intravitreal polymer matrix without a preservative.

TABLE 8

$K_i$ Values of Dexamethasone and Various Glucocorticoids

| Compound | $K_i$ Value (mol/L) |
|---|---|
| Prednisolone | $3.4 \times 10^{-9} \pm 7.3 \times 10^{-10}$ |
| Betamethasone | $1.7 \times 10^{-9} \pm 3.2 \times 10^{-10}$ |
| Dexamethasone | $1.9 \times 10^{-9} \pm 2.3 \times 10^{-10}$ |

The synthetic glucocorticoid dexamethasone is widely used for systemic and ocular inflammatory conditions. While effective for some types of posterior segment eye disease including uveitis, systemic corticosteroid therapy results in a high rate of serious adverse events and is avoided when possible. Extensive clinical experience attests to the efficacy of corticosteroids for treating ocular anterior segment inflammation (Gaudio 2004). However, topical delivery of corticosteroids, including dexamethasone, is generally ineffective for treatment of posterior ocular disease because the tight cellular junctions at the ocular surface and blood-retinal barrier prevent the medication from reaching the target tissues. Therefore, direct intravitreal injection is the most widely used route of administration for posterior segment eye disease. The disadvantage of this mode of administration is the need for frequent injections, as dexamethasone is a small molecule that is rapidly cleared from the vitreous, with an estimated vitreal half-life of 5.5 hours in humans. To overcome this limitation, sustained-release preparations for intravitreal use have been developed. Glucocorticoids such as dexamethasone exert their anti-inflammatory effects by influencing multiple signal transduction pathways, including VEGF. By binding to cytoplasmic glucocorticoid receptors, corticosteroids in high doses increase the activation of anti-inflammatory genes, whereas at lower concentrations they have a role in the suppression of activated anti-inflammatory genes (Chang-Lin 2011).

While there is much published data regarding the efficacy of OZURDEX in humans, little nonclinical pharmacology data has been published. Existing data demonstrates that dexamethasone was effective in a rabbit model of VEGF-induced vascular leakage (Edelman 2005).

Pharmacokinetics of Dexamethasone Ocular Formulations

Dexamethasone is a synthetic glucocorticoid with minimal or no metabolism in rabbit, monkey, or human ocular tissues, and dexamethasone does not bind to synthetic melanin. OZURDEX is formulated as an intravitreal implant containing dexamethasone 0.7 mg in the NOVADUR solid polymer drug delivery system, which is made up of PLGA matrix material. PLGA and PLA have been extensively investigated polymers for drug delivery purposes. The biodegradable polyester family has been regarded as one of the few synthetic biodegradable polymers with controllable biodegradability, excellent biocompatibility, and high safety. PLGA and PLA have been approved for human use by the FDA. PLGA and PLA are known to degrade via backbone hydrolysis (bulk erosion) and the degradation products, lactic acid and glycolic acid, are ultimately metabolized into carbon dioxide and water via the Krebs cycle (OZURDEX NDA 22-315, Anderson 1997).

Data described in OZURDEX NDA 22-315 indicates that an in vitro (implants in buffer) to in vivo correlation for dexamethasone release from the implant was established. In rabbit, the majority of the dexamethasone (>70%) was released from the implant by ~1 month post-dose. In a separate study, the in vivo release of dexamethasone in rabbits was unaffected by the administration of intact compared with fragmented implants over 28 days, and both implant formulations had released nearly 100% of dexamethasone by Day 28 (Bhagat 2014).

In contrast, OZURDEX NDA 22-315 describes that in monkey the majority of dexamethasone was released (>90%) from the implant by ~3 months post-dose. In a separate published monkey study, dexamethasone was detected in the retina and vitreous humor for 6 months, with peak concentrations during the first two months (Chang-Lin 2011).

Nonclinical Tolerability and Pharmacokinetics of ENV1105

Two nonclinical tolerability and pharmacokinetics studies of ENV1105, ENVRES-PRE-002 and ENV1105-PRE-003, were conducted in the albino rabbit to assess the duration of dexamethasone exposure following administration of various formulations of ENV1105. New Zealand White rabbits, 2 males/group/terminal time point, were administered a single bilateral intravitreal injection of either ENV1105 or OZURDEX and were followed for up 1, 2, 3, and/or 5 months. Animals were examined via slit lamp ophthalmoscopy and indirect ophthalmoscopy.

Bioanalytical Methods in Support of ENVRES-PRE-002

Ocular tissues, including aqueous humor, vitreous humor, and retina, were processed and analyzed for dexamethasone or FA by two of three methods. Dexamethasone present in ocular tissue samples was quantified by ELISA and HPLC. FA present in ocular tissues was quantified by HPLC and mass spectrometry. Prior to analysis, implants or particles were separated from vitreous humor samples via manual removal or centrifugation. Vitreous humor and aqueous humor tissue samples were analyzed as received or diluted with ACN for LC MS/MS or PBS for ELISA. Dexamethasone or FA were extracted from retinal tissue samples by using 95% methanol and then reconstituting in acetonitrile (ACN).

Bioanalytical Methods in Support of ENV1105-PRE-003

Bioanalytical methods for dexamethasone were developed and qualified in albino rabbit matrices by Covance Laboratories (Durham, N.C.) using liquid-liquid extraction and high performance liquid chromatography and tandem mass spectrometry (LC-MS/MS). Methods in rabbit aqueous humor, vitreous humor, vitreous humor containing implants, retina, choroid, and plasma were qualified for range of reliable response, selectivity, carryover assessment, and precision and accuracy. The formulations tested in the ENV1105-PRE-003 study are provided below in Table 9.

TABLE 9

Formulations Tested in Nonclinical Tolerability and Pharmacokinetics Studies

| Formulation ID | Test Article | Form Factor/ Size | No. of Implants/ Eye | Total Dose (μg / Eye) | Polymer Content (Ratio) | Study Number | Matrices Analyzed |
|---|---|---|---|---|---|---|---|
| ENV-1R-0159-82A | Dexamethasone | Suspension (25 × 25 × 50 μm) | NA | 700 | 203S | ENVRES-PRE-002 | Aqueous Humor, Vitreous Humor, Retina/Choroid |
| ENV-1R-0159-82B | Dexamethasone | Suspension (25 × 25 × 50 μm) | NA | 700 | 504S | | |
| ENV-1R-0159-82C | Dexamethasone | Suspension (25 × 25 × 50 μm) | NA | 700 | 203S/504S (50/50) | | |
| ENV-1R-0119-7-5 | Dexamethasone | Implant (225 × 225 × 2925 μm) | 6 | 270 | 203S/502S (50/50) | | |
| ENV-1R-0119-33-7 | Fluocinolone Acetonide | Implant (225 × 225 × 2925 μm) | NA | 40.7 | 203/DLG 1A (95/5) | | |
| ENV-1R-0119-33-9 | Fluocinolone Acetonide | Implant (225 × 225 × 2925 μm) | NA | 57.9 | 502S/502H (85/15) | | |
| ENV-1D-209-10-1 | Dexamethasone | Implant (200 × 200 × 4500 μm) | 4 | 355.6 | 203S/752S (85/15) | ENV1105-PRE-003 | Aqueous Humor, Vitreous Humor, Retina, Choroid, Plasma |
| ENV-1D-209-10-1 | Dexamethasone | Implant (200 × 200 × 4500 μm) | 2 | 177.8 | 203S/752S (85/15) | | |
| NA | Dexamethasone | Implant | 1 | 700 | 502H/502S (25:75) | | |
| ENV-1D-0209-12-3-G | Dexamethasone | Implant (200 × 200 × 4500 μm) | 2 | 201.6 | 203S/752S (85/15) | | |
| RES-DME-0005-27-2 | Dexamethasone | Implant (200 × 200 × 4500 μm) | 2 | 192.4 | 504H/203S (70/30) | | |
| RES-DME-0005-27-2 | Dexamethasone | Implant (200 × 200 × 4500 μm) | 2 | 192.4 | 504H/203S (70/30) | | |
| ENV-1D-0015-6-19 | Dexamethasone | Implant (200 × 200 × 4500 μm) | 2 | 193 | 203S/653H (60/40) | | |

Ocular Pharmacokinetics and Tolerability from Pharmacokinetics Study ENVRES-PRE-002

New Zealand White rabbits (2 males per group per terminal time point) were administered either a single bilateral administration of a particle suspension (50 μL, 0.7 mg/eye) or six implants (0.27 mg/eye) of dexamethasone, or one implant of one of two different implant formulations (0.0407 mg/eye; 0.0579 mg/eye) of fluocinolone acetonide via intravitreal injection. Animals were followed for up to 3 months, with ocular matrices (retina/choroid, vitreous humor and aqueous humor) collected to determine ocular pharmacokinetics at Months 2 and 3. Ocular exams were conducted on Days 2, 3, 6, 10, weekly through Day 28, and then biweekly through Month 3 to determine tolerability. A summary of the study designed is provided below in Table 10.

TABLE 10

Study Design for ENVRES-PRE-002 Nonclinical Tolerability and Pharmacokinetics Study

| Group | Number of Animals | Formulation ID | Test Article | Test Article Concentration (mg/eye) | Ophthalmic Exams | Terminal Time Points | Terminal Samples |
|---|---|---|---|---|---|---|---|
| 1 | 6 | ENV-1R-0159-82A | Dexamethasone Suspension | 700 | Baseline, Days 2, 3, 6, 10, Weeks 2, 3, 4, 6, 8, 10, 12 | Months 2 and 3 | Aqueous Humor, Vitreous Humor, Retina/Choroid |
| 2 | 6 | ENV-1R-0159-82B | Dexamethasone Suspension | 700 | | | |
| 3 | 6 | ENV-1R-0159-82C | Dexamethasone Suspension | 700 | | | |
| 4 | 6 | ENV-1R-0119-7-5 | Dexamethasone Implant | 270 (6 implants) | | | |
| 5 | 6 | ENV-1R-0119-33-7 | Fluocinolone acetonide Implant | 40.7 | | | |
| 6 | 6 | ENV-1R-0119-33-9 | Fluocinolone acetonide Implant | 57.9 | | | |

All formulations were generally well tolerated, with observations limited to findings related to the injection procedure. The pharmacokinetic data is provided below in Table 11 and in FIGS. 22-25.

TABLE 11

Ocular Pharmacokinetic Data from Nonclinical Study ENVRES-PRE-002

| Group | Formulation | Test Article Concentration (ug/eye) | Matrix | Cmax (ng/ g or mL) | Tmax (Day) | Clast (ng/ g or mL) | Tlast (Day) |
|---|---|---|---|---|---|---|---|
| Group 1 | ENV-1R-0159-82A | 700 dexamethasone | Aqueous Humor | 0.107 | 28 | 0.095 | 84 |
| | | | Vitreous Humor | 264.380 | 56 | 53.247 | 84 |
| | | | Retina/Choroid | 16271.888 | 28 | 36.375 | 84 |
| Group 2 | ENV-1R-0159-82B | 700 dexamethasone | Aqueous Humor | 2.610 | 28 | 0.210 | 84 |
| | | | Vitreous Humor | 4997.078 | 28 | 192.295 | 56 |
| | | | Retina/Choroid | 6993.380 | 56 | 18.194 | 84 |
| Group 3 | ENV-1R-0159-82C | 700 dexamethasone | Aqueous Humor | 0.970 | 28 | 0.125 | 84 |
| | | | Vitreous Humor | 2313.409 | 28 | 88.452 | 84 |
| | | | Retina/Choroid | 21149.675 | 28 | 10288.416 | 84 |
| Group 4 | ENV-1R-0119-7-5 | 270 dexamethasone | Aqueous Humor | 5.903 | 28 | 0.217 | 28 |
| | | | Vitreous Humor | 3075.170 | 28 | 232.176 | 84 |
| | | | Retina/Choroid | 28146.544 | 56 | 6678.204 | 84 |
| Group 5 | ENV-1R-0119-33-7 | 40.7 FA | Aqueous Humor | BLQ | NA | BLQ | NA |
| | | | Vitreous Humor | 297.863 | 90 | 297.863 | 84 |
| | | | Retina/Choroid | 3954.404 | 90 | 3954.404 | 84 |
| Group 6 | ENV-1R-0119-33-9 | 57.9 FA | Aqueous Humor | BLQ | NA | BLQ | NA |
| | | | Vitreous Humor | 295.829 | 28 | 295.829 | 28 |
| | | | Retina/Choroid | 1554.272 | 56 | 1554.272 | 56 |

Note:
BLQ: below limit of quantification;
NA: not applicable

Dexamethasone was present at high concentrations in the retina/choroid (Group 4 Cmax 28146 ng/mL), lower concentrations in vitreous humor (Group 4 Cmax 3075 ng/mL), and was present at very low concentrations in aqueous humor (Group 4 Cmax 5.9 ng/mL), and peaked on Day 28 or 56. Quantifiable levels of fluocinolone acetonide were present in the retina/choroid and vitreous humor samples (Group 5 Cmax 3954 ng/g and 298 ng/g, respectively), and peaked on Day 84 for Group 5 and Day 28 or 56 for Group 6. Presence of dexamethasone and FA in ocular tissues at later time points suggests successful extended release of test article over up to 3 months in the albino rabbit.

Ocular Tolerability and Ocular and Systemic Pharmacokinetics From Pharmacokinetics Study ENV1105-PRE-003

New Zealand White rabbits (2 males per group per terminal time point) were administered a single bilateral administration of either ENV1105 or OZURDEX. Animals were followed for up to 5 months, with ocular matrices (aqueous humor, vitreous humor, retina ("macula" punch), choroid ("macula" punch), and retina/choroid (remaining)) and plasma collected to determine pharmacokinetics on Week 1, Months 1, 2, 3, and/or 5. Vitreous humor was divided into 2 samples, one including the remaining implants and one without. Ocular exams were conducted on Week 1, Months 1, 2, 3, 4, and/or 5 to determine tolerability. A summary of the study design is presented below in Table 12.

TABLE 12

Study Design for ENV1105-PRE-003 Nonclinical Tolerability and Pharmacokinetics Study

| Group | Number of Animals | Test Article | Formulation ID | Dose (ug/eye) | No of Implants/ Eye | Ophthalmic Exams | Terminal Time Points | Terminal Samples |
|---|---|---|---|---|---|---|---|---|
| 1 | 8 | ENV1105 | ENV-1D-209-10-1 | 355.6 | 4 | Baseline, Week 1, Months 1, 2, 3, 4, 5 | Week 1, Months 1, 3, 5 | Aqueous Humor, Vitreous Humor, Retina, Choroid, Plasma |
| 2 | 8 | ENV1105 | ENV-1D-209-10-1 | 177.8 | 2 | | | |
| 3 | 6 | OZURDEX | NA | 700 | 1 | Baseline, Week 1, Months 1, 2, 3 | Week 1, Months 1, 2, 3 | |
| 4 | 8 | ENV1105 | ENV-1D-0209-12-3-G | 201.6 | 2 | | | |
| 5 | 8 | ENV1105 | RES-DME-0005-27-2 | 192.4 | 2 | | | |
| 6 | 8 | ENV1105 | RES-DME-0005-27-2 | 192.4 | 2 | | | |
| 7 | 8 | ENV1105 | ENV-1D-0015-6-19 | 193 | 2 | | | |

All formulations were generally well tolerated, with observations limited to findings related to the injection procedure. The concentration data is provided below in Tables 13, 14, 15, and 16, and in FIGS. 26-33.

TABLE 13

Dexamethasone Concentration Data From Nonclinical Study
ENV1105-PRE-002: Week 1

| Matrix | Parameter | Group 1 | 2 | 3 | 4 | 5 | 6 | 7 |
|---|---|---|---|---|---|---|---|---|
| Aqueous | Mean | BLQ | BLQ | 10.71 | 0.00 | 10.63 | BLQ | BLQ |
| Humor | SD | NA | NA | 9.48 | 0.00 | 21.25 | NA | NA |
|  | N | 4 | 4 | 4 | 4 | 4 | 4 | 4 |
| Vitreous | Mean | 331500.00 | 184250.00 | 462000.00 | 201000.00 | 161775.00 | 140000.00 | 165500.00 |
| Humor - With | SD | 98716.77 | 21868.93 | 95404.41 | 25664.50 | 59842.04 | 28178.01 | 32603.68 |
| Implants | N | 4 | 4 | 4 | 4 | 4 | 4 | 4 |
| Vitreous | Mean | 11.66 | 4.44 | 81.43 | 7.85 | 7.56 | 5.60 | 51.03 |
| Humor - No | SD | 4.56 | 6.22 | 39.98 | 10.15 | 6.04 | 4.79 | 33.74 |
| Implants | N | 4 | 4 | 3 | 4 | 4 | 4 | 4 |
| Retina-Punch | Mean | 54.43 | 7.43 | 1094.68 | 34.15 | 32.70 | 45.25 | 70.45 |
|  | SD | 28.15 | 14.85 | 1492.78 | 23.91 | 24.84 | 31.63 | 48.71 |
|  | N | 4 | 4 | 4 | 4 | 4 | 4 | 4 |
| Choroid-Punch | Mean | 9.45 | 0.00 | 264.43 | 13.13 | 0.00 | 12.25 | 6.80 |
|  | SD | 18.90 | 0.00 | 367.76 | 26.25 | 0.00 | 24.50 | 13.60 |
|  | N | 4 | 4 | 4 | 4 | 4 | 4 | 4 |
| Retina/Choroid | Mean | 44.80 | 6.50 | 736.75 | 27.50 | 42.70 | 23.98 | 104.05 |
| Non-punch | SD | 8.46 | 13.00 | 584.99 | 31.78 | 31.47 | 27.69 | 31.40 |
|  | N | 4 | 4 | 4 | 4 | 4 | 4 | 4 |
| Plasma | Mean | BLQ | BLQ | BLQ | BLQ | BLQ | BLQ | BLQ |
|  | SD | NA | NA | NA | NA | NA | NA | NA |
|  | N | 2 | 2 | 2 | 6 | 6 | 6 | 6 |

Note:
BLQ: below limit of quantification;
NA: not applicable

TABLE 14

Dexamethasone Concentration Data From Nonclinical Study
ENV1105-PRE-002: Month 1

| Matrix | Parameter | Group 1 | 2 | 3 | 4 | 5 | 6 | 7 |
|---|---|---|---|---|---|---|---|---|
| Aqueous | Mean | BLQ | BLQ | 9.40 | BLQ | 2.04 | 2.40 | 0.00 |
| Humor | SD | NA | NA | 14.41 | NA | 4.07 | 4.80 | 0.00 |
|  | N | 4 | 4 | 4 | 4 | 4 | 4 | 4 |
| Vitreous | Mean | 239750.00 | 142075.00 | 57120.50 | 121375.00 | 67500.00 | 42700.00 | 118450.00 |
| Humor - With | SD | 61070.32 | 54833.29 | 66666.40 | 18874.03 | 55753.09 | 15553.14 | 20383.24 |
| Implants | N | 4 | 4 | 4 | 4 | 4 | 4 | 4 |
| Vitreous | Mean | 136.57 | 95.57 | 237.95 | 68.90 | 196.88 | 321.50 | 53.60 |
| Humor - No | SD | 52.11 | 116.77 | 220.48 | 52.64 | 128.08 | 102.84 | 27.69 |
| Implants | N | 3 | 3 | 4 | 4 | 4 | 4 | 4 |
| Retina-Punch | Mean | 2986.80 | 98.67 | 4978.67 | 355.25 | 765.50 | 912.75 | 152.08 |
|  | SD | 5609.15 | 170.90 | 4901.73 | 370.64 | 326.65 | 369.83 | 151.12 |
|  | N | 4 | 3 | 3 | 4 | 4 | 4 | 4 |
| Choroid-Punch | Mean | 17.13 | 52.67 | 1010.00 | 112.48 | 237.75 | 272.25 | 50.28 |
|  | SD | 29.68 | 91.22 | 990.61 | 99.82 | 91.36 | 109.31 | 59.08 |
|  | N | 3 | 3 | 4 | 4 | 4 | 4 | 4 |
| Retina/Choroid | Mean | 2677.33 | 349.25 | 11351.50 | 430.75 | 882.50 | 889.50 | 249.00 |
| Non-punch | SD | 2228.92 | 326.95 | 15862.27 | 226.97 | 211.06 | 397.70 | 89.61 |
|  | N | 3 | 4 | 4 | 4 | 4 | 4 | 4 |
| Plasma | Mean | BLQ | BLQ | 0.80 | BLQ | BLQ | BLQ | BLQ |
|  | SD | NA | NA | 1.00 | NA | NA | NA | NA |
|  | N | 6 | 6 | 4 | 4 | 4 | 4 | 4 |

Note:
BLQ: below limit of quantification;
NA: not applicable

TABLE 15

Dexamethasone Concentration Data From Nonclinical Study ENV1105-PRE-002: Month 3

| Matrix | Parameter | Group 1 | 2 | 3 | 4 | 5 |
|---|---|---|---|---|---|---|
| Aqueous | Mean | BLQ | 2.55 | BLQ | BLQ | BLQ |
| Humor | SD | NA | 5.10 | NA | NA | NA |
|  | N | 4 | 4 | 4 | 4 | 4 |
| Vitreous | Mean | 27050.00 | 16381.73 | BLQ | 60600.00 | 39.25 |
| Humor - With Implants | SD | 21553.42 | 14052.84 | NA | 17212.21 | 7.58 |
|  | N | 4 | 4 | 4 | 4 | 4 |
| Vitreous | Mean | 36.50 | 16.58 | BLQ | 17.70 | BLQ |
| Humor - No Implants | SD | 35.45 | 20.86 | NA | 35.40 | NA |
|  | N | 4 | 4 | 4 | 4 | 4 |
| Retina-Punch | Mean | 112.78 | 52.05 | 12.00 | 8.80 | BLQ |
|  | SD | 106.11 | 16.88 | 24.00 | 17.60 | NA |
|  | N | 4 | 4 | 4 | 4 | 4 |
| Choroid-Punch | Mean | 81.75 | 12.88 | BLQ | BLQ | BLQ |
|  | SD | 163.50 | 25.75 | NA | NA | NA |
|  | N | 4 | 4 | 4 | 4 | 4 |
| Retina/Choroid | Mean | 5110.00 | 68.93 | 7.83 | 22.60 | BLQ |
| Non-punch | SD | 7243.92 | 26.76 | 15.65 | 4.20 | NA |
|  | N | 3 | 4 | 4 | 4 | 4 |
| Plasma | Mean | BLQ | BLQ | BLQ | BLQ | BLQ |
|  | SD | NA | NA | NA | NA | NA |
|  | N | 1 | 1 | 2 | 2 | 2 |

Note:
BLQ: below limit of quantification;
NA: not applicable;
ND: no data

TABLE 16

Dexamethasone Concentration Data From Nonclinical Study ENV1105-PRE-002: Month 5

| Matrix | Parameter | Group 1 | 2 |
|---|---|---|---|
| Aqueous | Mean | BLQ | BLQ |
| Humor | SD | NA | NA |
|  | N | 4 | 4 |
| Vitreous | Mean | BLQ | 204.25 |
| Humor-With | SD | NA | 408.50 |
| Implants | N | 4 | 4 |
| Vitreous | Mean | BLQ | 2.05 |
| Humor-No | SD | NA | 4.11 |
| Implants | N | 4 | 4 |
| Retina-Punch | Mean | BLQ | BLQ |
|  | SD | NA | NA |
|  | N | 4 | 4 |
| Choroid-Punch | Mean | BLQ | BLQ |
|  | SD | NA | NA |
|  | N | 4 | 4 |
| Retina/Choroid | Mean | BLQ | 8.65 |
| Non-punch | SD | NA | 17.30 |
|  | N | 4 | 4 |
| Plasma | Mean | BLQ | BLQ |
|  | SD | NA | NA |
|  | N | 2 | 2 |

Note:
BLQ: below limit of quantification; NA: not applicable

Figure 34:
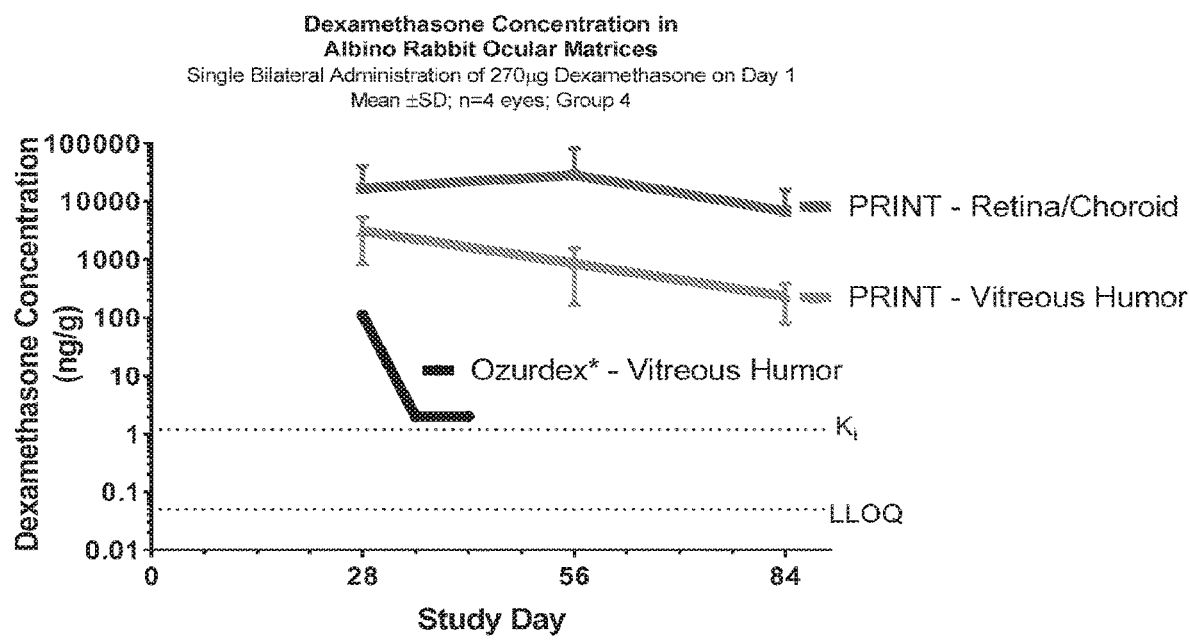
FIG. 34 illustrates the concentration and duration of dexamethasone in the vitreous human and retina/choroid achieved utilizing an intravitreal implant disclosed herein compared the concentration and duration of dexamethasone measured for OZURDEX®.

Data collected to date demonstrate that dexamethasone concentrations in vitreous humor, vitreous humor with implants, retina, and choroid were at or above therapeutically relevant concentrations in all groups at Week 1 and Month 1. By Month 3, little to no dexamethasone remained in the eyes administered OZURDEX, with no detectable dexamethasone in the vitreous samples and only individual samples of retina and choroid detectable at that time point. In contrast, high concentrations remained in the vitreous humor with implants samples in all ENV1105 groups at Month 3, indicating that the implants had not yet released all test article at that time point; dexamethasone was also detectable in vitreous humor, retina, and choroid in Groups 1, 2, and 4. Month 5 data is currently only available for Groups 1 and 2, with detectable dexamethasone observed in vitreous humor with implants and in retina/choroid in Group 2 samples; other samples were below the limit of quantitation. FIG. 34 illustrates the concentration and duration of dexamethasone in the vitreous human and retina/choroid achieved utilizing an intravitreal implant disclosed herein compared the concentration and duration of dexamethasone measured for OZURDEX®.

Exposure to dexamethasone in the aqueous humor was observed in most samples in the OZURDEX group during Week 1 and Month 1, and was generally undetectable in all other samples from all ENV1105 groups. This indicates decreased exposure to dexamethasone in the anterior segment following ENV1105 administration when compared with OZURDEX.

Dexamethasone was detected in 2 out of 4 plasma samples at Month 1 in the OZURDEX group, and was below the limit of quantitation in all other samples from all groups at all time points. These data demonstrate slightly increased systemic exposure following OZURDEX administration compared with ENV1105, as there were no quantifiable plasma samples after ENV1105 dose administration.

Data from these two studies indicate that ENV1105 retains and releases dexamethasone for as many as about 5 months, while OZURDEX retains no dexamethasone at the Month 3 time point. The trend suggests that ENV1105 implants will continue to release dexamethasone for about 6 months.

| Polymer Blend and wt./wt. ratio | Mass Biodegradable Polymer Matrix | Polymer blend % wt | Implant Size (um) | Implant Volume (mm³) | Wt. % API | Mass API (ug) | Total Implant (ug) | Needle Gauge |
|---|---|---|---|---|---|---|---|---|
| Lead Intravitreal Implant Formulations | | | | | | | | |
| 203S/752S (85/15) | 139-153 | 203S: 118-131<br>725S: 20-23 | 200 × 200 × 4500 | 0.18 | 35-45 | 86-92 | 225-245 | 27 |
| 203S/653H (60/40) | 135-145 | 203S: 81-87<br>653H: 54-58 | 200 × 200 × 4500 | | | 90-100 | | |
| 203S/502S (50/50) | 149-151 | 203S: 74-76<br>502S: 74-76 | 200 × 200 × 4500 | | | 76-94 | | |
| 203S/504H (30/70) | 133-136 | 203S: 40-41<br>504H: 93-95 | 200 × 200 × 4500 | | | 89-112 | | |
| 205S/653H (50/50) | 152-160 | 205S: 76-80<br>653H: 76-80 | 200 × 200 × 4500 | | | 73-85 | | |
| 203S/1A (95/5) | 136-148 | 203S: 129-141<br>DLG1A: 68-74 | 200 × 200 × 4500 | | | 89-97 | | |
| 203S/503H (15/85) | 60-72 | 203S: 9-11<br>503H: 51-61 | 225 × 225 × 4000 | 0.02 | | 50-58 | 110-130 | 25 |

Prophetic Example 1. ENV1105 Study in Patients with Diabetic Macular Edema

Clinical efficacy and safety is evaluated in randomized, active comparator controlled study in which subjects with diabetic macular edema are treated with OZURDEX (intravitreal dexamethasone 700 µg) or ENV1105 containing smaller dose of dexamethasone vs. what is administered to the patient via OZURDEX. OZURDEX is administered as indicated once every 6 months as is ENV1105. The mean change in best corrected visual acuity (BCVA) letters from baseline and gain of ≥15 letter in BCVA from baseline is assessed over 6 months. All adverse events are tracked and evaluated, including adverse event of intraocular pressure (IOP) elevation and cataract formation. The efficacy evaluation based on mean change in BCVA letters or gain of ≥15 BCVA letters as described above show non-inferior or superior control of macular edema as measured via BCVA in patients dosed with ENV1105. However, it is observed that the incidence of adverse events of IOP elevation, cataract formation, and systemic hypertension is lower in patients dosed with ENV1105 compared to patients dosed with OZURDEX. Adverse events associated with OZURDEX were obtained from the "Highlights of Prescribing Information," revised September 2014, which is available at http://www.allergan.com/assets/pdf/ozurdex_pi.pdf.

As generally applicable to Examples 1 above, the adverse event of IOP elevation is often characterized as IOP elevation by more than 10 mmHg. It has been shown for OZURDEX that the adverse event of IOP elevation occurs approximately in the range of 28% percent of the patients on OZURDEX while the incidence rate of IOP elevation in the placebo arm in the studied patient populations was in the range of 4%. ENV1105 at dexamethasone doses below the dexamethasone contained in OZURDEX (700 µg), while demonstrating non-inferior or superior treatment effect, demonstrates an improved safety and lesser incidence of adverse event of IOP elevation compared to OZURDEX's incidence. When ENV1105 is studied in the same patient population as OZURDEX, the level of IOP elevation by more than 10 mmHg is below 28% in this patient population.

Additionally, IOP elevation of higher than ≥30 mmHg at any time is also considered clinically undesirable. It has been shown for OZURDEX that the adverse event of IOP elevation of ≥30 mmHg occurs approximately in the range of 15% percent of the patients on OZURDEX while the incidence rate of IOP elevation in the placebo arm in the studied patient populations was in the range of 2%. ENV1105 at dexamethasone doses below the dexamethasone contained in OZURDEX (700 µg), while demonstrating non-inferior or superior treatment effect, demonstrates an improved safety and lesser incidence of adverse event of IOP elevation compared to OZURDEX's incidence. When ENV1105 is studied in the same patient population as OZURDEX, the level of IOP elevation of higher ≥30 mmHg below 15% in this patient population.

Furthermore, cataract formation at any time is also considered clinically undesirable. It has been shown for OZURDEX that the adverse event of cataract formation, including cataract, cataract nuclear, cataract subcapsular, lenticular opacities in patients who were phakic at baseline, occurs approximately in the range of 68% percent of the patients on OZURDEX while the incidence rate of cataract formation in the placebo arm in the studied patient populations was in the range of 21%. ENV1105 at dexamethasone doses below the dexamethasone contained in OZURDEX (750 µg), while demonstrating non-inferior or superior treatment effect, demonstrates an improved safety and lesser incidence of adverse event of cataract formation compared to OZURDEX's incidence. When ENV1105 is studied in the same patient population as OZURDEX, the level of cataract formation is below 68% in this patient population.

Lastly, systemic hypertension at any time is also considered clinically undesirable. It has been shown for OZURDEX that the adverse event of hypertension occurs approximately in the range of 13% percent of the patients on OZURDEX while the incidence rate of cataract formation in the placebo arm in the studied patient populations was in the range of 6%. ENV1105 at dexamethasone doses below the dexamethasone contained in OZURDEX (700 µg), while demonstrating non-inferior or superior treatment effect, demonstrates an improved safety and lesser incidence of adverse event of hypertension compared to OZURDEX's incidence. When ENV1105 is studied in the same patient population as OZURDEX, the level of hypertension is below 13% in this patient population.

Prophetic Example 2. Dexamethasone Implant Fabrication

A series of implants are fabricated utilizing the polymer matrix/therapeutic agent blends obtained using the method described in Example 1.1 with mold dimensions of 265×265×4500 µm and 255×255×4500 µm. The therapeutic agent is dexamethasone. A portion of polymer matrix/therapeutic agent blend is spread over a PET sheet and heated. Once heated, the blend is covered with the mold. Light pressure is applied using a roller to spread the blend over the mold area. The mold/blend laminate is then passed through a commercially available thermal laminator. The blend flows into the mold cavities and assumes the shape of the mold cavities. The blend is allowed to cool to room temperature and creates individual implants in the mold cavities. The mold is then removed leaving a two-dimensional array of implants resting on the film. Individual implants are removed from the PET film utilizing forceps.

265×265×4500 µm and 255×255×4500 µm implants demonstrate an in-vitro release of dexamethasone for about 4 to about 6 months in 1×PBS containing 0.1% TRITON-X surfactant.

Example embodiments have been described herein. As may be noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments, but should be defined only in accordance with features and claims supported by the present disclosure and their equivalents. Moreover, embodiments of the subject disclosure may include formulations, compounds, methods, systems, and devices which may further include any and all elements/features from any other disclosed formulations, compounds, methods, systems, and devices, including the manufacture and use thereof. In other words, features from one and/or another disclosed embodiment may be interchangeable with features from other disclosed embodiments, which, in turn, correspond to yet other embodiments. One or more features/elements of disclosed embodiments may be removed and still result in patentable subject matter (and thus, resulting in yet more embodiments of the subject disclosure). Furthermore, some embodiments of the present disclosure may be distinguishable from the prior art by specifically lacking one and/or another feature, functionality, ingredient or structure, which is included in the prior art (i.e., claims directed to such embodiments may include "negative limitations" or "negative provisos").

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. A method of treating an ocular condition in a subject in need thereof, comprising administering to an eye of the subject an effective amount of a composition comprising:
   A) a biodegradable polymer matrix, comprising a first biodegradable poly(D,L-lactide-co-glycolide) (PLGA) copolymer, a second biodegradable PLGA copolymer, and a third biodegradable PLGA copolymer; and
   B) at least one corticosteroid homogenously dispersed within the biodegradable polymer matrix.

2. The method of claim 1, wherein the composition is administered to the vitreous humor of an eye of the subject.

3. The method of claim 1, wherein the pharmaceutical composition is formulated to release the at least one corticosteroid for at least about 4 months.

4. The method of claim 1, wherein the at least one corticosteroid is dexamethasone, fluocinolone acetonide, or a combination thereof.

5. The method of claim 1, wherein the at least one corticosteroid is fluocinolone acetonide.

6. The method of claim 1, wherein the at least one corticosteroid is dexamethasone.

7. The method of claim 1, wherein the at least one corticosteroid comprises about 35 weight percent to about 45 weight percent of the pharmaceutical composition.

8. The method of claim 1, wherein the the first biodegradable PLGA copolymer has an inherent viscosity of 0.45 to 0.60 dlg measured at 0.1% w/v in $CHCl_3$ at 25° C. with an Ubbelhode size 0c glass capillary viscometer, and is 85±5 wt % of the biodegradable polymer matrix.

9. The method of claim 1, wherein the the first biodegradable PLGA copolymer has an inherent viscosity of 0.32-0.44 dL/g measured at 0.1% w/v in $CHCl_3$ at 25° C. with an Ubbelhode size 0c glass capillary viscometer, and is 85±5 wt % of the biodegradable polymer matrix.

10. The method of claim 1, wherein the subject is a dog, cat, horse, livestock, or human.

11. The method of claim 1, wherein the subject is a human.

12. The method of claim 1, wherein the ocular condition is macular edema, retinal vein occlusion, or uveitis.

13. The method of claim 2, wherein the ocular condition is macular edema, retinal vein occlusion, or uveitis.

14. The method of claim 1, wherein the ocular condition is macular edema, retinal vein occlusion, or uveitis.

15. The method of claim 4, wherein the ocular condition is macular edema, retinal vein occlusion, or uveitis.

16. The method of claim 5, wherein the ocular condition is macular edema, retinal vein occlusion, or uveitis.

17. The method of claim 6, wherein the ocular condition is macular edema, retinal vein occlusion, or uveitis.

18. The method of claim 7, wherein the ocular condition is macular edema, retinal vein occlusion, or uveitis.

19. The method of claim 8, wherein the ocular condition is macular edema, retinal vein occlusion, or uveitis.

20. The method of claim 9, wherein the ocular condition is macular edema, retinal vein occlusion, or uveitis.

21. The method of claim 10, wherein the ocular condition is macular edema, retinal vein occlusion, or uveitis.

22. The method of claim 11, wherein the ocular condition is macular edema, retinal vein occlusion, or uveitis.

23. The method of claim 2, wherein the at least one corticosteroid is dexamethasone.

24. The method of claim 3, wherein the at least one corticosteroid is dexamethasone.

25. The method of claim 7, wherein the at least one corticosteroid is dexamethasone.

26. The method of claim 11, wherein the at least one corticosteroid is dexamethasone.

* * * * *